United States Patent
Zawistoski et al.

(10) Patent No.: US 10,072,017 B2
(45) Date of Patent: Sep. 11, 2018

(54) COMPOUNDS AND METHODS FOR THE TREATMENT OF CYSTIC FIBROSIS

(71) Applicant: Flatley Discovery Lab, LLC, Charlestown, MA (US)

(72) Inventors: Michael P. Zawistoski, West Warwick, RI (US); Asmita Deshpande, Natick, MA (US); Bridget M. Cole, Quincy, MA (US)

(73) Assignee: Flatley Discovery Lab, LLC, Charlestown, MA (US)

( * ) Notice: Subject to any disclaimer, the term of this patent is extended or adjusted under 35 U.S.C. 154(b) by 0 days.

(21) Appl. No.: 15/392,727

(22) Filed: Dec. 28, 2016

(65) Prior Publication Data

US 2017/0204110 A1    Jul. 20, 2017

Related U.S. Application Data

(60) Provisional application No. 62/272,856, filed on Dec. 30, 2015.

(51) Int. Cl.
| | | |
|---|---|---|
| C07D 487/22 | (2006.01) | |
| C07D 491/22 | (2006.01) | |
| C07D 487/20 | (2006.01) | |
| C07D 487/14 | (2006.01) | |

(52) U.S. Cl.
CPC ......... *C07D 487/22* (2013.01); *C07D 487/14* (2013.01); *C07D 487/20* (2013.01); *C07D 491/22* (2013.01)

(58) Field of Classification Search
CPC .. C07D 487/22; C07D 487/14; C07D 487/20; C07D 491/22
USPC ....................................................... 514/278
See application file for complete search history.

(56) References Cited

U.S. PATENT DOCUMENTS 5,686,459 A    11/1997    Diederich et al.

FOREIGN PATENT DOCUMENTS

| CN | 105412089 A | 3/2016 |
|---|---|---|
| WO | 2016201440 A1 | 12/2016 |

OTHER PUBLICATIONS

Ardill, H., et al., "X=Y-ZH Compounds as Potential 1,3=Dipoles. Part 28. The Iminium Ion Route to Azomethine Ylides. Background and Reaction of Amines With Bifunctional Ketones," Tetrahedron, 46(18): 6443: 6448 (1990).
Azizian, J., et al., "One-Pot Highly Diastereo-Selective Synthesis of New 2-Substituted 8-(Sprio-3'-Indolino-2'-One)-Pyrrolo[3,4-a]-Pyrrolizine-1,3-Diones Mediated by Azomethine Ylide Induced by Microwave Irradiation," Synthetic Communications, 31:18, 2727-2733, DOI: 10.1081/SCC-100105318 (2001).
Rehn, S., et al., "The Three-Component Reaction between Isatin, α-Amino Acids, and Dipolarophiles," Eur. J. Org. Chem. 2004, 413-418.
Dondas, H. A., "1,3-Dipolar cycloaddition of stabilised and non-stabilised azomethine ylides derived from uracil polyoxin C (UPoC): access to nikkomycin analogues," Tetrahedron, 60 (2004) 3473-3485.
Karthikeyan, K., et al., "Synthesis of Spiropyrrolidines and Spiropyrrolizidines by Azomethine Ylide Cycloaddition of Baylis—Hillman Adducts Derived from N-Methyl Maleimide," Synlett, 2010, No. 18, pp. 2751-2754.
Rajkumar, V., et al., "Unactivated Norbornenes in [3+2] Cycload-ditions: Remarkably Stereo-controlled Entry into Norbornane-Fused Spirooxindolopyrrolidines, Spiro-1,3-indandionolylpyr-rolidines, and Spirooxindolopyrrolizidines," Synlett 2012, 23, 549-556.
Ruiz, F. M., "Receptor-Based Virtual Screening and Biological Characterization of Human Apurinic/Apyrimidinic Endonuclease (Ape1) Inhibitors," ChemMedChem 2012, 7, 2168-2178.
Pavlovskaya, T.L., et al., "Synthesis and Chemical Properties of New Derivatives of 3a',6a'-Dihydro-2'H-Spiro[Indole-3,1'-Pyr-rolo[3,4-c]Pyrrole]-2,4',6'(1H,3'H,5'H)-Trione," Chemistry of Het-erocyclic Compounds, vol. 49, No. 6, Sep. 2013 (Russian Original vol. 49, No. 6, Jun. 2013).

(Continued)

*Primary Examiner* — Kristin A Vajda
(74) *Attorney, Agent, or Firm* — Elmore Patent Law Group, P.C.; Edgar W. Harlan; Carolyn S. Elmore

(57) ABSTRACT

The invention relates to a compound of Formula I or IA compositions comprising compounds of Formula I or IA, and methods of treating cystic fibrosis comprising the step of administering a therapeutically effective amount of a compound of Formula I or IA to a patient in need thereof:

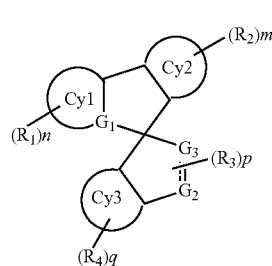

Formula I

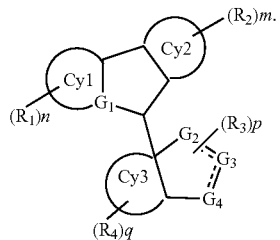

Formula IA

19 Claims, No Drawings

(56) References Cited

OTHER PUBLICATIONS

He, L., et al., "Ligand-based 3D pharmacophore design, virtual screening and molecular docking for novel p38 MAPK inhibitors," Med Chem Res (2015) 24:797-809.

Al-As'ad, R.M., et al., "A facile synthesis of novel pyridone-annelated spirooxindolepyrrolidines via 1,3-dipolar cycloaddition," Monatsh Chem (2015) 146:621-629.

Wang, Q.-L., et al., "An unprecedented base-promoted domino reaction of methyleneindolinones and N-tosyloxycarbamates for the construction of bispirooxindoles and spiroaziridine oxindoles," Chem. Commun., 2015, 51, 10726.

Zhao, H.-W., et al., "Diastereo- and Enantioselective Synthesis of Chiral Pyrrolidine-Fused Spirooxindoles via Organocatalytic [3+2] 1,3-Dipolar Cycloaddition of Azomethine Ylides with Maleimides," Adv. Synth. Catal. 2015, 357, 2492-2502.

Premachandra, I.D.U.A., et al., "Potent Synergy between Spirocyclic Pyrrolidinoindolinones and Fluconazole against Candida albicans," ChemMedChem 2015, 10, 1672-1686.

Muthusamy, S., et al., "Copper(I) catalyzed diastereoselective multicomponent synthesis of spiroindolo/pyrrolidines/-imidazolidines/-triazolidines from diazoamides via azomethine ylides," Org. Biomol. Chem., 2016, 14, 2228.

Ponce, A., et al., "Stereoselective Ag-Catalyzed 1,3-Dipolar Cycloaddition of Activated Trifluoromethyl-Substituted Azomethine Ylides," Chem. Eur. J. 2016, 22, 4952-4959.

Liu, L., et al., "Organocatalytic Asymmetric Michael/Cyclization Cascade Reaction of 3-Isothiocyanato Oxindoles with Maleimides for the Efficient Construction of Pyrrolidonyl Spirooxindoles," Eur. J. Org. Chem. 2016, 4711-4718.

Wang, X., et al., "Isatin N,N'-Cyclic Azomethine Imine 1,3-Dipole and Abnormal [3+2]-Cycloaddition with Maleimide in the Presence of 1,4-Diazabicyclo[2.2.2]octane," Org. Lett. 2017, 19, 646-649.

Girgis, A. S., et al., "Synthesis and QSAR study of novel cytotoxic spiro[3H-indole-3,2'(1'H)-pyrrolo [3,4-c pyrrole]-2,3',5'(1H,2'aH,4'H)-triones," European Journal of Medicinal Chemistry 47 (2012) 312-322.

PubChem, ZINC2364600, Jul. 13, 2005, pp. 1-11 [online], [retrieved on Feb. 6, 2017]. Retrieved from the Internet <URL: https://pubchem.ncbi.nlm.nih.gov/compound/1976377#section=Top>.

PubChem, CID 666133, Jun. 29, 2005, pp. 1-12 [online], [retrieved on Feb. 6, 2017]. Retrieved from the Internet <URL: https://pubchem.ncbi.nlm.nih.gov/compound/666133#section=1 op>.

PubChem, ZINC2415714, Jul. 13, 2005, pp. 1-11 [online], [retrieved on Feb. 6, 2017]. Retrieved from the Internet <URL: https://pubchem.ncbi.nlm.nih.gov/compound/2012794#section=2DSructure>.

Moreno, P. R., et al., "Coronary Composition and Macrophage Infiltration in Atherectomy Specimens From Patients With Diabetes Mellitus," Circulation, 102: 2180-2184 (2000).

COMPOUNDS AND METHODS FOR THE TREATMENT OF CYSTIC FIBROSIS

BACKGROUND

Cystic fibrosis (CF) is a lethal, recessive, genetic disease affecting approximately 1 in 2500 live births among Caucasians. (Cohen-Cymberknoh, M. et al., *Am. J. Respir. Crit. Care Med.* 1463-1471, 2011; Boat et al., The Metabolic Basis of Inherited Disease, 6th ed., pp 2649-2680, McGraw Hill, NY (1989)). Approximately 1 in 25 persons are carriers of the disease. The major symptoms of cystic fibrosis include chronic pulmonary disease, pancreatic exocrine insufficiency, and elevated sweat electrolyte levels. The symptoms are consistent with cystic fibrosis being an exocrine disorder. (Hantash F: U.S. Patent Application No. 20060057593). The CF gene codes for a cAMP/PKA-dependent, ATP-requiring, membrane chloride ion channel, generally found in the apical membranes of many secreting epithelia and is known as CFTR (cystic fibrosis transmembrane conductance regulator). There are currently over 1900 known mutations affecting CFTR, many of which give rise to a disease phenotype. Around 75% of CF alleles contain the ΔF508 mutation in which a triplet codon has been lost, leading to a missing phenylalanine at position 508 in the protein. This altered protein fails to be trafficked to the correct location in the cell and is generally destroyed by the proteasome. The small amount that does reach the correct location functions poorly. (Cuthbert A W, *British Journal of Pharmacology*, 163(1), 173-183, 2011).

Mutations in the CFTR gene result in absence or dysfunction of the protein that regulates ion transport across the apical membrane at the surface of certain epithelia. Although CFTR functions mainly as a chloride channel, it has many other roles, including inhibition of sodium transport through the epithelial sodium channel, regulation of the outwardly rectifying chloride channel, ATP channels, intracellular vesicle transport, and inhibition of endogenous calcium-activated chloride channels. CFTR is also involved in bicarbonate-chloride exchange. A deficiency in bicarbonate secretion leads to poor solubility and aggregation of luminal mucins. Obstruction of intrapancreatic ducts with thickened secretions causes autolysis of pancreatic tissue with replacement of the body of the pancreas with fat, leading to pancreatic insufficiency with subsequent malnutrition. In the lungs, CFTR dysfunction leads to airway surface liquid (ASL) depletion and thickened and viscous mucus that adheres to airway surfaces. The result is decreased mucociliary clearance (MCC) and impaired host defenses. Dehydrated, thickened secretions lead to endobronchial infection with a limited spectrum of distinctive bacteria, mainly *Staphylococcus aureus* and *Pseudomonas aeruginosa*, and an exaggerated inflammatory response leading to development of bronchiectasis and progressive obstructive airways disease. Pulmonary insufficiency is responsible for most CF-related deaths. (Cohen-Cymberknoh, M et al., *Am. J. Respir. Crit. Care Med.* 1463-1471, 2011).

The prognosis for the treatment of CF has improved over the last 40 years. This was achieved by improving pancreatic enzyme supplements, drugs designed to treat pulmonary infection, reduce inflammation and enhance mucociliary clearance. Currently the therapeutic challenges are to correct the biochemical defect of CF and to identify effective treatments for chronic respiratory infection. (Frerichs C. et al., *Expert Opin Pharmacother.* 10(7), 1191-202, 2009).

SUMMARY OF THE INVENTION

In one embodiment, the invention relates to a compound of Formula I and methods of treating CFTR mediated diseases, in particular cystic fibrosis, comprising the step of administering a therapeutically effective amount of a compound of Formula I, IA, IB or IC, or a pharmaceutically acceptable salt thereof, to a patient in need thereof:

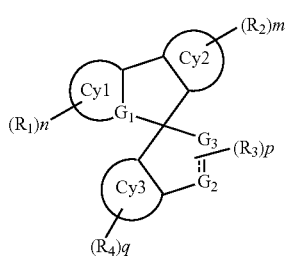

Formula I

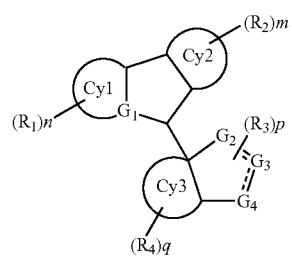

Formula IA

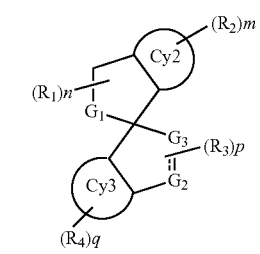

Formula IB

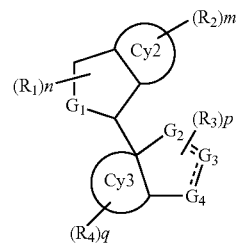

Formula IC

Wherein

Each n, m, p and q is independently selected from 0,1,2,3, 4,5, or 6;

Each Cy1, Cy2 and Cy3 is in dependently selected from absent and an optionally substituted 3, 4,5,6 or 7 membered carbocycyl, heterocyclyl and aryl;

$G_1$ is selected from $C(R_{10})$ and N;

$G_2$ is selected from absent, $[C(R_{10})_2]_z$, $CH_2$, $C(O)$, $C(S)$ $N(R_{11})$, $S(O)$, and $S(O)_2$;

z is 1, 2 or 3;

$G_3$ is selected from absent, $[C(R_{10})_2]_z$, $CH_2$, $C(R_{10})_2$, $C(O)$, $C(S)$ $N(R_{11})$, $S(O)$, and $S(O)_2$;

$G_4$ is selected from absent, $[C(R_{10})_2]_z$, $CH_2$, $C(R_{10})_2$, $C(O)$, $C(S)$ $N(R_{11})$, $S(O)$, and $S(O)_2$;

Each $R_{10}$ is independently selected from absent, hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl;

R₁₁ is selected from absent, hydrogen, deuterium, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl;

Each $R_1$, $R_2$, $R_3$ and $R_4$ is independently selected from hydrogen, deuterium, halogen, —$OR_{12}$, —$SR_{12}$, —$NR_{10}R_{13}$, —$N(R_{10})SO_2R_{13}$, —$CF_3$, —CN, —$NO_2$, —$N_3$, —C(O)$OR_{12}$, —C(O)$R_{12}$, —C(O)N $R_{12}R_{13}$, —S(O)$R_{12}$, —S(O)$NR_{12}$, —S(O)$_2R_{12}$, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl and substituted heteroaryl; Alternatively, two $R_1$ groups, or two $R_2$ groups, or two $R_3$ groups or two $R_4$ groups together with the atoms to which they are attached form an oxo (=O) or a vinyl group (=C); Alternatively, two $R_1$ groups, or two $R_2$ groups, or two $R_3$ groups or two $R_4$ groups together with the atoms to which they are attached forms a 3 4,5,6 or 7 membered, optionally substituted carbocyclic, heterocyclic or aryl group;

Each $R_{12}$ and $R_{13}$ is independently selected from absent, hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl; Alternatively two $R_{12}$ groups, or two $R_{13}$ groups, or one $R_{12}$ and one $R_{13}$ groups, together with the atoms to which they are attached forms a 3,4,5,6 or 7 membered, optionally substituted carbocyclic, heterocyclic or aryl group.

In one embodiment, the invention relates to a compound of Formula II or Formula IIA, and pharmaceutically acceptable slats thereof, and methods of treating CFTR mediated diseases, in particular cystic fibrosis, comprising the step of administering a therapeutically effective amount of a compound of Formula II or IIA, or a pharmaceutically acceptable salt thereof, to a patient in need thereof:

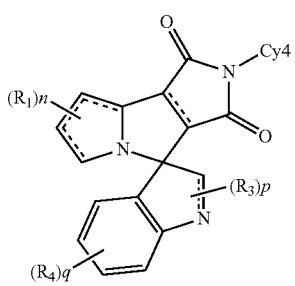

Formula II

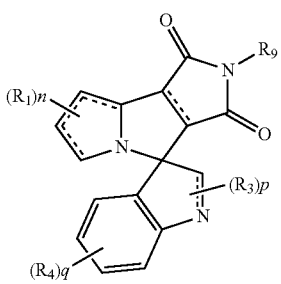

Formula IIA

Wherein:
Each ------ independently represents a single bond or a double bond; preferably each ------ represents a single bond;

$Cy_4$ is selected from optionally substituted aryl, heteroaryl or carbocyclyl wherein the aryl, heteroaryl or carbocylyl is optionally fused to an optionally substituted carbocyclyl, heterocyclyl or aryl;

Each n, p and q is independently selected from 0,1,2,3,4,5, or 6;

Each $R_1$, $R_3$ and $R_4$ is independently selected from hydrogen, deuterium, halogen, —$OR_{12}$, —$SR_{12}$, —$NR_{10}R_{13}$, —$CF_3$, —CN, —$NO_2$, —$N_3$, —C(O)$OR_{12}$, —C(O)$R_{12}$, —C(O)$NR_{12}R_{13}$, —S(O)$R_{12}$, —S(O)$NR_{12}$, —S(O)$_2R_{12}$, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl and substituted heteroaryl; Alternatively, two $R_1$ groups, or two $R_3$ groups together with the atoms to which they are attached form a carbonyl (C=O) or a vinyl group (C=CH$_2$);

preferably p is 3, ------ is a single bond in the ring to which the $R_3$ groups are attached, one $R_3$ is attached to the nitrogen atom and is hydrogen and two $R_3$ groups are attached to the carbon atom and, together with the carbon atom, form a carbonyl group. Alternatively, two $R_1$ groups, or two $R_3$ groups or two $R_4$ groups together with the atoms to which they are attached forms a 3,4,5,6 or 7 membered, optionally substituted carbocyclic, heterocyclic or aryl group;

Each $R_{12}$ and $R_{13}$ is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl; Alternatively two $R_{12}$ groups, or two $R_{13}$ groups, or one $R_{12}$ and one $R_{13}$ groups, together with the atoms to which they are attached, form a 3,4,5,6 or 7 membered, optionally substituted carbocyclic, heterocyclic or aryl group;

$R_9$ is selected from hydrogen, deuterium, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, and substituted heteroaryl.

DETAILED DESCRIPTION OF THE INVENTION

In one embodiment, the invention relates to a compound of Formula I or Formula IA, and pharmaceutically acceptable salts thereof, and methods of treating CFTR mediated diseases, in particular cystic fibrosis, comprising the step of administering a therapeutically effective amount of a compound of Formula I or Formula IA, or a pharmaceutically acceptable salt thereof, to a patient in need thereof:

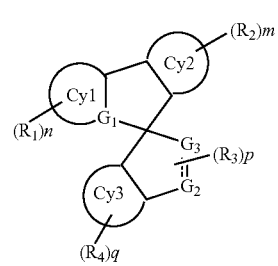

Formula I

-continued

Formula IA

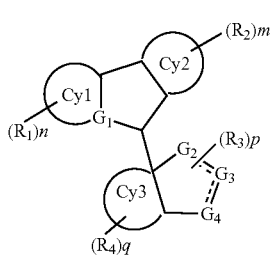

Wherein

Each n, m, p and q is independently selected from 0,1,2,3, 4,5, or 6;

Each Cy1, Cy2 and Cy3 is independently selected from an optionally substituted 3,4,5,6 or 7 membered carbocycyl, heterocyclyl and aryl;

$G_1$ is selected from $C(R_{10})$ and N;

$G_2$ is selected from absent, $[C(R_{10})_2]_z$, $CH_2$, $C(O)$, $C(S)$ $N(R_{11})$, $S(O)$, and $S(O)_2$; wherein z is 1, 2 or 3;

$G_3$ is selected from absent, $[C(R_{10})_2]_z$, $CH_2$, $C(R_{10})_2$, $C(O)$, $C(S)$ $N(R_{11})$, $S(O)$, and $S(O)_2$;

$G_4$ is selected from absent, $[C(R_{10})_2]_z$, $CH_2$, $C(R_{10})_2$, $C(O)$, $C(S)$ $N(R_{11})$, $S(O)$, and $S(O)_2$;

Each $R_{10}$ is independently selected from absent, hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl;

$R_{11}$ is selected from absent, hydrogen, deuterium, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl;

Each $R_1$, $R_2$, $R_3$ and $R_4$ is independently selected from hydrogen, deuterium, halogen, —$OR_{12}$, —$SR_{12}$, —$NR_{10}R_{13}$, —$CF_3$, —CN, —$NO_2$, —$N_3$, —$C(O)OR_{12}$, —$C(O)R_{12}$, —$C(O)NR_{12}R_{13}$, —$S(O)R_{12}$, —$S(O)NR_{12}R_{13}$, —$S(O)_2R_{12}$, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl and substituted heteroaryl; Alternatively, two $R_1$ groups, or two $R_2$ groups, or two $R_3$ groups or two $R_4$ groups together with the atoms to which they are attached form an oxo (=O) or a vinyl group (=C); Alternatively, two $R_1$ groups, or two $R_2$ groups, or two $R_3$ groups or two $R_4$ groups together with the atoms to which they are attached forms a 3,4,5,6 or 7 membered, optionally substituted carbocyclic, heterocyclic or aryl group;

Each $R_{12}$ and $R_{13}$ is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl; Alternatively two $R_{12}$ groups, or two $R_{13}$ groups, or one $R_{12}$ and one $R_{13}$ groups, together with the atoms to which they are attached forms a 3,4,5,6 or 7 membered, optionally substituted carbocyclic, heterocyclic or aryl group.

In a preferred embodiment, Cy1 is selected from:

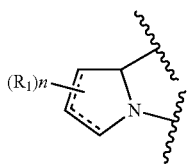
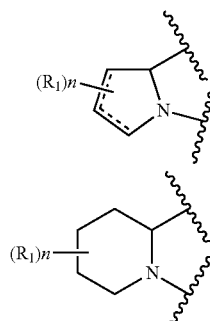
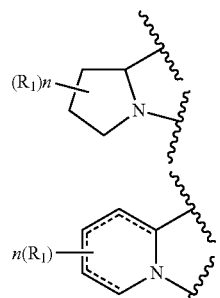
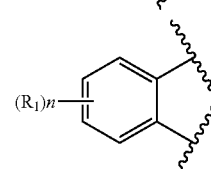
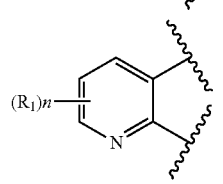
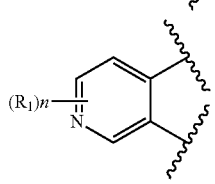

and,

More preferably, Cy1 is

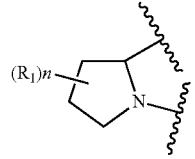

In a preferred embodiment, Cy2 is selected from:

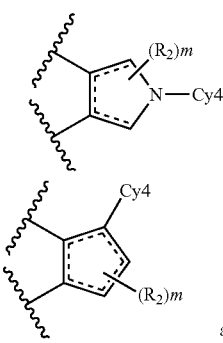
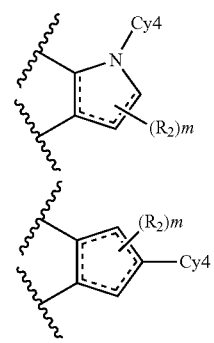

and,

More preferably, Cy2 is:

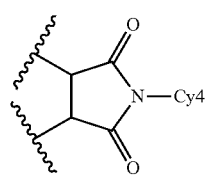

In a preferred embodiment, Cy3 is selected from:

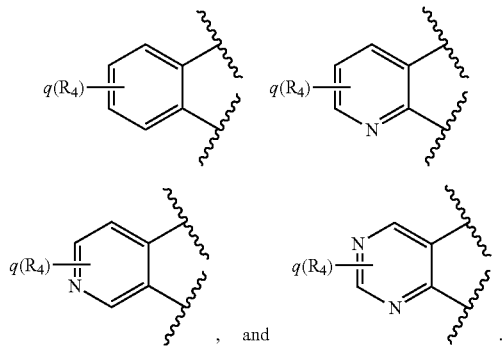

, and

In a preferred embodiment, Cy4 is selected from:

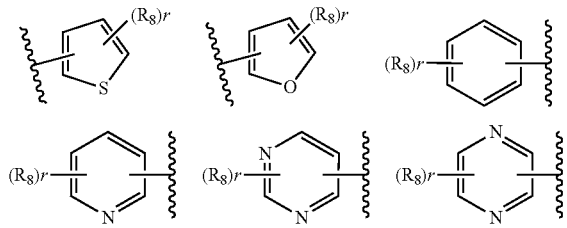

where r is 0 to 4 and each $R_8$ is independently selected from hydrogen, deuterium, halogen, —$OR_{12}$, —$SR_{12}$, —$NR_{10}R_{13}$, —$CF_3$, —CN, —$NO_2$, —$N_3$, —$C(O)OR_{12}$, —$C(O)R_{12}$, —$C(O)NR_{12}R_{13}$, —$S(O)R_{12}$, —$S(O)NR_{12}R_{13}$, —$S(O)_2R_{12}$, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl and substituted heteroaryl; Alternatively, two $R_8$ groups, together with the atoms to which they are attached forms a 3,4,5,6 or 7 membered, optionally substituted carbocyclic, heterocyclic or aryl group.

In a preferred embodiment, the invention relates to a compound of Formula II or Formula IIA, and pharmaceutically acceptable salts thereof, and methods of treating CFTR mediated diseases, in particular cystic fibrosis, comprising the step of administering a therapeutically effective amount of a compound of Formula II or IIA, or a pharmaceutically acceptable salt thereof, to a patient in need thereof:

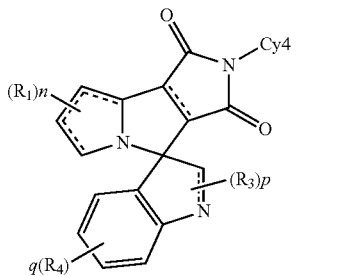

Formula II

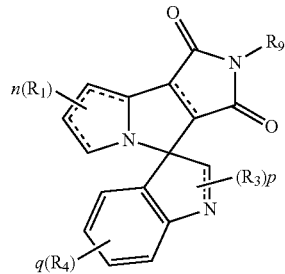

Formula IIA

Wherein
$Cy_4$ is selected from optionally substituted aryl, heteroaryl or carbocyclyl wherein the aryl, heteroaryl or carbocylyl is optionally fused to an optionally substituted carbocyclyl, heterocyclyl or aryl, Each n, p, r and q is independently selected from 0,1,2,3,4,5, or 6;

Each $R_1$, $R_3$, $R_4$ and $R_8$ is independently selected from hydrogen, deuterium, halogen, —$OR_{12}$, —$SR_{12}$, —$NR_{10}R_{13}$, —$CF_3$, —CN, —$NO_2$, —$N_3$, —$C(O)OR_{12}$, —$C(O)R_{12}$, —$C(O)NR_{12}R_{13}$, —$S(O)R_{12}$, —$S(O)NR_{12}R_{13}$, —$S(O)_2R_{12}$, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl and substituted heteroaryl; Alternatively, two $R_1$ groups, or two $R_3$ groups together with the atoms to which they are attached form an oxo (=O) or a vinyl group (=C); Alternatively, two $R_1$ groups, or two $R_3$ groups or two $R_4$ groups together with the atoms to which they are attached forms a 3,4,5,6 or 7 membered, optionally substituted carbocyclic, heterocyclic or aryl group;

Each $R_{12}$ and $R_{13}$ is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl; Alternatively two $R_{12}$ groups, or two $R_{13}$ groups, or one $R_{12}$ group and one $R_{13}$ group, together with the atoms to which they are attached, form a 3,4,5,6 or 7 membered, optionally substituted carbocyclic, heterocyclic or aryl group;

$R_9$ is selected from hydrogen, deuterium, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl.

In a preferred embodiment, the invention relates to a compound of Formula III or IIIA or a pharmaceutically acceptable salt thereof:

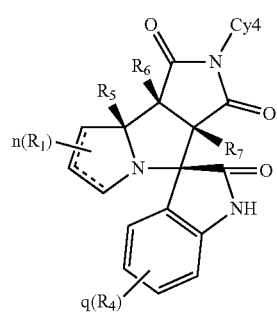

Formula III

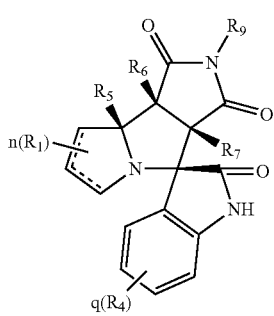

Formula IIIA

Wherein

Cy$_4$ is selected from optionally substituted aryl, heteroaryl or carbocyclyl wherein the aryl, heteroaryl or carbocylyl is optionally fused to an optionally substituted carbocyclyl, heterocyclyl or aryl. Each n and q is independently selected from 0,1,2,3,4,5, or 6;

Each $R_1$, $R_4$, $R_5$, $R_6$ and $R_7$ is independently selected from hydrogen, deuterium, halogen, —OR$_{12}$, —SR$_{12}$, —NR$_{10}$R$_{13}$, —CF$_3$, —CN, —NO$_2$, —N$_3$, —C(O)OR$_{12}$, —C(O)R$_{12}$, —C(O)NR$_{12}$R$_{13}$, —S(O)R$_{12}$, —S(O)NR$_{12}$R$_{13}$, —S(O)$_2$R$_{12}$, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl and substituted heteroaryl; Alternatively, two $R_1$ groups together with the atoms to which they are attached form an oxo (=O) or a vinyl group (=C);

Alternatively, two $R_1$ groups, or two $R_3$ groups or two $R_4$ groups together with the atoms to which they are attached form a 3,4,5,6 or 7 membered, optionally substituted carbocyclic, heterocyclic or aryl group;

Each $R_{12}$ and $R_{13}$ is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl; Alternatively two $R_{12}$ groups, or two $R_{13}$ groups, or one $R_{12}$ and one $R_{13}$ groups, together with the atoms to which they are attached, form a 3,4,5,6 or 7 membered, optionally substituted carbocyclic, heterocyclic or aryl group;

$R_9$ is selected from hydrogen, deuterium, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl.

In a preferred embodiment, the invention relates to a compound of Formula IV or Formula IVA, or a pharmaceutically acceptable salt thereof:

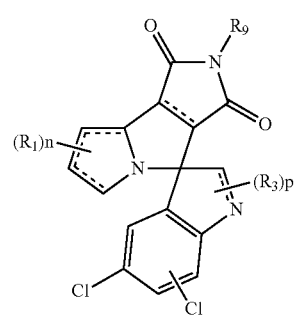

Formula IVA

Wherein

Cy$_4$ is selected from optionally substituted aryl, heteroaryl or carbocyclyl wherein the aryl, heteroaryl or carbocylyl is optionally fused to an optionally substituted carbocyclyl, heterocyclyl or aryl, Each n and p is independently selected from 0,1,2,3,4,5, or 6;

Each $R_1$, and $R_3$ is independently selected from hydrogen, deuterium, halogen, —OR$_{12}$, —SR$_{12}$, —NR$_{10}$R$_{13}$, —CF$_3$, —CN, —NO$_2$, —N$_3$, —C(O)OR$_{12}$, —C(O)R$_{12}$, —C(O)NR$_{12}$R$_{13}$, —S(O)R$_{12}$, —S(O)NR$_{12}$R$_{13}$, —S(O)$_2$R$_{12}$, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl and substituted heteroaryl; Alternatively, two $R_1$ groups, or two $R_3$ groups together with the atoms to which they are attached form an oxo (=O) or a vinyl group (=C);

Alternatively, two $R_1$ groups, or two $R_3$ groups or two $R_4$ groups together with the atoms to which they are attached forms a 3,4,5,6 or 7 membered, optionally substituted carbocyclic, heterocyclic or aryl group; and Each $R_{12}$ and $R_{13}$ is independently selected from absent, hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl; Alternatively two $R_{12}$ groups, or two $R_{13}$ groups, or one $R_{12}$ and one $R_{13}$ groups, together with the atoms to which they are attached forms a 3,4,5,6 or 7 membered, optionally substituted carbocyclic, heterocyclic or aryl group.

In another embodiment, the invention relates to a compound of Formula V or VA,

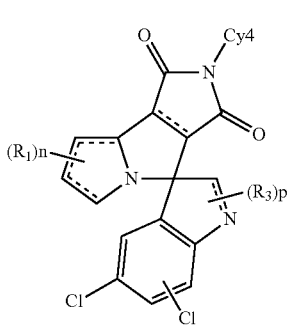

Formula IV

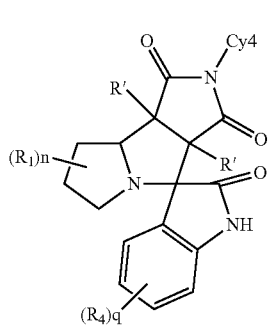

(V)

-continued

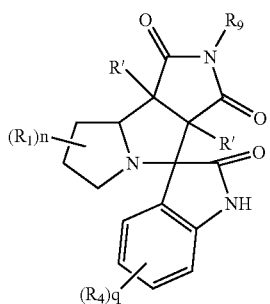
(VA)

or a pharmaceutically acceptable salt thereof, where each R' is independently hydrogen or deuterium, and $Cy_4$, $R_1$, $R_4$, $R_9$, n and q are as defined above. Preferably, each R' is hydrogen. Preferably, the compounds of Formula V have the stereochemistry shown in Formulas VB and VC below.

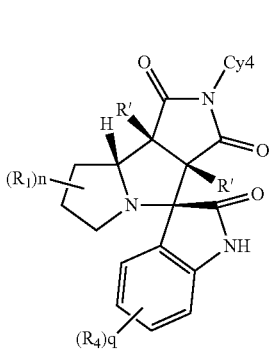
(VB)

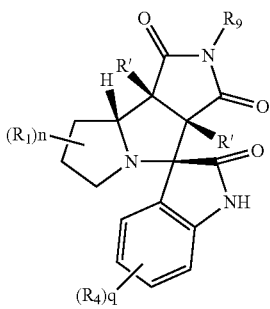
(VC)

In another embodiment, the invention relates to a compound of Formula VI or VIA, or a pharmaceutically acceptable salt thereof,

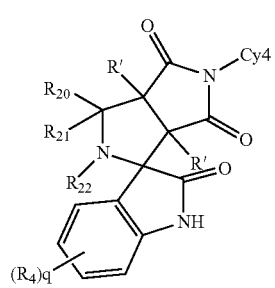
(VI)

-continued

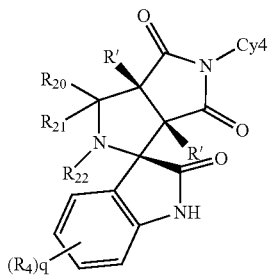
(VIA)

where $Cy_4$, R', $R_4$ and q are as defined above, and $R_{20}$, $R_{21}$ and $R_{22}$ are each, independently hydrogen, alkyl, substituted alkyl, alkenyl, substituted alkenyl, alkynyl, cycloalkyl, substituted cycloalkyl, substituted alkynyl, aryl, substituted aryl, heteroaryl or substituted heteroaryl.

Alternatively, $R_{20}$ and $R_{21}$, together with the carbon atom to which they are attached, form a spiro-cycloalkyl or spiro-heterocyclyl group, such as a spiro-$C_3$-$C_6$-cycloalkyl. In one embodiment, $R_{20}$ and $R_{21}$ are both hydrogen and $R_{22}$ is not hydrogen. In another embodiment, $R_{21}$ and $R_{22}$ are both hydrogen and $R_{20}$ is not hydrogen. In certain embodiments, $R_{21}$ and $R_{22}$ are both hydrogen and $R_{20}$ is $C_1$-$C_6$-alkyl, substituted $C_1$-$C_6$-alkyl, $C_3$-$C_6$-cycloalkyl, substituted $C_3$-$C_6$-cycloalkyl, aryl-$C_1$-$C_6$-alkyl, substituted aryl-$C_1$-$C_6$-alkyl, heteroaryl-$C_1$-$C_6$-alkyl, or substituted heteroaryl-$C_1$-$C_6$-alkyl. Preferably, the aryl-$C_1$-$C_6$-alkyl group is an arylmethyl group and the heteroaryl-$C_1$-$C_6$-alkyl group is a heteroarylmethyl group. In one embodiment, $R_{20}$ is a $C_1$-$C_4$-alkyl group optionally substituted with one or more substituents selected from halogen, hydroxyl, carboxyl; a phenylmethyl (benzyl) group, wherein the phenyl group is optionally substituted with halogen, cyano, hydroxyl, amino, methyl, methoxy, trifluoromethoxy, and trifluoromethyl; or a heteroarylmethyl group, where the heteroaryl is pyridyl, pyrimidyl, pyrazyl or a five-membered nitrogen containing heteroaryl or fused 5/6 heteroaryl, such as thiazolyl, isoxazolyl, indolyl or benzimidazole; and the heteroaryl is optionally substituted, for example, with a $C_1$-$C_4$-alkyl group, halogen, hydroxyl or amino.

In a preferred embodiment, the invention relates to a compound of Formula VII, or a pharmaceutically acceptable salt thereof;

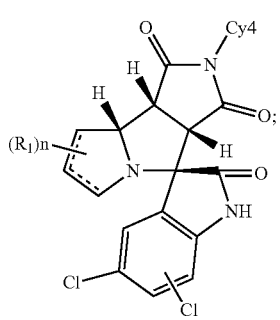
Formula VII wherein n, $R_1$, and $Cy_4$ are as defined above.

In a preferred embodiment, the invention relates to a compound of Formula VIII, or a pharmaceutically acceptable salt thereof;

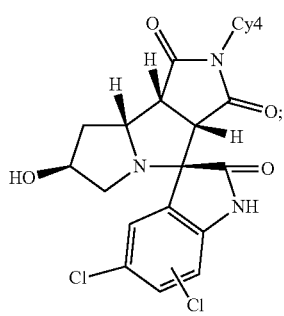

Formula VIII

Wherein Cy₄ is as defined above.

In preferred embodiments, the invention relates to a compound of Formula II, III, IV, V, VA, VB, VC, VI, VIA, VII or VIII, wherein Cy4 is selected from:

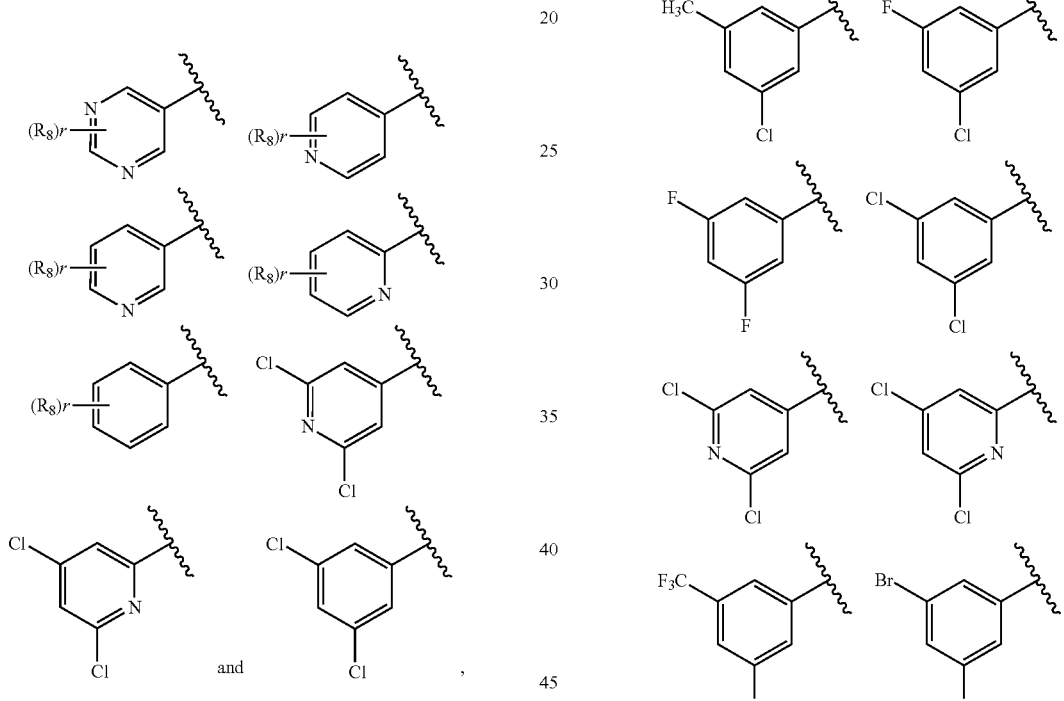

wherein r is selected from 0,1,2, and 3; preferably r is 1, 2 or 3; and, each $R_8$ is independently selected from deuterium, halogen, —$OR_{12}$, —$SR_{12}$, —$NR_{10}R_{13}$ —$CF_3$, —CN, —$NO_2$, —$N_3$, —C(O)$OR_{12}$, —C(O)$R_{12}$, —C(O)$NR_{12}R_{13}$, —S(O)$R_{12}$, —S(O)$NR_{12}R_{13}$, —S(O)$_2R_{12}$, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl and substituted heteroaryl; Alternatively, two $R_8$ groups together with the atoms to which they are attached forms a 3,4,5,6 or 7 membered, optionally substituted, carbocyclic, heterocyclic or aryl group; in certain embodiments, r is 1 or 2 and each $R_8$ is independently halogen, preferably chloro, bromo or fluoro; methoxy; trifluoromethoxy; difluoromethoxy; methyl; —C(O)OCH₃; —C(O)NH₂, CN; or hydroxyl.

Each $R_{12}$ and $R_{13}$ is independently selected from hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl; Alternatively two $R_{12}$ groups, or two $R_{13}$ groups, or one $R_{12}$ and one $R_{13}$ groups, together with the atoms to which they are attached forms a 3,4,5,6 or 7 membered, optionally substituted carbocyclic, heterocyclic or aryl group.

In certain embodiments of the compounds of Formulas I, IA, II, IIA, III, IIIA and V, q is 1, 2 or 3, and each $R_4$ is independently halogen, preferably fluoro, chloro, or bromo; methyl; trifluoromethyl; difluoromethyl; carboxy; —SO₂NH₂; or —C(O)NH₂.

In certain embodiments of the compounds of Formulas I, IA, II, IIA, III, IIIA, V, VA, VB, VC, VI, VIA, VII and VIII, Cy4 is selected from the groups set forth below.

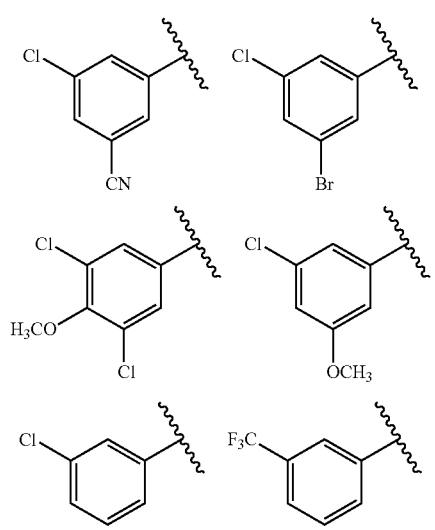

-continued

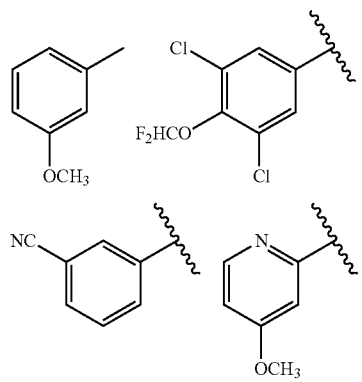

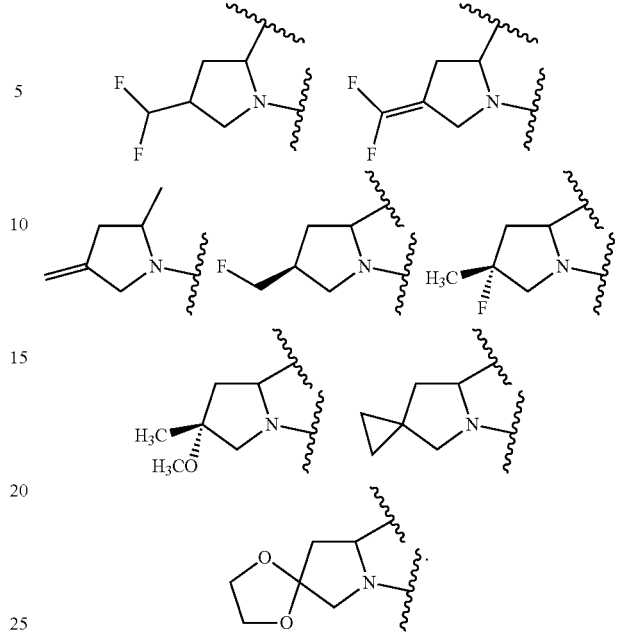

In certain embodiments of the compounds of Formulas I, IA, II, IIA, III, IIIA, IV, IVA, V, VA, VB, VC and VII, n is 0,1 or 2, preferably 1 or 2, and each $R_1$ is independently selected from halogen, preferably fluoro, chloro or bromo; methyl; hydroxyl; trifluoromethyl; trideuteromethyl; BnO—; CN; $CH_3C(O)O$—; $NH_2$; difluoromethyl; fluoromethyl; or $CH_3C(O)NH$—. Alternatively, two adjacent $R_1$ moieties, together with the carbon atoms to which they are attached, form an epoxide ring or two geminal $R_1$ moieties, together with the carbon atom to which they are attached, form a spiro-cycloalkyl group, preferably a spiro-cyclopropyl group, a C=$CH_2$ group or a C=$CF_2$ group.

In certain embodiments of the compounds of Formulas V, VA, VB, VC, VD, VII and IX

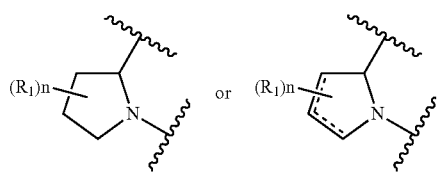

is selected from the groups shown below:

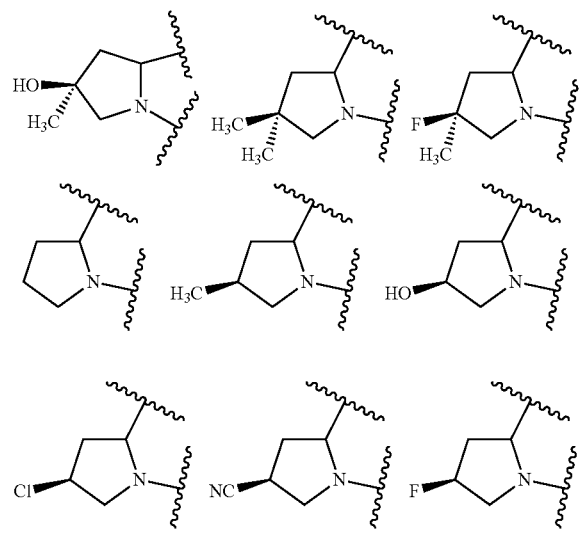

In a preferred embodiment, the invention relates to a compound of Formula IX, or a pharmaceutically acceptable salt thereof;

Formula IX

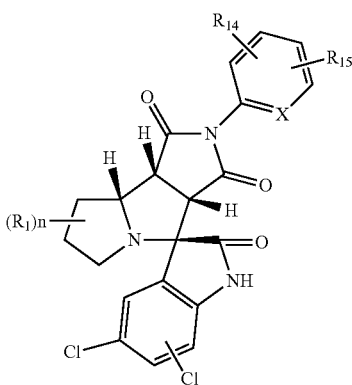

wherein n and $R_1$ are as defined above;
X is $CR_{10}$ or N;
Wherein each $R_{14}$ and $R_{15}$ is independently, hydrogen, deuterium, halogen, —$OR_{12}$, —$SR_{12}$, —$NR_{10}R_{13}$, —$CF_3$, —CN, —$NO_2$, —$N_3$, —$C(O)OR_{12}$, —$C(O)R_{12}$, —$C(O)NR_{12}R_{13}$, —$S(O)R_{12}$, —$S(O)NR_{12}R_{13}$, —$S(O)_2R_{12}$, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl and substituted heteroaryl; Alternatively, $R_{14}$ and $R_{15}$ together with the atoms to which they are attached forms a 3,4,5,6 or 7 membered, optionally substituted carbocyclic, heterocyclic or aryl group; or a pharmaceutically acceptable salt thereof;
Each $R_{12}$ and $R_{13}$ is independently selected from absent, hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl; Alternatively two $R_{12}$ groups, or two $R_{13}$ groups, or one $R_{12}$ and one $R_{13}$ groups, together with the atoms to which they are attached forms a 3,4,5,6 or 7 membered, optionally substituted carbocyclic, heterocyclic or aryl group.

In a preferred embodiment, the invention relates to a compound of Formula VII, wherein $R_{14}$ is —Cl, —Br, —F, —CF$_3$, —OCH$_3$, —OCH$_2$CH$_3$, —OCH$_2$C(CH$_3$)$_3$, —C(O)OCH$_3$, —CH$_3$, —CH$_2$CH$_3$, —C(O)NH$_2$.

In a preferred embodiment, the invention relates to a compound of Formula VII, wherein $R_{15}$ is —Cl, —Br, —F, —CF$_3$, —OCH$_3$, —OCH$_2$CH$_3$, —OCH$_2$C(CH$_3$)$_3$, —C(O)OCH$_3$, —CH$_3$, —CH$_2$CH$_3$, —C(O)NH$_2$.

In a preferred embodiment, the invention relates to a compound of Formula VII, wherein $R_{14}$ is —Cl.

In a preferred embodiment, the invention relates to a compound of Formula VII, wherein $R_{15}$ is —Cl.

In a preferred embodiment, the invention relates to a compound of Formula VII, wherein $R_{14}$ and $R_{15}$ are —Cl.

In a preferred embodiment, the invention relates to a compound of Formula VII, wherein n is 0.

The compounds of this invention may be prepared by methods known in the art. Exemplary synthetic routes to prepare compounds of this invention are illustrated in Schemes I-IV below:

Scheme I:

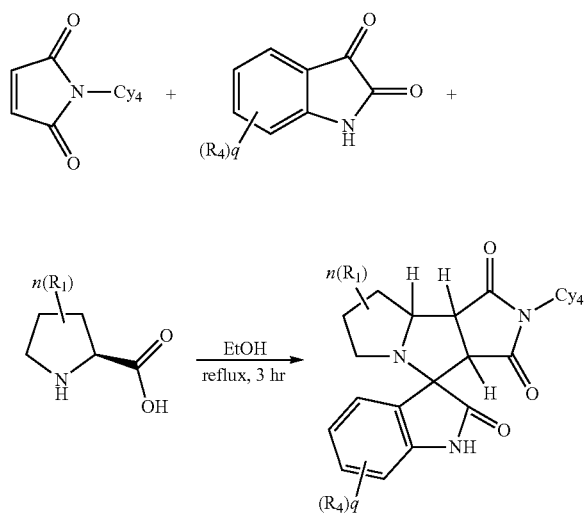

Scheme II:

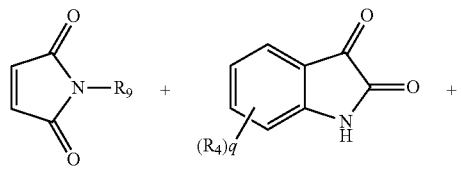

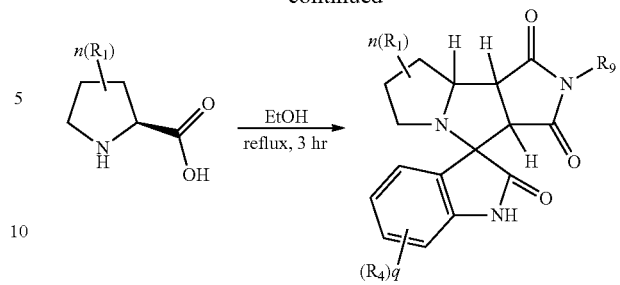

Scheme III:

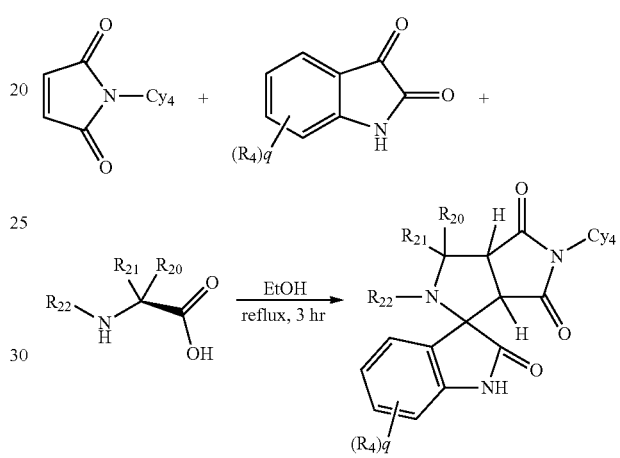

Scheme IV:

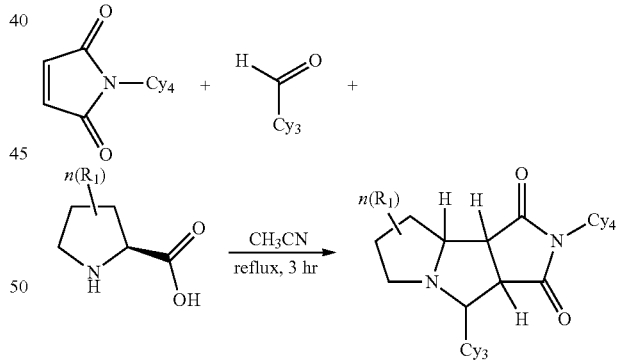

In one embodiment, the invention relates to a compound or a pharmaceutically acceptable composition of Formula I, IA, II, IIA, III, IIIA, IV, IVA, V, VA, VB, VC, VI, VIA, VII, VIII or IX, or a pharmaceutical acceptable salt thereof, and methods of treating cystic fibrosis comprising the step of administering a therapeutically effective amount of a compound of Formula I, IA, II, IIA, III, IIIA, IV, IVA, V, VA, VB, VC, VI, VIA, VII, VIII or IX to a patient in need thereof.

Compounds of the invention are useful as modulators of CFTR and treating diseases or disorders mediated by CFTR such as for the treatment of disease, disorders or conditions such as Cystic fibrosis, Asthma, Constipation, Pancreatitis, Gastrointestinal diseases or disorders, Infertility, Hereditary emphysema, Hereditary hemochromatosis, Coagulation-Fibrinolysis deficiencies, such as Protein C deficiency, Type 1 hereditary angioedema, Lipid processing deficiencies, such as Familial hypercholesterolemia, Type 1 chylomicronemia, Abetalipoproteinemia, Lysosomal storage diseases, such as I-cell disease/Pseudo-Hurler, Mucopolysaccharidoses, Sandhof/Tay-Sachs, Crigler-Najjar type II, Polyendocrinopathy/Hyperinsulemia, Diabetes mellitus, Laron dwarfism, Myeloperoxidase deficiency, Primary hypoparathyroidism, Melanoma, Glycanosis CDG type 1, Hereditary emphysema, Congenital hyperthyroidism, Osteogenesis imperfecta, Hereditary hypofibrinogenemia, ACT deficiency, Diabetes insipidus (DI), Neurophyseal DI, Neprogenic DI, Charcot-Marie Tooth syndrome, Perlizaeus-Merzbacher disease, neurodegenerative diseases such as Alzheimer's disease, Parkinson's disease, Amyotrophic lateral sclerosis, Progressive supranuclear plasy, Pick's disease, several polyglutamine neurological disorders such as Huntington's disease, Spinocerebullar ataxia type I, Spinal and bulbar muscular atrophy, Dentororubal pallidoluysian, and Myotic dystrophy, as well as spongiform encephalopathies such as Hereditary Creutzfeldt-Jakob disease, Fabry disease, Straussler-Scheinker disease, secretory diarrhea, polycystic kidney disease, chronic obstructive pulmonary disease (COPD), dry eye disease, or Sjogren's Syndrome, Spongiform encephalopathies, such as Hereditary Creutzfeldt-Jakob disease (due to Prion protein processing defect), Fabry disease and Straussler-Scheinker syndrome.

The compounds of the invention may be administered in combination with antibiotics, anti-inflammatory medicines, bronchodilators, or mucus-thinning medicines. In particular antibiotics for the treatment of bacteria mucoid *Pseudomonas* may be used in combination with compounds of the invention. Inhaled antibiotics such as tobramycin, colistin, and aztreonam can be used in combination with treatment with compounds of the invention. Anti-inflammatory medicines may also be used in combination with compounds of the invention to treat CFTR related diseases. Bronchodilators can be used in combination with compounds of the invention to treat CFTR related diseases.

In one embodiment, the invention provides a method of treating cystic fibrosis or a symptom thereof in a subject in need thereof, comprising administering to the subject a therapeutically effective amount of a compound of the invention. The compound of the invention is optionally administered in combination with one or more additional pharmaceutical agents useful for the treatment of CF. In a preferred embodiment, the additional pharmaceutical agent is the aminoglycoside gentamicin. In a preferred embodiment, the additional pharmaceutical agent is ataluren, Ivacaftor (Kalydeco), or VX-809. In another embodiment, a compound of the invention is administered in combination with a second compound selected from FDL-169 and FDL-176. In one embodiment, the compound of the invention is administered in combination with both FDL-169 and FDL-176. In one embodiment, the invention relates to pharmaceutical compositions comprising compounds of the invention and pharmaceutically acceptable carriers. The compositions may include compounds of the invention, and optionally a pharmaceutically acceptable carrier, adjuvant or vehicle. In certain embodiments, these compositions optionally further comprise one or more additional therapeutic agents useful for the treatment of CFTR mediated diseases or disorders.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid, gel or liquid filler, diluent, encapsulating material or formulation auxiliary of any type. Some examples of materials which can serve as pharmaceutically acceptable carriers are sugars such as lactose, glucose and sucrose; cyclodextrins such as alpha-($\alpha$), beta-($\beta$) and gamma-($\gamma$) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir. In a preferred embodiment, administration is oral administration. Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

In another embodiment, administration is parenteral administration by injection. Injectable preparations, for example, sterile injectable aqueous or oleaginous suspensions, may be formulated according to the known art using suitable dispersing or wetting agents and suspending agents. The sterile injectable preparation may also be a sterile injectable suspension or emulsion, such as INTRALIPID®, LIPOSYN® or OMEGAVEN®, or solution, in a nontoxic parenterally acceptable diluent or solvent, for example, as a solution in 1,3-butanediol. INTRALIPID® is an intravenous fat emulsion containing 10-30% soybean oil, 1-10% egg yolk phospholipids, 1-10% glycerin and water. LIPOSYN® is also an intravenous fat emulsion containing 2-15% safflower oil, 2-15% soybean oil, 0.5-5% egg phosphatides 1-10% glycerin and water. OMEGAVEN® is an emulsion for infusion containing about 5-25% fish oil, 0.5-10% egg phosphatides, 1-10% glycerin and water. Among the acceptable vehicles and solvents that may be employed are water, Ringer's solution, USP and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics is known in the art (see, for example U.S. Pat. No. 5,767,068 to Van Devanter et al., U.S. Pat. No. 5,508,269 to Smith et al., and WO 98/43650 by Montgomery).

The compositions described herein can be formulated in a unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose. The amount of the active compound in a unit dosage form will vary depending upon, for example, the host treated, and the particular mode of administration. In one embodiment, the unit dosage form can have one of the compounds of the invention as an active ingredient in an amount of about 10 mg, 20 mg, 30 mg, 40 mg, 50 mg, 100 mg, 150 mg, 200 mg, 250 mg, 300 mg, 400 mg, 500 mg, 600 mg, 700 mg, 750 mg, 800 mg, 900 mg, 1000 mg, or 1,250 mg.

In some embodiments, the compounds of the invention can be administered in a dose of at least about 10 mg/day to at least about 1500 mg/day. In some embodiments, the compounds of the invention are administered in a dose of at least about 300 mg (e.g., at least about 450 mg, at least about 500 mg, at least about 750 mg, at least about 1,000 mg, at least about 1250 mg, or at least about 1500 mg).

Dose adjustments can be made for patients with mild, moderate or severe hepatic impairment (Child-Pugh Class A). Furthermore, dosage adjustments can be made for patients taking one or more Cytochrome P450 inhibitors and inducers, in particular CYP3A4, CYP2D6, CYP2C9, CYP2C19 and CYP2B6 inhibitors and inducers. Dose adjustments can also be made for patients with impaired Cytochrome P450 function such as poor, intermediate, extensive and ultra-rapid metabolizers.

Definitions

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include both branched and straight chain, substituted or unsubstituted saturated aliphatic hydrocarbon radicals/groups having the specified number of carbons. Preferred alkyl groups comprise about 1 to about 24 carbon atoms ("$C_1$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$").

The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$"). The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means an aromatic system containing one, two or three rings wherein such rings may be attached together in a pendent manner or may be fused. The term "aryl" embraces aromatic radicals such as phenyl, naphthyl, tetrahydronaphthyl, indane furanyl, quinazolinyl, pyridyl and biphenyl.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like. The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N, N-alkylamino, such as N-methylamino, N-ethylamino, N, N-dimethylamino, N, N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkyl sulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g., $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms "alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The terms "compound" "drug," and "prodrug" as used herein all include pharmaceutically acceptable salts, co-crystals, solvates, hydrates, polymorphs, enantiomers, diastereoisomers, racemates and the like of the compounds, drugs and prodrugs having the formulas as set forth herein.

The present invention includes all pharmaceutically acceptable isotopically-labeled or enriched compounds of the invention. The compounds include one or more atoms that are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^2H$ and $^3H$, carbon, such as $^{11}C$, $^{13}C$ and $^{14}C$, nitrogen, such as $^{13}N$ and $^{15}N$, oxygen, such as $^{15}O$, $^{17}O$ and $^{18}O$, chlorine, such as $^{36}Cl$, fluorine, such as $^{18}F$, iodine, $^{123}I$ and $^{125}I$, phosphorus, such as $^{32}P$, and sulfur, such as $^{35}S$.

Substituents indicated as attached through variable points of attachments can be attached to any available position on the ring structure.

As used herein, the term "effective amount of the subject compounds," with respect to the subject method of treatment, refers to an amount of the subject compound which, when delivered as part of desired dose regimen, brings about management of the disease or disorder to clinically acceptable standards.

"Treatment" or "treating" refers to an approach for obtaining beneficial or desired clinical results in a patient. For purposes of this invention, beneficial or desired clinical results include, but are not limited to, one or more of the following: alleviation of symptoms, diminishment of extent of a disease, stabilization (i.e., not worsening) of a state of disease, preventing spread (i.e., metastasis) of disease, preventing occurrence or recurrence of disease, delay or slowing of disease progression, amelioration of the disease state, and remission (whether partial or total).

EXAMPLES

List of Abbreviations:
All temperatures are in degrees Centigrade
CF—cystic fibrosis
CFTR—cystic fibrosis transmembrane conductance regulator
$CH_2Cl_2$—methylene chloride
DIPEA—N,N-diisopropylethylamine
DMF—dimethylformamide
DMSO—dimethylsulfoxide
ENaC—epithelial sodium channel
$Et_2O$—diethyl ether
$Et_3N$—triethylamine
EtOAc—ethyl acetate
$H_2O$—water
HATU—(1-[Bis(dimethylamino)methylene]-1H-1,2,3-triazolo[4,5-b]pyridinium 3-oxid hexafluorophosphate)
HBS—Hepes-buffered saline
HCl—hydrochloric acid
HOAc—acetic acid
HPLC—high pressure liquid chromatography
hr—hours
HTS—high throughput screen
$K_2CO_3$—potassium carbonate
$Na_2SO_4$—sodium sulfate
NaH—sodium hydride
NaH—sodium hydride
$NaHCO_3$—sodium bicarbonate
NAUC—normalized area under the curve
$NH_4Cl$—ammonium chloride
NMR—nuclear magnetic resonance
PBS—Phosphate buffered saline
$POCl_3$—phosphorus oxychloride
rt—room temperature
TFA—trifluoroacetic acid
THF—tetrahydrofuran
YFP— yellow fluorescent protein
THF—tetrahydrofuran
$Ac_2O$—acetic anhydride
NaOAc—sodium acetate
EtOH—ethanol
MeOH—methanol
$CH_3CN$—acetonitrile
NaOH—sodium hydroxide
$CH_3I$—methyl iodide
$SnCl_2.2H_2O$—tin(II) chloride dihydrate
EDC—1-Ethyl-3-(3-dimethylaminopropyl)carbodiimide
HOBT—Hydroxybenzotriazole
TEMPO—(2,2,6,6-Tetramethylpiperidin-1-yl)oxyl
DAST—Diethylaminosulfur trifluoride Example 1

(3R,3a'S,8a'R,8b'R)-5,7-dichloro-2'-(3,5-dichlorophenyl)-3a',6',7',8',8a',8b'-hexahydro-1'H-spiro[indoline-3,4'-pyrrolo[3,4-a]pyrrolizine]-1',2,3'(2'H)-trione (10)

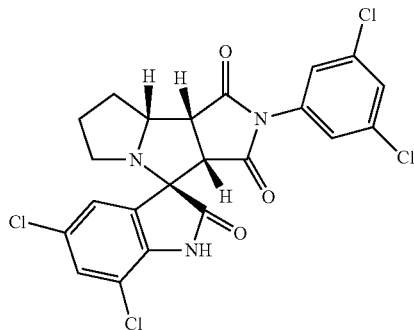 [SMILES: O=C1[C@H]2[C@H]3CCCN3[C@]3(C(=O)Nc4c(Cl)cc(Cl)cc43)[C@H]2C(=O)N1c1cc(Cl)cc(Cl)c1]

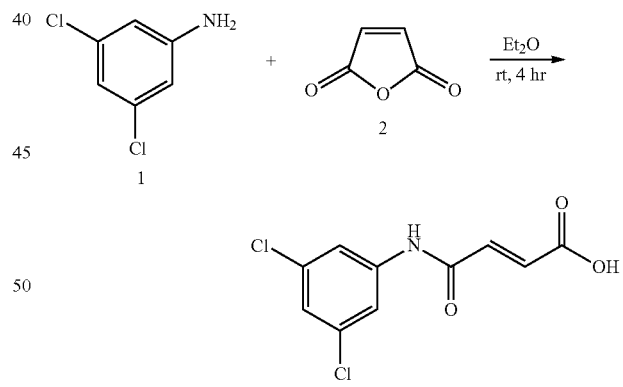

(E)-4-((3,5-Dichlorophenyl)amino)-4-oxobut-2-enoic acid (3). 3,5-Dichloroaniline (1) (30 g, 185.2 mmol) was added to a stirred solution of maleic anhydride (2) (18.1 g, 185.2 mmol) in $Et_2O$ (500 mL) at rt. The reaction mixture was stirred at rt for 4 hr. The resulting suspension was filtered and the solid was dried in vacuo to give the crude product. This was triturated with $Et_2O$ and dried in vacuo to give 40 g (83.1% yield) of pure product as an off-white solid, which was used without further purification in the next step. LCMS m/z 260 [M+H−1], 262 [M+H+1], 264 [M+H+3]; (98.4% purity).

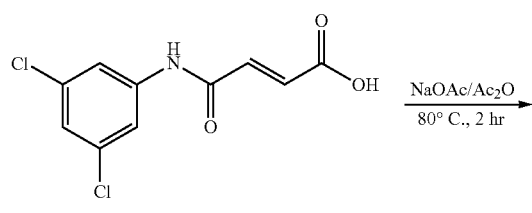

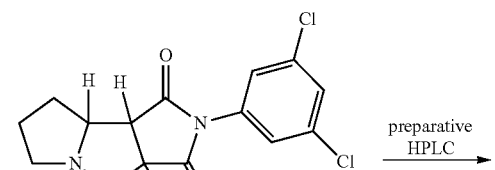

1-(3,5-Dichlorophenyl)-1H-pyrrole-2,5-dione (4). 3 (45 g, 173.0 mmol) was added to a mixture of NaOAc (14.19 g, 173.0 mmol) and Ac$_2$O (500 mL) at rt. The resulting mixture was stirred at 80° for 2 hr, then cooled to rt. Ice-cold H$_2$O was added and the resulting solid was collected and dried in vacuo to give 25 g (59.8% yield) of white was used without further purification. $^1$H NMR (400 MHz, DMSO-d$_6$) δ 7.69-7.68 (dd, J=2.0 Hz, J=2.0 Hz, 1H), 7.51-7.50 (d, J=2.0 Hz, 2H), 7.25 (s, 2H).

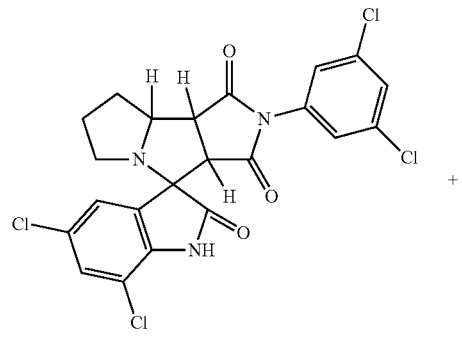

racemate 1

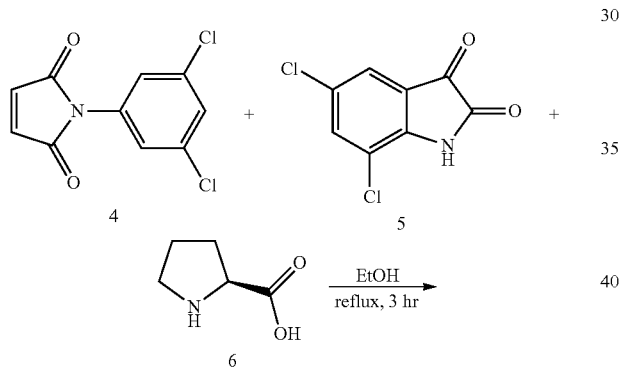

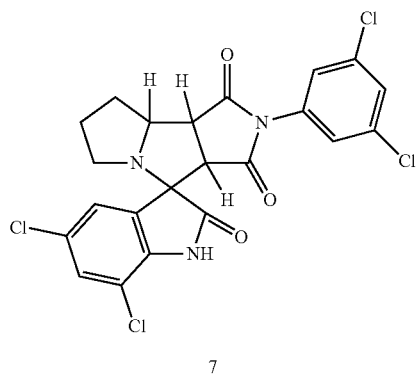

5,7-Dichloro-2'-(3,5-dichlorophenyl)-3a',6',7',8',8a ', 8b'-hexahydro-1'H-spiro[indoline-3,4'-pyrrolo[3,4-a]pyrrolizine]-1',2,3'(2'H)-trione (7).
To a stirred solution of 4 (5 g, 20.65 mmol) in EtOH (50 mL) was added 5,7-dichloroisatin (5) (4.46 g, 20.65 mmol) and L-Proline (6) (2.37 g, 20.65 mmol) at rt. The reaction mixture was stirred at 80° for 3 hr, then cooled to rt, and evaporated in vacuo to give 4.4 g of 7 as a brown solid.

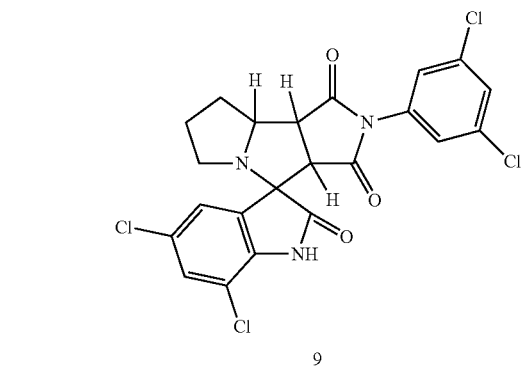

racemate 2

(3R,3a'S,8a'R,8b'R)-5,7-dichloro-2'-(3,5-dichlorophenyl)-3a',6',7',8',8a ',8b'-hexahydro-1'H-spiro[indoline-3,4'-pyrrolo[3,4-a]pyrrolizine]-1',2,3'(2'H)-trione (10) and (3S,3a'R,8a'S,8b'S)-5,7-dichloro-2'-(3,5-dichlorophenyl)-3a',6',7',8',8a',8b'-hexahydro-1'H-spiro[indoline-3,4'-pyrrolo[3,4-a]pyrrolizine]-1',2,3'(2'H)-trione (11). The mixture of crude products 7 (1.5 g) was purified by preparative HPLC using the following conditions: Acquisition Method—RND-FA-4.5 MIN; Column—Acquity BEH C18 (50 mm×2.1 mm, 1.7 uM); Mobile Phase—A—0.1% Formic Acid in H$_2$O, B—0.1% Formic Acid in CH$_3$CN; Time (min)/% B: 0/3, 0.4/3, 3.2/98, 3.8/98, 4.2/3, 4.5/3; Column Temp—35°; Flow Rate—0.6 mL/min. The following fractions were collected: 8 (racemate 1)—340 mg; LCMS m/z 510 [M$^+$−1], 512 [M$^+$+1], 514 [M$^+$+3] 516 [M$^+$+5] (98.6% purity); HPLC (99.8% purity); 9 (racemate 2)—770 mg; LCMS m/z 510 [M−1], 512 [M+1], 514 [M+3] 516 [M+5], (97.6% purity); HPLC (99.6% purity).

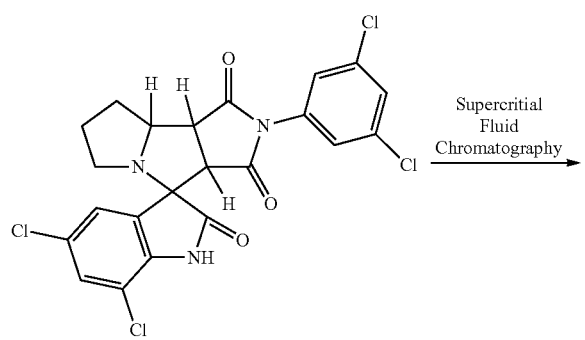

9
racemate 2

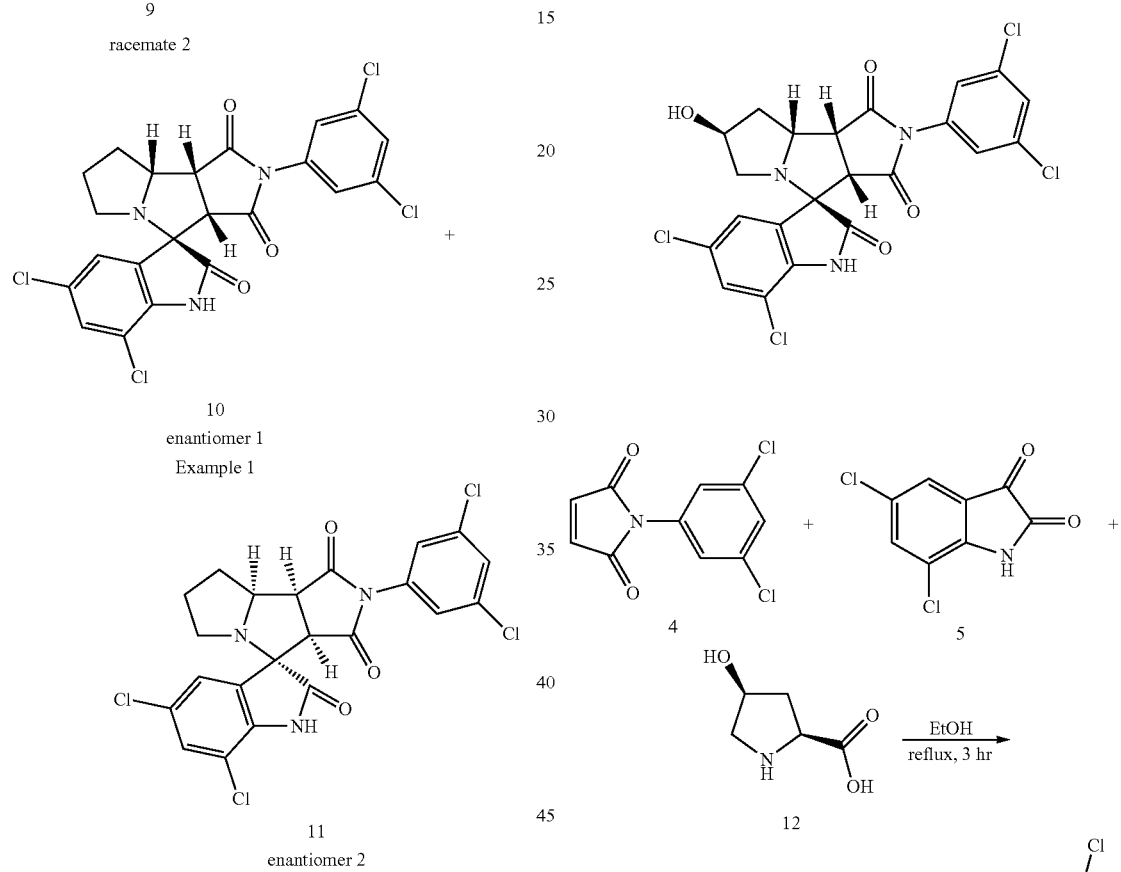

1H), 7.45 (d, J=1.2 Hz, 2H), 7.03 (m, 1H), 4.32-4.27 (m, 1H), 3.86 (d, J=8.0 Hz, 1H), 3.72-3.68 (t, J=7.6 Hz, 1H), 2.58-2.52 (m, 1H), 2.39-2.32 (m, 1H), 1.97-1.84 (m, 4H); Optical rotation $[\alpha]_D^{20}=-48.200°$.

Example 2

(3R,3a'S,7'S,8a'R,8b'R)-5,7-dichloro-2'-(3,5-dichlorophenyl)-7'-hydroxy-3a',6',7',8',8a',8b'-hexahydro-1'H-spiro[indoline-3,4'-pyrrolo[3,4-a]pyrrolizine]-1',2,3'(2'H)-trione (14)

9 (770 mg) was submitted to Supercritical Fluid Chromatography, using the following conditions: Column—Chiralpak-IC (4.5 mm×250 mm); Solvent—MeOH. The following fractions were collected: 10 (enantiomer 1, Example 1)—200 mg; LCMS m/z 510 [M−1], 512 [M+1], 514 [M+3] 516 [M+5], (99.2% purity); HPLC (97.3% purity); Chiral HPLC (99.8% purity); $^1$H NMR (300 MHz, DMSO-d$_6$) δ 11.22 (s, 1H), 7.77-7.76 (t, J=1.8 Hz, 1H), 7.55 (d, J=1.8 Hz, 1H), 7.45 (d, J=1.8 Hz, 2H), 7.04 (d, J=1.8 Hz, 1H), 4.32-4.25 (m, 1H), 3.86 (d, J=8.4 Hz, 1H), 3.72-3.66 (t, J=8.1 Hz, 1H), 2.59-2.52 (m, 1H), 2.39-2.32 (m, 1H), 1.97-1.84 (m, 4H); Optical rotation $[\alpha]_D^{20}=+49.200°$. The structure and absolute stereochemistry of 10 were determined by single crystal x-ray diffraction.

11 (enantiomer 2)—118 mg; LCMS m/z 510 [M−1], 512 [M+1], 514 [M+3] 516 [M+5], (83.9% purity); HPLC (91.7% purity); Chiral HPLC (95.5% purity); $^1$H NMR (400 MHz, DMSO-d$_6$) δ 11.21 (s, 1H), 7.76 (m, 1H), 7.54 (m, (7'S)-5,7-dichloro-2'-(3,5-dichlorophenyl)-7'-hydroxy-3a',6',7',8',8a',8b'-hexahydro-1'H-spiro[indoline-3,4'-pyrrolo[3,4-a]pyrrolizine]-1',2,3'(2'H)-trione (13) To a stirred solution of 4 (5 g, 20.65 mmol) in EtOH (50 mL) was added 5 (4.46 g, 20.65 mmol) and cis-4-hydroxy-L-proline (12) (2.70 g, 20.65 mmol) at rt. The reaction mixture was stirred at 80° for 3 hr, then cooled to rt, and evaporated in vacuo to give 4.5 g of 13 as a brown solid.

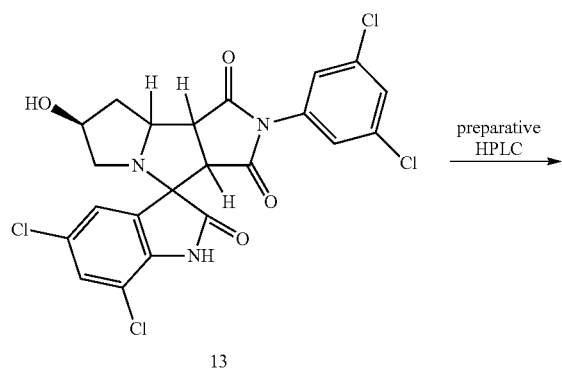

13

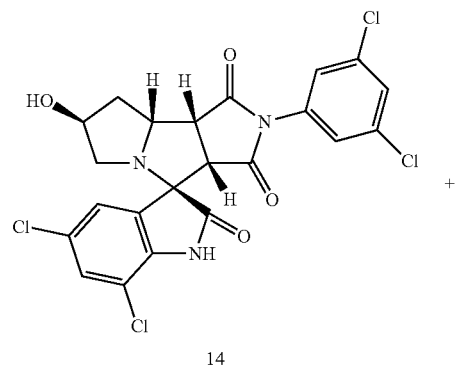

14
enantiomer 1
Example 2

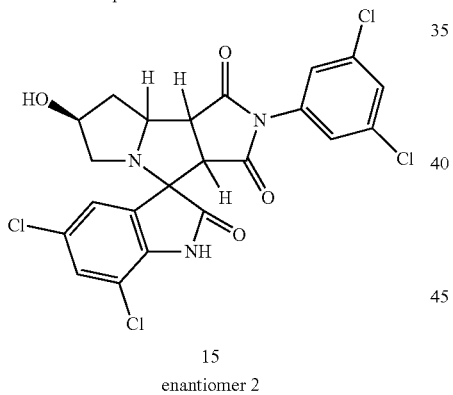

15
enantiomer 2

(3R,3a'S,7'S,8a'R,8b'R)-5,7-dichloro-2'-(3,5-dichlorophenyl)-7'-hydroxy-3a',6',7',8',8a',8b'-hexahydro-1'H-spiro[indoline-3,4'-pyrrolo[3,4-a]pyrrolizine]-1',2,3'(2'H)-trione (14) and 5,7-dichloro-2'-(3,5-dichlorophenyl)-7'-hydroxy-3a',6',7',8',8a',8b'-hexahydro-1'H-spiro[indoline-3,4'-pyrrolo[3,4-a]pyrrolizine]-1',2,3'(2'H)-trione (15) The mixture of crude products 13 (4.5 g) was purified by preparative HPLC. The following fractions were collected: 14 (enantiomer 1, Example 2)—100 mg; LCMS m/z 526 [M−1], 528 [M+1], 530 [M+3] 532 [M+5], (99.9% purity); HPLC (99.2% purity); Chiral HPLC (98.8% purity); 15 (enantiomer 2)—225 mg; LCMS m/z 526 [M−1], 528 [M+1], 530 [M+3] 532 [M+5], (99.0% purity); HPLC (98.7% purity); Chiral HPLC (98.6% purity); $^1$H NMR (300 MHz, DMSO-d$_6$) δ 11.26 (s, 1H), 7.81 (d, J=1.8 Hz, 1H), 7.77-7.75 (t, J=1.8 Hz, 1H), 7.62 (d, J=1.8 Hz, 1H), 7.30 (d, J=1.8 Hz, 1H), 4.71 (d, J=4.2 Hz, 1H), 4.35-4.31 (m, 4H), 3.60-3.55 (dd, J=3.3 Hz, J=9.9 Hz, 1H), 3.14-3.10 (dd, J=3.9 Hz, J=9.9 Hz, 1H), 2.45 (d, J=9.6 Hz, 1H), 2.35-2.26 (m, 1H), 2.10-2.02 (dd, J=8.4 Hz, J=14.1 Hz, 1H).

An additional larger batch of 14 was prepared by the same chemistry above to give 10 g of crude 13, which was first purified by column chromatography using 100-200 silica gel, eluting with EtOAc:Pet. Ether (1:1) to give 4 g of purified 14; LCMS m/z 526 [M$^+$−1], 528 [M$^+$+1], 530 [M$^+$+3] 532 [M$^+$+5], (87.5% purity). This was purified further by preparative HPLC purification using the following conditions: Column—X-Bridge-C8 (250 mm×19 mm, 10 um); Mobile Phase—A—0.1% Formic Acid in H$_2$O, B—CH$_3$CN; Isocratic method: A (45%)/B (55%); Flow Rate—15 mL/min. The following fractions were collected: 14 (enantiomer 1 Example 2)—1.5 g; LCMS m/z 526 [M−1], 528 [M+1], 530 [M+3] 532 [M+5], (99.6% purity); HPLC (99.2% purity); Chiral HPLC (99.8% purity); $^1$H NMR (300 MHz, DMSO-d$_6$) δ 11.23 (s, 1H), 7.77 (t, J=1.8 Hz, 1H), 7.55 (d, J=1.8 Hz, 1H), 7.44 (d, J=1.8 Hz, 2H), 6.97 (d, J=1.8 Hz, 1H), 4.91 (d, J=4.0 Hz, 1H), 4.49-4.34 (m, 2H), 3.86 (d, J=8.1 Hz, 1H), 3.76-3.68 (m, 1H), 2.82 (br dd, J=6.2 Hz, J=9.2 Hz, 1H), 2.17 (br dd, J=2.9 Hz, J=9.2 Hz, 1H), 2.12-2.01 (m, 1H), 1.74 (br dd, J=6.2 Hz, J=12.8 Hz, 1H); Optical rotation $[\alpha]_D^{20}$=+59.800°.

Example 3

5,7-Dichloro-2'-(4,6-dichloropyridin-2-yl)-3a',6',7', 8',8a',8b'-hexahydro-1'H-spiro[indoline-3,4'-pyrrolo[3,4-a]pyrrolizine]-1',2,3'(2'H)-trione (20)

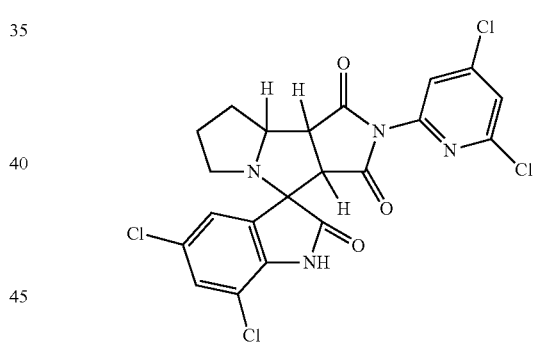

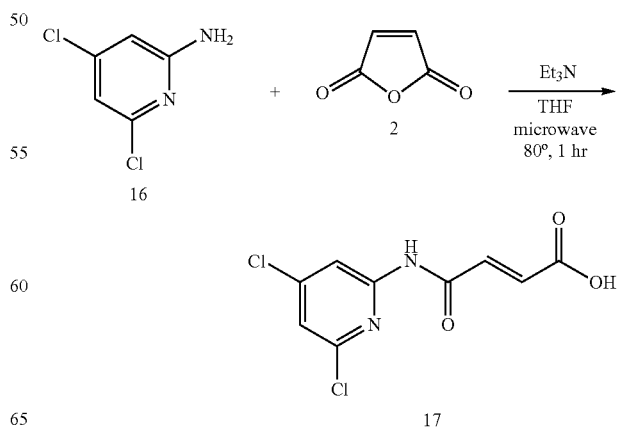

(E)-4-((4,6-Dichloropyridin-2-yl)amino)-4-oxobut-2-enoic acid (17). 4,6-Dichloropyridin-2-amine (16) (500 mg, 3.067 mmol) was added to a stirred solution of 2 (300 mg, 3.067 mmol) and Et$_3$N (0.86 mL, 6.134 mmol) in THF (5 mL) at rt. The reaction mixture was heated at 80° in a microwave for 1 hr. This was repeated seven more times for a total of eight runs, and the resulting reaction mixtures were combined and evaporated in vacuo to give the crude product, which was purified by prep HPLC to give 250 mg of product, suitable for use in the next step. LCMS m/z 261 [M+H−1], 263 [M+H+1], 265 [M+H+3]; (96.8% purity).

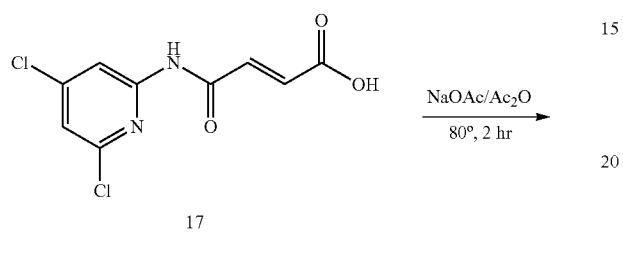

1-(4,6-Dichloropyridin-2-yl)-1H-pyrrole-2,5-dione (18). 17 (125 mg, 0.48 mmol) was added to a mixture of NaOAc (39.2 mg, 0.48 mmol) and Ac$_2$O (3.0 mL) at rt. The resulting mixture was stirred at 80° for 2 hr, then cooled to rt. Ice-cold H$_2$O was added and the resulting solid was collected and dried in vacuo to give 75 mg (64.6% yield) of white was used without further purification. $^1$H NMR (400 MHz, DMSO-d$_6$) δ 7.93 (d, J=1.6 Hz, 1H), 7.62 (d, J=1.6 Hz, 1H), 7.28 (s, 2H).

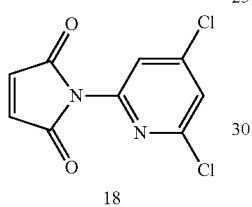

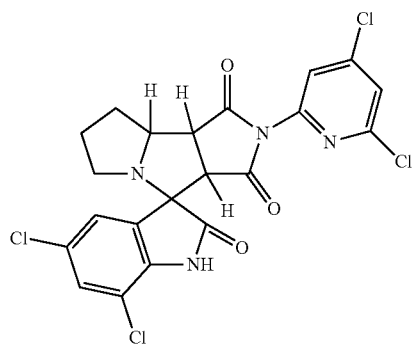

5,7-Dichloro-2'-(4,6-dichloropyridin-2-yl)-3a',6',7',8',8a',8b'-hexahydro-1'H-spiro[indoline-3,4'-pyrrolo[3,4-a]pyrrolizine]-1',2,3'(2'H)-trione (19) To a stirred solution of 18 (400 mg, 1.65 mmol) in EtOH (12 mL) was added 5 (356.9 mg, 1.65 mmol) and 6 (190.1 mg, 1.65 mmol) at rt. The reaction mixture was stirred at 80° for 3 hr, then cooled to rt, and evaporated in vacuo to give 480 mg of 19 as an off-white solid. LCMS m/z 511 [M−1], 513 [M+1], 515 [M+3], 515 [M+5]; (99.5% purity).

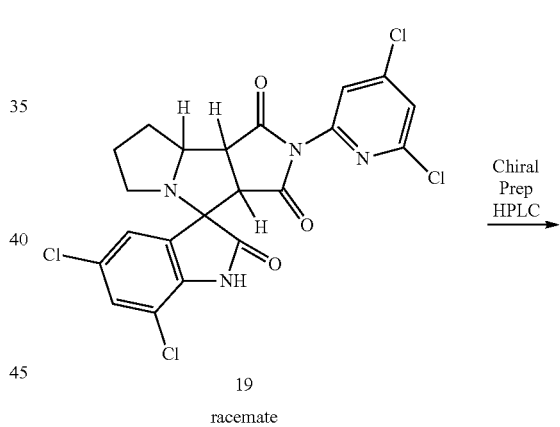

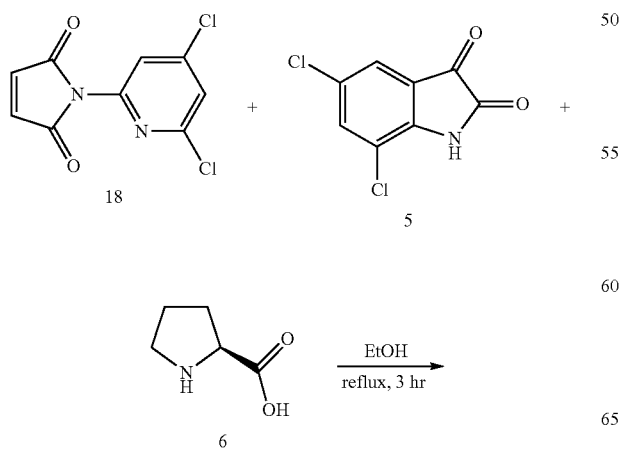

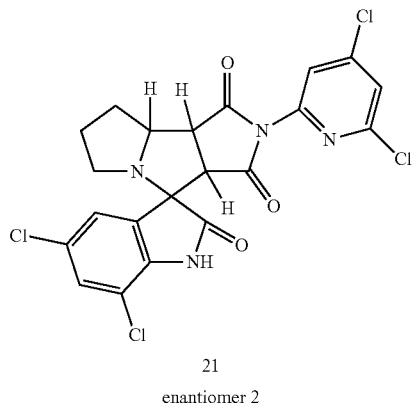

21
enantiomer 2

19 (400 mg) was submitted to Chiral prep HPLC, using the following conditions: Column—Chiralpak-IC (30 mm×250 mm, 5 um); Mobile Phase—A—Hexane, B—Isopropyl alcohol; Isocratic method: A (70%)/B (30%); Flow Rate—41 mL/min; Wave Length 210 nm. The following fractions were collected: 20 (active enantiomer 1, Example 3)—36 mg; LCMS m/z 511 [M−1], 513 [M+1], 515 [M+3], 515 [M+5]; (96.9% purity); HPLC (97.1% purity); Chiral HPLC (97% purity); $^1$H NMR (400 MHz, DMSO-$d_6$) δ 11.25 (s, 1H), 8.04 (d, J=1.2 Hz, 1H), 7.67 (d, J=1.6 Hz, 1H), 7.54 (d, J=2.0 Hz, 1H), 7.54 (d, J=2.0 Hz, 1H), 4.27-4.25 (m, 1H), 3.94 (d, J=7.6 Hz, 1H), 3.72 (t, J=7.6 Hz, 1H), 2.34-2.26 (m, 1H), 1.98-1.83 (m, 5H); 21 (enantiomer 2)—20 mg; LCMS m/z 511 [M−1], 513 [M+1], 515 [M+3], 515 [M+5]; (98.0% purity); HPLC (98.4% purity); Chiral HPLC (98% purity); $^1$H NMR (400 MHz, DMSO-$d_6$) δ 11.25 (s, 1H), 8.04 (d, J=1.2 Hz, 1H), 7.67 (d, J=1.6 Hz, 1H), 7.54 (d, J=2.0 Hz, 1H), 7.54 (d, J=2.0 Hz, 1H), 4.27-4.25 (m, 1H), 3.94 (d, J=7.6 Hz, 1H), 3.72 (t, J=7.6 Hz, 1H), 2.34-2.26 (m, 1H), 1.98-1.83 (m, 5H).

Example 4

5,7-dichloro-2'-(3,5-dichloro-4-methoxyphenyl)-7',7'-dimethyl-3a',6',7',8',8a',8b'-hexahydro-1'H-spiro[indoline-3,4'-pyrrolo[3,4-a]pyrrolizine]-1',2,3'(2'H)-trione (29)

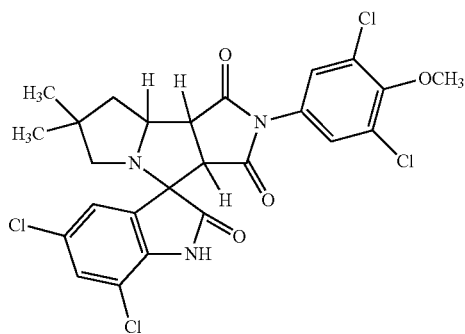 [SMILES: COc1c(Cl)cc(N2C(=O)C3C4CC(C)(C)CN4C4(C(=O)Nc5c(Cl)cc(Cl)cc54)C3C2=O)cc1Cl]

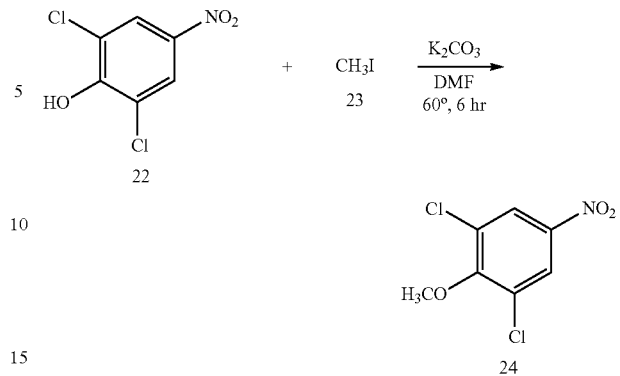

1,3-dichloro-2-methoxy-5-nitrobenzene (24). To a stirred solution of 2,6-dichloro-4-nitrophenol (22) (6.0 g, 28.84 mmoles) in anhydrous DMF (60 mL) was added anhydrous $K_2CO_3$ (15.9 g, 115.36 mmoles) and methyl iodide (23) (8.18 g, 57.69 mmoles) at 0°. The reaction mixture was heated at 60° for 6 hr. The resulting mixture was cooled to rt and poured into ice-water. The resulting solid was collected and dried in vacuo to give the crude product. This was purified by column chromatography, eluting with Pet. Ether: EtOAc (85:15) to give 2.5 g (39.0% yield) of pure product as an off-white solid. $^1$H NMR (400 MHz, $CDCl_3$) δ 8.22 (s, 2H), 4.01 (s, 3H).

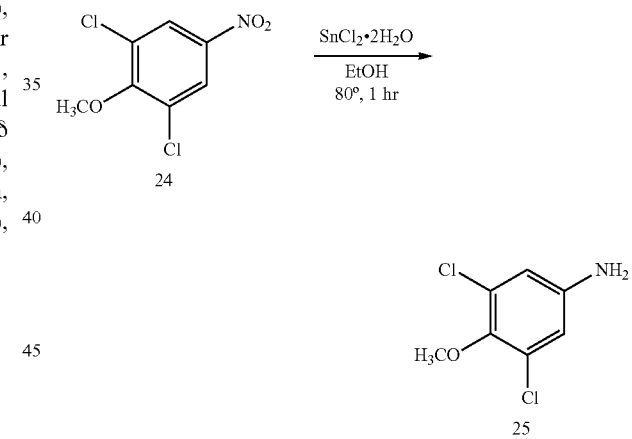

3,5-dichloro-4-methoxyaniline (25). To a stirred solution of 24 (1.5 g, 6.76 mmole) in EtOH (25 mL) was added $SnCl_2 \cdot 2H_2O$ (7.62 g, 33.77 mmole) portion-wise over a period of 5 min. at rt. The reaction mixture was heated at 80° for 1 hr, then cooled to rt. This reaction was repeated 3 additional times, and all of the crude reaction mixtures were combined and poured into ice-water. The resulting mixture was basified to pH=12 with 2N NaOH solution, then filtered through a pad of Celite. The aqueous filtrate was extracted with EtOAc (2×500 mL). The combined organic extracts were dried over $Na_2SO_4$ and evaporated in vacuo to give 3.0 g (57.9% yield) of product as a brown solid. LCMS m/z 192 [M+H−1], 194 [M+H+1], 196 [M+H+3]; (99.1% purity). $^1$H NMR (400 MHz, DMSO-$d_6$) δ 6.59 (s, 2H), 5.39 (s, 2H), 3.67 (s, 3H).

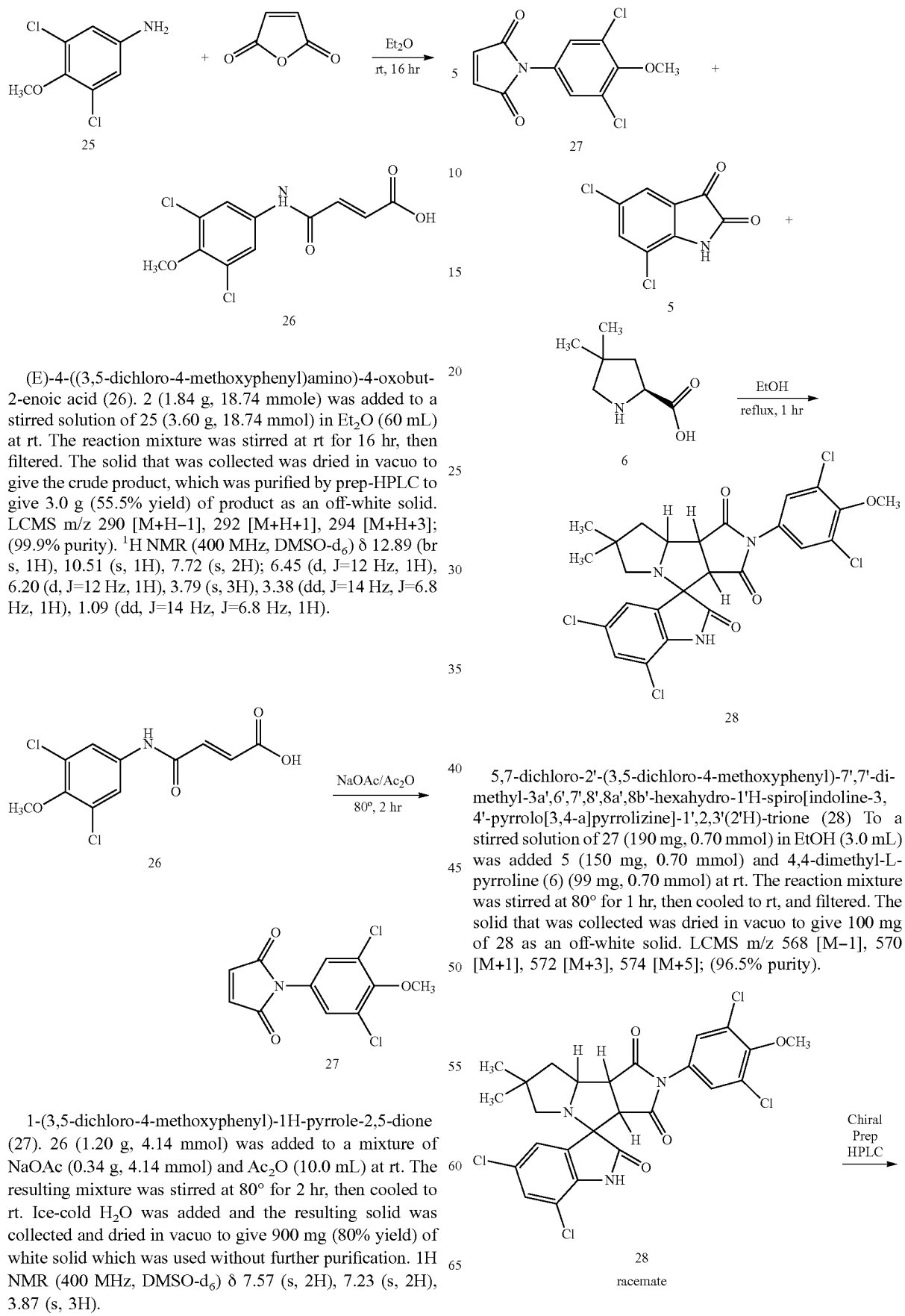

(E)-4-((3,5-dichloro-4-methoxyphenyl)amino)-4-oxobut-2-enoic acid (26). 2 (1.84 g, 18.74 mmole) was added to a stirred solution of 25 (3.60 g, 18.74 mmol) in Et$_2$O (60 mL) at rt. The reaction mixture was stirred at rt for 16 hr, then filtered. The solid that was collected was dried in vacuo to give the crude product, which was purified by prep-HPLC to give 3.0 g (55.5% yield) of product as an off-white solid. LCMS m/z 290 [M+H−1], 292 [M+H+1], 294 [M+H+3]; (99.9% purity). $^1$H NMR (400 MHz, DMSO-d$_6$) δ 12.89 (br s, 1H), 10.51 (s, 1H), 7.72 (s, 2H); 6.45 (d, J=12 Hz, 1H), 6.20 (d, J=12 Hz, 1H), 3.79 (s, 3H), 3.38 (dd, J=14 Hz, J=6.8 Hz, 1H), 1.09 (dd, J=14 Hz, J=6.8 Hz, 1H).

1-(3,5-dichloro-4-methoxyphenyl)-1H-pyrrole-2,5-dione (27). 26 (1.20 g, 4.14 mmol) was added to a mixture of NaOAc (0.34 g, 4.14 mmol) and Ac$_2$O (10.0 mL) at rt. The resulting mixture was stirred at 80° for 2 hr, then cooled to rt. Ice-cold H$_2$O was added and the resulting solid was collected and dried in vacuo to give 900 mg (80% yield) of white solid which was used without further purification. 1H NMR (400 MHz, DMSO-d$_6$) δ 7.57 (s, 2H), 7.23 (s, 2H), 3.87 (s, 3H).

5,7-dichloro-2'-(3,5-dichloro-4-methoxyphenyl)-7',7'-dimethyl-3a',6',7',8',8a',8b'-hexahydro-1'H-spiro[indoline-3,4'-pyrrolo[3,4-a]pyrrolizine]-1',2,3'(2'H)-trione (28) To a stirred solution of 27 (190 mg, 0.70 mmol) in EtOH (3.0 mL) was added 5 (150 mg, 0.70 mmol) and 4,4-dimethyl-L-pyrroline (6) (99 mg, 0.70 mmol) at rt. The reaction mixture was stirred at 80° for 1 hr, then cooled to rt, and filtered. The solid that was collected was dried in vacuo to give 100 mg of 28 as an off-white solid. LCMS m/z 568 [M−1], 570 [M+1], 572 [M+3], 574 [M+5]; (96.5% purity).

41
-continued

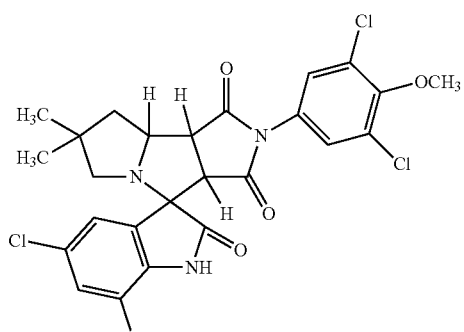

29
enantiomer 1
Example 4

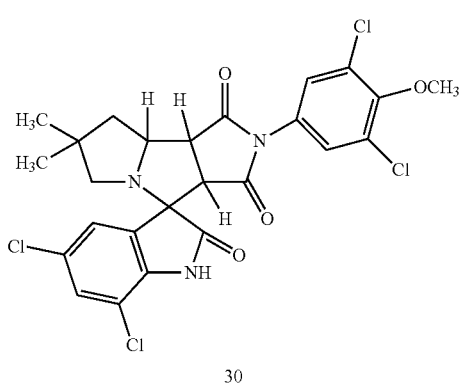

30
enantiomer 2

28 (90 mg) was submitted to Chiral prep HPLC, using the following conditions: Column—Chiralpak-IC (30 mm×250 mm, 5 um); Mobile Phase—CH$_3$CN; Flow Rate—20 mL/min; Wave Length 215 nm. The following fractions were collected: 29 (active enantiomer 1, Example 4)—25 mg; LCMS m/z 568 [M−1], 570 [M+1], 572 [M+3], 574 [M+5]; (98.3% purity); Chiral HPLC (>99% purity); $^1$H NMR (DMSO-d$_6$) δ 11.21 (s, 1H), 7.56 (s, 1H), 7.51 (s, 2H), 7.10 (s, 1H), 4.39 (q, J=7.8 Hz, 1H), 3.89 (s, 3H), 3.82 (d, J=8.1 Hz, 1H), 3.68 (t, J=7.8 Hz, 1H), 2.37 (d, J=8.4 Hz, 1H), 2.13 (d, J=8.1 Hz, 1H), 1.77-1.63 (m, 2H), 1.03 (s, 3H), 1.01 (s, 3H); 30 (enantiomer 2)—25 mg; LCMS m/z 568 [M−1], 570 [M+1], 572 [M+3], 574 [M+5]; (98.3% purity); Chiral HPLC (96.7% purity); $^1$H NMR (400 MHz, DMSO-d$_6$) δ 11.20 (s, 1H), 7.56 (d, J=2.0 Hz, 1H), 7.51 (s, 2H), 7.10 (s, 1H), 4.39 (q, J=7.2 Hz, 1H), 3.89 (s, 3H), 3.82 (d, J=8.4 Hz, 1H), 3.68 (t, J=8.0 Hz, 1H), 2.37 (d, J=8.4 Hz, 1H), 2.13 (d, J=8.4 Hz, 1H), 1.76-1.65 (m, 2H), 1.03 (s, 3H), 1.02 (s, 3H).

42
Example 5

(7'S)-5,7-Dichloro-2'-(3,5-dichlorophenyl)-7'-hydroxy-3a',6',7',8',8a',8b'-hexahydro-1'H-spiro[indoline-3,4'-pyrrolo[3,4-a]pyrrolizine]-1',2,3'(2'H)-trione-3a',8b'-d$_2$ (35)

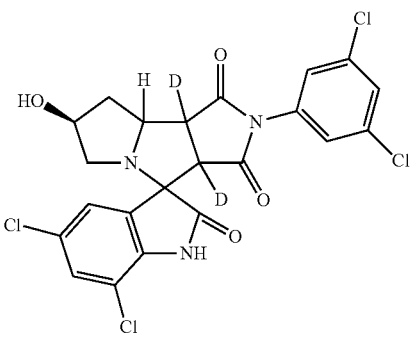

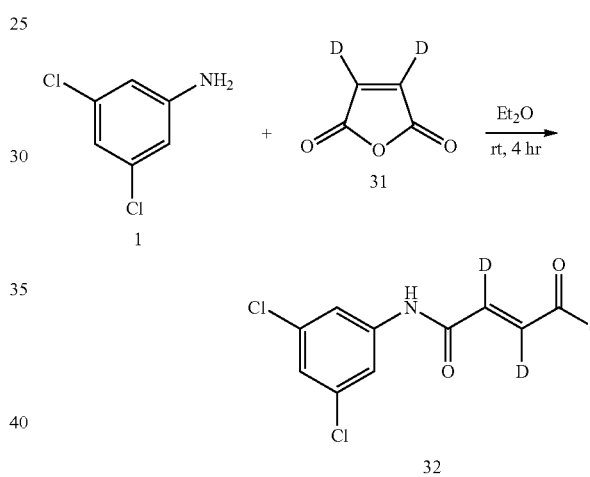

(E)-4-((3,5-Dichlorophenyl)amino)-4-oxobut-2-enoic-2,3-d$_2$ acid (32). (1) (4.85 g, 29.93 mmol) was added to a stirred solution of maleic anhydride-d$_2$ (31) (2.99 g, 29.93 mmol) in Et$_2$O (60 mL) at rt. The reaction mixture was stirred at rt for 4 hr, then evaporated in vacuo to give the crude product. This was triturated with Et$_2$O and dried in vacuo to give 4.0 g (51.0% yield) of pure product as an off-white solid, which was used without further purification in the next step. LCMS m/z 262 [M+H−1], 264 [M+H+1], 266 [M+H+3]; (99.8% purity). $^1$H NMR (400 MHz, DMSO-d$_6$) δ 12.88 (br s, 1H), 10.60 (s, 1H), 7.68 (d, J=1.6 Hz, 2H), 7.31 (s, 1H).

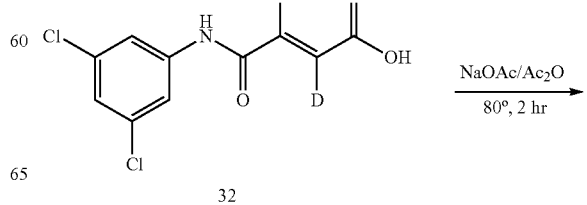

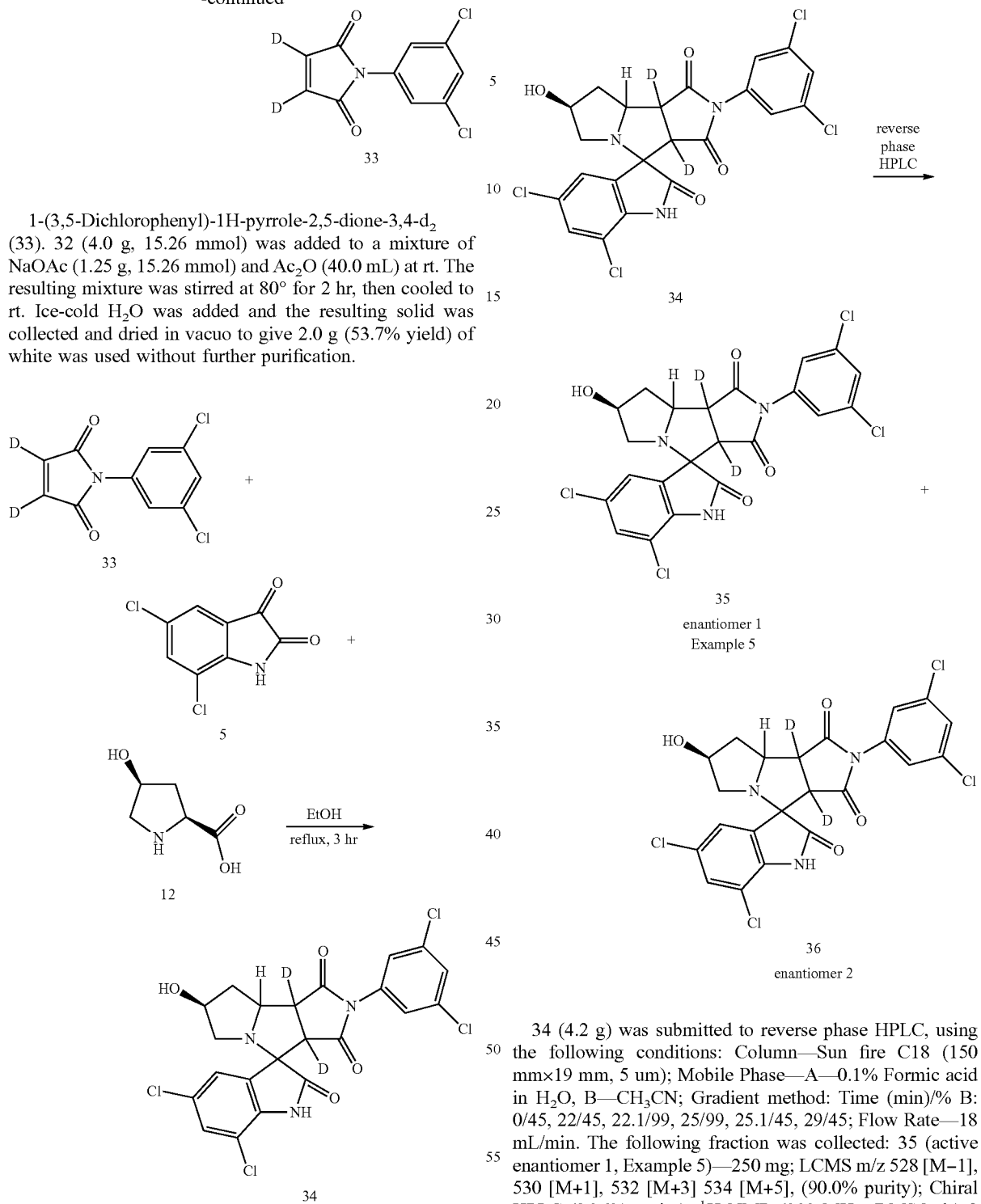

1-(3,5-Dichlorophenyl)-1H-pyrrole-2,5-dione-3,4-$d_2$ (33). 32 (4.0 g, 15.26 mmol) was added to a mixture of NaOAc (1.25 g, 15.26 mmol) and $Ac_2O$ (40.0 mL) at rt. The resulting mixture was stirred at 80° for 2 hr, then cooled to rt. Ice-cold $H_2O$ was added and the resulting solid was collected and dried in vacuo to give 2.0 g (53.7% yield) of white was used without further purification.

(7'S)-5,7-Dichloro-2'-(3,5-dichlorophenyl)-7'-hydroxy-3a',6',7',8',8a',8b'-hexahydro-1'H-spiro[indoline-3,4'-pyrrolo[3,4-a]pyrrolizine]-1',2,3'(2'H)-trione-3a',8b'-$d_2$ (34). To a stirred solution of 33 (1.88 g, 7.70 mmol) in EtOH (20 mL) was added 5 (1.66 g, 7.70 mmol) and (12) (0.886 g, 7.70 mmol) at rt. The reaction mixture was stirred at 80° for 3 hr, then cooled to rt, and evaporated in vacuo to give 4.2 g of 34 as a brown solid.

34 (4.2 g) was submitted to reverse phase HPLC, using the following conditions: Column—Sun fire C18 (150 mm×19 mm, 5 um); Mobile Phase—A—0.1% Formic acid in $H_2O$, B—$CH_3CN$; Gradient method: Time (min)/% B: 0/45, 22/45, 22.1/99, 25/99, 25.1/45, 29/45; Flow Rate—18 mL/min. The following fraction was collected: 35 (active enantiomer 1, Example 5)—250 mg; LCMS m/z 528 [M−1], 530 [M+1], 532 [M+3] 534 [M+5], (90.0% purity); Chiral HPLC (86.6% purity); $^1$H NMR (300 MHz, DMSO-$d_6$) δ 11.24 (s, 1H), 7.77 (dd, J=2.1 Hz, J=1.8 Hz, 1H), 7.55 (d, J=1.8 Hz, 1H), 7.44 (d, J=1.8 Hz, 2H), 6.97 (d, J=1.8 Hz, 1H), 4.91 (d, J=4.2 Hz, 1H), 4.43 (dd, J=8.7 Hz, J=6.6 Hz, 1H), 4.38 (br s, 1H), 2.82 (dd, J=9.3 Hz, J=6.9 Hz, 1H), 2.15 (dd, J=6.6 Hz, J=3.0 Hz, 1H), 2.11-2.02 (m, 1H), 1.74 (dd, J=12.9 Hz, J=6.6 Hz, 1H).

35 (50 mg) was further purified by SFC purification to give 15 mg of pure material. LCMS m/z 528 [M−1], 530 [M+1], 532 [M+3] 534 [M+5], (99.8% purity); Chiral HPLC (99.5% purity); $^1$H NMR (300 MHz, DMSO-d$_6$) δ 11.23 (s, 1H), 7.77 (dd, J=2.1 Hz, J=1.8 Hz, 1H), 7.55 (d, J=2.1 Hz, 1H), 7.44 (d, J=1.8 Hz, 2H), 6.97 (d, J=1.8 Hz, 1H), 4.91 (d, J=4.2 Hz, 1H), 4.43 (dd, J=8.7 Hz, J=6.3 Hz, 1H), 4.38 (br s, 1H), 2.82 (dd, J=9.6 Hz, J=6.3 Hz, 1H), 2.17 (dd, J=6.3 Hz, J=3.0 Hz, 1H), 2.11-2.02 (m, 1H), 1.74 (dd, J=12.6 Hz, J=6.3 Hz, 1H).

Example 6

(7'S)-5,7-Dichloro-2'-(3-chloro-5-methoxyphenyl)-7'-fluoro-3a',6',7',8',8a',8b'-hexahydro-1'H-spiro[indoline-3,4'-pyrrolo[3,4-a]pyrrolizine]-1',2,3'(2'H)-trione (42)

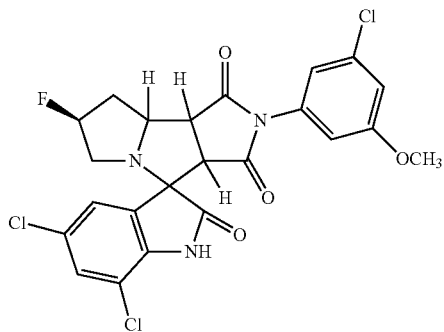 [SMILES: COc1cc(Cl)cc(N2C(=O)C3C4C[C@H](F)CN4C4(C(=O)Nc5c(Cl)cc(Cl)cc54)C3C2=O)c1]

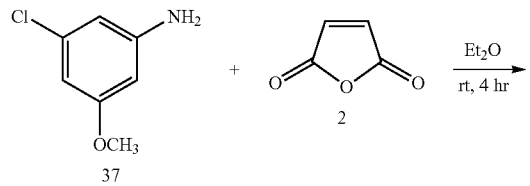

(E)-4-((3-Chloro-5-methoxyphenyl)amino)-4-oxobut-2-enoic acid (38). 3-chloro-5-methoxyaniline (37) (5.0 g, 31.72 mmol) was added to a stirred solution of (2) (3.11 g, 31.72 mmol) in Et$_2$O (60 mL) at rt. The reaction mixture was stirred at rt for 4 hr. The resulting mixture was evaporated in vacuo to give the crude product. This was triturated with Et$_2$O and dried in vacuo to give 5.0 g (61.7% yield) of pure product as an off-white solid, which was used without further purification in the next step. LCMS m/z 256 [M+H−1], 25 [M+H+1], 264 [M+H+3]; (99.4% purity). 1H NMR (400 MHz, DMSO-d$_6$) δ 12.89 (br s, 1H), 10.43 (s, 1H), 7.36 (dd, J=2.0 Hz, J=1.6 Hz, 1H), 7.16 (dd, J=2.0 Hz, J=2.0 Hz, 1H), 6.76 (dd, J=2.4 Hz, J=2.0 Hz, 1H), 6.44 (d, J=12 Hz, 1H), 6.31 (d, J=12 Hz, 1H), 3.75 (s, 3H).

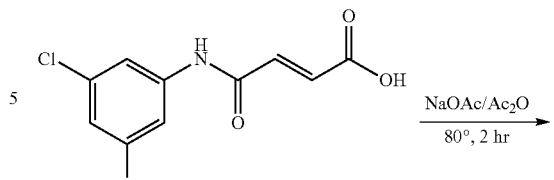

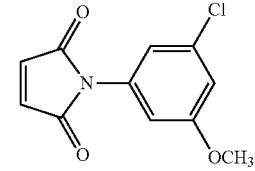

1-(3-chloro-5-methoxyphenyl)-1H-pyrrole-2,5-dione (39). 38 (5.0 g, 19.55 mmol) was added to a mixture of NaOAc (1.6 g, 19.55 mmol) and Ac$_2$O (50.0 mL) at rt. The resulting mixture was stirred at 80° for 2 hr, then cooled to rt. Ice-cold H$_2$O was added and the resulting solid was collected and dried in vacuo to give 3.0 g (53.5% yield) of white solid which was used without further purification. LCMS m/z 238 [M+H−1], 240 [M+H+1], 242 [M+H+3]; (87.5% purity). $^1$H NMR (400 MHz, DMSO-d$_6$) δ 7.20 (s, 2H), 7.10 (m, 1H), 7.04 (m, 1H), 6.95 (m, 1H), 3.79 (s, 3H).

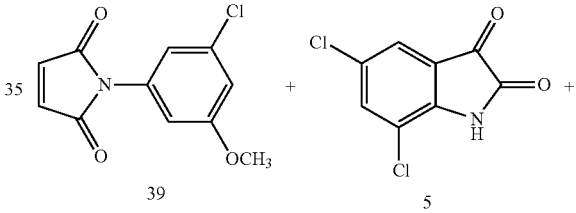

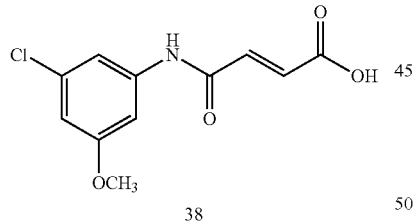

(7'S)-5,7-Dichloro-2'-(3-chloro-5-methoxyphenyl)-7'-fluoro-3a',6',7',8',8a',8b'-hexahydro-1'H-spiro[indoline-3,4'-pyrrolo[3,4-a]pyrrolizine]-1',2,3'(2'H)-trione (41). To a stirred solution of 39 (800 mg, 3.277 mmol) in EtOH (12 mL) was added 5 (707 mg, 3.277 mmol) and (40) (436 mg, 3.277 mmol) at rt. The reaction mixture was stirred at 80° for 3 hr, then cooled to rt, and evaporated in vacuo to give 1.65 g of 41 as a brown solid.

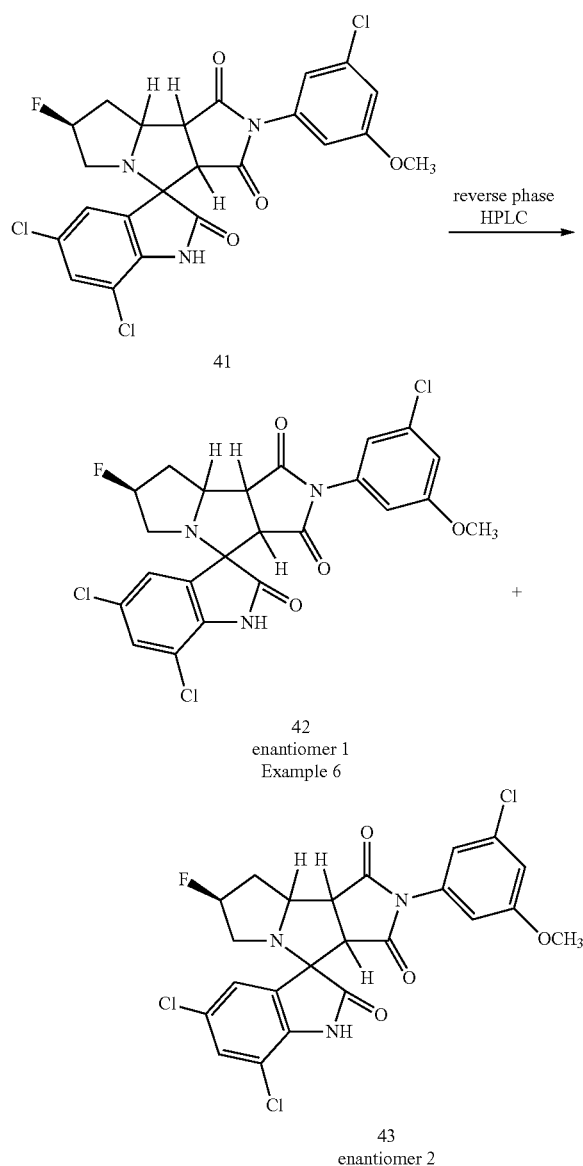

41 (1.65 g) was submitted to reverse phase HPLC, using the following conditions: Column—X-Bridge C18 (150 mm×30 mm, 5 um); Mobile Phase—A—0.1% Formic acid in H$_2$O, B—CH$_3$CN; Gradient method: Time (min)/% B: 0/55, 13/55, 13.1/99, 14/99, 14.1/55, 18/55; Flow Rate—25 mL/min. The following fraction was collected: 42 (active enantiomer 1, Example 6)—380 mg; LCMS m/z 524 [M−1], 526 [M+1], 528 [M+3] 530 [M+5], (99.3% purity); Chiral HPLC (86.3% purity).

42 (75 mg) was further purified by Chiral prep HPLC purification to give 20 mg of pure material, using the following conditions: Column—Chiralpak-ASH (250 mm×21 mm, 5 um); Mobile Phase—A—Hexane, B—EtOH; Isocratic method: A (70%)/B (30%); Flow Rate—21 mL/min; Wave Length 215 nm. LCMS m/z 524 [M−1], 526 [M+1], 528 [M+3] 530 [M+5], (99.7% purity);

Chiral HPLC (>99.9% purity); $^1$H NMR (400 MHz, DMSO-d$_6$) δ 11.28 (br s, 1H), 7.57 (d, J=2.0 Hz, 1H), 7.16 (dd, J=2.4 Hz, J=2.0 Hz, 1H), 6.98 (dd, J=2.0 Hz, J=1.6 Hz, 1H), 6.97 (d, J=2.0 Hz, 1H), 6.85 (dd, J=2.0 Hz, J=1.6 Hz, 1H), 5.45-5.27 (ddd, J=54 Hz, J 3.6 Hz, J=3.6 Hz, 1H), 4.50 (dd, J=14.4 Hz, J=8.4 Hz, 1H), 3.84 (dd, J=46 Hz, J=8.4 Hz, 2H), 3.82 (s, 3H), 3.01 (ddd, J=26.8 Hz, J=10.8 Hz, J=4.8 Hz, 1H), 2.50-2.45 (m, 1H), 2.30-2.07 (m, 2H).

Example 7

3'-(Sec-butyl)-5,7-dichloro-5'-(3-chloro-5-methoxyphenyl)-2',3',3a',6a'-tetrahydro-4'H-spiro[indoline-3,1'-pyrrolo[3,4-c]pyrrole]-2,4',6'(5'H)-trione (45)

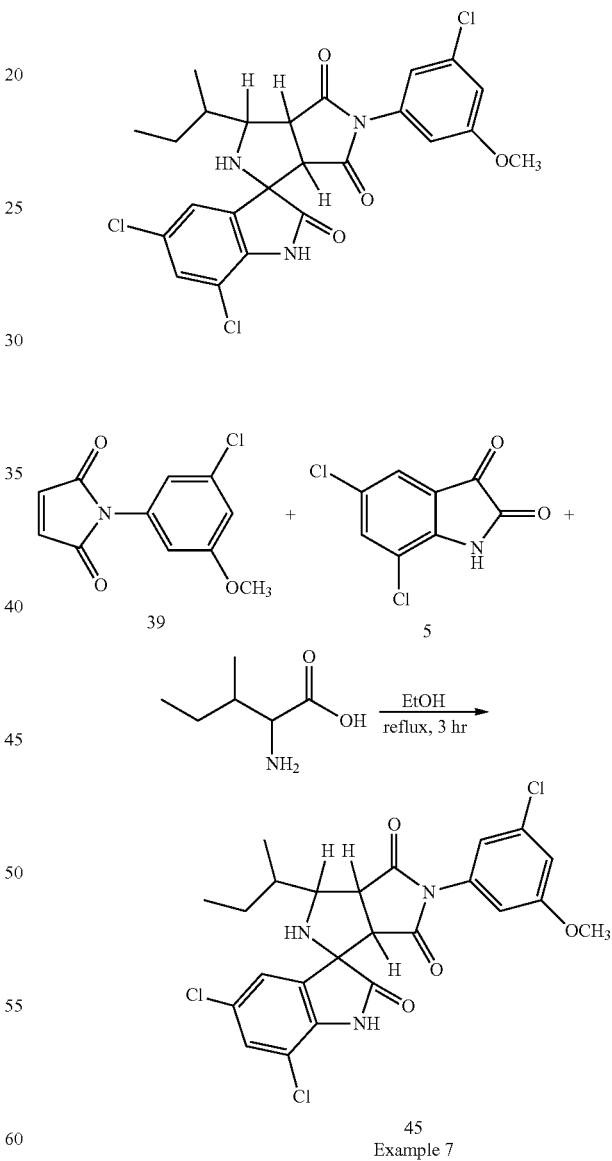

3'-(Sec-butyl)-5,7-dichloro-5'-(3-chloro-5-methoxyphenyl)-2',3',3a',6a'-tetrahydro-4'H-spiro[indoline-3,1'-pyrrolo[3,4-c]pyrrole]-2,4',6'(5'H)-trione (45). To a stirred solution of 39 (50 mg, 0.20 mmol) in anhydrous DMF (1.5 mL) was added 5 (43 mg, 0.20 mmol) and isoleucine (44) (26 mg, 0.20 mmol) at rt. The reaction mixture was stirred at 110° for 5 hr, then cooled to rt and diluted with ice-cold H$_2$O (20 mL). The resulting mixture was extracted with EtOAc (2×20 mL). The combined organic extracts were washed with brine (10 mL), dried over anhydrous Na$_2$SO$_4$ and evaporated in vacuo to give 0.045 g (42%) of 45 (Example 7) as a brown solid. LCMS m/z 524 [M−H]; (76.3% purity).

Example 8

(7'S)-5,7-Dichloro-7'-hydroxy-7'-methyl-2'-(1H-tetrazol-5-yl)-3a',6',7',8',8a',8b'-hexahydro-1'H-spiro[indoline-3,4'-pyrrolo[3,4-a]pyrrolizine]-1',2,3'(2'H)-trione (53)

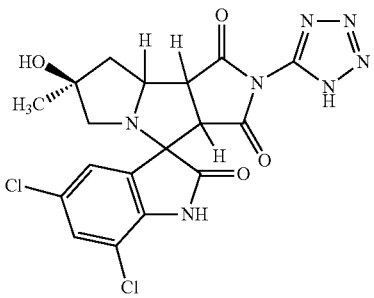 [SMILES: C[C@]1(O)CC2C3C(=O)N(c4nnn[nH]4)C(=O)C3C3(C(=O)Nc4c(Cl)cc(Cl)cc43)N2C1]

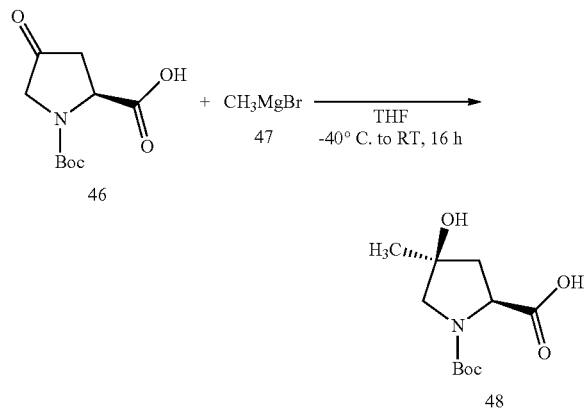

(2S,4S)-1-(tert-butoxycarbonyl)-4-hydroxy-4-methylpyrrolidine-2-carboxylic acid (48). Methyl magnesium bromide (47) (3.0 M in Et$_2$O, 43.6 mL, 130.85 mmol) was added to anhydrous THF (200 mL) and then cooled to −40° for 30 min. with stirring. A cold solution of (S)-1-(Tert-butoxycarbonyl)-4-oxopyrrolidine-2-carboxylic acid (46) (12.0 g, 52.34 mmol) in anhydrous THF (100 mL) was added dropwise over 1 hr, and then the resulting mixture was warmed to rt and stirred at rt for 16 hr. The reaction mixture was cooled to −5° and quenched by the addition of 1N HCl until the reaction mixture turned into a clear solution. This was extracted with EtOAc (3×300 mL), and the combined extracts were washed with H$_2$O and dried over anhydrous Na$_2$SO$_4$ then evaporated in vacuo to give the crude product. This was purified by column chromatography, eluting with MeOH:CH$_2$Cl$_2$ (1:49) to give 4.8 g (37% yield) of pure 48 as an off-white solid. LCMS m/z 268 [M+Na]$^+$; (84.2% purity). $^1$H NMR (300 MHz, DMSO-d$_6$) δ 12.50-12.20 (br s, 1H), 4.92-4.76 (m, 1H), 4.14-4.05 (m, 1H), 3.28-3.17 (m, 2H), 2.19-2.05 (m, 1H), 1.98-1.88 (m, 1H), 1.37 (d, J=15 Hz, 9H), 1.22 (s, 3H).

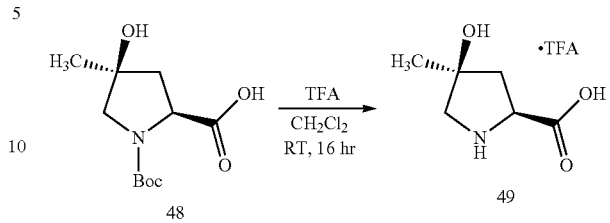

(2S,4S)-4-hydroxy-4-methylpyrrolidine-2-carboxylic acid, TFA salt (49). To a stirred solution of 48 (4.8 g, 19.57 mmol) in anhydrous CH$_2$Cl$_2$ (50 mL) at 0° was added TFA (9.6 mL) and the reaction mixture was stirred at rt for 16 hr. The reaction mixture was evaporated in vacuo to the crude product, which was then co-distilled with CHCl$_3$ followed by Et$_2$O to give 4.0 g of the crude TFA salt of 49 as a gummy brown liquid, which was suitable for use in the next step without further purification. LCMS m/z 146 (free amine) [M+H]$^+$; (97.4% purity). $^1$H NMR (300 MHz, DMSO-d$_6$) δ 9.97-9.72 (br s, 1H), 8.78-8.50 (br s, 1H), 4.52-4.33 (m, 1H), 3.24-3.12 (m, 1H), 3.11-2.93 (m, 1H), 2.21 (d, J=6 Hz, 2H), 1.33 (s, 3H).

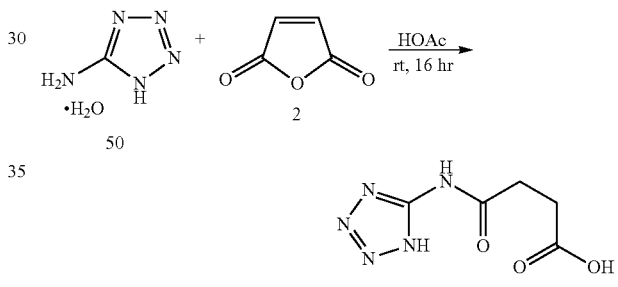

4-((1H-Tetrazol-5-yl)amino)-4-oxobutanoic acid (51). A mixture of 5-aminotetrazole hydrate (50) (5.00 g, 48.5 mmol) and 2 (4.70 g, 48.5 mmol) in glacial HOAC (10 mL) was stirred at rt for 16 hr. The reaction mixture was concentrated in vacuo to give the crude product, which was washed with CH$_2$Cl$_2$ to give 2.0 g (22.5% yield) of 51 as an off-white solid, which was suitable for use in the next step without further purification. LCMS m/z 184 [M+H]$^+$; (98.6% purity).

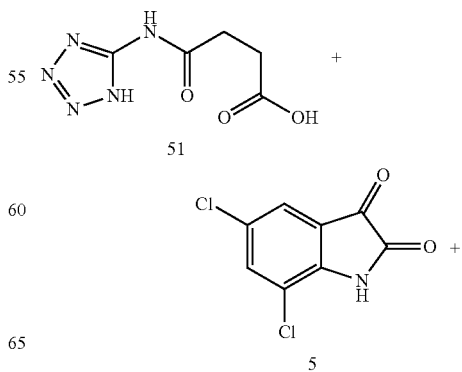

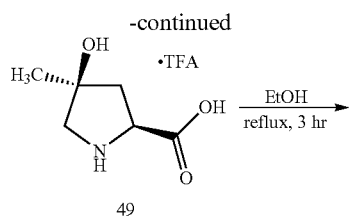

49

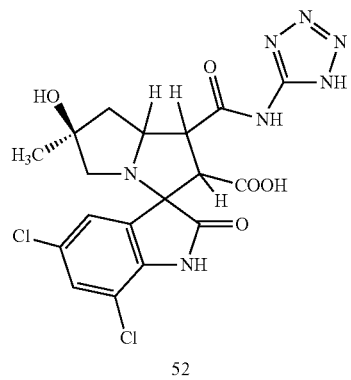

52

(6'S)-1'-((1H-Tetrazol-5-yl)carbamoyl)-5,7-dichloro-6'-hydroxy-6'-methyl-2-oxo-1',2',5',6',7',7a'-hexahydrospiro[indoline-3,3'-pyrrolizine]-2'-carboxylic acid (52). To a stirred solution of 51 (1.0 g, 5.46 mmol) in EtOH (10 mL) was added 5 (1.17 g, 5.46 mmol) and 49 (0.792 g, 5.46 mmol) at rt. The reaction mixture was stirred at 80° for 3 hr, then cooled to rt, and evaporated in vacuo to give the product as a brown solid. This was purified by preparative HPLC to give 0.150 g (6% yield) of 52 as a light brown solid. LCMS m/z 482 [M+H]⁺; (92.1% purity). ¹H NMR (400 MHz, DMSO-d₆) δ 15.96 (br s, 1H), 12.53 (br s, 1H), 11.81 (br s, 1H), 11.08 (s, 1H), 6.70 (s, 1H), 6.40 (s, 1H), 4.52-4.19 (m, 2H), 4.03 (q, J=7.3 Hz, 1H), 3.58 (d, J=7.3 Hz, 1H), 3.15 (d, J=8.3 Hz, 1H), 2.37-2.22 (m, 2H), 1.92-1.85 (m, 1H), 1.27 (s, 3H).

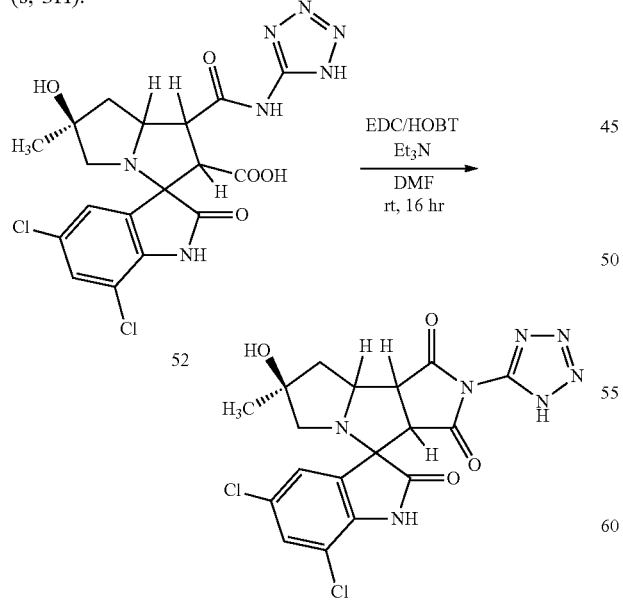

53
Example 8

(7'S)-5,7-Dichloro-7'-hydroxy-7'-methyl-2'-(1H-tetrazol-5-yl)-3a',6',7',8',8a',8b'-hexahydro-1'H-spiro[indoline-3,4'-pyrrolo[3,4-a]pyrrolizine]-1',2,3'(2'H)-trione (53). To a stirred solution of 52 (0.15 g, 0.311 mmol) in anhydrous DMF (3 mL) at 0° was added Et₃N (0.08 mL, 0.622 mmol), EDC (0.048 g, 0.373 mmol) and HOBT (0.042 g, 0.435 mmol). The resulting mixture was warmed to rt and stirred at rt for 16 hr. The reaction mixture was evaporated in vacuo to give the crude product, which was purified by preparative HPLC to give 0.020 g (14% yield) of pure 53 (Example 8) as a pale pink solid. LCMS m/z 464 [M+H]⁺; (95% purity). ¹H NMR (300 MHz, DMSO-d₆) δ 11.29 (s, 1H), 7.56 (d, J=1.8 Hz, 1H), 7.01 (d, J=1.5 Hz, 1H), 4.53-4.43 (m, 1H), 3.99 (d, J=7.7 Hz, 1H), 3.89-3.82 (m, 1H), 3.35 (s, 1H), 3.38 (br s, 1H), 2.44 (d, J=8.4 Hz, 1H), 2.31 (d, J=8.4 Hz, 1H), 1.90-1.75 (m, 2H), 1.3 (s, 3H).

Example 9

2-(3,5-Dichlorophenyl)-4-(6-fluoropyridin-3-yl)hexahydropyrrolo[3,4-a]pyrrolizine-1,3(2H,4H)-dione (55)

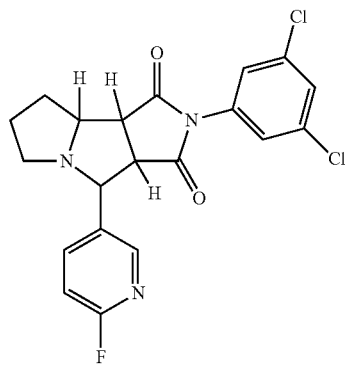 [SMILES: O=C1C2C(C(=O)N1c1cc(Cl)cc(Cl)c1)C(c1ccc(F)nc1)N1CCCC21]

55

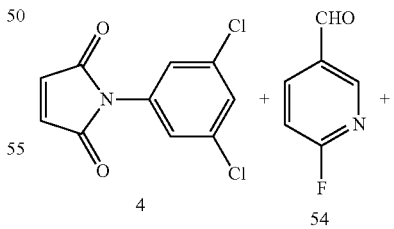

4

54

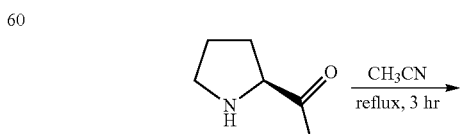

6

-continued

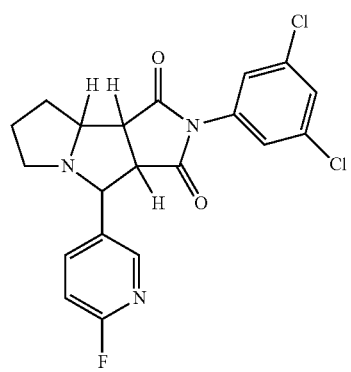

55
Example 9

2-(3,5-Dichlorophenyl)-4-(6-fluoropyridin-3-yl)hexahydropyrrolo[3,4-a]pyrrolizine-1,3(2H,4H)-dione (55). To a stirred solution of 4 (0.1 g, 0.413 mmol) in CH₃CN (2 mL) was added 6-fluoronicotinaldehyde (54) (0.51 g, 0.413 mmol) and 6 (0.047 g, 0.413 mmol) at rt. The reaction mixture was stirred at 80° for 3 hr, then cooled to rt, and evaporated in vacuo to give the crude product. This was purified by preparative TLC, eluting with Pet. Ether:EtOAc (70:30) to give 0.05 g (29% yield) of 55 (Example 9) as a brown solid. LCMS m/z 420 [M+H]⁺; (95.2% purity).

Example 10

(7'S)-5,7-dichloro-2'-(3,5-dichlorophenyl)-7'-fluoro-7'-methyl-3a',6',7',8',8a',8b'-hexahydro-1'H-spiro[indoline-3,4'-pyrrolo[3,4-a]pyrrolizine]-1',2,3'(2'H)-trione (61)

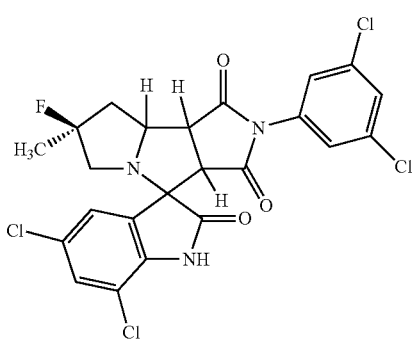 [SMILES: C[C@]1(F)CC2C3C(=O)N(c4cc(Cl)cc(Cl)c4)C(=O)C3C3(C(=O)Nc4c(Cl)cc(Cl)cc43)N2C1]

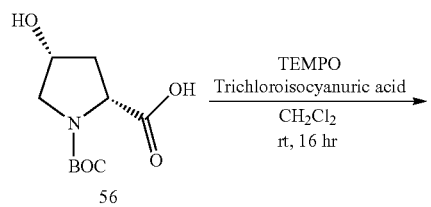

-continued

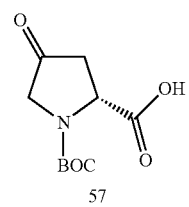

57

(R)-1-(tert-butoxycarbonyl)-4-oxopyrrolidine-2-carboxylic acid (57). To a stirred solution of (2R,4R)-1-(tert-butoxycarbonyl)-4-hydroxypyrrolidine-2-carboxylic acid (56) (20.0 g, 86.45 mmol) in CH₂Cl₂ (300 mL) was added TEMPO (0.12 g, 0.77 mmol), followed by the addition of trichloroisocyanuric acid (20.1 g, 86.45 mmol). The resulting reaction mixture was stirred at rt for 16 hr. The reaction mixture was diluted with H₂O and stirred for 1 hr, then concentrated in vacuo to remove the CH₂Cl₂. The remaining solution was filtered through a pad of Celite and the pad was washed with an excess of EtOAc. The resulting filtrate was acidified with 1N HCl and extracted with EtOAc (3×300 mL). The combined organic extracts were dried over anhydrous Na₂SO₄ and concentrated in vacuo to give the crude product. This was washed with n-pentane to give 18.0 g (90% yield) of pure 57 as an off-white solid. This was suitable for use in the next step without further purification. LCMS m/z 228 [M−H]⁺; (85.9% purity). ¹H NMR (300 MHz, DMSO-d₆) δ 13.40-12.20 (br s, 1H), 4.60-4.48 (m, 1H), 3.91-3.60 (m, 2H), 3.20-3.03 (m, 1H), 2.58-2.41 (m, 1H), 1.40 (s, 9H).

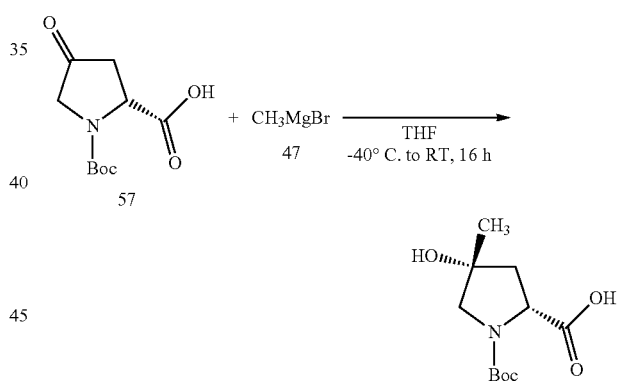

(2R,4R)-1-(tert-butoxycarbonyl)-4-hydroxy-4-methylpyrrolidine-2-carboxylic acid (58). Methyl magnesium bromide (47) (3.0 M in Et₂O, 65.4 mL, 196.3 mmol) was added to anhydrous THF (600 mL) and then cooled to −40° for 30 min. with stirring. A cold solution of 57 (18.0 g, 78.5 mmol) in anhydrous THF (200 mL) was added dropwise over 1 hr, and then the resulting mixture was warmed to rt and stirred at rt for 16 hr. The reaction mixture was cooled to −5° and quenched by the addition of 1N HCl until the reaction mixture turned into a clear solution. This was extracted with EtOAc (3×300 mL), and the combined extracts were washed with H₂O and dried over anhydrous Na₂SO₄ then evaporated in vacuo to give the crude product. This was purified by column chromatography, eluting with MeOH:CH₂Cl₂ (1:49) to give 4.8 g (25% yield) of pure 58 as an off-white solid. LCMS m/z 246 [M+H]⁺; (81.1% purity). ¹H NMR (300 MHz, DMSO-d₆) δ 12.58-12.17 (br s, 1H), 5.00-4.64 (br s, 1H), 4.14-4.05 (m, 1H), 3.28-3.17 (m, 2H), 2.19-2.05 (m, 1H), 1.98-1.88 (m, 1H), 1.37 (d, J=15 Hz, 9H), 1.22 (s, 3H).

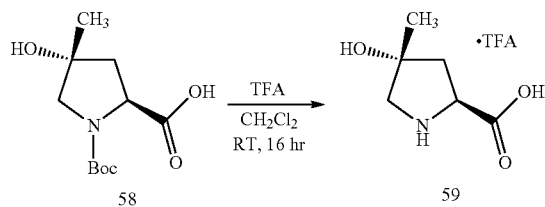

(2S,4R)-4-hydroxy-4-methylpyrrolidine-2-carboxylic acid, TFA salt (59). To a stirred solution of 58 (4.8 g, 19.57 mmol) in anhydrous CH$_2$Cl$_2$ (100 mL) at 0° was added TFA (14 mL) and the reaction mixture was stirred at rt for 16 hr. The reaction mixture was evaporated in vacuo to the crude product, which was then co-distilled with CHCl$_3$ followed by Et$_2$O to give 2.8 g (100% yield) of the crude TFA salt of 59 as a gummy brown liquid, which was suitable for use in the next step without further purification. LCMS m/z 146 (free amine) [M+H]$^+$; (98.8% purity). $^1$H NMR (300 MHz, DMSO-d$_6$) δ 10.00-9.60 (br s, 1H), 9.00-8.45 (br s, 1H), 4.42 (t, J=12 Hz, 1H), 3.18 (d, J=12 Hz, 1H), 3.03 (d, J=12 Hz, 1H), 2.20 (d, J=12 Hz, 2H), 1.33 (s, 3H).

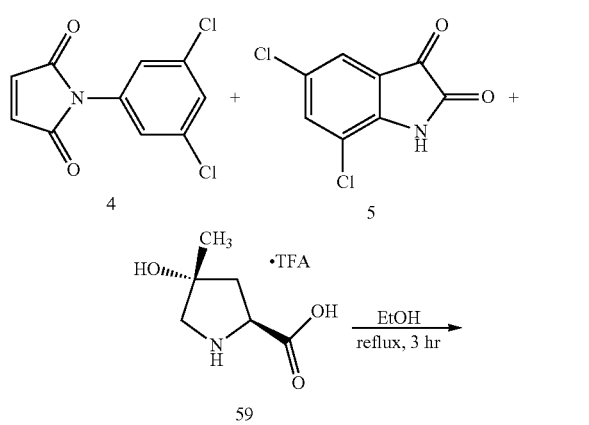

(7'R)-5,7-dichloro-2'-(3,5-dichlorophenyl)-7'-hydroxy-7'-methyl-3a',6',7',8',8a',8b'-hexahydro-1'H-spiro[indoline-3,4'-pyrrolo[3,4-a]pyrrolizine]-1',2,3'(2'H)-trione (60). To a stirred solution of 4 (5.50 g, 22.73 mmol) in EtOH (50 mL) was added 5 (4.90 g, 22.73 mmol) and (59) (3.30 g, 22.73 mmol) at rt. The reaction mixture was stirred at 80° for 3 hr, then cooled to rt, and evaporated in vacuo to give the crude product. This was purified by column chromatography, eluting with Pet. Ether:EtOAc (60:40) to give 3.5 g (28% yield) of (60) as a light pink solid. LCMS m/z 542 [M+H]$^+$; 94% purity). $^1$H NMR (300 MHz, DMSO-d$_6$) δ 11.21 (s, 1H), 7.79 (m, 1H), 7.58 (m, 1H), 7.42 (m, 2H), 7.01 (m, 1H), 4.78 (s, 1H), 4.50 (dd, J=9 Hz, J=3 Hz, 1H), 3.82 (d, J=4.5 Hz, 1H), 3.74 (t, J=4.5 Hz, 1H), 2.50 (d, J=4.5 Hz, 1H), 2.34 (d, J=4.5 Hz, 1H), 1.90-1.80 (m, 2H), 1.22 (s, 3H).

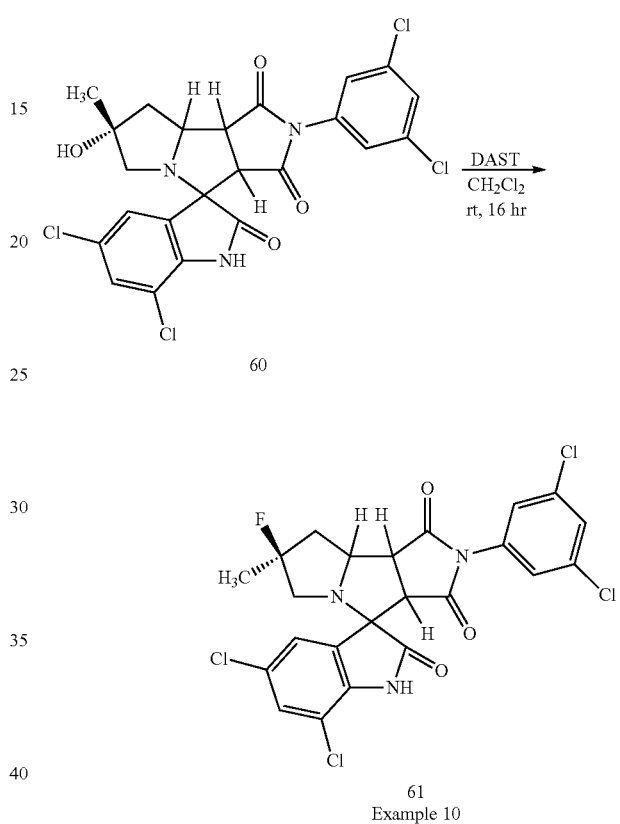

(7'S)-5,7-dichloro-2'-(3,5-dichlorophenyl)-7'-fluoro-7'-methyl-3a',6',7',8',8a',8b'-hexahydro-1'H-spiro[indoline-3,4'-pyrrolo[3,4-a]pyrrolizine]-1',2,3'(2'H)-trione (61). To a stirred solution of 60 (4.80 g, 8.86 mmol) in CH$_2$Cl$_2$ (100 mL) at 0° was added DAST (1.2 mL, 8.86 mmol). The reaction mixture was warmed to rt and stirred at rt for 16 hr. The reaction mixture was cooled to 0° and quenched with H$_2$O. The resulting mixture was extracted with CH$_2$Cl$_2$ (3×200 mL). The combined organic extracts were dried over anhydrous Na$_2$SO$_4$ and evaporated in vacuo to give the crude product. This was purified by column chromatography, eluting with Pet. Ether:EtOAc (60:40) to give 250 mg (5% yield) of pure 61 (Example 10). LCMS m/z 544 [M+H]$^+$; (96% purity); Chiral HPLC (95.0% purity). $^1$H NMR (400 MHz, DMSO-d$_6$) δ 11.24 (s, 1H), 7.77 (t, J=2.0 Hz, 1H), 7.55 (d, J=2.0 Hz, 1H), 7.47 (d, J=2.0 Hz, 2H), 7.11 (d, J=2.0 Hz, 1H), 4.56-4.48 (m, 1H), 3.89 (d, J=7.8 Hz, 1H), 3.82-3.75 (m, 1H), 2.83-2.73 (m, 1H), 2.63-2.53 (m, 1H), 2.28-1.91 (m, 2H), 1.51-1.28 (m, 3H).

The compounds set forth in Table 1 were prepared using the general methods described in Schemes I to IV and Examples 1 to 10 above.

TABLE 1

| Example No. | Structure | M/Z | Single enantiomer (s) or mixture of stereoisomers (m) |
|---|---|---|---|
| 11 | 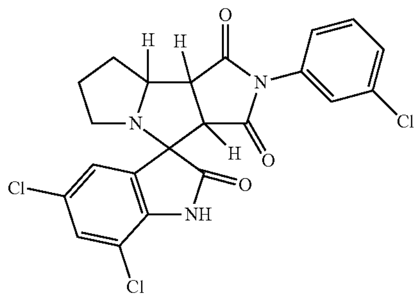 [SMILES: O=C1C2C3CCCN3C3(C(=O)Nc4c(Cl)cc(Cl)cc43)C2C(=O)N1c1cccc(Cl)c1] | 476.00 [M + H]$^+$ | m |
| 12 | 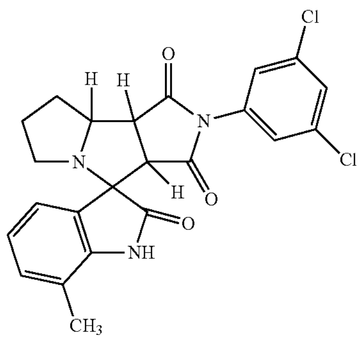 [SMILES: Cc1cccc2c1NC(=O)C21C2C(=O)N(c3cc(Cl)cc(Cl)c3)C(=O)C2C2CCCN21] | 456.09 [M + H]$^+$ | m |
| 13 | 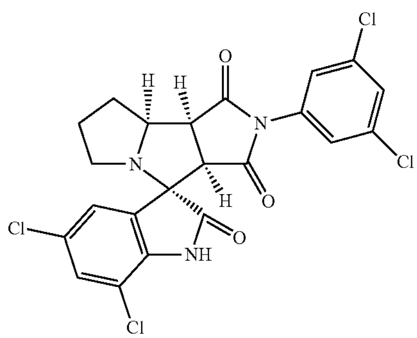 [SMILES: O=C1[C@H]2[C@@H](C(=O)N1c1cc(Cl)cc(Cl)c1)[C@]1(C(=O)Nc3c(Cl)cc(Cl)cc31)N1CCC[C@@H]21] | 510.18 [M + H]$^-$ | s |
| 14 | 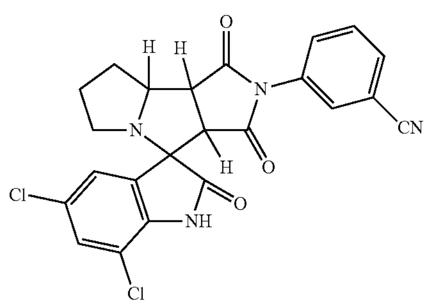 [SMILES: N#Cc1cccc(N2C(=O)C3C4CCCN4C4(C(=O)Nc5c(Cl)cc(Cl)cc54)C3C2=O)c1] | 467.28 [M + H]$^+$ | m |
| 15 | 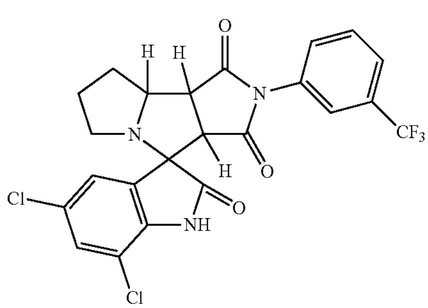 [SMILES: O=C1C2C3CCCN3C3(C(=O)Nc4c(Cl)cc(Cl)cc43)C2C(=O)N1c1cccc(C(F)(F)F)c1] | 510.28 [M + H]$^+$ | m |

TABLE 1-continued

| Example No. | Structure | M/Z | Single enantiomer(s) or mixture of stereoisomers (m) |
|---|---|---|---|
| 16 | 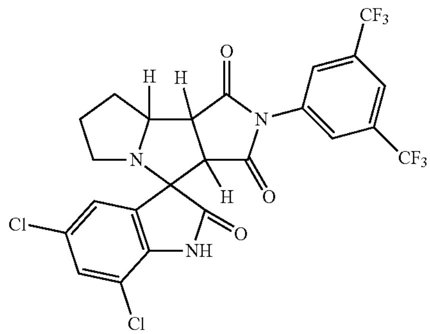 [SMILES: O=C1C2C3CCCN3C3(C(=O)Nc4c(Cl)cc(Cl)cc43)C2C(=O)N1c1cc(C(F)(F)F)cc(C(F)(F)F)c1] | 578.17 [M + H]+ | m |
| 17 | 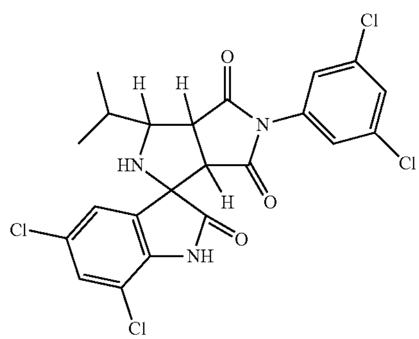 [SMILES: CC(C)C1NC2(C(=O)Nc3c(Cl)cc(Cl)cc32)C2C(=O)N(c3cc(Cl)cc(Cl)c3)C(=O)C12] | 512.20 [M + H]− | m |
| 18 | 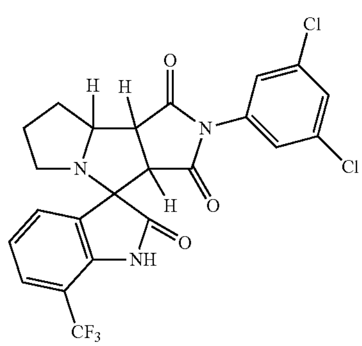 [SMILES: O=C1C2C3CCCN3C3(C(=O)Nc4c(C(F)(F)F)cccc43)C2C(=O)N1c1cc(Cl)cc(Cl)c1] | 510.34 [M + H]+ | m |
| 19 | 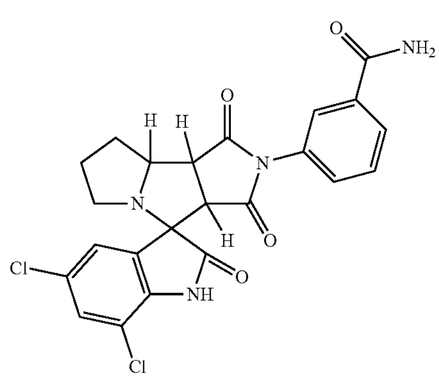 [SMILES: NC(=O)c1cccc(N2C(=O)C3C4CCCN4C4(C(=O)Nc5c(Cl)cc(Cl)cc54)C3C2=O)c1] | 485.32 [M + H]+ | m |

TABLE 1-continued

| Example No. | Structure | M/Z | Single enantiomer(s) or mixture of stereoisomers (m) |
|---|---|---|---|
| 20 | 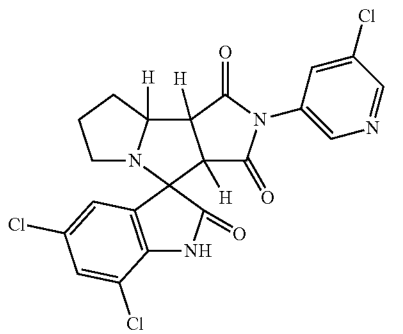 [SMILES: O=C1C2C3CCCN3C3(C(=O)Nc4c(Cl)cc(Cl)cc43)C2C(=O)N1c1cncc(Cl)c1] | 477.24 [M + H]⁺ | m |
| 21 | 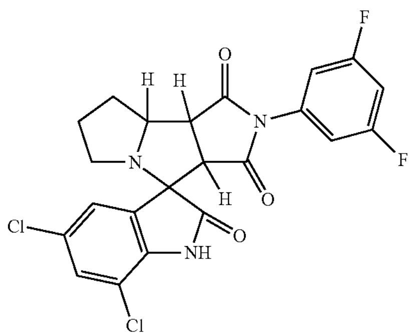 [SMILES: O=C1C2C3CCCN3C3(C(=O)Nc4c(Cl)cc(Cl)cc43)C2C(=O)N1c1cc(F)cc(F)c1] | 478.29 [M + H]⁺ | m |
| 22 | 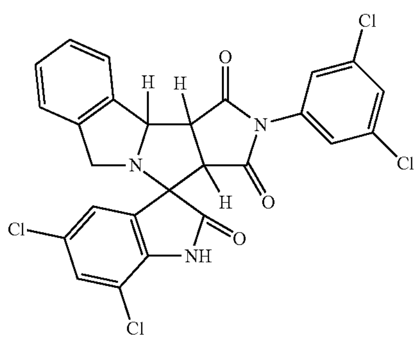 [SMILES: O=C1C2C3c4ccccc4CN3C3(C(=O)Nc4c(Cl)cc(Cl)cc43)C2C(=O)N1c1cc(Cl)cc(Cl)c1] | 558.16 [M + H]⁻ | m |
| 23 | 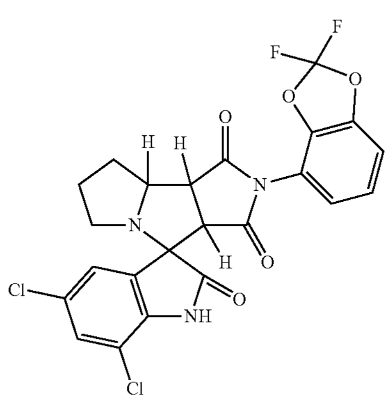 [SMILES: O=C1C2C3CCCN3C3(C(=O)Nc4c(Cl)cc(Cl)cc43)C2C(=O)N1c1cccc2c1OC(F)(F)O2] | 522.25 [M + H]⁺ | m |

TABLE 1-continued

| Example No. | Structure | M/Z | Single enantiomer (s) or mixture of stereoisomers (m) |
|---|---|---|---|
| 24 | 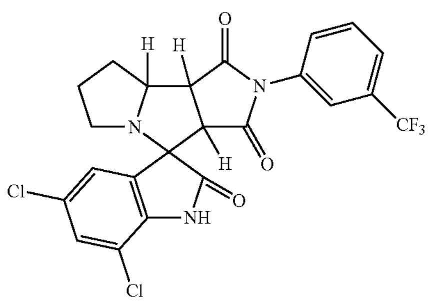 [SMILES: O=C1C2C3CCCN3C3(C(=O)Nc4c(Cl)cc(Cl)cc43)C2C(=O)N1c1cccc(C(F)(F)F)c1] | 510.37 [M + H]+ | s |
| 25 | 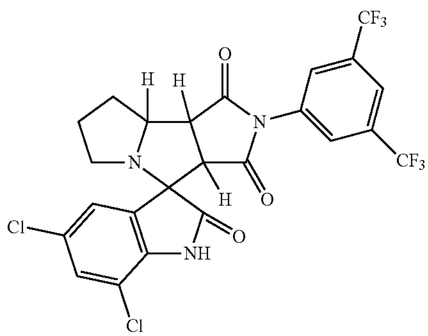 [SMILES: O=C1C2C3CCCN3C3(C(=O)Nc4c(Cl)cc(Cl)cc43)C2C(=O)N1c1cc(C(F)(F)F)cc(C(F)(F)F)c1] | 578.68 [M + H]+ | s |
| 26 | 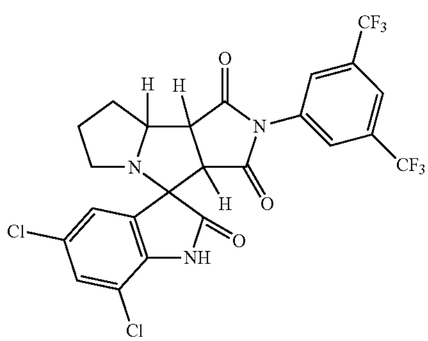 [SMILES: O=C1C2C3CCCN3C3(C(=O)Nc4c(Cl)cc(Cl)cc43)C2C(=O)N1c1cc(C(F)(F)F)cc(C(F)(F)F)c1] | 578.68 [M + H]+ | s |
| 27 | 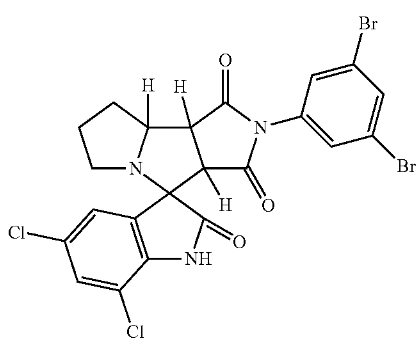 [SMILES: O=C1C2C3CCCN3C3(C(=O)Nc4c(Cl)cc(Cl)cc43)C2C(=O)N1c1cc(Br)cc(Br)c1] | 600.09 [M + H]+ | m |

TABLE 1-continued

| Example No. | Structure | M/Z | Single enantiomer (s) or mixture of stereoisomers (m) |
|---|---|---|---|
| 28 | 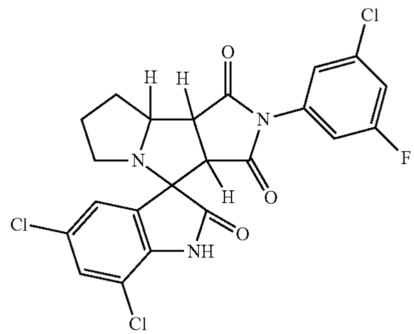 | 494.73 [M + H]$^+$ | m |
| 29 | 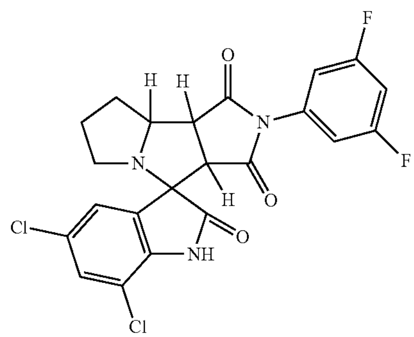 | 445.37 [M + H]$^+$ | m |
| 30 | 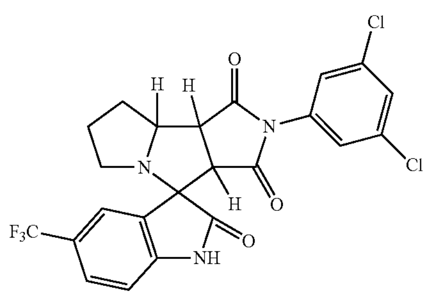 [SMILES: O=C1C2C3CCCN3C3(C(=O)Nc4ccc(C(F)(F)F)cc43)C2C(=O)N1c1cc(Cl)cc(Cl)c1] | 510.29 [M + H]$^+$ | m |
| 31 | 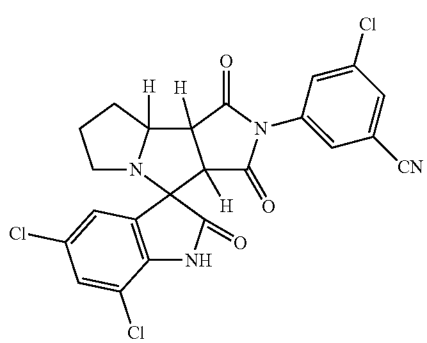 [SMILES: N#Cc1cc(Cl)cc(N2C(=O)C3C4CCCN4C4(C(=O)Nc5c(Cl)cc(Cl)cc54)C3C2=O)c1] | 501.75 [M + H]$^+$ | m |

TABLE 1-continued

| Example No. | Structure | M/Z | Single enantiomer(s) or mixture of stereoisomers (m) |
|---|---|---|---|
| 32 | 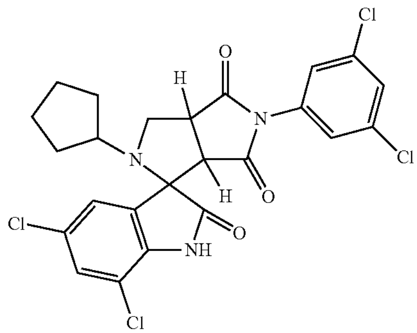 [SMILES: O=C1C2CN(C3CCCC3)C3(C(=O)Nc4c(Cl)cc(Cl)cc43)C2C(=O)N1c1cc(Cl)cc(Cl)c1] | 538.22 [M + H]⁻ | m |
| 33 | 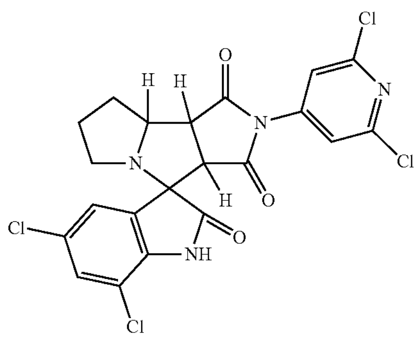 | 511.20 [M + H]⁻ | m |
| 34 | 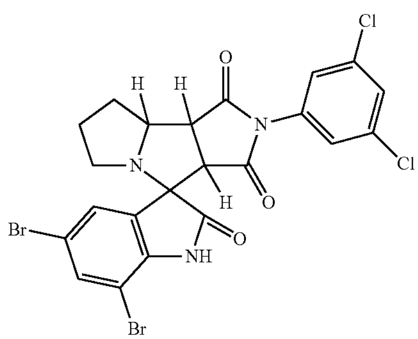 | 598.06 [M + H]⁻ | m |
| 35 | 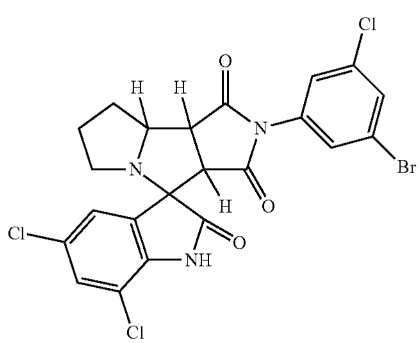 [SMILES: O=C1C2C3CCCN3C3(C(=O)Nc4c(Cl)cc(Cl)cc43)C2C(=O)N1c1cc(Cl)cc(Br)c1] | 554.10 [M + H]⁻ | m |

TABLE 1-continued

| Example No. | Structure | M/Z | Single enantiomer(s) or mixture of stereoisomers (m) |
|---|---|---|---|
| 36 | 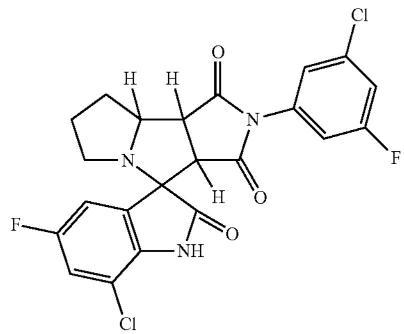 [SMILES: O=C1C2C3CCCN3C3(C(=O)Nc4c(Cl)cc(F)cc43)C2C(=O)N1c1cc(F)cc(Cl)c1] | 478.29 [M + H]⁺ | m |
| 37 | 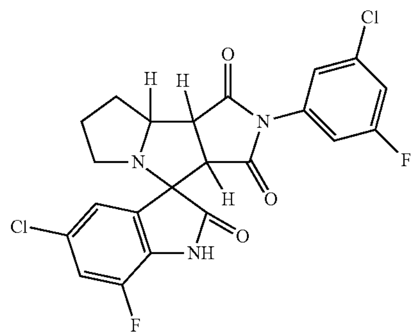 [SMILES: O=C1C2C3CCCN3C3(C(=O)Nc4c(F)cc(Cl)cc43)C2C(=O)N1c1cc(F)cc(Cl)c1] | 478.33 [M + H]⁺ | m |
| 38 | 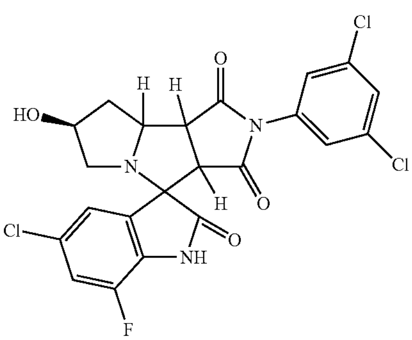 | 526.25 [M + H]⁻ | m |
| 39 | 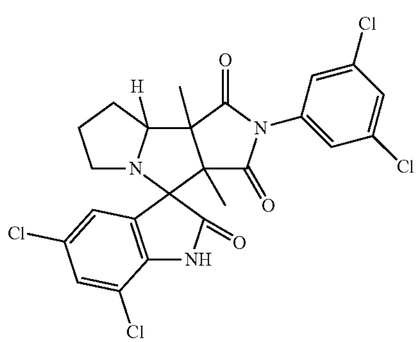 [SMILES: CC12C(=O)N(c3cc(Cl)cc(Cl)c3)C(=O)C1(C)C1(C(=O)Nc3c(Cl)cc(Cl)cc31)N1CCCC12] | 539.23 [M + H]⁺ | m |

TABLE 1-continued

| Example No. | Structure | M/Z | Single enantiomer(s) or mixture of stereoisomers (m) |
|---|---|---|---|
| 40 | 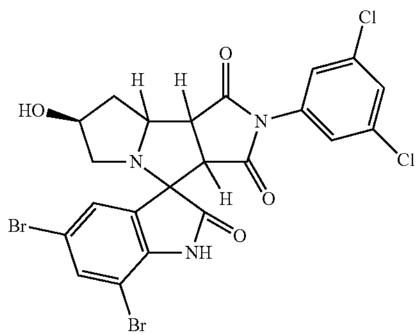 | 616.09 [M + H]⁺ | m |
| 41 | 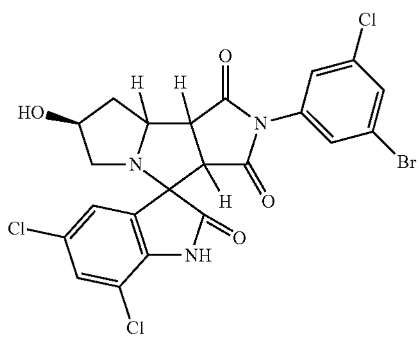 [SMILES: O=C1C2C3C[C@H](O)CN3C3(C(=O)Nc4c(Cl)cc(Cl)cc43)C2C(=O)N1c1cc(Cl)cc(Br)c1] | 572.22 [M + H]⁺ | m |
| 42 | 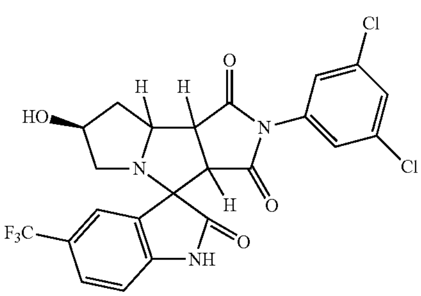 [SMILES: O=C1C2C3C[C@H](O)CN3C3(C(=O)Nc4ccc(C(F)(F)F)cc43)C2C(=O)N1c1cc(Cl)cc(Cl)c1] | 526.29 [M + H]⁺ | m |
| 43 | 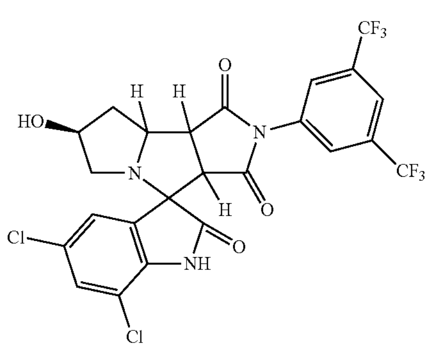 [SMILES: O=C1C2C3C[C@H](O)CN3C3(C(=O)Nc4c(Cl)cc(Cl)cc43)C2C(=O)N1c1cc(C(F)(F)F)cc(C(F)(F)F)c1] | 594.29 [M + H]⁺ | m |

TABLE 1-continued

| Example No. | Structure | M/Z | Single enantiomer (s) or mixture of stereoisomers (m) |
|---|---|---|---|
| 44 | 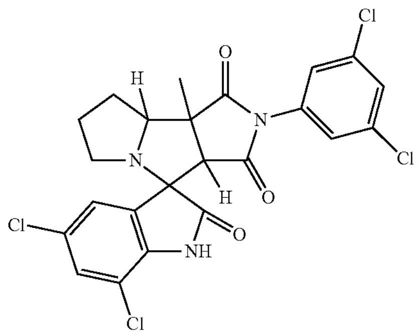 [SMILES: CC12C(=O)N(c3cc(Cl)cc(Cl)c3)C(=O)C1C1(C(=O)Nc3c(Cl)cc(Cl)cc31)N1CCCC12] | 524.20 [M + H]⁻ | m |
| 45 | 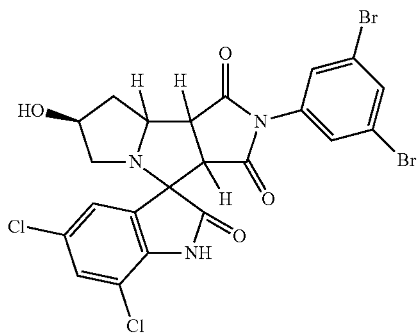 | 614.09 [M + H]⁻ | m |
| 46 | 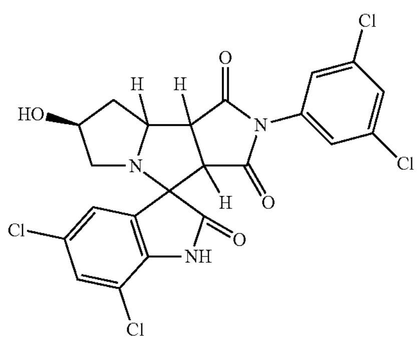 [SMILES: O=C1C2C3C[C@H](O)CN3C3(C(=O)Nc4c(Cl)cc(Cl)cc43)C2C(=O)N1c1cc(Cl)cc(Cl)c1] | 526.21 [M + H]⁻ | s |
| 47 | 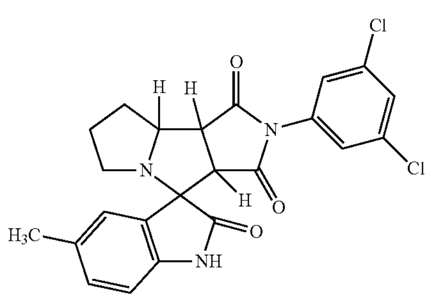 [SMILES: Cc1ccc2c(c1)C1(C(=O)N2)C2C(=O)N(c3cc(Cl)cc(Cl)c3)C(=O)C2C2CCCN21] | 456.32 [M + H]⁺ | m |

TABLE 1-continued

| Example No. | Structure | M/Z | Single enantiomer (s) or mixture of stereoisomers (m) |
|---|---|---|---|
| 48 | 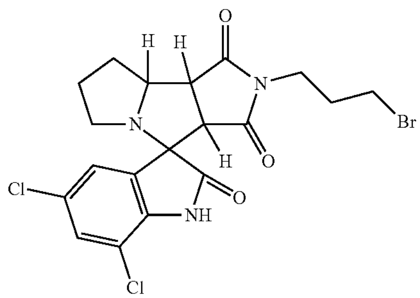 [SMILES: O=C1C2C3CCCN3C3(C(=O)Nc4c(Cl)cc(Cl)cc43)C2C(=O)N1CCCBr] | 486.33 [M + H]⁻ | m |
| 49 | 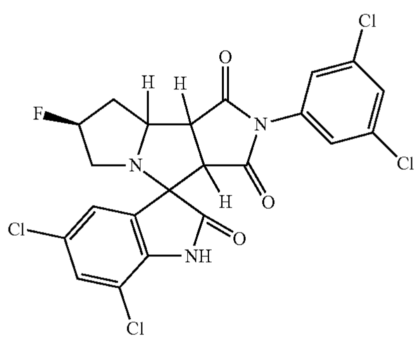 [SMILES: O=C1C2C3C[C@H](F)CN3C3(C(=O)Nc4c(Cl)cc(Cl)cc43)C2C(=O)N1c1cc(Cl)cc(Cl)c1] | 528.38 [M + H]⁻ | m |
| 50 | 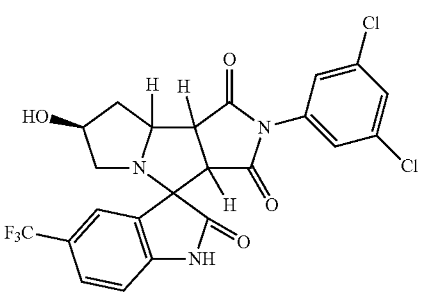 [SMILES: O=C1C2C3C[C@H](O)CN3C3(C(=O)Nc4ccc(C(F)(F)F)cc43)C2C(=O)N1c1cc(Cl)cc(Cl)c1] | 526.49 [M + H]⁺ | s |
| 51 | 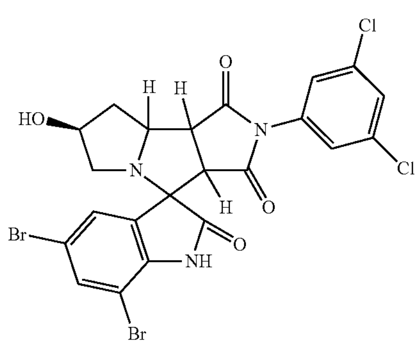 | 614.23 [M + H]⁻ | s |

TABLE 1-continued

| Example No. | Structure | M/Z | Single enantiomer(s) or mixture of stereoisomers (m) |
|---|---|---|---|
| 52 | 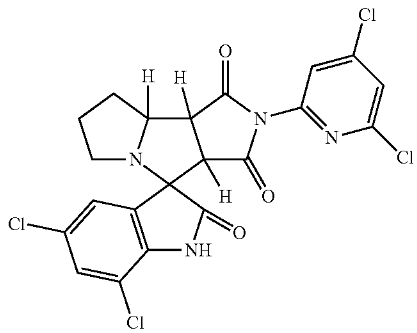 [SMILES: O=C1C2C3CCCN3C3(C(=O)Nc4c(Cl)cc(Cl)cc43)C2C(=O)N1c1cc(Cl)cc(Cl)n1] | 511.00 [M + H]⁻ | m |
| 53 | 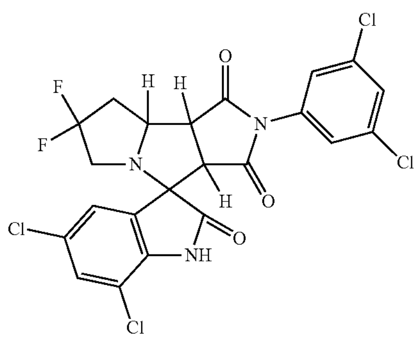 [SMILES: O=C1C2C3CC(F)(F)CN3C3(C(=O)Nc4c(Cl)cc(Cl)cc43)C2C(=O)N1c1cc(Cl)cc(Cl)c1] | 545.90 [M + H]⁻ | m |
| 54 | 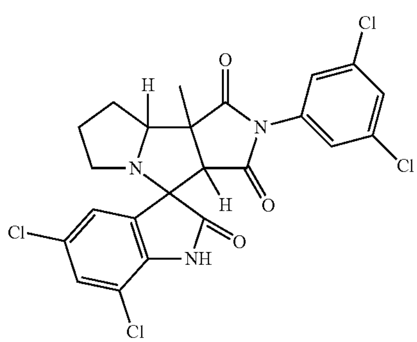 [SMILES: CC12C(=O)N(c3cc(Cl)cc(Cl)c3)C(=O)C1C1(C(=O)Nc3c(Cl)cc(Cl)cc31)N1CCCC12] | 524.00 [M + H]⁻ | s |
| 55 | 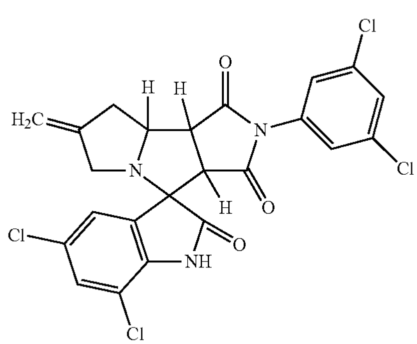 [SMILES: C=C1CC2C3C(=O)N(c4cc(Cl)cc(Cl)c4)C(=O)C3C3(C(=O)Nc4c(Cl)cc(Cl)cc43)N2C1] | 522.00 [M + H]⁻ | m |

TABLE 1-continued

| Example No. | Structure | M/Z | Single enantiomer (s) or mixture of stereoisomers (m) |
|---|---|---|---|
| 56 | 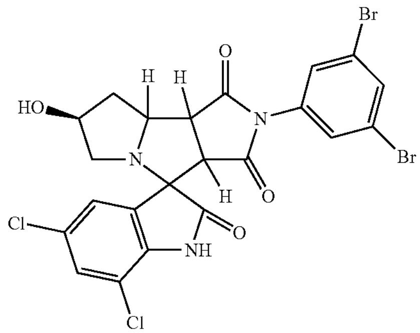 [SMILES: O=C1C2C3C[C@H](O)CN3C3(C(=O)Nc4c(Cl)cc(Cl)cc43)C2C(=O)N1c1cc(Br)cc(Br)c1] | 613.90 [M + H]⁻ | s |
| 57 | 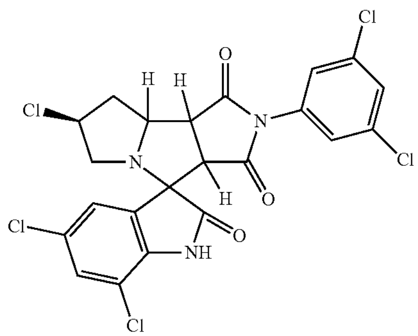 | 543.90 [M + H]⁻ | m |
| 58 | 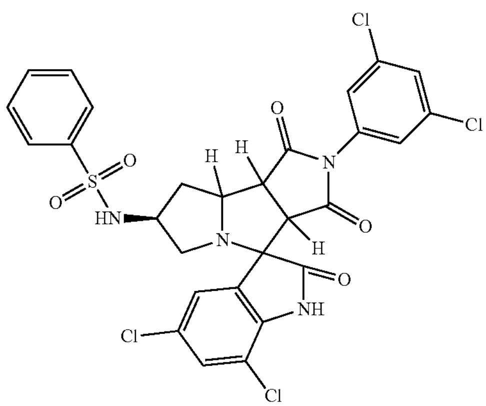 [SMILES: O=C1C2C3C[C@H](NS(=O)(=O)c4ccccc4)CN3C3(C(=O)Nc4c(Cl)cc(Cl)cc43)C2C(=O)N1c1cc(Cl)cc(Cl)c1] | 665.30 [M + H]⁻ | s |
| 59 | 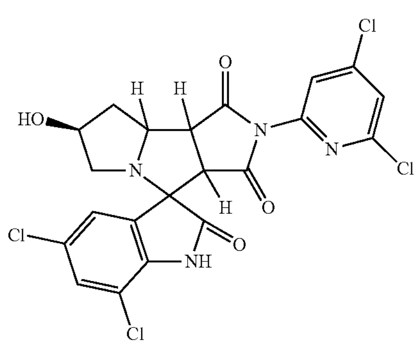 [SMILES: O=C1C2C3C[C@H](O)CN3C3(C(=O)Nc4c(Cl)cc(Cl)cc43)C2C(=O)N1c1cc(Cl)cc(Cl)n1] | 527.00 [M + H]⁻ | m |

TABLE 1-continued

| Example No. | Structure | M/Z | Single enantiomer (s) or mixture of stereoisomers (m) |
|---|---|---|---|
| 60 | 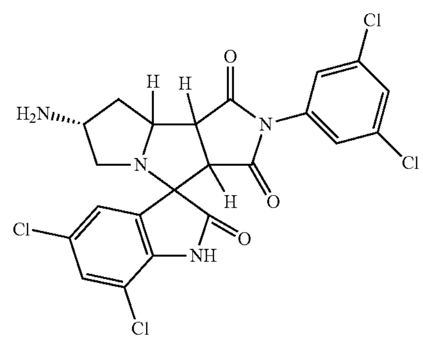 [SMILES: N[C@@H]1CC2C3C(=O)N(c4cc(Cl)cc(Cl)c4)C(=O)C3C3(C(=O)Nc4c(Cl)cc(Cl)cc43)N2C1] | 526.20 [M + H]+ | m |
| 61 | 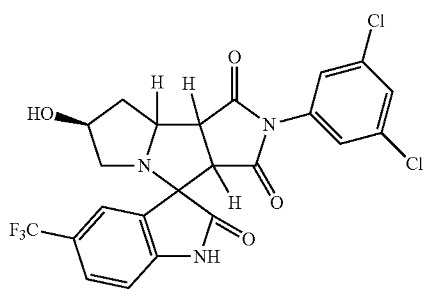 [SMILES: O=C1C2C3C[C@H](O)CN3C3(C(=O)Nc4ccc(C(F)(F)F)cc43)C2C(=O)N1c1cc(Cl)cc(Cl)c1] | 526.40 [M + H]+ | s |
| 62 | 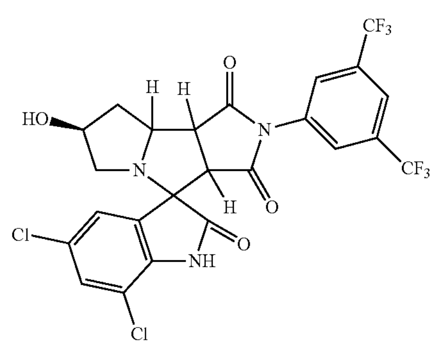 [SMILES: O=C1C2C3C[C@H](O)CN3C3(C(=O)Nc4c(Cl)cc(Cl)cc43)C2C(=O)N1c1cc(C(F)(F)F)cc(C(F)(F)F)c1] | 594.36 [M + H]+ | s |
| 63 | 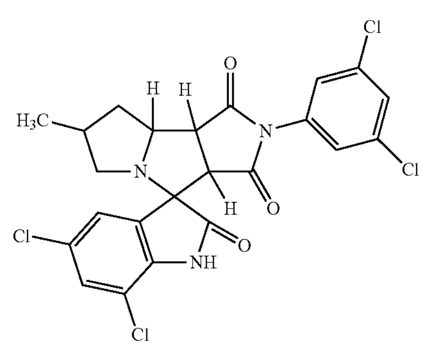 [SMILES: CC1CC2C3C(=O)N(c4cc(Cl)cc(Cl)c4)C(=O)C3C3(C(=O)Nc4c(Cl)cc(Cl)cc43)N2C1] | 524.00 [M + H]− | m |

TABLE 1-continued

| Example No. | Structure | M/Z | Single enantiomer (s) or mixture of stereoisomers (m) |
| --- | --- | --- | --- |
| 64 | 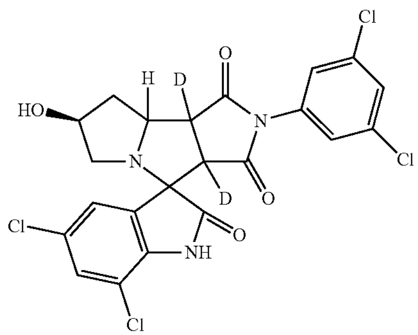 [SMILES: [2H]C12C(=O)N(c3cc(Cl)cc(Cl)c3)C(=O)C1([2H])C1(C(=O)Nc3c(Cl)cc(Cl)cc31)N1C[C@@H](O)CC12] | 530.28 [M + H]+ | m |
| 65 | 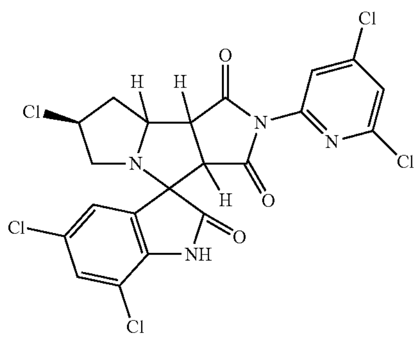 [SMILES: O=C1C2C3C[C@H](Cl)CN3C3(C(=O)Nc4c(Cl)cc(Cl)cc43)C2C(=O)N1c1cc(Cl)cc(Cl)n1] | 545.00 [M + H]− | m |
| 66 | 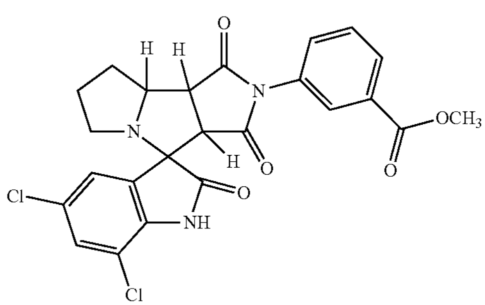 [SMILES: COC(=O)c1cccc(N2C(=O)C3C4CCCN4C4(C(=O)Nc5c(Cl)cc(Cl)cc54)C3C2=O)c1] | 500.32 [M + H]+ | m |
| 67 | 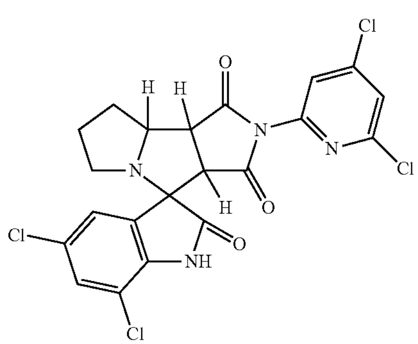 [SMILES: O=C1C2C3CCCN3C3(C(=O)Nc4c(Cl)cc(Cl)cc43)C2C(=O)N1c1cc(Cl)cc(Cl)n1] | 511.00 [M + H]− | s |

TABLE 1-continued

| Example No. | Structure | M/Z | Single enantiomer (s) or mixture of stereoisomers (m) |
|---|---|---|---|
| 68 | 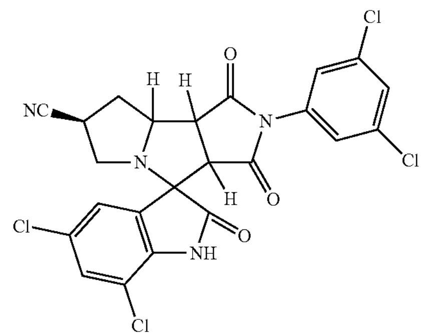 [SMILES: N#C[C@H]1CC2C3C(=O)N(c4cc(Cl)cc(Cl)c4)C(=O)C3C3(C(=O)Nc4c(Cl)cc(Cl)cc43)N2C1] | 536.19 [M + H]+ | m |
| 69 | 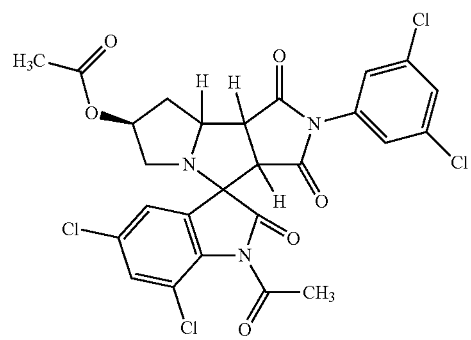 [SMILES: CC(=O)O[C@H]1CC2C3C(=O)N(c4cc(Cl)cc(Cl)c4)C(=O)C3C3(C(=O)N(C(C)=O)c4c(Cl)cc(Cl)cc43)N2C1] | 611.25 [M + H]+ | m |
| 70 | 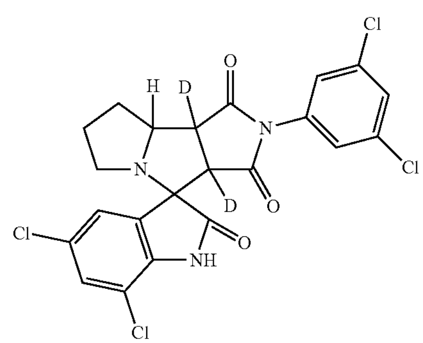 [SMILES: [2H]C12C(=O)N(c3cc(Cl)cc(Cl)c3)C(=O)C1([2H])C1(C(=O)Nc3c(Cl)cc(Cl)cc31)N1CCCC12] | 512.00 [M + H]− | s |
| 71 | 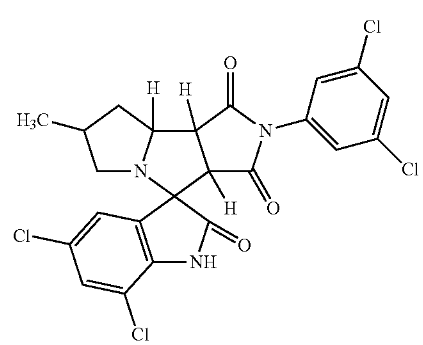 | 524.00 [M + H]+ | m |

TABLE 1-continued

| Example No. | Structure | M/Z | Single enantiomer (s) or mixture of stereoisomers (m) |
|---|---|---|---|
| 72 | 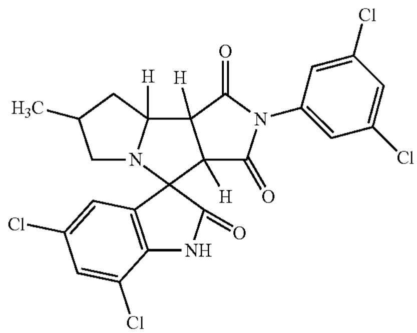 [SMILES: CC1CC2C3C(=O)N(c4cc(Cl)cc(Cl)c4)C(=O)C3C3(C(=O)Nc4c(Cl)cc(Cl)cc43)N2C1] | 524.00 [M + H]+ | s |
| 73 | 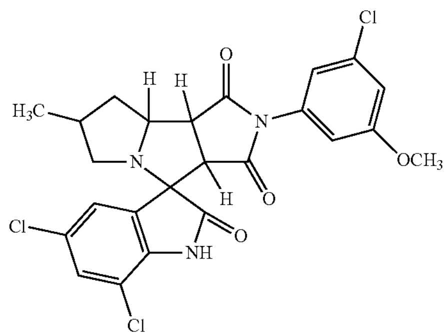 | 506.10 [M + H]+ | m |
| 74 | 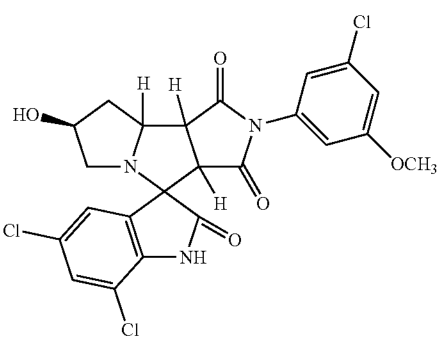 [SMILES: COc1cc(Cl)cc(N2C(=O)C3C4C[C@H](O)CN4C4(C(=O)Nc5c(Cl)cc(Cl)cc54)C3C2=O)c1] | 522.10 [M + H]+ | m |
| 75 | 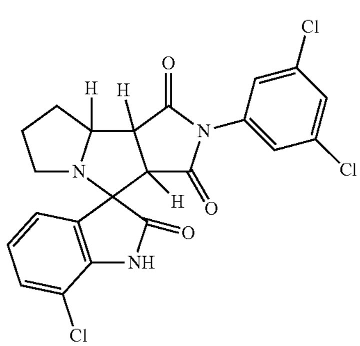 [SMILES: O=C1C2C3CCCN3C3(C(=O)Nc4c(Cl)cccc43)C2C(=O)N1c1cc(Cl)cc(Cl)c1] | 476.17 [M + H]+ | m |

TABLE 1-continued

| Example No. | Structure | M/Z | Single enantiomer(s) or mixture of stereoisomers (m) |
|---|---|---|---|
| 76 | 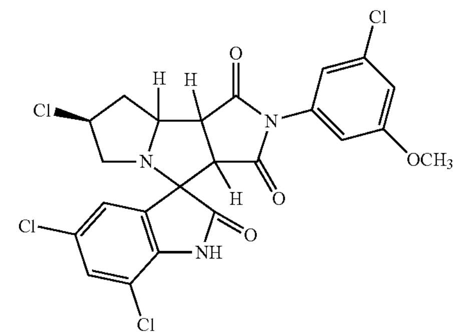 [SMILES: COc1cc(Cl)cc(N2C(=O)C3C4C[C@H](Cl)CN4C4(C(=O)Nc5c(Cl)cc(Cl)cc54)C3C2=O)c1] | 540.10 [M + H]⁻ | m |
| 77 | 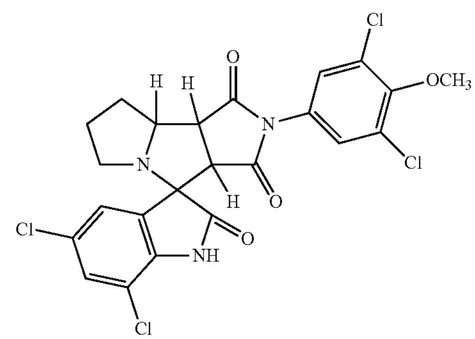 [SMILES: COc1c(Cl)cc(N2C(=O)C3C4CCCN4C4(C(=O)Nc5c(Cl)cc(Cl)cc54)C3C2=O)cc1Cl] | 540.00 [M + H]⁻ | m |
| 78 | 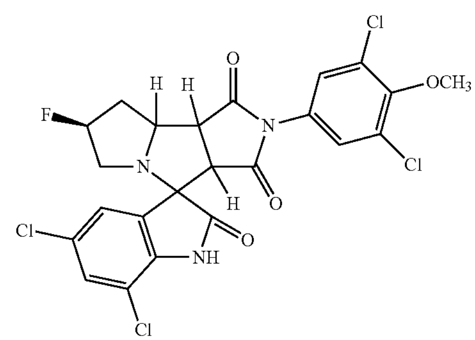 [SMILES: COc1c(Cl)cc(N2C(=O)C3C4C[C@H](F)CN4C4(C(=O)Nc5c(Cl)cc(Cl)cc54)C3C2=O)cc1Cl] | 558.00 [M + H]⁻ | m |
| 79 | 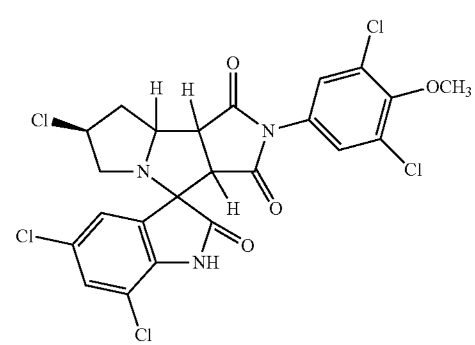 | 574.00 [M + H]⁻ | m |

TABLE 1-continued
| Example No. | Structure | M/Z | Single enantiomer(s) or mixture of stereoisomers (m) |
|---|---|---|---|
| 80 | 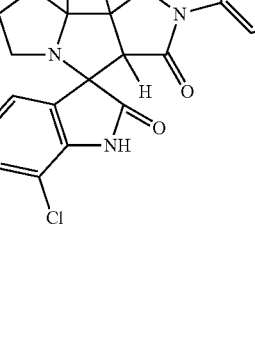 | 510.00 [M + H]⁺ | m |
| 81 | 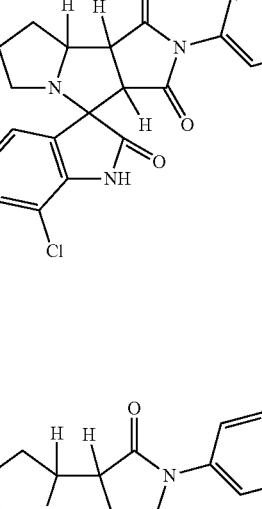 | 526.00 [M + H]⁻ | m |
| 82 | 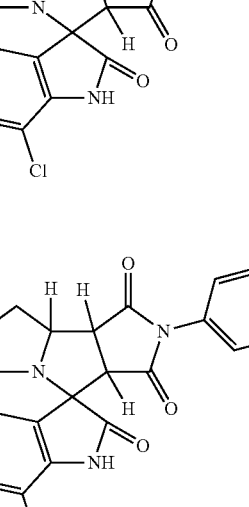 | 542.00 [M + H]⁻ | m |
| 83 | 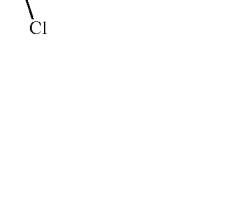 | 560.00 [M + H]⁻ | m |

TABLE 1-continued

| Example No. | Structure | M/Z | Single enantiomer (s) or mixture of stereoisomers (m) |
|---|---|---|---|
| 84 | 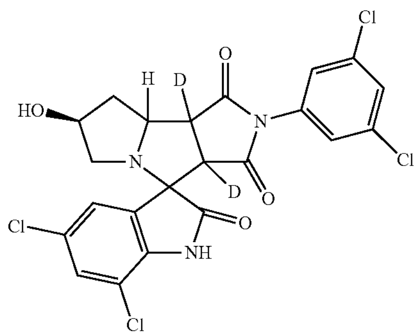 [SMILES: [2H]C12C(=O)N(c3cc(Cl)cc(Cl)c3)C(=O)C1([2H])C1(C(=O)Nc3c(Cl)cc(Cl)cc31)N1C[C@@H](O)CC12] | 528.00 [M + H]− | s |
| 85 | 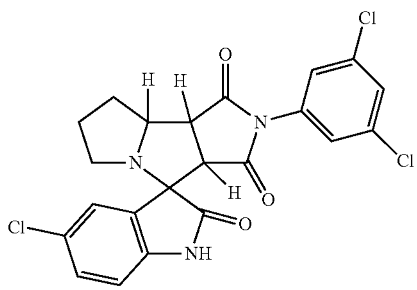 [SMILES: O=C1C2C3CCCN3C3(C(=O)Nc4ccc(Cl)cc43)C2C(=O)N1c1cc(Cl)cc(Cl)c1] | 476.17 [M + H]+ | m |
| 86 | 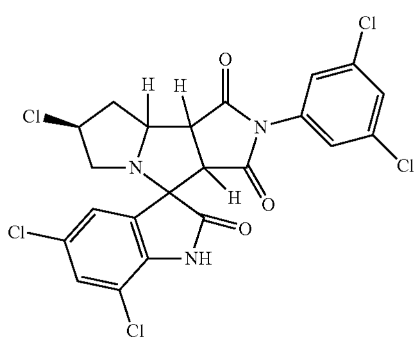 [SMILES: O=C1C2C3C[C@H](Cl)CN3C3(C(=O)Nc4c(Cl)cc(Cl)cc43)C2C(=O)N1c1cc(Cl)cc(Cl)c1] | 544.00 [M + H]− | s |
| 87 | 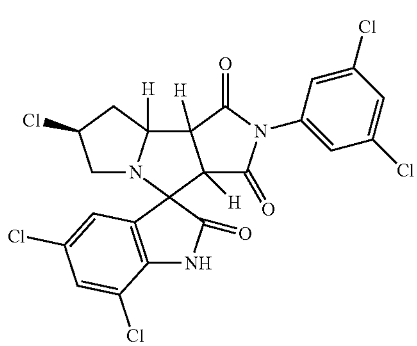 [SMILES: O=C1C2C3C[C@H](Cl)CN3C3(C(=O)Nc4c(Cl)cc(Cl)cc43)C2C(=O)N1c1cc(Cl)cc(Cl)c1] | 544.00 [M + H]− | s |

TABLE 1-continued

| Example No. | Structure | M/Z | Single enantiomer (s) or mixture of stereoisomers (m) |
|---|---|---|---|
| 88 | 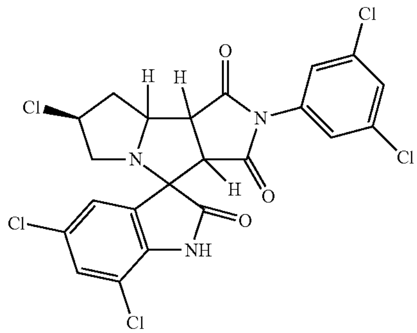 [SMILES: O=C1C2C3C[C@H](Cl)CN3C3(C(=O)Nc4c(Cl)cc(Cl)cc43)C2C(=O)N1c1cc(Cl)cc(Cl)c1] | 544.00 [M + H]⁻ | s |
| 89 | 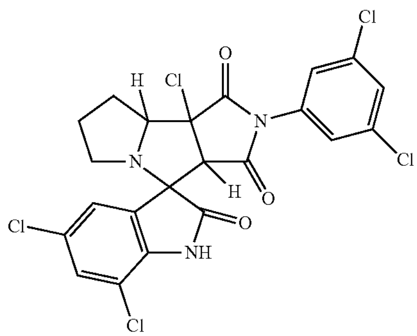 [SMILES: O=C1C2C(Cl)(C(=O)N1c1cc(Cl)cc(Cl)c1)C1CCCN1C21C(=O)Nc2c(Cl)cc(Cl)cc21] | 544.00 [M + H]⁻ | m |
| 90 | 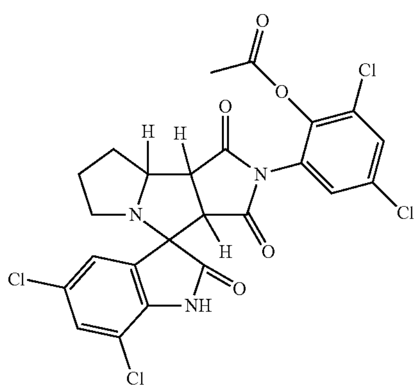 [SMILES: CC(=O)Oc1c(Cl)cc(Cl)cc1N1C(=O)C2C3CCCN3C3(C(=O)Nc4c(Cl)cc(Cl)cc43)C2C1=O] | 568.10 [M + H]⁻ | m |
| 91 | 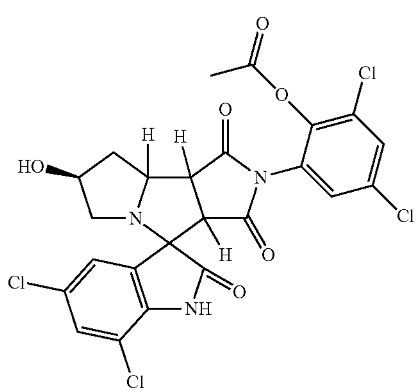 [SMILES: CC(=O)Oc1c(Cl)cc(Cl)cc1N1C(=O)C2C3C[C@H](O)CN3C3(C(=O)Nc4c(Cl)cc(Cl)cc43)C2C1=O] | 584.10 [M + H]⁻ | m |

TABLE 1-continued

| Example No. | Structure | M/Z | Single enantiomer(s) or mixture of stereoisomers (m) |
|---|---|---|---|
| 92 | 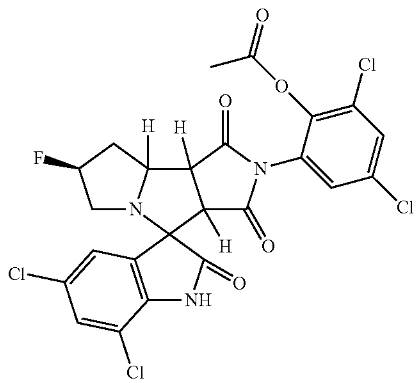 [SMILES: CC(=O)Oc1c(Cl)cc(Cl)cc1N1C(=O)C2C3C[C@H](F)CN3C3(C(=O)Nc4c(Cl)cc(Cl)cc43)C2C1=O] | 586.00 [M + H]⁻ | m |
| 93 | 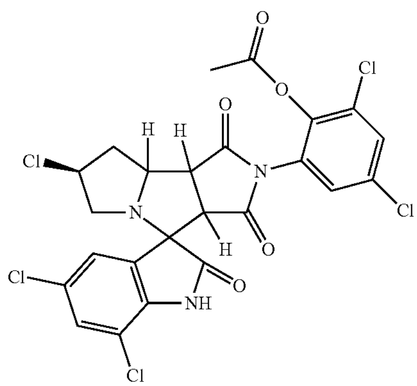 [SMILES: CC(=O)Oc1c(Cl)cc(Cl)cc1N1C(=O)C2C3C[C@H](Cl)CN3C3(C(=O)Nc4c(Cl)cc(Cl)cc43)C2C1=O] | 602.00 [M + H]⁻ | m |
| 94 | 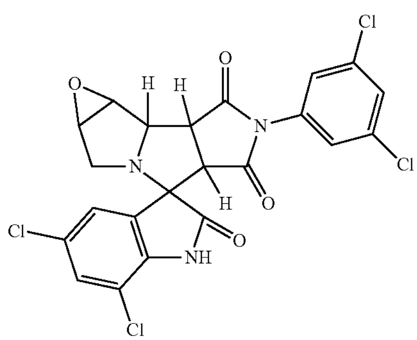 [SMILES: O=C1C2C3C4OC4CN3C3(C(=O)Nc4c(Cl)cc(Cl)cc43)C2C(=O)N1c1cc(Cl)cc(Cl)c1] | 526.00 [M + H]⁺ | m |
| 95 | 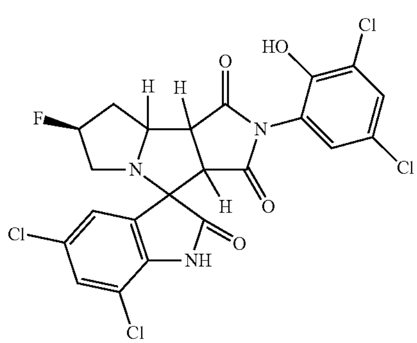 [SMILES: O=C1C2C3C[C@H](F)CN3C3(C(=O)Nc4c(Cl)cc(Cl)cc43)C2C(=O)N1c1cc(Cl)cc(Cl)c1O] | 544.00 [M + H]⁻ | m |

TABLE 1-continued

| Example No. | Structure | M/Z | Single enantiomer(s) or mixture of stereoisomers (m) |
|---|---|---|---|
| 96 | 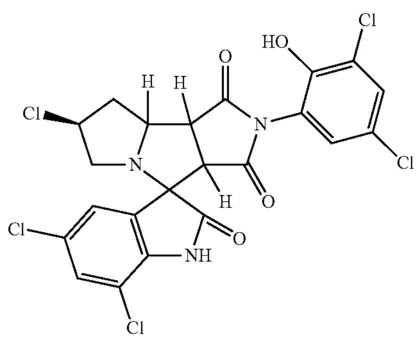 [SMILES: O=C1C2C3C[C@H](Cl)CN3C3(C(=O)Nc4c(Cl)cc(Cl)cc43)C2C(=O)N1c1cc(Cl)cc(Cl)c1O] | 560.00 [M + H]⁻ | m |
| 97 | 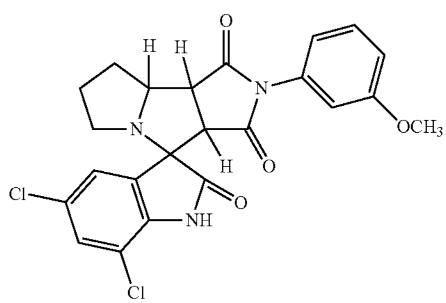 [SMILES: COc1cccc(N2C(=O)C3C4CCCN4C4(C(=O)Nc5c(Cl)cc(Cl)cc54)C3C2=O)c1] | 472.10 [M + H]⁺ | m |
| 98 | 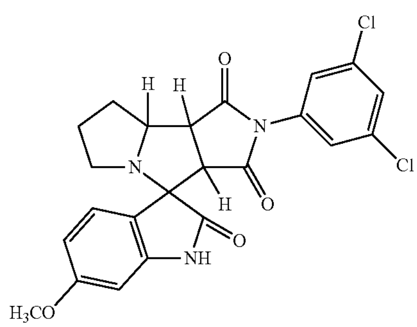 [SMILES: COc1ccc2c(c1)NC(=O)C21C2C(=O)N(c3cc(Cl)cc(Cl)c3)C(=O)C2C2CCCN21] | 472.10 [M + H]⁺ | m |
| 99 | 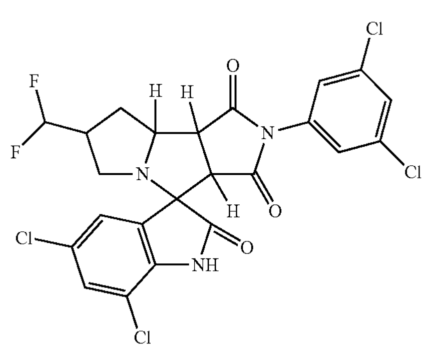 [SMILES: O=C1C2C3CC(C(F)F)CN3C3(C(=O)Nc4c(Cl)cc(Cl)cc43)C2C(=O)N1c1cc(Cl)cc(Cl)c1] | 560.00 [M + H]⁻ | m |

TABLE 1-continued

| Example No. | Structure | M/Z | Single enantiomer(s) or mixture of stereoisomers (m) |
|---|---|---|---|
| 100 | 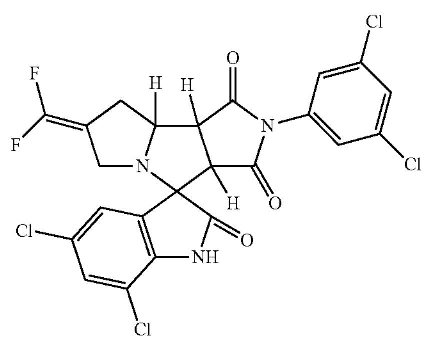 [SMILES: O=C1C2C3CC(=C(F)F)CN3C3(C(=O)Nc4c(Cl)cc(Cl)cc43)C2C(=O)N1c1cc(Cl)cc(Cl)c1] | 558.00 [M + H]⁻ | m |
| 101 | 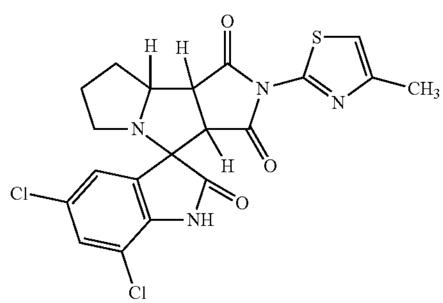 [SMILES: Cc1csc(N2C(=O)C3C4CCCN4C4(C(=O)Nc5c(Cl)cc(Cl)cc54)C3C2=O)n1] | 463.00 [M + H]⁺ | m |
| 102 | 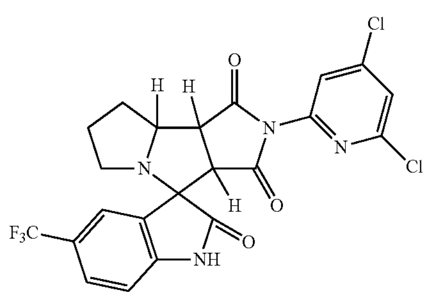 [SMILES: O=C1C2C3CCCN3C3(C(=O)Nc4ccc(C(F)(F)F)cc43)C2C(=O)N1c1cc(Cl)cc(Cl)n1] | 511.10 [M + H]⁺ | m |
| 103 | 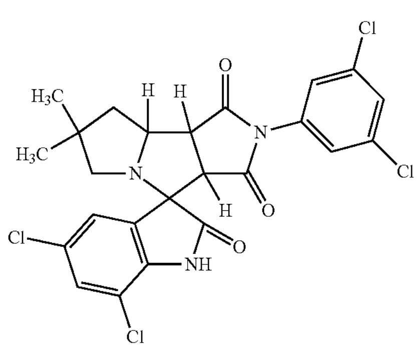 | 538.00 [M + H]⁻ | m |

TABLE 1-continued

| Example No. | Structure | M/Z | Single enantiomer (s) or mixture of stereoisomers (m) |
|---|---|---|---|
| 104 | 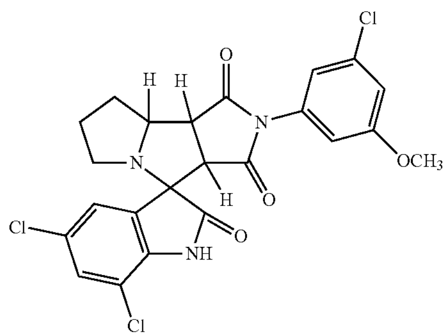 [SMILES: COc1cc(Cl)cc(N2C(=O)C3C4CCCN4C4(C(=O)Nc5c(Cl)cc(Cl)cc54)C3C2=O)c1] | 506.00 [M + H]⁻ | s |
| 105 | 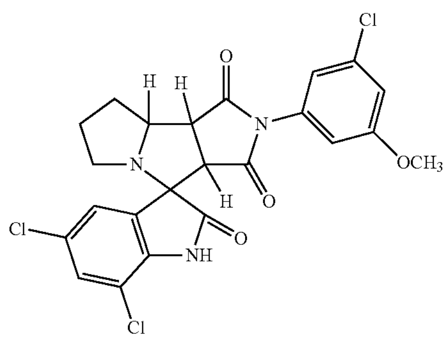 [SMILES: COc1cc(Cl)cc(N2C(=O)C3C4CCCN4C4(C(=O)Nc5c(Cl)cc(Cl)cc54)C3C2=O)c1] | 506.00 [M + H]⁻ | s |
| 106 | 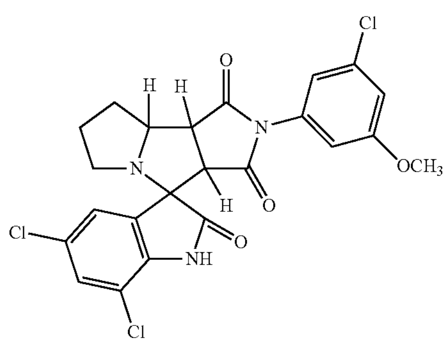 [SMILES: COc1cc(Cl)cc(N2C(=O)C3C4CCCN4C4(C(=O)Nc5c(Cl)cc(Cl)cc54)C3C2=O)c1] | 506.00 [M + H]⁻ | s |
| 107 | 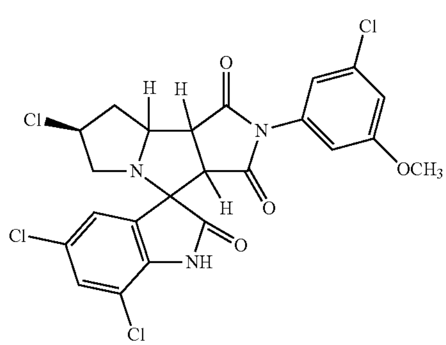 [SMILES: COc1cc(Cl)cc(N2C(=O)C3C4C[C@H](Cl)CN4C4(C(=O)Nc5c(Cl)cc(Cl)cc54)C3C2=O)c1] | 540.00 [M + H]⁻ | s |

TABLE 1-continued

| Example No. | Structure | M/Z | Single enantiomer (s) or mixture of stereoisomers (m) |
|---|---|---|---|
| 108 | 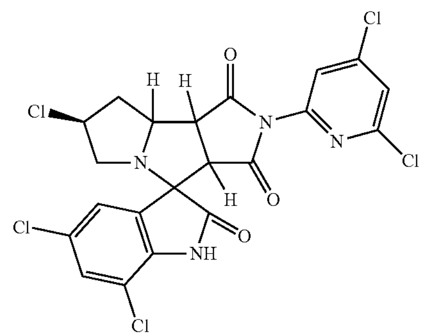 [SMILES: O=C1C2C3C[C@H](Cl)CN3C3(C(=O)Nc4c(Cl)cc(Cl)cc43)C2C(=O)N1c1cc(Cl)cc(Cl)n1] | 544.90 [M + H]⁻ | s |
| 109 | 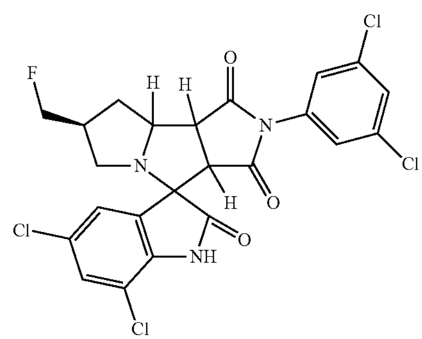 [SMILES: O=C1C2C3C[C@H](CF)CN3C3(C(=O)Nc4c(Cl)cc(Cl)cc43)C2C(=O)N1c1cc(Cl)cc(Cl)c1] | 541.90 [M + H]⁻ | m |
| 110 | 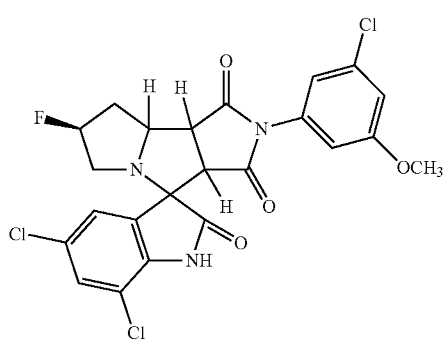 [SMILES: COc1cc(Cl)cc(N2C(=O)C3C4C[C@H](F)CN4C4(C(=O)Nc5c(Cl)cc(Cl)cc54)C3C2=O)c1] | 524.00 [M + H]⁺ | s |
| 111 | 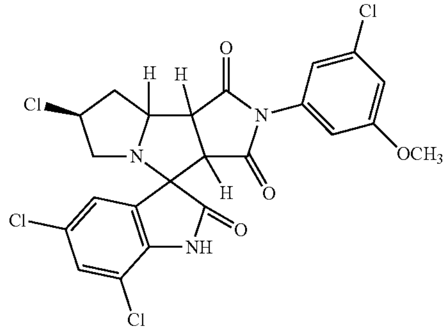 [SMILES: COc1cc(Cl)cc(N2C(=O)C3C4C[C@H](Cl)CN4C4(C(=O)Nc5c(Cl)cc(Cl)cc54)C3C2=O)c1] | 540.00 [M + H]⁻ | s |

TABLE 1-continued

| Example No. | Structure | M/Z | Single enantiomer (s) or mixture of stereoisomers (m) |
|---|---|---|---|
| 112 | 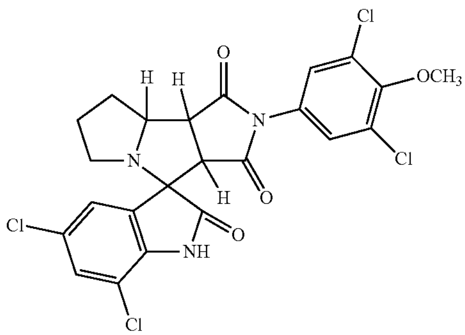 [SMILES: COc1c(Cl)cc(N2C(=O)C3C4CCCN4C4(C(=O)Nc5c(Cl)cc(Cl)cc54)C3C2=O)cc1Cl] | 540.16 [M + H]⁻ | s |
| 113 | 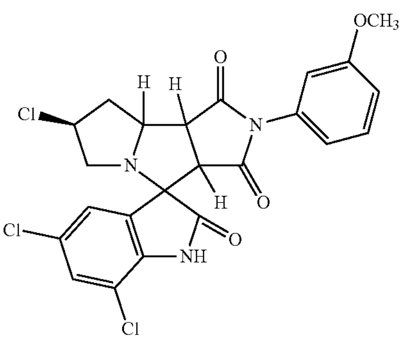 [SMILES: COc1cccc(N2C(=O)C3C4C[C@H](Cl)CN4C4(C(=O)Nc5c(Cl)cc(Cl)cc54)C3C2=O)c1] | 506.19 [M + H]⁺ | m |
| 114 | 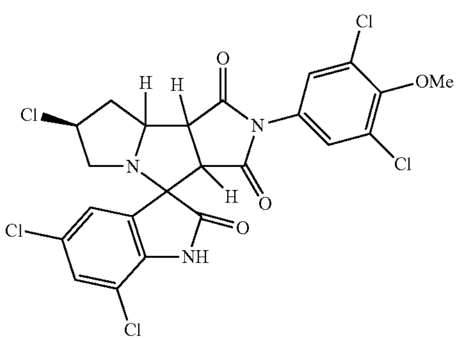 [SMILES: COc1c(Cl)cc(N2C(=O)C3C4C[C@H](Cl)CN4C4(C(=O)Nc5c(Cl)cc(Cl)cc54)C3C2=O)cc1Cl] | 576.14 [M + H]⁺ | s |
| 115 | 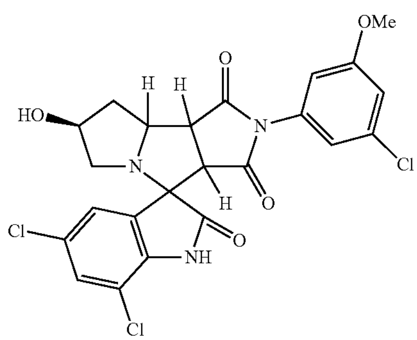 [SMILES: COc1cc(Cl)cc(N2C(=O)C3C4C[C@H](O)CN4C4(C(=O)Nc5c(Cl)cc(Cl)cc54)C3C2=O)c1] | 524.15 [M + H]⁺ | s |

TABLE 1-continued

| Example No. | Structure | M/Z | Single enantiomer (s) or mixture of stereoisomers (m) |
|---|---|---|---|
| 116 | 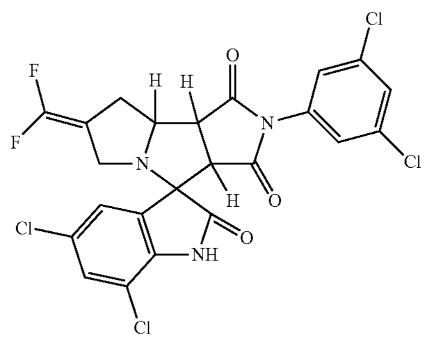 | 560.13 [M + H]⁺ | s |
| 117 | 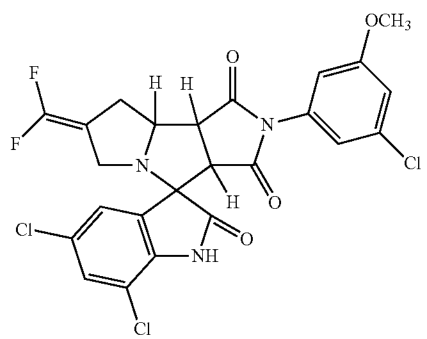 [SMILES: COc1cc(Cl)cc(N2C(=O)C3C4CC(=C(F)F)CN4C4(C(=O)Nc5c(Cl)cc(Cl)cc54)C3C2=O)c1] | 554.23 [M + H]⁺ | m |
| 118 | 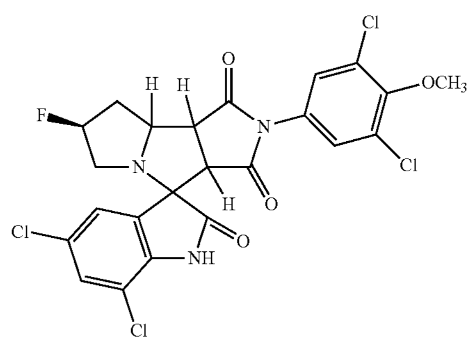 [SMILES: COc1c(Cl)cc(N2C(=O)C3C4C[C@H](F)CN4C4(C(=O)Nc5c(Cl)cc(Cl)cc54)C3C2=O)cc1Cl] | 558.28 [M + H]⁻ | s |
| 119 | 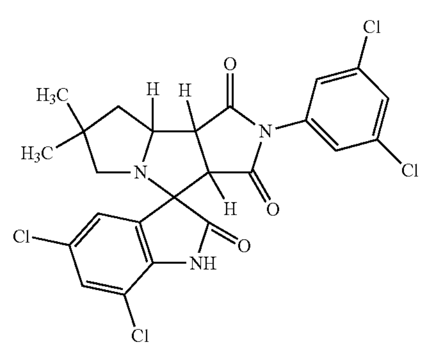 [SMILES: CC1(C)CC2C3C(=O)N(c4cc(Cl)cc(Cl)c4)C(=O)C3C3(C(=O)Nc4c(Cl)cc(Cl)cc43)N2C1] | 538.38 [M + H]⁻ | s |

TABLE 1-continued

| Example No. | Structure | M/Z | Single enantiomer (s) or mixture of stereoisomers (m) |
| --- | --- | --- | --- |
| 120 | 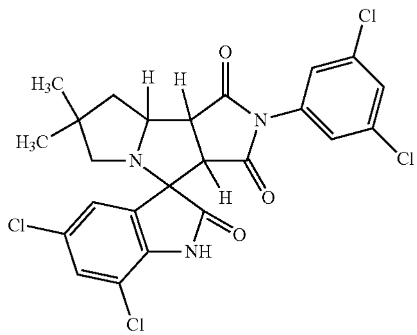 | 538.37 [M + H]⁻ | s |
| 121 | 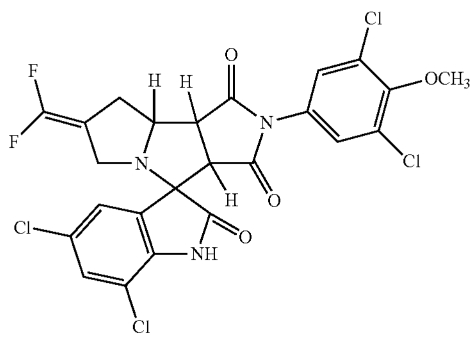 [SMILES: COc1c(Cl)cc(N2C(=O)C3C4CC(=C(F)F)CN4C4(C(=O)Nc5c(Cl)cc(Cl)cc54)C3C2=O)cc1Cl] | 590.07 [M + H]⁺ | m |
| 122 | 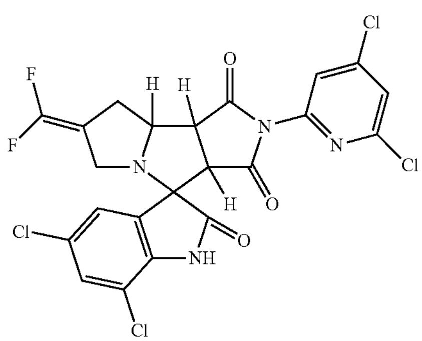 | 561.18 [M + H]⁺ | m |
| 123 | 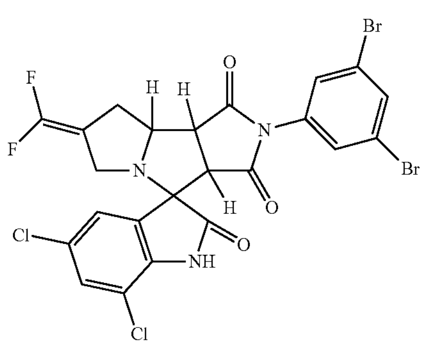 [SMILES: O=C1C2C3CC(=C(F)F)CN3C3(C(=O)Nc4c(Cl)cc(Cl)cc43)C2C(=O)N1c1cc(Br)cc(Br)c1] | 648.12 [M + H]⁺ | m |

TABLE 1-continued

| Example No. | Structure | M/Z | Single enantiomer (s) or mixture of stereoisomers (m) |
|---|---|---|---|
| 124 | 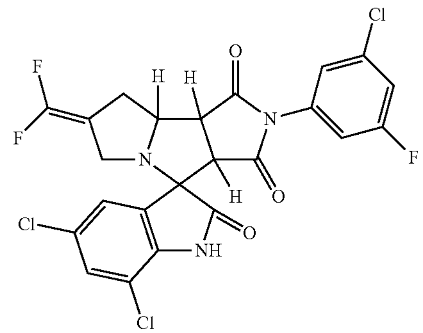 [SMILES: O=C1C2C3CC(=C(F)F)CN3C3(C(=O)Nc4c(Cl)cc(Cl)cc43)C2C(=O)N1c1cc(F)cc(Cl)c1] | 542.25 [M + H]+ | m |
| 125 | 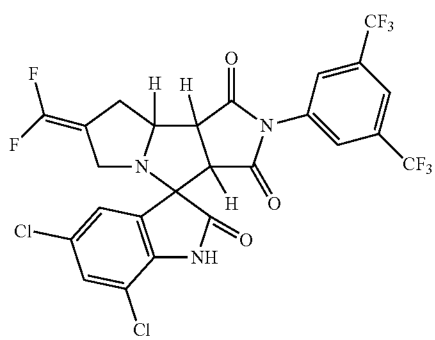 [SMILES: O=C1C2C3CC(=C(F)F)CN3C3(C(=O)Nc4c(Cl)cc(Cl)cc43)C2C(=O)N1c1cc(C(F)(F)F)cc(C(F)(F)F)c1] | 626.28 [M + H]+ | m |
| 126 | 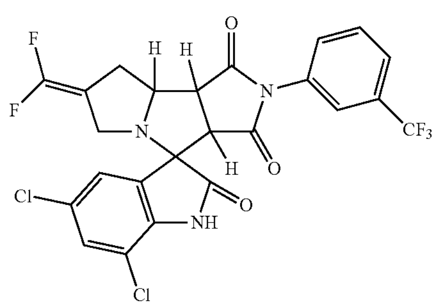 [SMILES: O=C1C2C3CC(=C(F)F)CN3C3(C(=O)Nc4c(Cl)cc(Cl)cc43)C2C(=O)N1c1cccc(C(F)(F)F)c1] | 558.28 [M + H]+ | m |
| 127 | 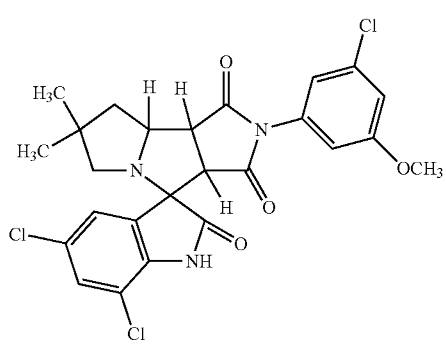 [SMILES: COc1cc(Cl)cc(N2C(=O)C3C4CC(C)(C)CN4C4(C(=O)Nc5c(Cl)cc(Cl)cc54)C3C2=O)c1] | 534.42 [M + H]+ | m |

TABLE 1-continued

| Example No. | Structure | M/Z | Single enantiomer(s) or mixture of stereoisomers (m) |
|---|---|---|---|
| 128 | 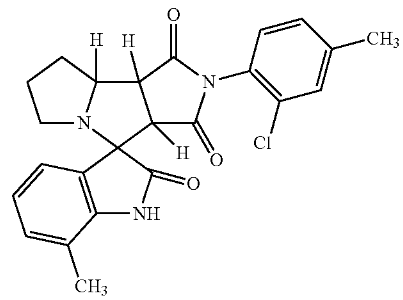 [SMILES: Cc1ccc(N2C(=O)C3C4CCCN4C4(C(=O)Nc5c(C)cccc54)C3C2=O)c(Cl)c1] | 435.73 [M + H]⁺ | m |
| 129 | 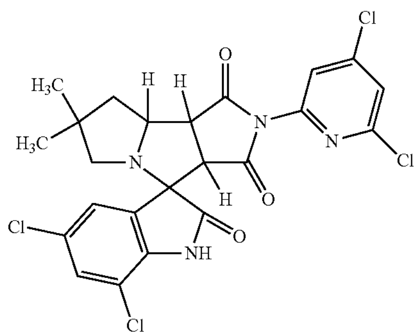 [SMILES: CC1(C)CC2C3C(=O)N(c4cc(Cl)cc(Cl)n4)C(=O)C3C3(C(=O)Nc4c(Cl)cc(Cl)cc43)N2C1] | 541.28 [M + H]⁺ | m |
| 130 | 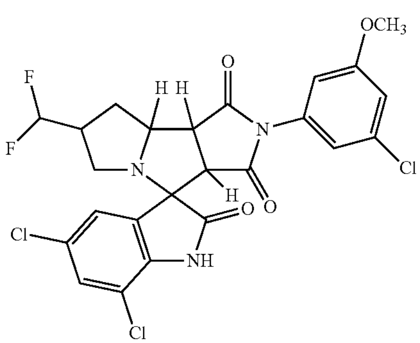 [SMILES: COc1cc(Cl)cc(N2C(=O)C3C4CC(C(F)F)CN4C4(C(=O)Nc5c(Cl)cc(Cl)cc54)C3C2=O)c1] | 556.28 [M + H]⁺ | m |
| 131 | 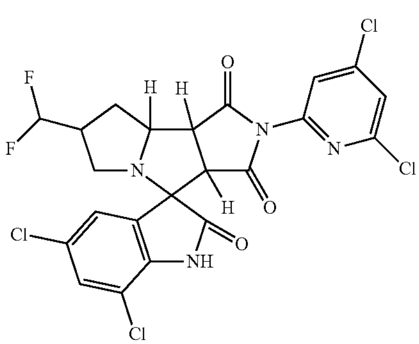 | 561.25 [M + H]⁻ | m |

TABLE 1-continued

| Example No. | Structure | M/Z | Single enantiomer(s) or mixture of stereoisomers (m) |
|---|---|---|---|
| 132 | 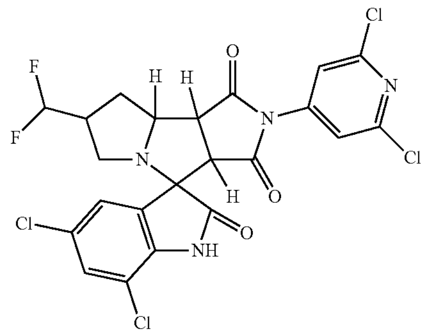 | 561.19 [M + H]⁻ | m |
| 133 | 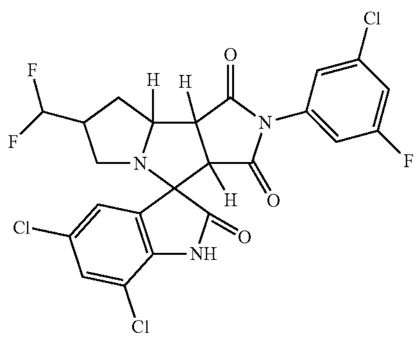 [SMILES: O=C1C2C3CC(C(F)F)CN3C3(C(=O)Nc4c(Cl)cc(Cl)cc43)C2C(=O)N1c1cc(F)cc(Cl)c1] | 544.27 [M + H]⁺ | m |
| 134 | 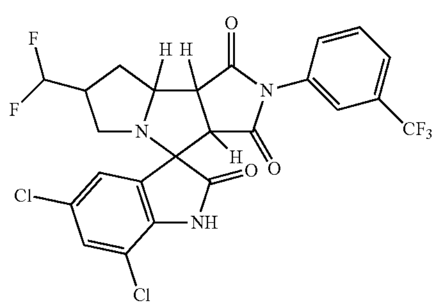 [SMILES: O=C1C2C3CC(C(F)F)CN3C3(C(=O)Nc4c(Cl)cc(Cl)cc43)C2C(=O)N1c1cccc(C(F)(F)F)c1] | 560.28 [M + H]⁺ | m |
| 135 | 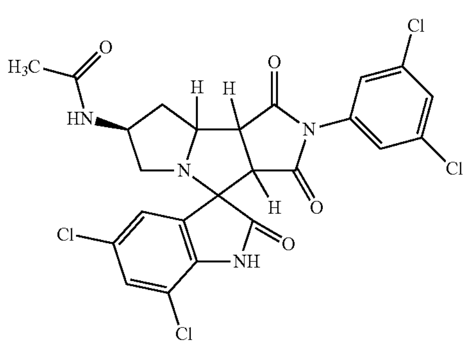 [SMILES: CC(=O)N[C@H]1CC2C3C(=O)N(c4cc(Cl)cc(Cl)c4)C(=O)C3C3(C(=O)Nc4c(Cl)cc(Cl)cc43)N2C1] | 567.10 [M + H]⁻ | m |

TABLE 1-continued

| Example No. | Structure | M/Z | Single enantiomer (s) or mixture of stereoisomers (m) |
|---|---|---|---|
| 136 | 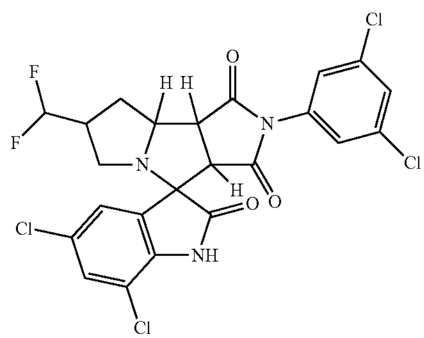 [SMILES: O=C1C2C3CC(C(F)F)CN3C3(C(=O)Nc4c(Cl)cc(Cl)cc43)C2C(=O)N1c1cc(Cl)cc(Cl)c1] | 560.31 [M + H]⁻ | m |
| 137 | 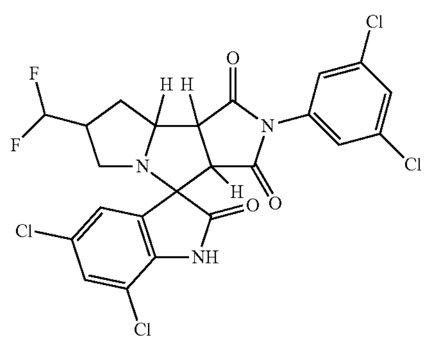 [SMILES: O=C1C2C3CC(C(F)F)CN3C3(C(=O)Nc4c(Cl)cc(Cl)cc43)C2C(=O)N1c1cc(Cl)cc(Cl)c1] | 562.17 [M + H]⁺ | m |
| 138 | 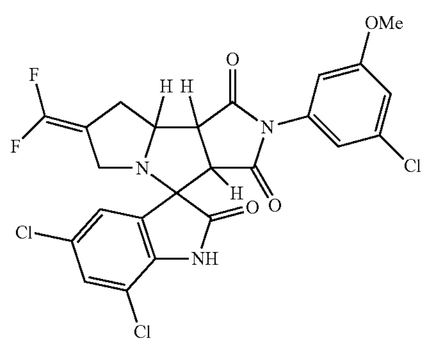 [SMILES: COc1cc(Cl)cc(N2C(=O)C3C4CC(=C(F)F)CN4C4(C(=O)Nc5c(Cl)cc(Cl)cc54)C3C2=O)c1] | 554.14 [M + H]⁺ | s |
| 139 | 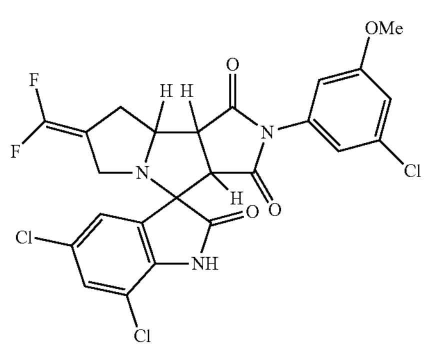 [SMILES: COc1cc(Cl)cc(N2C(=O)C3C4CC(=C(F)F)CN4C4(C(=O)Nc5c(Cl)cc(Cl)cc54)C3C2=O)c1] | 554.10 [M + H]⁺ | s |

TABLE 1-continued

| Example No. | Structure | M/Z | Single enantiomer (s) or mixture of stereoisomers (m) |
|---|---|---|---|
| 140 | 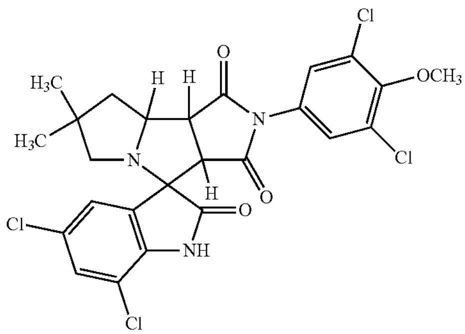 [SMILES: COc1c(Cl)cc(N2C(=O)C3C4CC(C)(C)CN4C4(C(=O)Nc5c(Cl)cc(Cl)cc54)C3C2=O)cc1Cl] | 568.09 [M + H]+ | s |
| 141 | 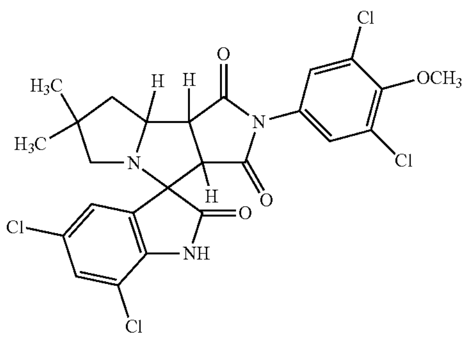 [SMILES: COc1c(Cl)cc(N2C(=O)C3C4CC(C)(C)CN4C4(C(=O)Nc5c(Cl)cc(Cl)cc54)C3C2=O)cc1Cl] | 568.09 [M + H]+ | s |
| 142 | 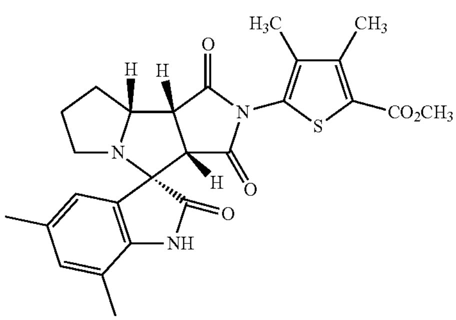 [SMILES: COC(=O)c1sc(N2C(=O)[C@H]3[C@H]4CCCN4[C@@]4(C(=O)Nc5c(C)cc(C)cc54)[C@H]3C2=O)c(C)c1C] | 493.17 [M + H]+ | s |
| 143 | 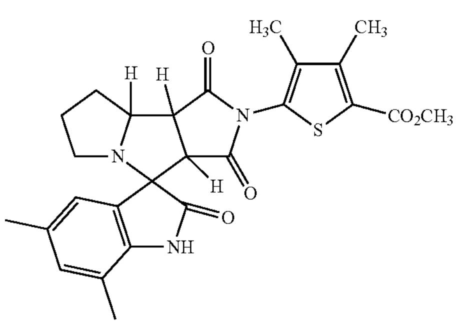 [SMILES: COC(=O)c1sc(N2C(=O)C3C4CCCN4C4(C(=O)Nc5c(C)cc(C)cc54)C3C2=O)c(C)c1C] | 493.17 [M + H]+ | m |

TABLE 1-continued

| Example No. | Structure | M/Z | Single enantiomer (s) or mixture of stereoisomers (m) |
|---|---|---|---|
| 144 | 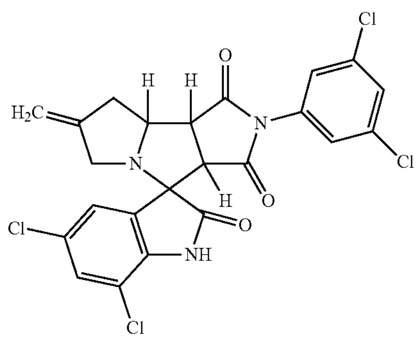 [SMILES: C=C1CC2C3C(=O)N(c4cc(Cl)cc(Cl)c4)C(=O)C3C3(C(=O)Nc4c(Cl)cc(Cl)cc43)N2C1] | 524.15 [M + H]⁺ | s |
| 145 | 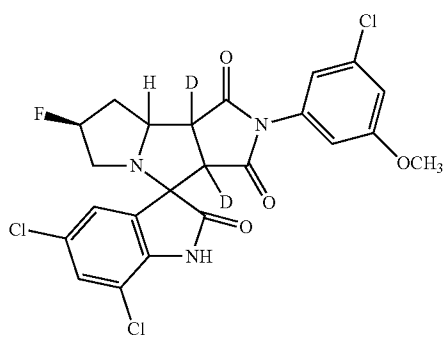 | 526.26 [M + H]⁺ | m |
| 146 | 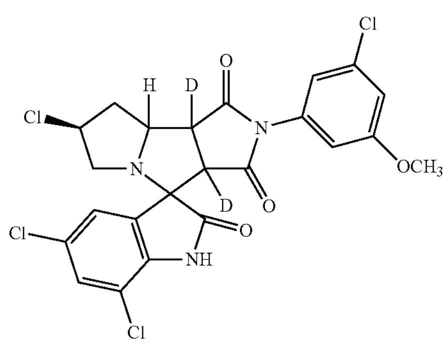 [SMILES: [2H]C12C(=O)N(c3cc(Cl)cc(OC)c3)C(=O)C1([2H])C1(C(=O)Nc3c(Cl)cc(Cl)cc31)N1C[C@@H](Cl)CC12] | 542.30 [M + H]⁻ | m |
| 147 | 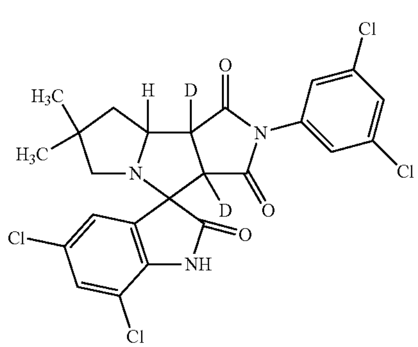 [SMILES: [2H]C12C(=O)N(c3cc(Cl)cc(Cl)c3)C(=O)C1([2H])C1(C(=O)Nc3c(Cl)cc(Cl)cc31)N1CC(C)(C)CC12] | 540.13 [M + H]⁻ | m |

TABLE 1-continued
| Example No. | Structure | M/Z | Single enantiomer(s) or mixture of stereoisomers (m) |
|---|---|---|---|
| 148 | 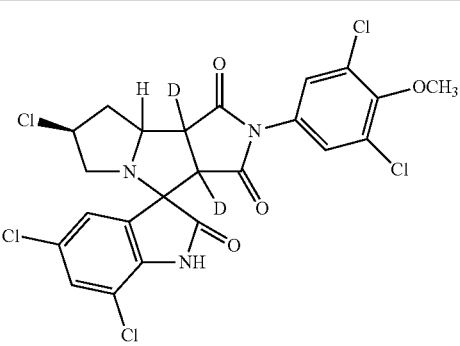 [SMILES: [2H]C12C(=O)N(c3cc(Cl)c(OC)c(Cl)c3)C(=O)C1([2H])C1(C(=O)Nc3c(Cl)cc(Cl)cc31)N1C[C@@H](Cl)CC12] | 576.30 [M + H]⁻ | m |
| 149 | 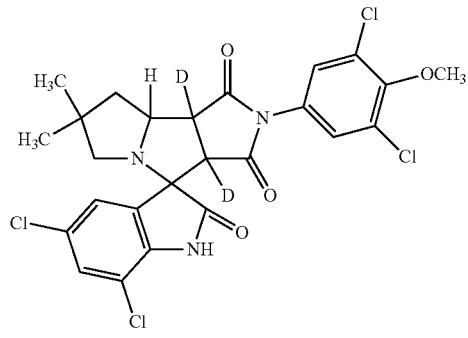 [SMILES: [2H]C12C(=O)N(c3cc(Cl)c(OC)c(Cl)c3)C(=O)C1([2H])C1(C(=O)Nc3c(Cl)cc(Cl)cc31)N1CC(C)(C)CC12] | 570.48 [M + H]⁻ | m |
| 150 | 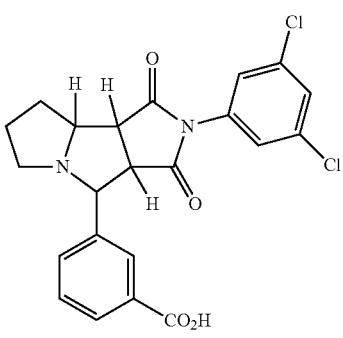 [SMILES: O=C(O)c1cccc(C2C3C(=O)N(c4cc(Cl)cc(Cl)c4)C(=O)C3C3CCCN32)c1] | 444.80 [M + H]⁻ | m |
| 151 | 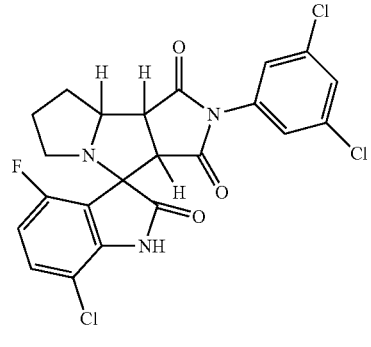 | 474.30 [M + H]⁺ | m |

TABLE 1-continued

| Example No. | Structure | M/Z | Single enantiomer(s) or mixture of stereoisomers (m) |
|---|---|---|---|
| 152 | 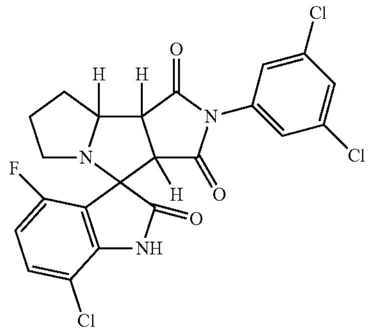 [SMILES: O=C1C2C3CCCN3C3(C(=O)Nc4c(Cl)ccc(F)c43)C2C(=O)N1c1cc(Cl)cc(Cl)c1] | 478.36 [M + H]⁺ | m |
| 153 | 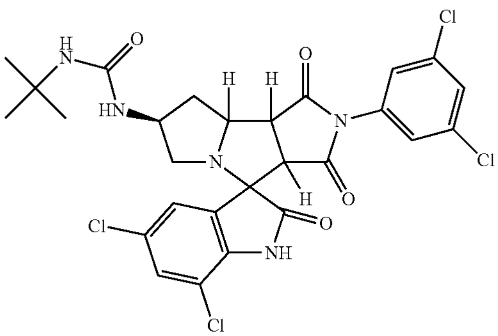 [SMILES: CC(C)(C)NC(=O)N[C@H]1CC2C3C(=O)N(c4cc(Cl)cc(Cl)c4)C(=O)C3C3(C(=O)Nc4c(Cl)cc(Cl)cc43)N2C1] | 624.40 [M + H]⁺ | m |
| 154 | 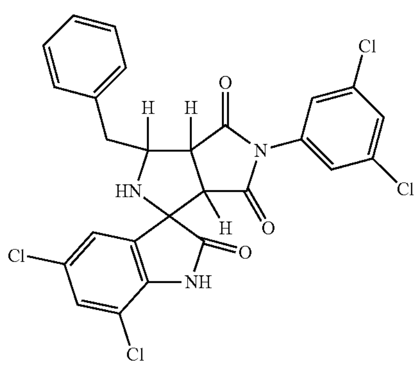 [SMILES: O=C1C2C(Cc3ccccc3)NC3(C(=O)Nc4c(Cl)cc(Cl)cc43)C2C(=O)N1c1cc(Cl)cc(Cl)c1] | 561.80 [M + H]⁺ | m |
| 155 | 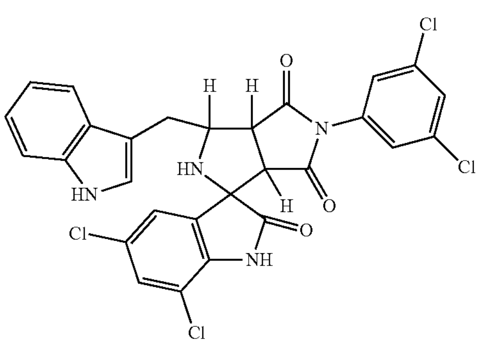 [SMILES: O=C1C2C(Cc3c[nH]c4ccccc34)NC3(C(=O)Nc4c(Cl)cc(Cl)cc43)C2C(=O)N1c1cc(Cl)cc(Cl)c1] | 600.80 [M + H]⁺ | m |

TABLE 1-continued

| Example No. | Structure | M/Z | Single enantiomer(s) or mixture of stereoisomers (m) |
|---|---|---|---|
| 156 | 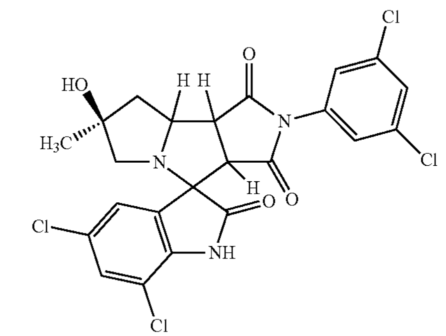 [SMILES: C[C@]1(O)CC2C3C(=O)N(c4cc(Cl)cc(Cl)c4)C(=O)C3C3(C(=O)Nc4c(Cl)cc(Cl)cc43)N2C1] | 540.10 [M + H]− | m |
| 157 | 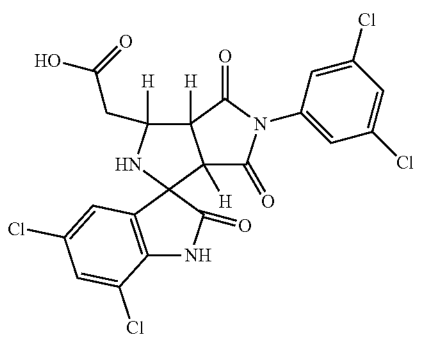 [SMILES: O=C(O)CC1NC2(C(=O)Nc3c(Cl)cc(Cl)cc32)C2C(=O)N(c3cc(Cl)cc(Cl)c3)C(=O)C12] | 529.70 [M + H]+ | m |
| 158 | 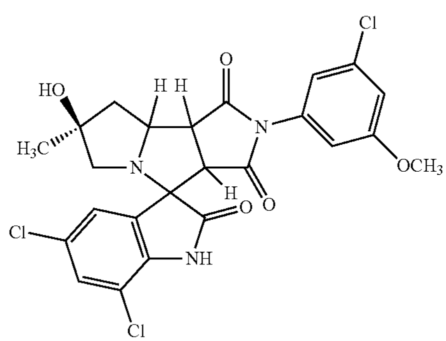 [SMILES: COc1cc(Cl)cc(N2C(=O)C3C4C[C@](C)(O)CN4C4(C(=O)Nc5c(Cl)cc(Cl)cc54)C3C2=O)c1] | 536.14 [M + H]+ | m |
| 159 | 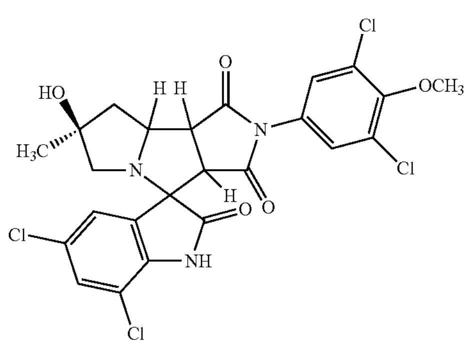 [SMILES: COc1c(Cl)cc(N2C(=O)C3C4C[C@](C)(O)CN4C4(C(=O)Nc5c(Cl)cc(Cl)cc54)C3C2=O)cc1Cl] | 570.07 [M + H]− | m |

TABLE 1-continued

| Example No. | Structure | M/Z | Single enantiomer (s) or mixture of stereoisomers (m) |
|---|---|---|---|
| 160 | 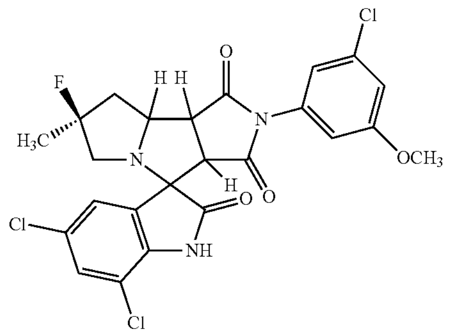 [SMILES: COc1cc(Cl)cc(N2C(=O)C3C4C[C@](C)(F)CN4C4(C(=O)Nc5c(Cl)cc(Cl)cc54)C3C2=O)c1] | 538.34 [M + H]+ | m |
| 161 | 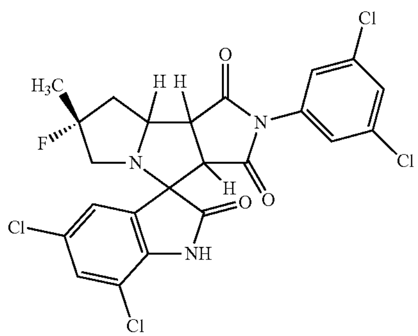 [SMILES: C[C@@]1(F)CC2C3C(=O)N(c4cc(Cl)cc(Cl)c4)C(=O)C3C3(C(=O)Nc4c(Cl)cc(Cl)cc43)N2C1] | 542.32 [M + H]− | s |
| 162 | 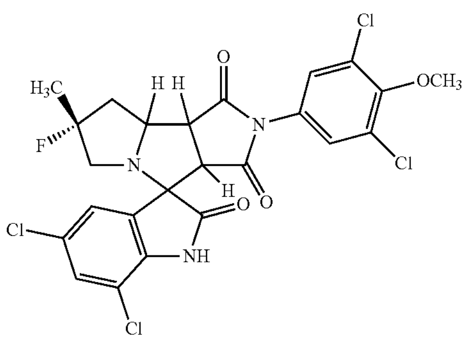 [SMILES: COc1c(Cl)cc(N2C(=O)C3C4C[C@@](C)(F)CN4C4(C(=O)Nc5c(Cl)cc(Cl)cc54)C3C2=O)cc1Cl] | 572.36 [M + H]− | s |
| 163 | 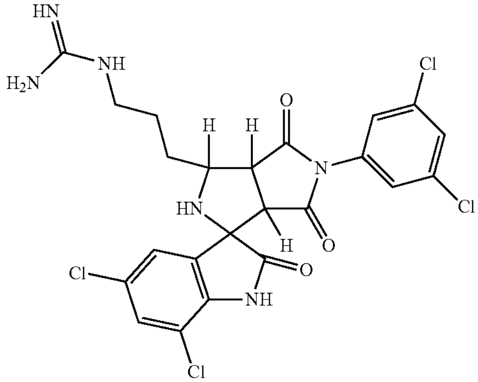 [SMILES: N=C(N)NCCCC1NC2(C(=O)Nc3c(Cl)cc(Cl)cc32)C2C(=O)N(c3cc(Cl)cc(Cl)c3)C(=O)C12] | 570.80 [M + H]+ | m |

TABLE 1-continued

| Example No. | Structure | M/Z | Single enantiomer (s) or mixture of stereoisomers (m) |
|---|---|---|---|
| 164 | 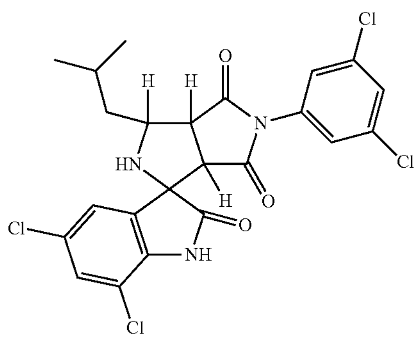 [SMILES: CC(C)CC1NC2(C(=O)Nc3c(Cl)cc(Cl)cc32)C2C(=O)N(c3cc(Cl)cc(Cl)c3)C(=O)C12] | 527.80 [M + H]⁺ | m |
| 165 | 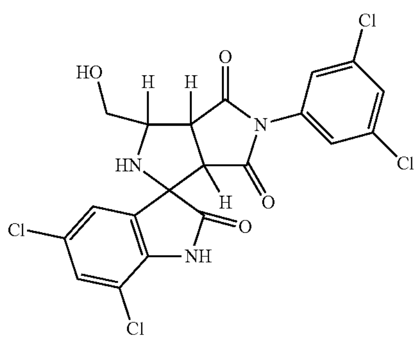 [SMILES: O=C1C2C(CO)NC3(C(=O)Nc4c(Cl)cc(Cl)cc43)C2C(=O)N1c1cc(Cl)cc(Cl)c1] | 500.00 [M + H]⁻ | m |
| 166 | 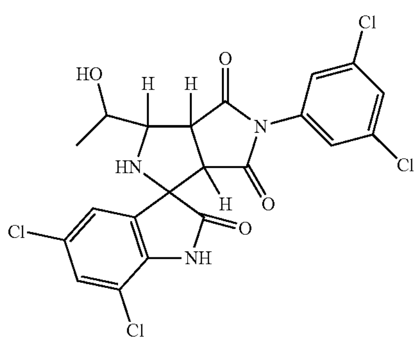 [SMILES: CC(O)C1NC2(C(=O)Nc3c(Cl)cc(Cl)cc32)C2C(=O)N(c3cc(Cl)cc(Cl)c3)C(=O)C12] | 514.20 [M + H]⁻ | m |
| 167 | 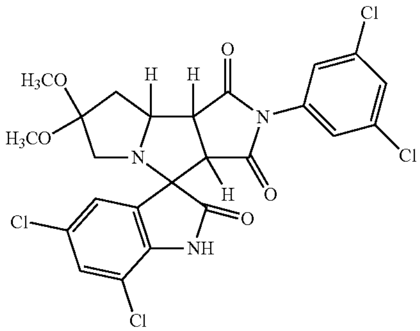 [SMILES: COC1(OC)CC2C3C(=O)N(c4cc(Cl)cc(Cl)c4)C(=O)C3C3(C(=O)Nc4c(Cl)cc(Cl)cc43)N2C1] | 570.13 [M + H]⁻ | m |

TABLE 1-continued

| Example No. | Structure | M/Z | Single enantiomer(s) or mixture of stereoisomers (m) |
|---|---|---|---|
| 168 | 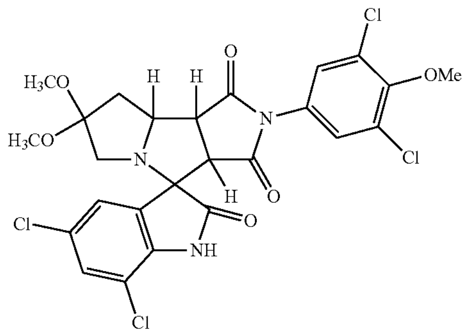 [SMILES: COc1c(Cl)cc(N2C(=O)C3C4CC(OC)(OC)CN4C4(C(=O)Nc5c(Cl)cc(Cl)cc54)C3C2=O)cc1Cl] | 600.10 [M + H]⁻ | m |
| 169 | 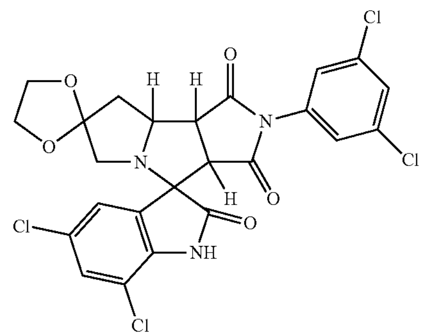 [SMILES: O=C1C2C3CC4(CN3C3(C(=O)Nc5c(Cl)cc(Cl)cc53)C2C(=O)N1c1cc(Cl)cc(Cl)c1)OCCO4] | 568.10 [M + H]⁻ | m |
| 170 | 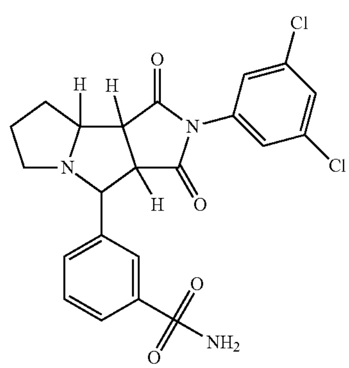 | 480.43 [M + H]⁺ | m |
| 171 | 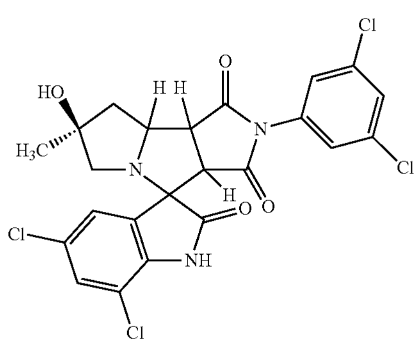 [SMILES: C[C@]1(O)CC2C3C(=O)N(c4cc(Cl)cc(Cl)c4)C(=O)C3C3(C(=O)Nc4c(Cl)cc(Cl)cc43)N2C1] | 540.62 [M + H]⁻ | s |

TABLE 1-continued

| Example No. | Structure | M/Z | Single enantiomer (s) or mixture of stereoisomers (m) |
|---|---|---|---|
| 172 | 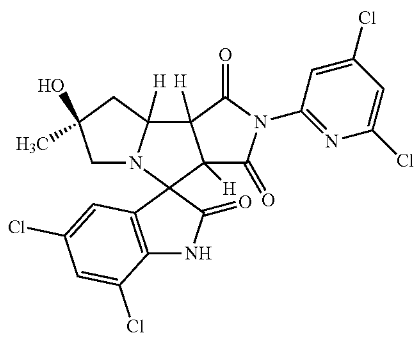 [SMILES: C[C@]1(O)CC2C3C(=O)N(c4cc(Cl)cc(Cl)n4)C(=O)C3C3(C(=O)Nc4c(Cl)cc(Cl)cc43)N2C1] | 541.59 [M + H]⁻ | m |
| 173 | 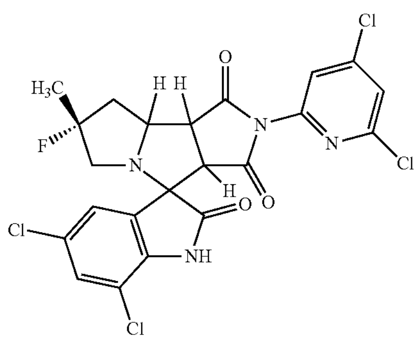 | 543.48 [M + H]⁻ | m |
| 174 | 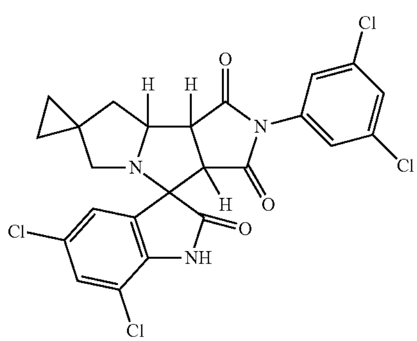 [SMILES: O=C1C2C3CC4(CC4)CN3C3(C(=O)Nc4c(Cl)cc(Cl)cc43)C2C(=O)N1c1cc(Cl)cc(Cl)c1] | 536.50 [M + H]⁻ | m |
| 175 | 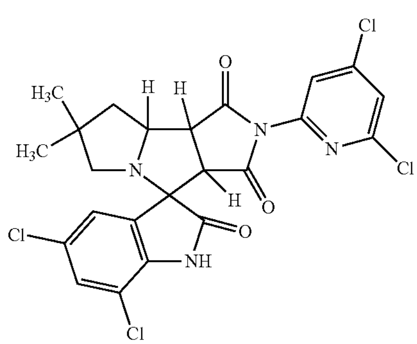 [SMILES: CC1(C)CC2C3C(=O)N(c4cc(Cl)cc(Cl)n4)C(=O)C3C3(C(=O)Nc4c(Cl)cc(Cl)cc43)N2C1] | 539.59 [M + H]⁻ | s |

TABLE 1-continued

| Example No. | Structure | M/Z | Single enantiomer (s) or mixture of stereoisomers (m) |
|---|---|---|---|
| 176 | 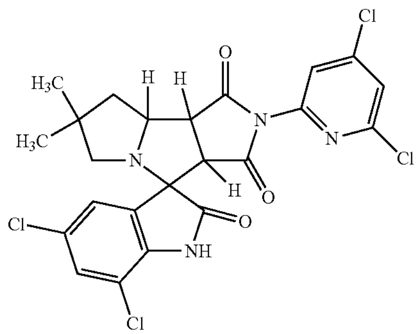 [SMILES: CC1(C)CC2C3C(=O)N(c4cc(Cl)cc(Cl)n4)C(=O)C3C3(C(=O)Nc4c(Cl)cc(Cl)cc43)N2C1] | 539.58 [M + H]⁻ | s |
| 177 | 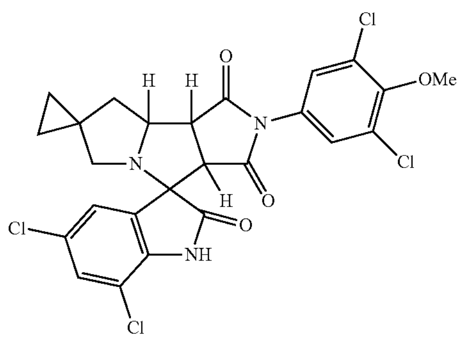 [SMILES: COc1c(Cl)cc(N2C(=O)C3C4CC5(CC5)CN4C4(C(=O)Nc5c(Cl)cc(Cl)cc54)C3C2=O)cc1Cl] | 566.57 [M + H]⁻ | m |
| 178 | 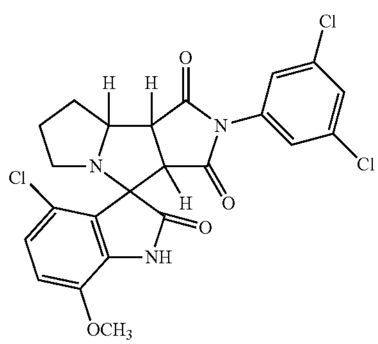 [SMILES: COc1ccc(Cl)c2c1NC(=O)C21C2C(=O)N(c3cc(Cl)cc(Cl)c3)C(=O)C2C2CCCN21] | 490.52 [M + H]⁺ | m |
| 179 | 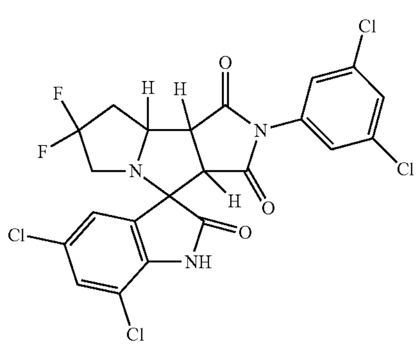 | 546.41 [M + H]⁻ | s |

TABLE 1-continued

| Example No. | Structure | M/Z | Single enantiomer (s) or mixture of stereoisomers (m) |
|---|---|---|---|
| 180 | 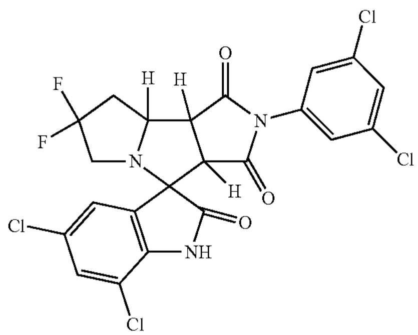 | 546.42 [M + H]⁻ | s |
| 181 | 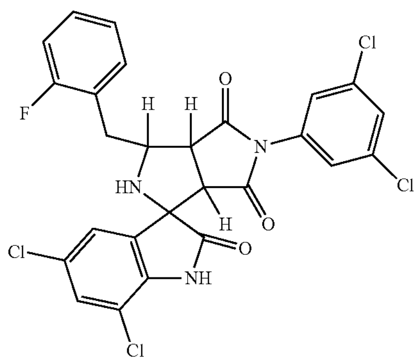 [SMILES: O=C1C2C(Cc3ccccc3F)NC3(C(=O)Nc4c(Cl)cc(Cl)cc43)C2C(=O)N1c1cc(Cl)cc(Cl)c1] | 578.00 [M + H]⁻ | m |
| 182 | 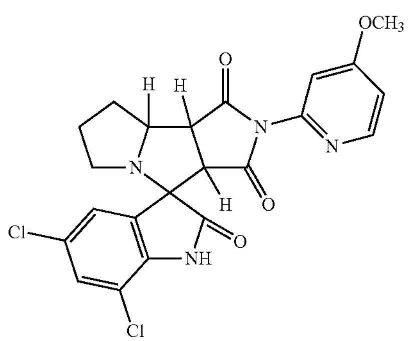 [SMILES: COc1ccnc(N2C(=O)C3C4CCCN4C4(C(=O)Nc5c(Cl)cc(Cl)cc54)C3C2=O)c1] | 573.19 [M + H]⁺ | m |
| 183 | 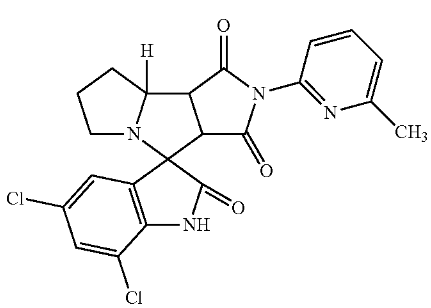 [SMILES: Cc1cccc(N2C(=O)C3C4CCCN4C4(C(=O)Nc5c(Cl)cc(Cl)cc54)C3C2=O)n1] | 457.27 [M + H]⁺ | m |

TABLE 1-continued

| Example No. | Structure | M/Z | Single enantiomer(s) or mixture of stereoisomers (m) |
|---|---|---|---|
| 184 | 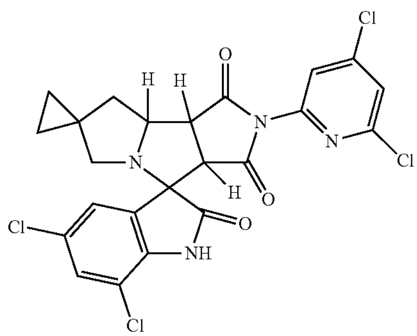 [SMILES: O=C1C2C3CC4(CC4)CN3C3(C(=O)Nc4c(Cl)cc(Cl)cc43)C2C(=O)N1c1cc(Cl)cc(Cl)n1] | 537.28 [M + H]⁻ | m |
| 185 | 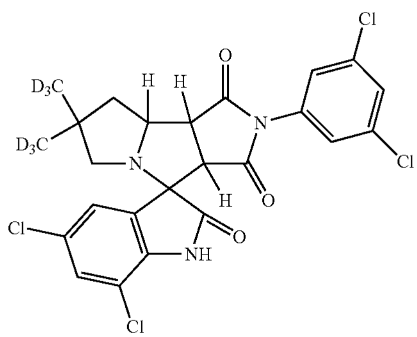 | 546.20 [M + H]⁻ | m |
| 186 | 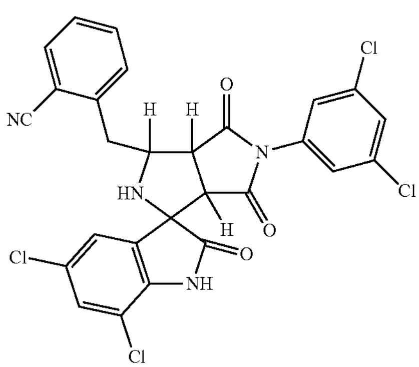 [SMILES: N#Cc1ccccc1CC1NC2(C(=O)Nc3c(Cl)cc(Cl)cc32)C2C(=O)N(c3cc(Cl)cc(Cl)c3)C(=O)C12] | 588.00 [M + H]⁺ | m |
| 187 | 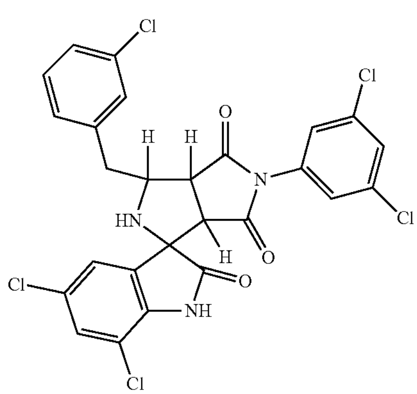 [SMILES: O=C1C2C(Cc3cccc(Cl)c3)NC3(C(=O)Nc4c(Cl)cc(Cl)cc43)C2C(=O)N1c1cc(Cl)cc(Cl)c1] | 596.00 [M + H]⁻ | m |

TABLE 1-continued

| Example No. | Structure | M/Z | Single enantiomer (s) or mixture of stereoisomers (m) |
|---|---|---|---|
| 188 | 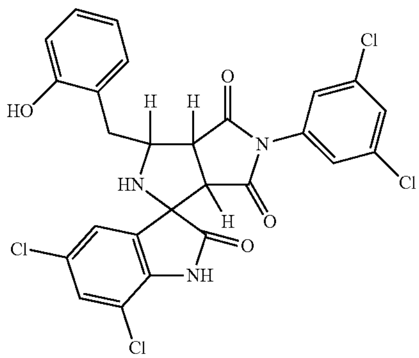 [SMILES: O=C1C2C(Cc3ccccc3O)NC3(C(=O)Nc4c(Cl)cc(Cl)cc43)C2C(=O)N1c1cc(Cl)cc(Cl)c1] | 578.00 [M + H]+ | m |
| 189 | 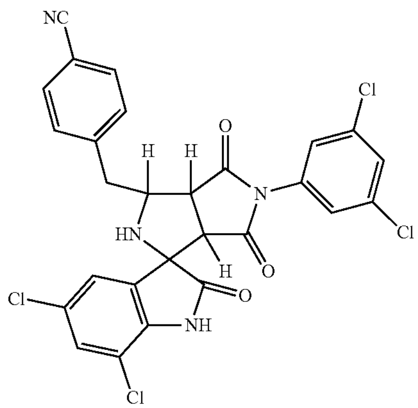 [SMILES: N#Cc1ccc(CC2NC3(C(=O)Nc4c(Cl)cc(Cl)cc43)C3C(=O)N(c4cc(Cl)cc(Cl)c4)C(=O)C23)cc1] | 585.60 [M + H]− | m |
| 190 | 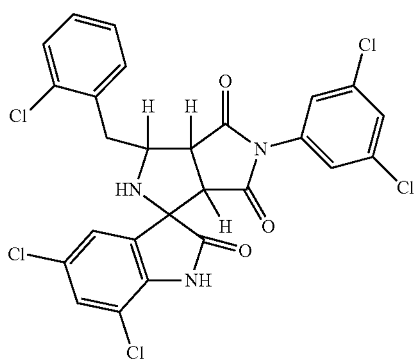 [SMILES: O=C1C2C(Cc3ccccc3Cl)NC3(C(=O)Nc4c(Cl)cc(Cl)cc43)C2C(=O)N1c1cc(Cl)cc(Cl)c1] | 592.20 [M + H]− | m |
| 191 | 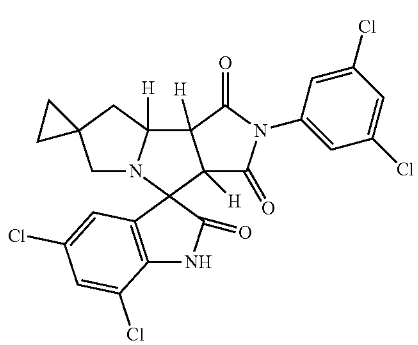 [SMILES: O=C1C2C3CC4(CC4)CN3C3(C(=O)Nc4c(Cl)cc(Cl)cc43)C2C(=O)N1c1cc(Cl)cc(Cl)c1] | 536.19 [M + H]− | s |

TABLE 1-continued

| Example No. | Structure | M/Z | Single enantiomer (s) or mixture of stereoisomers (m) |
|---|---|---|---|
| 192 | 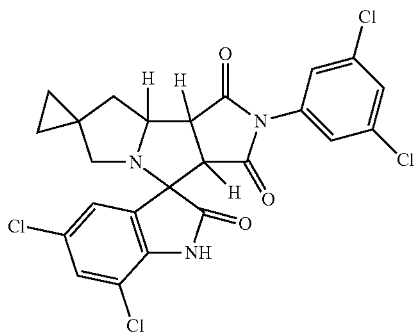 [SMILES: O=C1C2C3CC4(CC4)CN3C3(C(=O)Nc4c(Cl)cc(Cl)cc43)C2C(=O)N1c1cc(Cl)cc(Cl)c1] | 536.19 [M + H]⁻ | s |
| 193 | 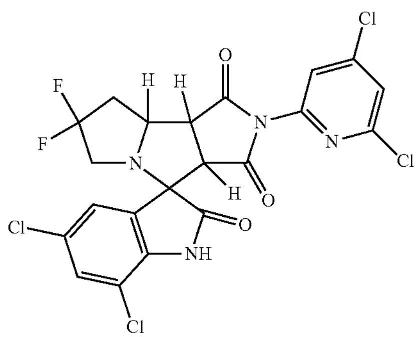 [SMILES: O=C1C2C3CC(F)(F)CN3C3(C(=O)Nc4c(Cl)cc(Cl)cc43)C2C(=O)N1c1cc(Cl)cc(Cl)n1] | 547.17 [M + H]⁻ | m |
| 194 | 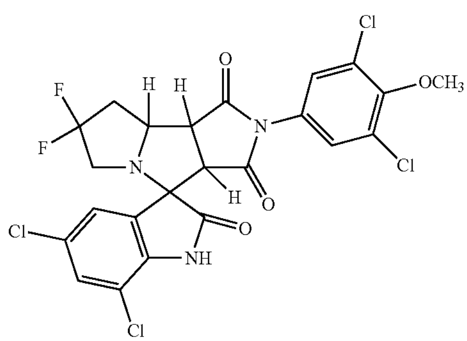 [SMILES: COc1c(Cl)cc(N2C(=O)C3C4CC(F)(F)CN4C4(C(=O)Nc5c(Cl)cc(Cl)cc54)C3C2=O)cc1Cl] | 576.16 [M + H]⁻ | m |
| 195 | 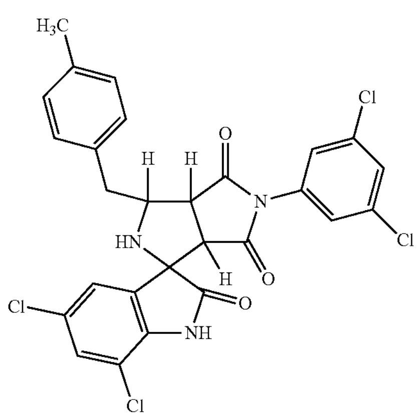 [SMILES: Cc1ccc(CC2NC3(C(=O)Nc4c(Cl)cc(Cl)cc43)C3C(=O)N(c4cc(Cl)cc(Cl)c4)C(=O)C23)cc1] | 572.00 [M + H]⁻ | m |

TABLE 1-continued

| Example No. | Structure | M/Z | Single enantiomer (s) or mixture of stereoisomers (m) |
|---|---|---|---|
| 196 | 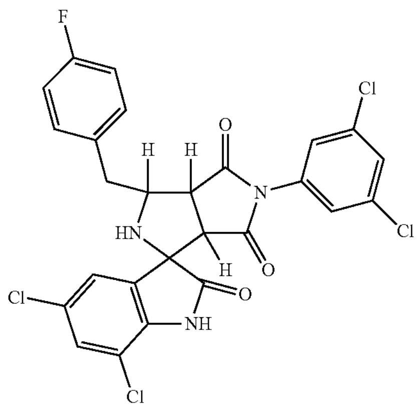 [SMILES: O=C1C2C(Cc3ccc(F)cc3)NC3(C(=O)Nc4c(Cl)cc(Cl)cc43)C2C(=O)N1c1cc(Cl)cc(Cl)c1] | 579.00 [M + H]⁻ | m |
| 197 | 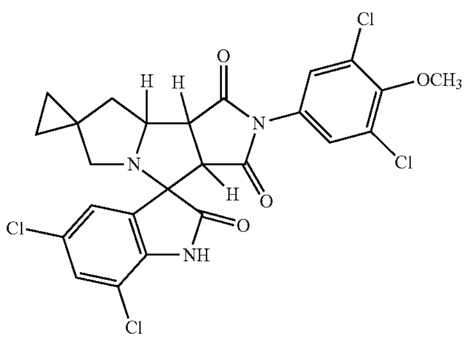 [SMILES: COc1c(Cl)cc(N2C(=O)C3C4CC5(CC5)CN4C4(C(=O)Nc5c(Cl)cc(Cl)cc54)C3C2=O)cc1Cl] | 565.93 [M + H]⁻ | s |
| 198 | 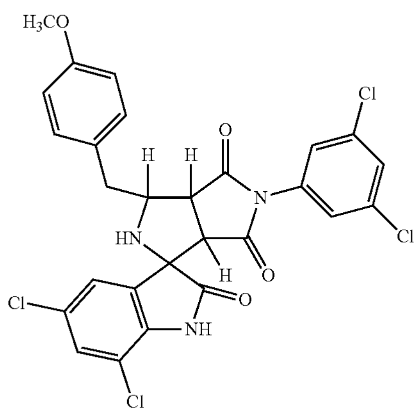 [SMILES: COc1ccc(CC2NC3(C(=O)Nc4c(Cl)cc(Cl)cc43)C3C(=O)N(c4cc(Cl)cc(Cl)c4)C(=O)C23)cc1] | 592.00 [M + H]⁺ | m |
| 199 | 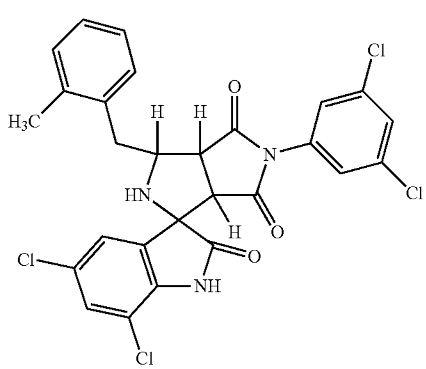 [SMILES: Cc1ccccc1CC1NC2(C(=O)Nc3c(Cl)cc(Cl)cc32)C2C(=O)N(c3cc(Cl)cc(Cl)c3)C(=O)C12] | 574.00 [M + H]⁻ | m |

TABLE 1-continued

| Example No. | Structure | M/Z | Single enantiomer (s) or mixture of stereoisomers (m) |
|---|---|---|---|
| 200 | 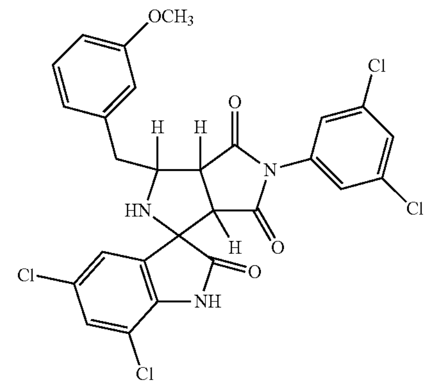 [SMILES: COc1cccc(CC2NC3(C(=O)Nc4c(Cl)cc(Cl)cc43)C3C(=O)N(c4cc(Cl)cc(Cl)c4)C(=O)C23)c1] | 587.90 [M + H]⁻ | m |
| 201 | 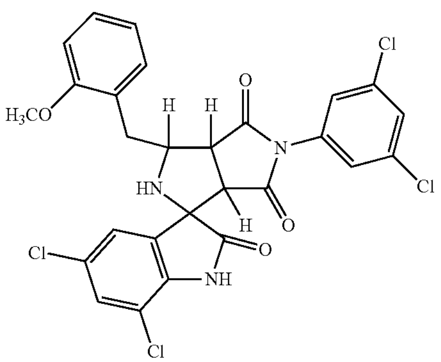 [SMILES: COc1ccccc1CC1NC2(C(=O)Nc3c(Cl)cc(Cl)cc32)C2C(=O)N(c3cc(Cl)cc(Cl)c3)C(=O)C12] | 591.90 [M + H]⁺ | m |
| 202 | 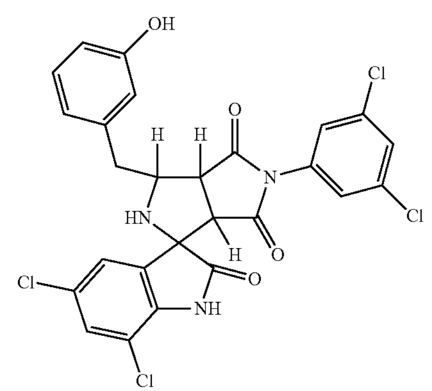 [SMILES: O=C1C2C(Cc3cccc(O)c3)NC3(C(=O)Nc4c(Cl)cc(Cl)cc43)C2C(=O)N1c1cc(Cl)cc(Cl)c1] | 578.00 [M + H]⁺ | m |
| 203 | 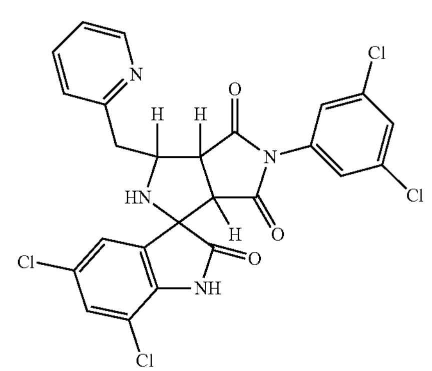 [SMILES: O=C1C2C(Cc3ccccn3)NC3(C(=O)Nc4c(Cl)cc(Cl)cc43)C2C(=O)N1c1cc(Cl)cc(Cl)c1] | 563.00 [M + H]⁺ | m |

TABLE 1-continued

| Example No. | Structure | M/Z | Single enantiomer(s) or mixture of stereoisomers (m) |
|---|---|---|---|
| 204 | 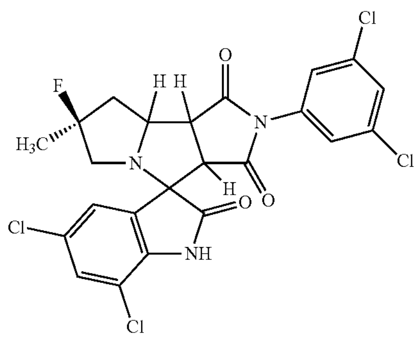 [SMILES: C[C@]1(F)CC2C3C(=O)N(c4cc(Cl)cc(Cl)c4)C(=O)C3C3(C(=O)Nc4c(Cl)cc(Cl)cc43)N2C1] | 542.17 [M + H]⁻ | m |
| 205 | 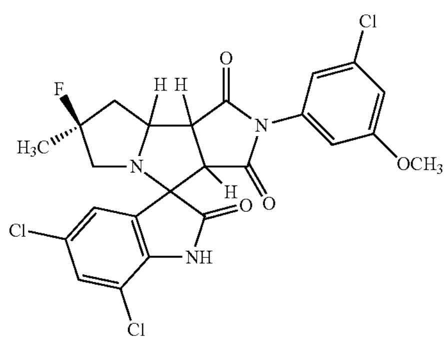 [SMILES: COc1cc(Cl)cc(N2C(=O)C3C4C[C@](C)(F)CN4C4(C(=O)Nc5c(Cl)cc(Cl)cc54)C3C2=O)c1] | 538.28 [M + H]⁺ | m |
| 206 | 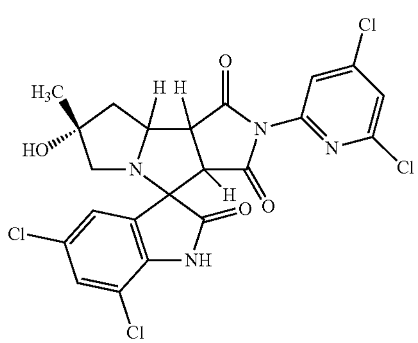 [SMILES: C[C@@]1(O)CC2C3C(=O)N(c4cc(Cl)cc(Cl)n4)C(=O)C3C3(C(=O)Nc4c(Cl)cc(Cl)cc43)N2C1] | 541.23 [M + H]⁻ | m |
| 207 | 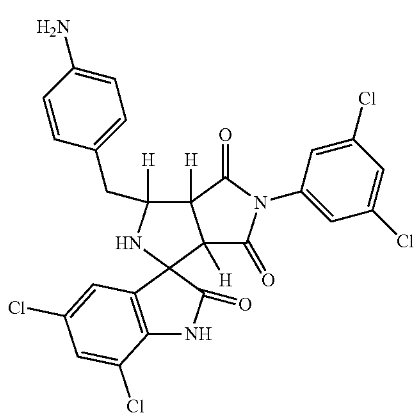 [SMILES: Nc1ccc(CC2NC3(C(=O)Nc4c(Cl)cc(Cl)cc43)C3C(=O)N(c4cc(Cl)cc(Cl)c4)C(=O)C23)cc1] | 577.60 [M + H]⁺ | m |

TABLE 1-continued

| Example No. | Structure | M/Z | Single enantiomer(s) or mixture of stereoisomers (m) |
|---|---|---|---|
| 208 | 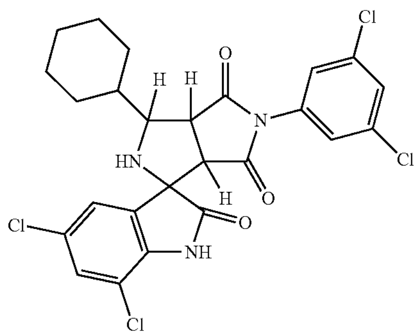 [SMILES: O=C1C2C(C3CCCCC3)NC3(C(=O)Nc4c(Cl)cc(Cl)cc43)C2C(=O)N1c1cc(Cl)cc(Cl)c1] | 554.60 [M + H]⁺ | m |
| 209 | 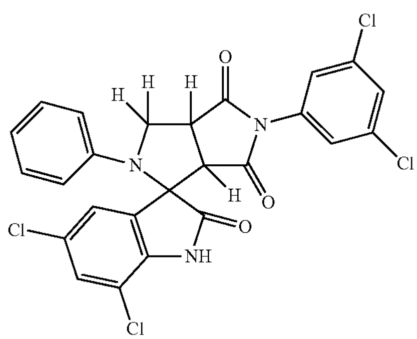 [SMILES: O=C1C2CN(c3ccccc3)C3(C(=O)Nc4c(Cl)cc(Cl)cc43)C2C(=O)N1c1cc(Cl)cc(Cl)c1] | 547.80 [M + H]⁺ | m |
| 210 | 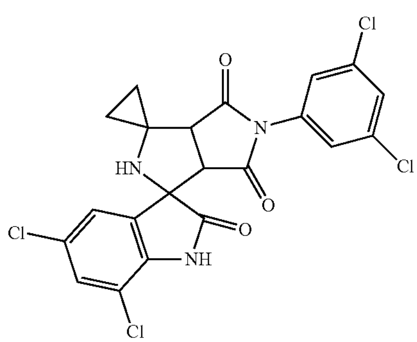 [SMILES: O=C1C2C(C(=O)N1c1cc(Cl)cc(Cl)c1)C1(NC23CC3)C(=O)Nc2c(Cl)cc(Cl)cc21] | 498.00 [M + H]⁺ | m |
| 211 | 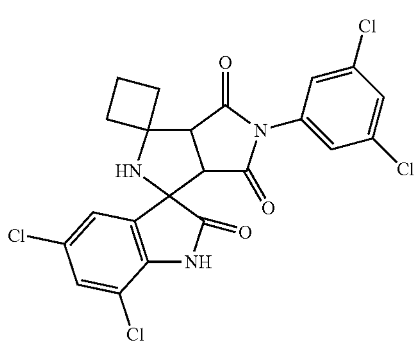 [SMILES: O=C1C2C(C(=O)N1c1cc(Cl)cc(Cl)c1)C1(NC23CCC3)C(=O)Nc2c(Cl)cc(Cl)cc21] | 512.00 [M + H]⁺ | m |

TABLE 1-continued

| Example No. | Structure | M/Z | Single enantiomer(s) or mixture of stereoisomers (m) |
|---|---|---|---|
| 212 | 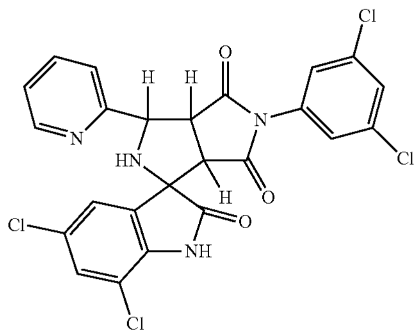 [SMILES: O=C1C2C(c3ccccn3)NC3(C(=O)Nc4c(Cl)cc(Cl)cc43)C2C(=O)N1c1cc(Cl)cc(Cl)c1] | 549.10 [M + H]⁺ | m |
| 213 | 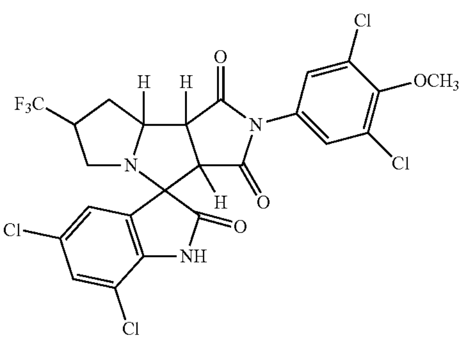 [SMILES: COc1c(Cl)cc(N2C(=O)C3C4CC(C(F)(F)F)CN4C4(C(=O)Nc5c(Cl)cc(Cl)cc54)C3C2=O)cc1Cl] | 610.00 [M + H]⁺ | m |
| 214 | 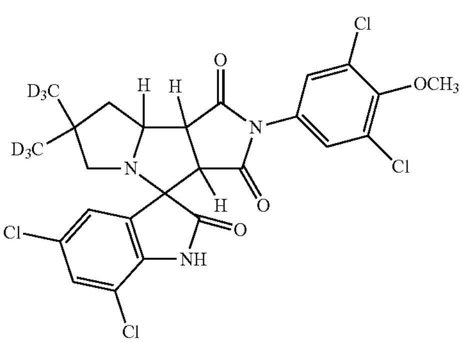 [SMILES: [2H]C([2H])([2H])C1(C([2H])([2H])[2H])CC2C3C(=O)N(c4cc(Cl)c(OC)c(Cl)c4)C(=O)C3C3(C(=O)Nc4c(Cl)cc(Cl)cc43)N2C1] | 576.70 [M + H]⁺ | m |
| 215 | 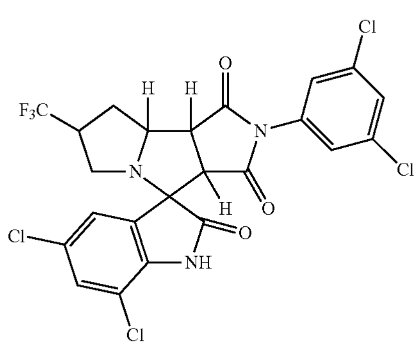 [SMILES: O=C1C2C3CC(C(F)(F)F)CN3C3(C(=O)Nc4c(Cl)cc(Cl)cc43)C2C(=O)N1c1cc(Cl)cc(Cl)c1] | 578.00 [M + H]⁻ | m |

TABLE 1-continued

| Example No. | Structure | M/Z | Single enantiomer (s) or mixture of stereoisomers (m) |
|---|---|---|---|
| 216 | 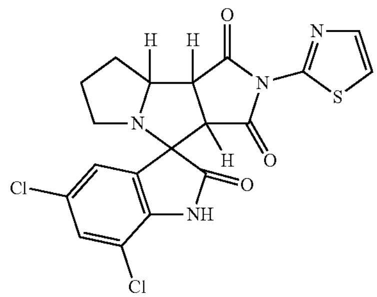 [SMILES: O=C1C2C3CCCN3C3(C(=O)Nc4c(Cl)cc(Cl)cc43)C2C(=O)N1c1nccs1] | 450.20 [M + H]+ | m |
| 217 | 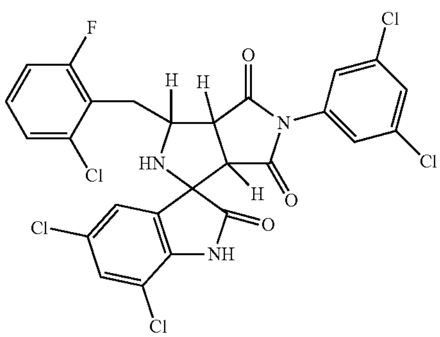 [SMILES: O=C1C2C(Cc3c(F)cccc3Cl)NC3(C(=O)Nc4c(Cl)cc(Cl)cc43)C2C(=O)N1c1cc(Cl)cc(Cl)c1] | 612.40 [M + H]− | m |
| 218 | 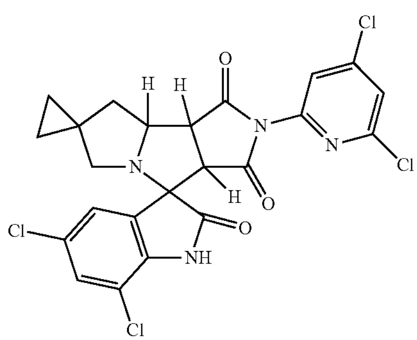 [SMILES: O=C1C2C3CC4(CC4)CN3C3(C(=O)Nc4c(Cl)cc(Cl)cc43)C2C(=O)N1c1cc(Cl)cc(Cl)n1] | 537.17 [M + H]− | s |
| 219 | 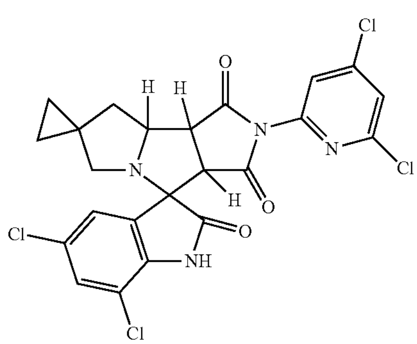 [SMILES: O=C1C2C3CC4(CC4)CN3C3(C(=O)Nc4c(Cl)cc(Cl)cc43)C2C(=O)N1c1cc(Cl)cc(Cl)n1] | 537.20 [M + H]− | s |

TABLE 1-continued

| Example No. | Structure | M/Z | Single enantiomer (s) or mixture of stereoisomers (m) |
|---|---|---|---|
| 220 | 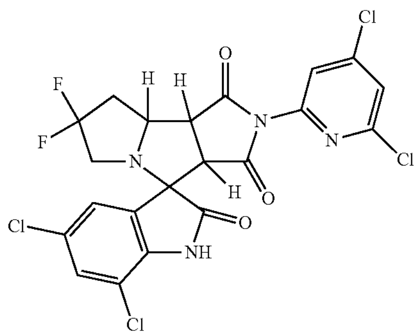 [SMILES: O=C1C2C3CC(F)(F)CN3C3(C(=O)Nc4c(Cl)cc(Cl)cc43)C2C(=O)N1c1cc(Cl)cc(Cl)n1] | 547.25 [M + H]⁻ | s |
| 221 | 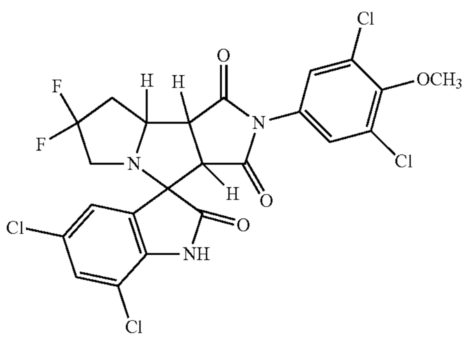 [SMILES: COc1c(Cl)cc(N2C(=O)C3C4CC(F)(F)CN4C4(C(=O)Nc5c(Cl)cc(Cl)cc54)C3C2=O)cc1Cl] | 576.34 [M + H]⁻ | s |
| 222 | 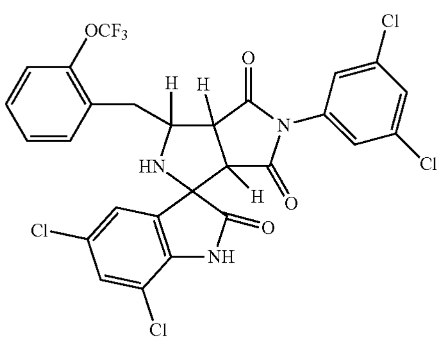 [SMILES: O=C1C2C(Cc3ccccc3OC(F)(F)F)NC3(C(=O)Nc4c(Cl)cc(Cl)cc43)C2C(=O)N1c1cc(Cl)cc(Cl)c1] | 646.20 [M + H]⁺ | m |
| 223 | 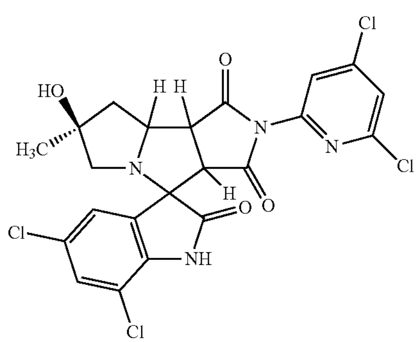 [SMILES: C[C@]1(O)CC2C3C(=O)N(c4cc(Cl)cc(Cl)n4)C(=O)C3C3(C(=O)Nc4c(Cl)cc(Cl)cc43)N2C1] | 541.59 [M + H]⁻ | s |

TABLE 1-continued

| Example No. | Structure | M/Z | Single enantiomer (s) or mixture of stereoisomers (m) |
|---|---|---|---|
| 224 | 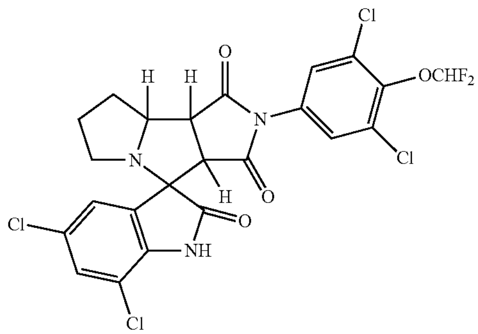 [SMILES: O=C1C2C3CCCN3C3(C(=O)Nc4c(Cl)cc(Cl)cc43)C2C(=O)N1c1cc(Cl)c(OC(F)F)c(Cl)c1] | 576.30 [M + H]⁻ | m |
| 225 | 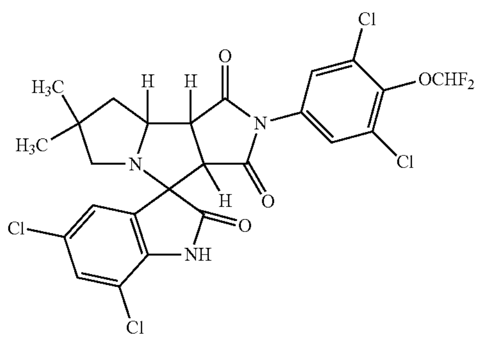 [SMILES: CC1(C)CC2C3C(=O)N(c4cc(Cl)c(OC(F)F)c(Cl)c4)C(=O)C3C3(C(=O)Nc4c(Cl)cc(Cl)cc43)N2C1] | 604.31 [M + H]⁻ | m |
| 226 | 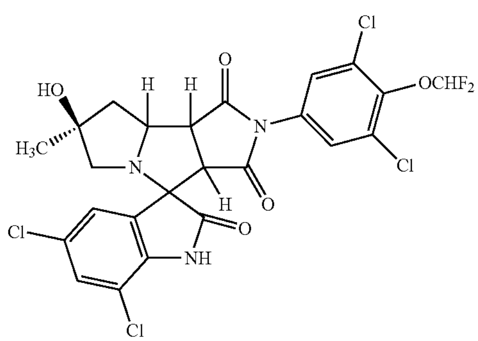 [SMILES: C[C@]1(O)CC2C3C(=O)N(c4cc(Cl)c(OC(F)F)c(Cl)c4)C(=O)C3C3(C(=O)Nc4c(Cl)cc(Cl)cc43)N2C1] | 606.29 [M + H]⁻ | m |
| 227 | 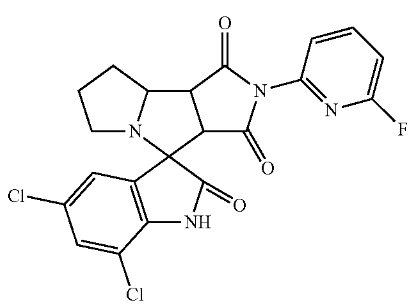 [SMILES: O=C1C2C3CCCN3C3(C(=O)Nc4c(Cl)cc(Cl)cc43)C2C(=O)N1c1cccc(F)n1] | 461.31 [M + H]⁺ | m |

TABLE 1-continued

| Example No. | Structure | M/Z | Single enantiomer(s) or mixture of stereoisomers (m) |
|---|---|---|---|
| 228 | 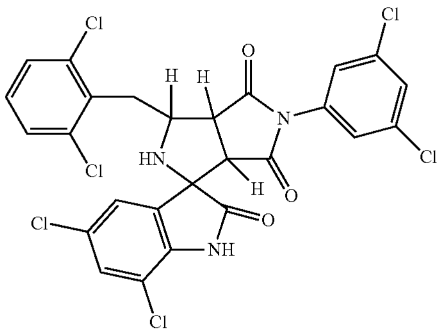 | 631.00 [M + H]⁺ | m |
| 229 | 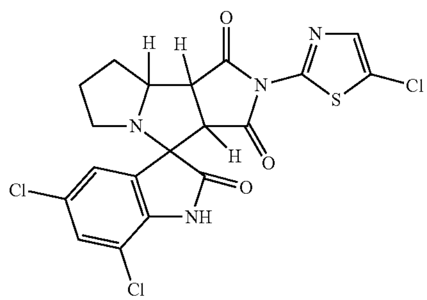 [SMILES: O=C1C2C3CCCN3C3(C(=O)Nc4c(Cl)cc(Cl)cc43)C2C(=O)N1c1ncc(Cl)s1] | 486.70 [M + H]⁺ | m |
| 230 | 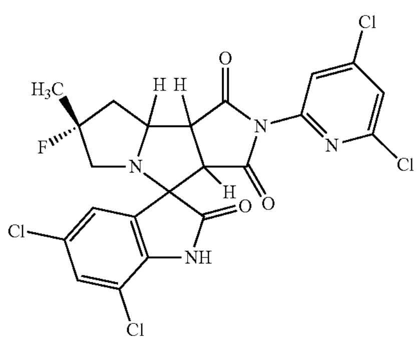 [SMILES: C[C@@]1(F)CC2C3C(=O)N(c4cc(Cl)cc(Cl)n4)C(=O)C3C3(C(=O)Nc4c(Cl)cc(Cl)cc43)N2C1] | 543.18 [M + H]⁻ | s |
| 231 | 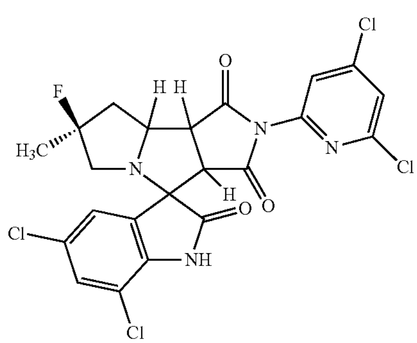 | 543.21 [M + H]⁻ | m |

TABLE 1-continued

| Example No. | Structure | M/Z | Single enantiomer (s) or mixture of stereoisomers (m) |
|---|---|---|---|
| 232 | 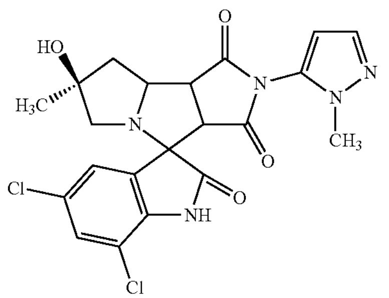 | 446.41 [M + H]⁺ | m |
| 233 | 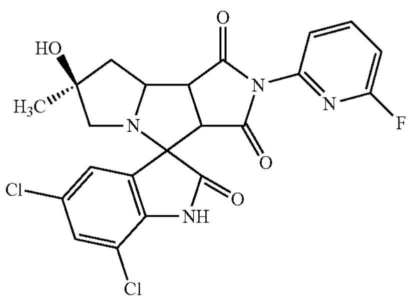 [SMILES: C[C@]1(O)CC2C3C(=O)N(c4cccc(F)n4)C(=O)C3C3(C(=O)Nc4c(Cl)cc(Cl)cc43)N2C1] | 491.37 [M + H]⁺ | m |
| 234 | 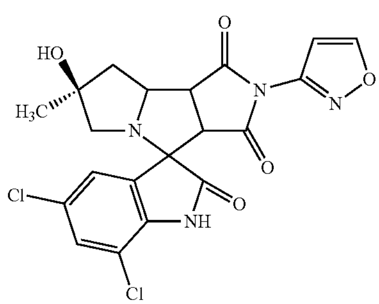 [SMILES: C[C@]1(O)CC2C3C(=O)N(c4ccon4)C(=O)C3C3(C(=O)Nc4c(Cl)cc(Cl)cc43)N2C1] | 463.36 [M + H]⁺ | m |
| 235 | 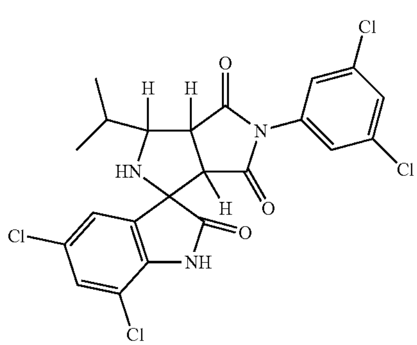 | 5111.20 [M + H]⁺ | m |

TABLE 1-continued

| Example No. | Structure | M/Z | Single enantiomer (s) or mixture of stereoisomers (m) |
|---|---|---|---|
| 236 | 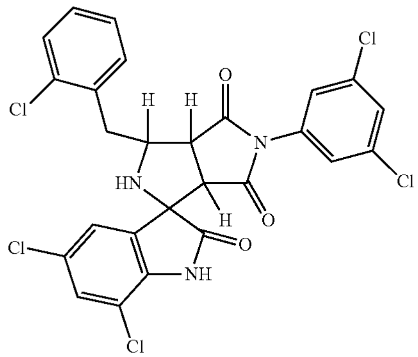 | 596.30 [M + H]+ | m |
| 237 | 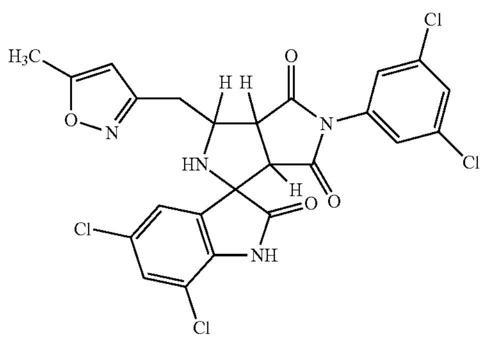 [SMILES: Cc1cc(CC2NC3(C(=O)Nc4c(Cl)cc(Cl)cc43)C3C(=O)N(c4cc(Cl)cc(Cl)c4)C(=O)C23)no1] | 567.40 [M + H]+ | m |
| 238 | 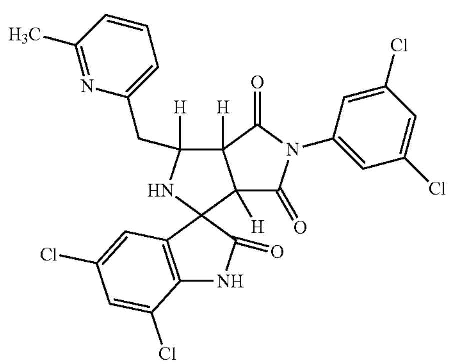 | 577.80 [M + H]+ | m |
| 239 | 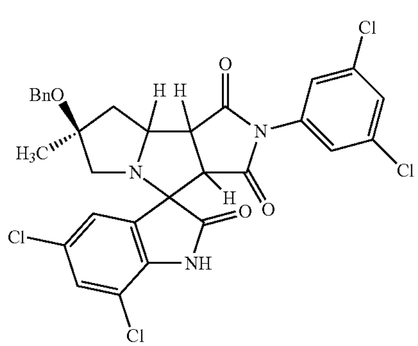 [SMILES: C[C@]1(OCc2ccccc2)CC2C3C(=O)N(c4cc(Cl)cc(Cl)c4)C(=O)C3C3(C(=O)Nc4c(Cl)cc(Cl)cc43)N2C1] | 630.22 [M + H]− | s |

TABLE 1-continued

| Example No. | Structure | M/Z | Single enantiomer (s) or mixture of stereoisomers (m) |
|---|---|---|---|
| 240 | 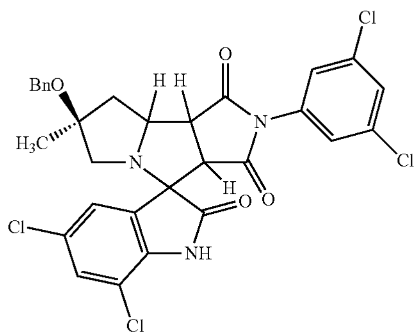 [SMILES: C[C@]1(OCc2ccccc2)CC2C3C(=O)N(c4cc(Cl)cc(Cl)c4)C(=O)C3C3(C(=O)Nc4c(Cl)cc(Cl)cc43)N2C1] | 630.34 [M + H]⁻ | s |
| 241 | 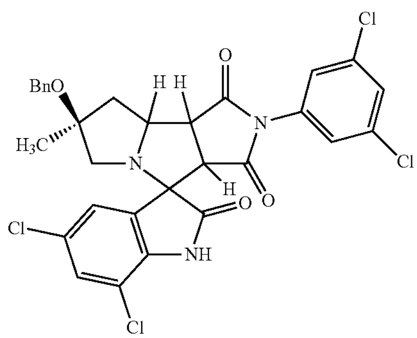 [SMILES: C[C@]1(OCc2ccccc2)CC2C3C(=O)N(c4cc(Cl)cc(Cl)c4)C(=O)C3C3(C(=O)Nc4c(Cl)cc(Cl)cc43)N2C1] | 630.37 [M + H]⁻ | s |
| 242 | 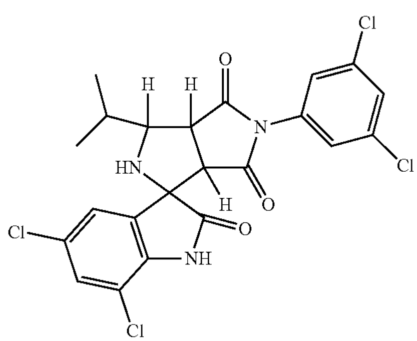 [SMILES: CC(C)C1NC2(C(=O)Nc3c(Cl)cc(Cl)cc32)C2C(=O)N(c3cc(Cl)cc(Cl)c3)C(=O)C12] | 514.00 [M + H]⁺ | s |
| 243 | 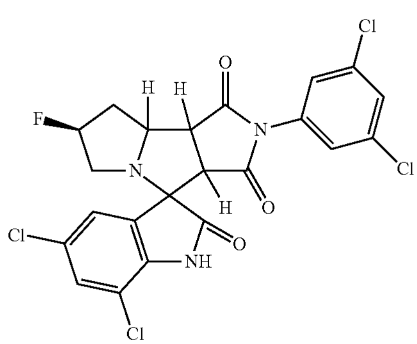 [SMILES: O=C1C2C3C[C@H](F)CN3C3(C(=O)Nc4c(Cl)cc(Cl)cc43)C2C(=O)N1c1cc(Cl)cc(Cl)c1] | 528.20 [M + H]⁻ | s |

TABLE 1-continued

| Example No. | Structure | M/Z | Single enantiomer (s) or mixture of stereoisomers (m) |
|---|---|---|---|
| 244 | 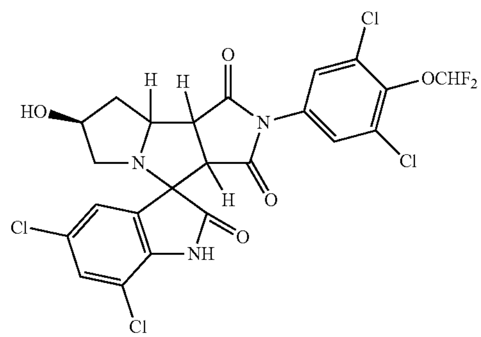 [SMILES: O=C1C2C3C[C@H](O)CN3C3(C(=O)Nc4c(Cl)cc(Cl)cc43)C2C(=O)N1c1cc(Cl)c(OC(F)F)c(Cl)c1] | 592.28 [M + H]⁻ | m |
| 245 | 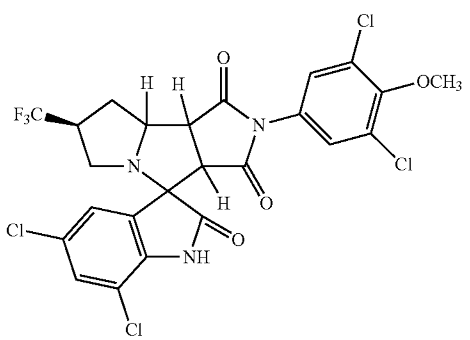 [SMILES: COc1c(Cl)cc(N2C(=O)C3C4C[C@H](C(F)(F)F)CN4C4(C(=O)Nc5c(Cl)cc(Cl)cc54)C3C2=O)cc1Cl] | 610.00 [M + H]⁺ | m |
| 246 | 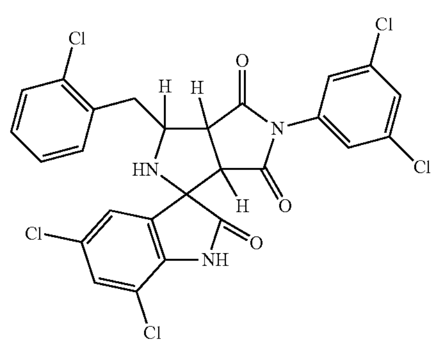 [SMILES: O=C1C2C(Cc3ccccc3Cl)NC3(C(=O)Nc4c(Cl)cc(Cl)cc43)C2C(=O)N1c1cc(Cl)cc(Cl)c1] | 596.70 [M + H]⁺ | s |
| 247 | 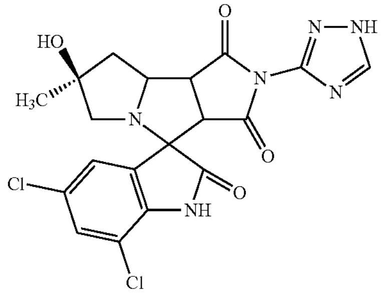 | 466.30 [M + H]⁺ | m |

TABLE 1-continued

| Example No. | Structure | M/Z | Single enantiomer(s) or mixture of stereoisomers (m) |
|---|---|---|---|
| 248 | 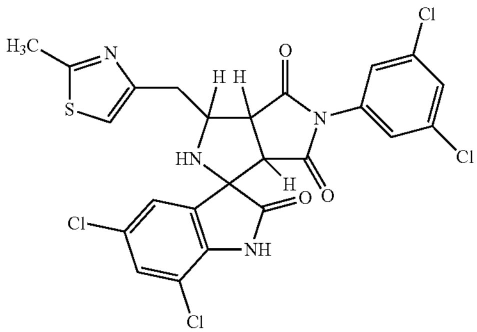 [SMILES: Cc1nc(CC2NC3(C(=O)Nc4c(Cl)cc(Cl)cc43)C3C(=O)N(c4cc(Cl)cc(Cl)c4)C(=O)C23)cs1] | 583.00 [M + H]+ | m |
| 249 | 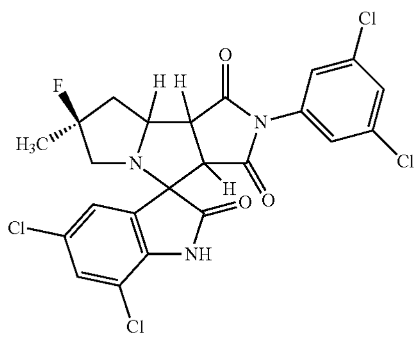 [SMILES: C[C@]1(F)CC2C3C(=O)N(c4cc(Cl)cc(Cl)c4)C(=O)C3C3(C(=O)Nc4c(Cl)cc(Cl)cc43)N2C1] | 542.42 [M + H]− | s |
| 250 | 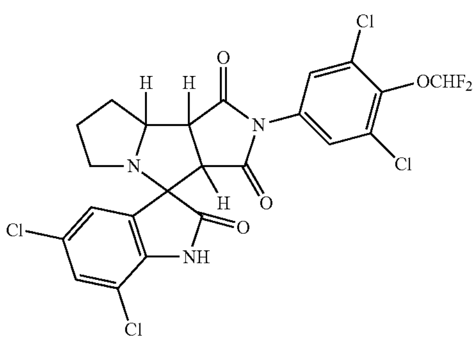 [SMILES: O=C1C2C3CCCN3C3(C(=O)Nc4c(Cl)cc(Cl)cc43)C2C(=O)N1c1cc(Cl)c(OC(F)F)c(Cl)c1] | 576.37 [M + H]+ | s |
| 251 | 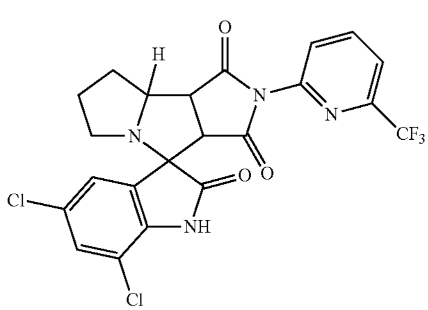 [SMILES: O=C1C2C3CCCN3C3(C(=O)Nc4c(Cl)cc(Cl)cc43)C2C(=O)N1c1cccc(C(F)(F)F)n1] | 511.32 [M + H]+ | m |

TABLE 1-continued

| Example No. | Structure | M/Z | Single enantiomer (s) or mixture of stereoisomers (m) |
|---|---|---|---|
| 252 | 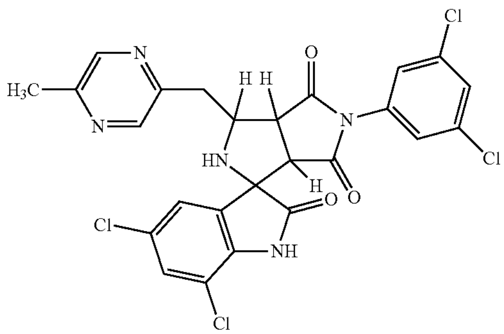 [SMILES: Cc1cnc(CC2NC3(C(=O)Nc4c(Cl)cc(Cl)cc43)C3C(=O)N(c4cc(Cl)cc(Cl)c4)C(=O)C23)cn1] | 577.30 [M + H]⁺ | m |
| 253 | 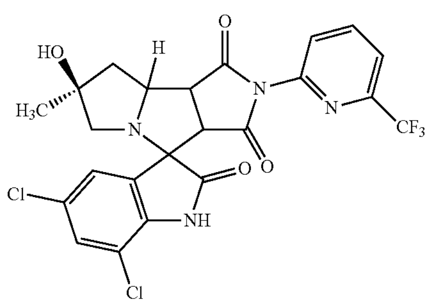 [SMILES: C[C@]1(O)CC2C3C(=O)N(c4cccc(C(F)(F)F)n4)C(=O)C3C3(C(=O)Nc4c(Cl)cc(Cl)cc43)N2C1] | 541.34 [M + H]⁺ | m |
| 254 | 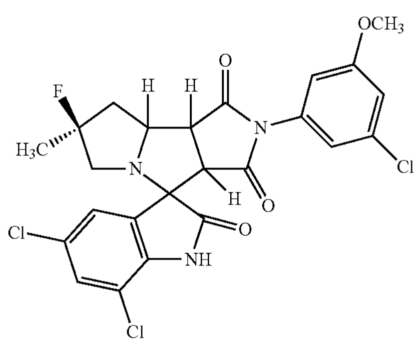 [SMILES: COc1cc(Cl)cc(N2C(=O)C3C4C[C@](C)(F)CN4C4(C(=O)Nc5c(Cl)cc(Cl)cc54)C3C2=O)c1] | 540.33 [M + H]⁺ | s |
| 255 | 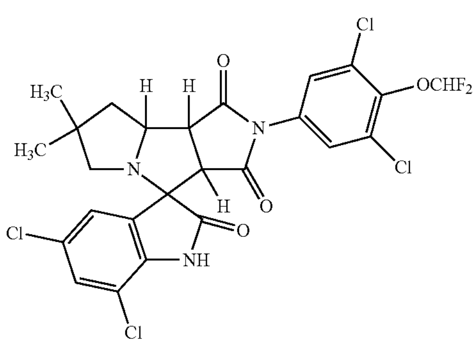 [SMILES: CC1(C)CC2C3C(=O)N(c4cc(Cl)c(OC(F)F)c(Cl)c4)C(=O)C3C3(C(=O)Nc4c(Cl)cc(Cl)cc43)N2C1] | 606.32 [M + H]⁺ | s |

TABLE 1-continued

| Example No. | Structure | M/Z | Single enantiomer(s) or mixture of stereoisomers (m) |
|---|---|---|---|
| 256 | 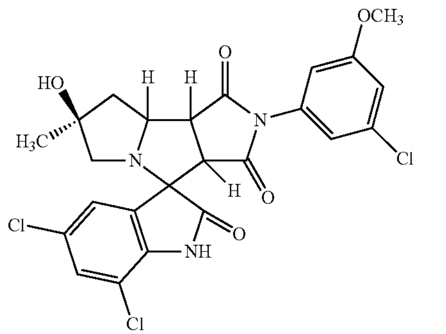 [SMILES: COc1cc(Cl)cc(N2C(=O)C3C4C[C@](C)(O)CN4C4(C(=O)Nc5c(Cl)cc(Cl)cc54)C3C2=O)c1] | 538.25 [M + H]$^+$ | s |

For each compound of Examples 1-10 and Table 1 in which the stereochemistry of the ring system is not indicated, the preferred stereoisomer has the stereochemistry shown in Formula VB, VC or VIA.

Assays for Detecting and Measuring the Effect of Compounds on dF508-CFTR Channels CFRT-YFP High Throughput Assay:

The following protocol is designed to selectively screen small molecule compounds for F508del CFTR corrector activities in the HTS YFP flux assay. In this protocol, the cells are incubated with test compounds for 24 hours, washed with PBS, stimulated with forskolin and a standard potentiator, and read on a 384-well HTS plate reader, such as the Hamamatsu FDDD-6000.

YFP fluorescence intensity is acquired at high speed before and after iodide buffer is injected to the assay cells. Iodide enters the cells via active CFTR channels in the plasma membrane, and quenches the YFP fluorescence. The rate of fluorescence quenching is proportionally related to the total CFTR activities in the cell membrane. dF508-CFTR corrector accelerates YFP quenching by increasing the number of CFTR molecules in the testing cell plasma membrane.

This method was initially developed for bench top plate readers (Galietta et al., 2001), and was adapted to the HTS format (Sui et al. Assay Drug Dev. Technol. 2010).

Fisher Rat Thyroid (FRT) cells stably expressing both human ΔF508-CFTR and a halide-sensitive yellow fluorescent protein (YFP-H148Q/I152L 25, 22) (Galietta et al., Am. J. Physiol Cell Physiol 281(5), C1734, 2001) were cultured on plastic surface in Coon's modified Ham's F12 medium supplemented with FBS 10%, L-glutamine 2 mM, penicillin 100 U/mL, and streptomycin 100 µg/mL. G418 (0.75-1.0 mg/mL) and zeocin (3.2 ug/mL) were used for selection of FRT cells expressing ΔF508-CFTR and YFP. For primary screening, FRT cells were plated into 384-well black wall, transparent bottom microtiter plates (Costar; Corning Inc.) at a cell density of 20,000-40,000 per well. Test compounds were applied to the cells at varying concentrations. Cells were incubated in a cell culture incubator at 37° C. with 5% $CO_2$ for 24-26 h. Assay plates were washed with DPBS media (Thermo, cat# SH30028.02) to remove unbound cells and compound. Stimulation media (25 µL) containing 20 µM Forskolin & 30 µM P3 [6-(Ethyl-phenyl-sulfonyl)-4-oxo-1, 4-dihydro-quinoline-3-carboxylic acid 2-methoxy-benzylamide] in Hams F-12 coon's modified media was added to the plate wells and incubated at room temperature for 60-120 min. 25 µL of HEPES-PBS-I buffer (10 mM HEPES, 1 mM $MgCl_2$, 3 mM KCl, 1 mM $CaCl_2$, 150 mM NaI) was then added and fluorescence quench curves (Excitation 500 nm/Emission 540 nm; exposure 136 ms) were immediately recorded on an FDSS-6000 plate reader (Hamamatsu). Quench rates were derived from least squares fitting of the data as described by Sui et al., (2010).

REFERENCES

Galietta, L. J., Jayaraman, S., and Verkman, A. S. Cell-based assay for high-throughput quantitative screening of CFTR chloride transport agonists. Am. J. Physiol Cell Physiol 281(5), C1734, 2001.

Sui J, Cotard S, Andersen J, Zhu P, Staunton J, Lee M, Lin S. (2010) Optimization of a Yellow fluorescent protein-based iodide influx high-throughput screening assay for cystic fibrosis transmembrane conductance regulator (CFTR) modulators. Assay Drug Dev Technol. 2010 December; 8(6):656-68.

Determination of Activity in Primary CF Cell:

Cell Culture:

Primary CF airway epithelial cells were obtained from the UNC Cystic Fibrosis Tissue Procurement and Cell Culture Core. The cells are grown at 37° C. in a Heracell 150i incubator using growth media (BEGM, Fischer). Cells were then transferred to differentiation media (ALI, UNC) for a minimum of 4 weeks on coated Costar snapwells. Two days before the Ussing assay the mucus on the apical surface of the cells was aspirated after incubating with 200 µL of differentiation Media for at least thirty (30) minutes. One day before the Ussing assay test compounds were added to the basolateral surface of the cells at various test concentrations dissolved in DMSO. Duplicate wells were prepared giving a n=3 or n=4 protocol.

6.1.2 Electrophysiological Procedures

Cells were treated for 24 hours with various combinations and concentrations of the test articles, reference standard (3 µM VX809, positive control). Compounds stock solutions were prepared in DMSO and diluted 1/1000 into ALI media to their final assay concentration. Cells were treated with combination solutions (2 mL of each dilution) and incubated at 37° C. for 24 h.

Ussing:

For an Ussing experiment, cells on four Snapwell (6-well) plates were treated 24 hours prior to experimentation. The next day filters from individual Snapwells were removed from the plates and mounted vertically in Ussing chambers pre-equilibrated at 37° C. in 5 ml of HBS (pH 7.4) both apical and basolateral sides and bubbled with room air to facilitate mixing upon addition of compounds. The resting current was recorded for 10 min to ensure a stable baseline. Resting current was blocked by the apical addition of 3 µM benzamil, an ENaC inhibitor. After 10 min, 10 µM forskolin was added to both the apical and basolateral side to stimulate CFTR. The increase in chloride current was detected as an upward deflection of the trace. After an additional 10 min, the potentiator VX770 (1 µM) was added, further increasing the chloride current. Finally CFTR-172 (a CFTR inhibitor, 20 µM) and/or bumetanide (20 uM) was added to block CFTR mediated chloride current, resulting in a decrease in the observed current.

For the equivalent current assay, cells on four Transwell (24-well) plates were treated. Each Transwell plate was filled with 200 µl of HBS on the apical surface and 2 ml on the basolateral surface. Plates were placed horizontally in a heated mount at 37° C., and equilibrated for several minutes. Resting current was measured for 15 min and then blocked by the apical addition of 5 µM benzamil. After 20 min, 10 µM forskolin and 1 µM VX770 were added to both the apical and basolateral side to stimulate CFTR. An increase in chloride current is seen as an upward deflection of the trace. After another 30 min, CFTR-172 (a CFTR inhibitor, 20 µM) and/or bumetanide (20 uM) was added to block CFTR mediated chloride current.

Data Collection and Analysis Methods

The raw data, current vs. time for the Ussing chamber (sampling interval: 10 s) and voltage vs. time and resistance vs. time for the equivalent current assay (sampling interval: 5 minutes) were transferred to Excel (Microsoft Office Professional, version 14.0.7106.5003) for analysis. CFTR specific current was measured as the average amplitude of the increase in current elicited upon addition forskolin and ending upon addition of the CFTR channel specific blocker CFTR-172. This average is equivalent to the sum of the average forskolin activated and the average VX770-potentiated currents. The average current measured in vehicle (0.1% DMSO) treated cells, Iv, was subtracted from the current for the test article, $I_{TA}$, or from the corrector reference standard VX809 (3 uM $I_{STD}$). For replicate measurements, the average vehicle subtracted response for the test article, was normalized to the average vehicle subtracted inhibitor response of the reference corrector VX809 (3 µM).

$$I_{NSC}=(I_{TA}-I_V)_{(ave)}/(I_{STD}-I_V)_{(ave)} \quad \text{(Equation 1)}$$

A second endpoint, for the equivalent current assay, evaluated was NAUC, the normalized area under the curve (AUC) measuring the response after addition of forskolin and VX770 to the time point right before the addition of the CFTR inhibitor. The AUC is effectively the average response multiplied by the duration of the response. The AUC of the test article, $AUC_{TA}$ was then corrected by subtracting the average vehicle response, $AUC_{V,ave}$ over the same time range, and normalized as for the inhibitor-sensitive current to the difference of the corrector reference standard VX809 (3 µM $_{VX809r,ave}$ and the vehicle response:

$$NAUC_{TA}=[AUC_{TA}-AUC_{V,ave}]/[AUC_{VX809r,ave}-AUC_{V,ave}] \quad \text{(Equation 2)}.$$

The normalized value for DMSO is 0.0 and for VX-809 alone is 1.0. Combinations of compounds with VX-809 that give normalized values greater than 1.0 show activity in the combination assay. A value of 2 means the test compound doubles the effect to VX-809 alone.

Experiments were run with a minimum of n=4 replicates per concentration. Since the distribution for the ratio of two normal distributions is a Cauchy distribution, the median value must be used for the average and the average deviation must be used for the error of all normalized data. Potency ($EC_{50}$) and efficacy (maximum response) were determined by fitting dose response data to a sigmoid dose response model (GraphPad Prism 5.04, Manufacturer) using Equation 3:

$$E=E_{min}+(E_{max}-E_{min})/(1+10^{((\text{Log } EC50-S)*n_H)}) \quad \text{(Equation 3)}$$

where E is the recorded response, and S is the concentration of test compound in combination with VX-809. Since there were at most 8 points in the dose response curve only $EC_{50}$ and maximum ($E_{max}$) were allowed to vary, while the minimum ($E_{min}$) was fixed equal to the VX-809 response of 1.0, and the Hill slope, $n_H$, was fixed equal to 1.

Statistical comparisons (t-test and Mann Whitney) and calculation of averages and errors were performed in Excel.

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

TABLE II

Equivalent current assay results in Primary CF airway epithelial cells; The following meanings apply:
NAUC "+++" refers to an observed NAUC >170% of positive control
NAUC "++" refers to an observed NAUC 170-140% of positive control
NAUC "+" refers to an observed NAUC <140% of positive control

| Example No. | Nauc @ 3 µM | Nauc @ 10 µM |
|---|---|---|
| 1 | +++ | +++ |
| 2 | +++ | +++ |
| 3 | +++ | +++ |
| 4 | +++ | ++ |
| 5 | +++ | +++ |
| 6 | +++ | +++ |
| 7 | ++ | ++ |
| 8 | +++ | + |
| 9 | + | ++ |
| 10 | +++ | +++ |
| 11 | + | +++ |
| 12 | + | ++ |
| 13 | +++ | +++ |
| 14 | + | ++ |
| 15 | ++ | +++ |
| 16 | +++ | +++ |
| 17 | + | ++ |
| 18 | ++ | + |
| 19 | + | ++ |
| 20 | + | ++ |
| 21 | ++ | ++ |
| 22 | +++ | +++ |
| 23 | ++ | + |
| 24 | +++ | +++ |
| 25 | +++ | +++ |
| 26 | + | +++ |
| 27 | ++ | ++ |
| 28 | ++ | +++ |
| 29 | + | ++ |
| 30 | ++ | +++ |
| 31 | + | +++ |
| 32 | ++ | +++ |

TABLE II-continued

Equivalent current assay results in Primary CF airway epithelial cells;
The following meanings apply:
NAUC "+++" refers to an observed NAUC >170% of positive control
NAUC "++" refers to an observed NAUC 170-140% of positive control
NAUC "+" refers to an observed NAUC <140% of positive control

| Example No. | Nauc @ 3 μM | Nauc @ 10 μM |
|---|---|---|
| 33 | ++ | +++ |
| 34 | +++ | +++ |
| 35 | + | +++ |
| 36 | + | +++ |
| 37 | + | ++ |
| 38 | +++ | +++ |
| 39 | + | ++ |
| 40 | +++ | +++ |
| 41 | ++ | +++ |
| 42 | ++ | ++ |
| 43 | ++ | +++ |
| 44 | ++ | + |
| 45 | + | +++ |
| 46 | ++ | + |
| 47 | ++ | ++ |
| 48 | ++ | + |
| 49 | ++ | +++ |
| 50 | ++ | + |
| 51 | +++ | ++ |
| 52 | ++ | +++ |
| 53 | ++ | ++ |
| 54 | ++ | + |
| 55 | + | +++ |
| 56 | ++ | +++ |
| 57 | +++ | +++ |
| 58 | ++ | +++ |
| 59 | + | +++ |
| 60 | + | ++ |
| 61 | +++ | +++ |
| 62 | ++ | ++ |
| 63 | +++ | +++ |
| 64 | + | ++ |
| 65 | ++ | +++ |
| 66 | ++ | ++ |
| 67 | +++ | +++ |
| 68 | + | +++ |
| 69 | +++ | + |
| 70 | +++ | +++ |
| 71 | + | +++ |
| 72 | +++ | + |
| 73 | +++ | ++ |
| 74 | +++ | +++ |
| 75 | ++ | + |
| 76 | +++ | +++ |
| 77 | +++ | +++ |
| 78 | +++ | +++ |
| 79 | +++ | +++ |
| 80 | ++ | ++ |
| 81 | + | ++ |
| 82 | + | ++ |
| 83 | ++ | +++ |
| 84 | ++ | ++ |
| 85 | ++ | +++ |
| 86 | + | +++ |
| 87 | +++ | +++ |
| 88 | + | +++ |
| 89 | + | ++ |
| 90 | + | +++ |
| 91 | + | +++ |
| 92 | +++ | + |
| 93 | ++ | +++ |
| 94 | ++ | +++ |
| 95 | ++ | + |
| 96 | ++ | + |
| 97 | + | ++ |
| 98 | +++ | +++ |
| 99 | +++ | +++ |
| 100 | +++ | +++ |
| 101 | + | +++ |
| 102 | + | ++ |
| 103 | ++ | +++ |
| 104 | + | ++ |
| 105 | ++ | ++ |
| 106 | +++ | +++ |
| 107 | +++ | +++ |
| 108 | +++ | ++ |
| 109 | ++ | ++ |
| 110 | +++ | +++ |
| 111 | +++ | +++ |
| 112 | +++ | +++ |
| 113 | + | ++ |
| 114 | +++ | +++ |
| 115 | + | ++ |
| 116 | +++ | +++ |
| 117 | +++ | +++ |
| 118 | ++ | ++ |
| 119 | +++ | +++ |
| 120 | +++ | + |
| 121 | ++ | ++ |
| 122 | +++ | + |
| 123 | + | +++ |
| 124 | + | ++ |
| 125 | +++ | + |
| 126 | +++ | +++ |
| 127 | ++ | + |
| 128 | ++ | + |
| 129 | ++ | ++ |
| 130 | + | ++ |
| 131 | + | ++ |
| 132 | + | ++ |
| 133 | ++ | ++ |
| 134 | + | ++ |
| 135 | +++ | + |
| 136 | +++ | +++ |
| 137 | +++ | +++ |
| 138 | +++ | + |
| 139 | ++ | + |
| 140 | +++ | +++ |
| 141 | + | ++ |
| 144 | +++ | +++ |
| 145 | + | +++ |
| 146 | +++ | +++ |
| 147 | +++ | +++ |
| 148 | +++ | +++ |
| 149 | +++ | +++ |
| 150 | + | ++ |
| 151 | ++ | + |
| 152 | +++ | + |
| 153 | + | ++ |
| 154 | +++ | +++ |
| 155 | ++ | + |
| 156 | ++ | +++ |
| 157 | +++ | + |
| 158 | ++ | +++ |
| 159 | +++ | +++ |
| 160 | + | ++ |
| 161 | +++ | +++ |
| 162 | + | ++ |
| 163 | ++ | + |
| 164 | ++ | +++ |
| 165 | ++ | ++ |
| 166 | ++ | ++ |
| 167 | + | ++ |
| 168 | + | ++ |
| 169 | + | ++ |
| 170 | ++ | + |
| 171 | +++ | +++ |
| 172 | ++ | +++ |
| 173 | +++ | +++ |
| 174 | +++ | +++ |
| 175 | +++ | +++ |
| 176 | ++ | ++ |

TABLE II-continued

Equivalent current assay results in Primary CF airway epithelial cells;
The following meanings apply:
NAUC "+++" refers to an observed NAUC >170% of positive control
NAUC "++" refers to an observed NAUC 170-140% of positive control
NAUC "+" refers to an observed NAUC <140% of positive control

| Example No. | Nauc @ 3 µM | Nauc @ 10 µM |
|---|---|---|
| 177 | ++ | +++ |
| 178 | + | ++ |
| 179 | +++ | +++ |
| 180 | ++ | + |
| 181 | +++ | +++ |
| 182 | +++ | +++ |
| 183 | ++ | + |
| 184 | +++ | +++ |
| 185 | +++ | +++ |
| 186 | + | +++ |
| 187 | +++ | ++ |
| 188 | + | +++ |
| 189 | + | +++ |
| 190 | +++ | +++ |
| 191 | +++ | +++ |
| 192 | + | ++ |
| 193 | +++ | +++ |
| 194 | +++ | ++ |
| 195 | + | ++ |
| 196 | + | ++ |
| 197 | +++ | +++ |
| 198 | + | ++ |
| 199 | +++ | ++ |
| 200 | ++ | + |
| 201 | + | +++ |
| 202 | + | ++ |
| 203 | ++ | ++ |
| 204 | + | +++ |
| 205 | ++ | +++ |
| 206 | ++ | +++ |
| 207 | ++ | + |
| 208 | ++ | + |
| 209 | + | +++ |
| 210 | + | ++ |
| 211 | ++ | ++ |
| 212 | + | ++ |
| 213 | ++ | +++ |
| 214 | +++ | +++ |
| 215 | +++ | ++ |
| 216 | ++ | + |
| 217 | ++ | ++ |
| 218 | +++ | +++ |
| 219 | ++ | + |
| 220 | +++ | +++ |
| 221 | +++ | +++ |
| 222 | +++ | ++ |
| 223 | + | +++ |
| 224 | +++ | +++ |
| 225 | +++ | +++ |
| 226 | ++ | ++ |
| 227 | + | ++ |
| 228 | +++ | ++ |
| 229 | + | ++ |
| 230 | +++ | +++ |
| 231 | + | +++ |
| 232 | ++ | + |
| 233 | +++ | ++ |
| 234 | + | ++ |
| 235 | +++ | +++ |
| 236 | +++ | ++ |
| 237 | ++ | + |
| 238 | + | ++ |
| 239 | ++ | ++ |
| 240 | +++ | + |
| 241 | +++ | +++ |
| 242 | +++ | +++ |
| 243 | +++ | +++ |
| 244 | ++ | ++ |
| 245 | +++ | +++ |
| 246 | +++ | +++ |
| 247 | + | ++ |
| 248 | + | ++ |
| 249 | ++ | + |
| 250 | +++ | +++ |
| 251 | +++ | +++ |
| 252 | ++ | ++ |
| 253 | + | ++ |
| 254 | +++ | +++ |
| 255 | +++ | +++ |
| 256 | ++ | +++ |

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

What is claimed:

1. A compound of Formula IV or IVA, or a pharmaceutically acceptable salt thereof;

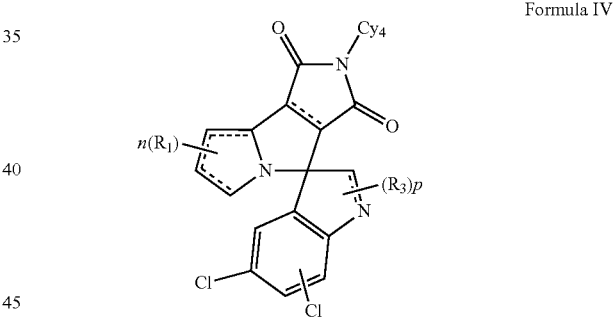

Formula IV

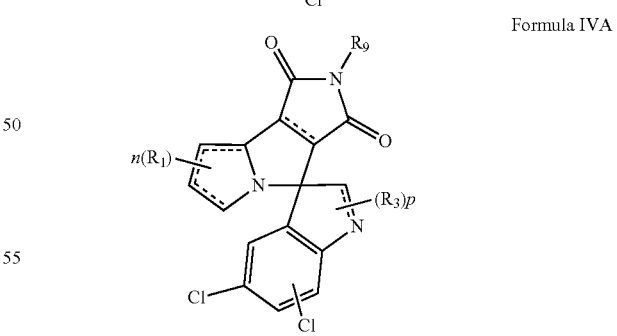

Formula IVA wherein
each ====== independently represents a single bond or a double bond;
Cy$_4$ is selected from optionally substituted aryl, heteroaryl or carbocyclyl wherein the aryl, heteroaryl or carbocyclyl is optionally fused to an optionally substituted carbocyclyl, heterocyclyl or aryl;
n and p are independently 0, 1, 2, 3, 4, 5, or 6;

each $R_1$ and $R_3$ is independently selected from hydrogen, deuterium, halogen, $-OR_{12}$, $-SR_{12}$, $-NR_{10}R_{13}$, $-CF_3$, $-CN$, $-NO_2$, $-N_3$, $-C(O)OR_{12}$, $-C(O)R_{12}$, $-C(O)NR_{12}R_{13}$, $-S(O)R_{12}$, $-S(O)NR_{12}$, $-S(O)_2R_{12}$, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl and substituted heteroaryl; alternatively, two $R_1$ groups, or two $R_3$ groups together with the atoms to which they are attached form an oxo (=O) or a vinyl group (=C); alternatively, two $R_1$ groups, or two $R_3$ groups or two $R_4$ groups together with the atoms to which they are attached form a 3, 4, 5, 6 or 7 membered, optionally substituted carbocyclic, heterocyclic or aryl group;

$R_{10}$ is hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl; and each $R_{12}$ and $R_{13}$ is independently selected from absent, hydrogen, deuterium, halogen, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl; alternatively two $R_{12}$ groups, or two $R_{13}$ groups, or one $R_{12}$ group and one $R_{13}$ group, together with the atoms to which they are attached form a 3, 4, 5, 6 or 7 membered, optionally substituted carbocyclic, heterocyclic or aryl group; and $R_9$ is selected from hydrogen, deuterium, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl, or substituted heteroaryl.

2. The compound of claim 1, selected from Table A, or a pharmaceutically acceptable salt thereof:

TABLE A

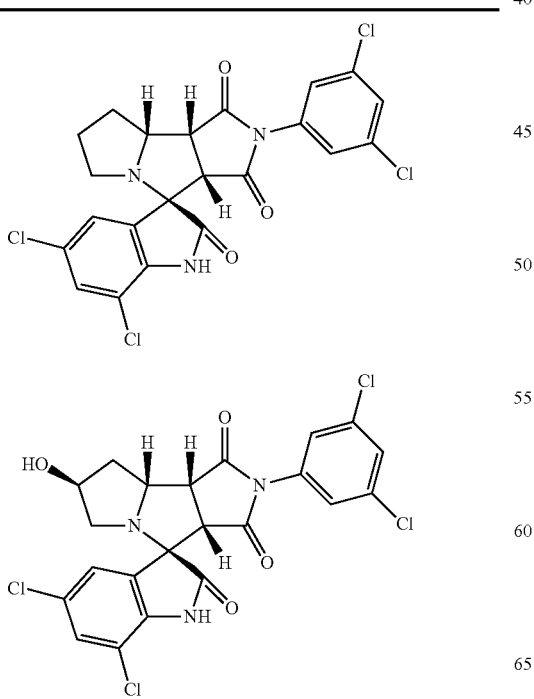

TABLE A-continued

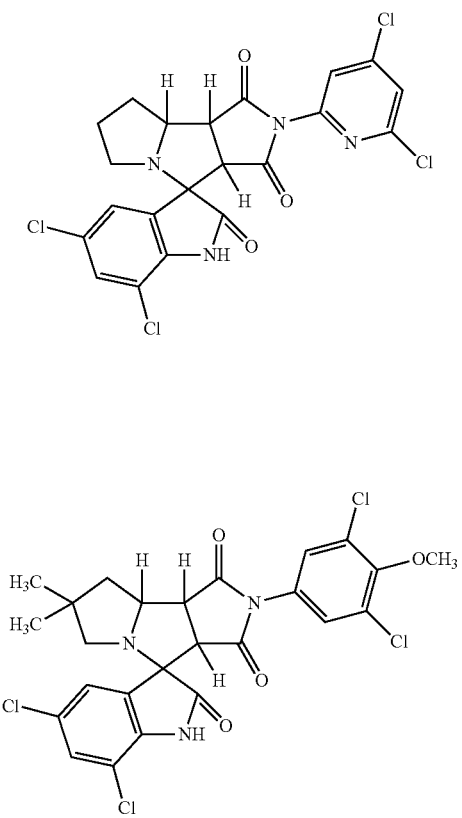

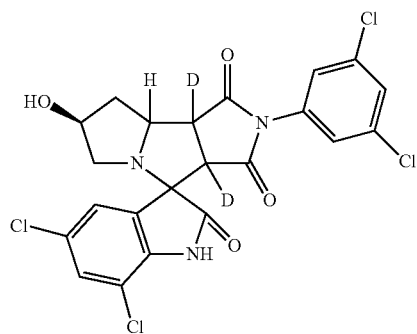 [SMILES: [2H]C12C(=O)N(c3cc(Cl)cc(Cl)c3)C(=O)C1([2H])C1(C(=O)Nc3c(Cl)cc(Cl)cc31)N1C[C@@H](O)CC12]

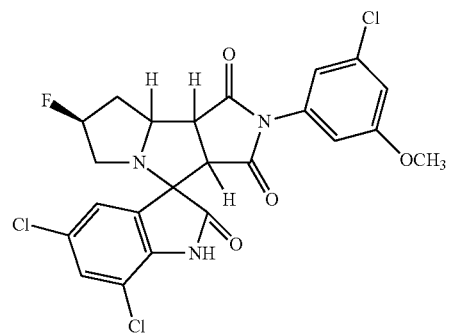 [SMILES: COc1cc(Cl)cc(N2C(=O)C3C4C[C@H](F)CN4C4(C(=O)Nc5c(Cl)cc(Cl)cc54)C3C2=O)c1]

TABLE A-continued
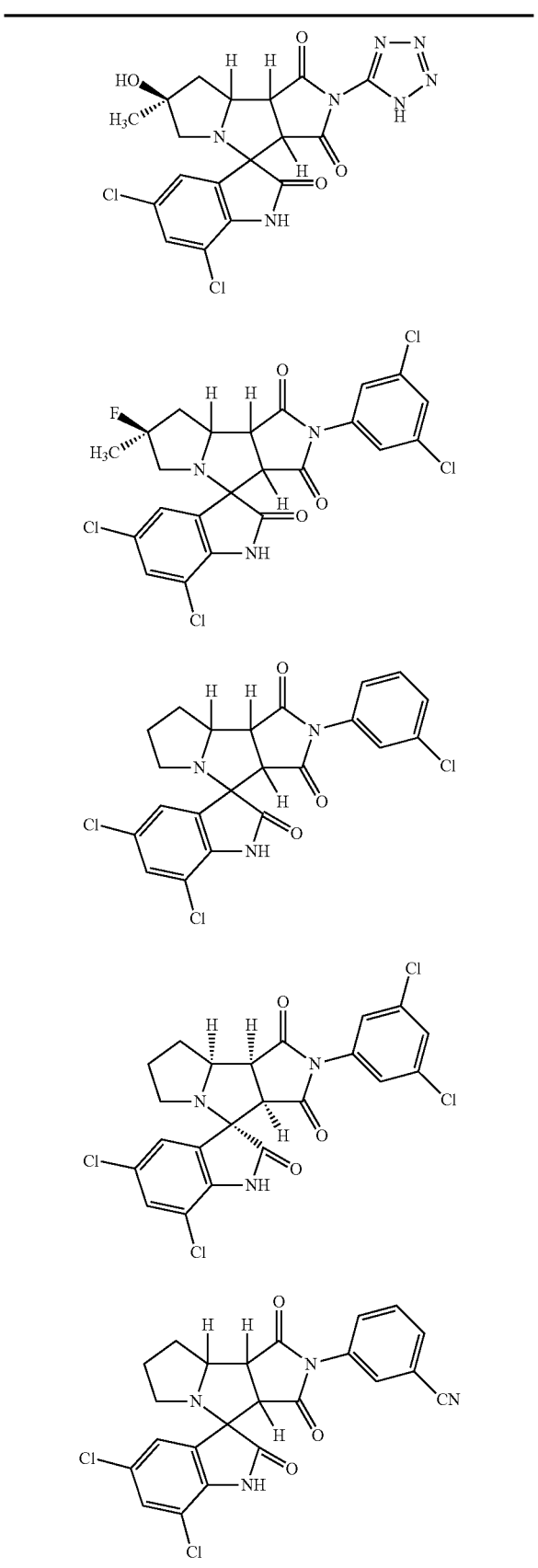
TABLE A-continued
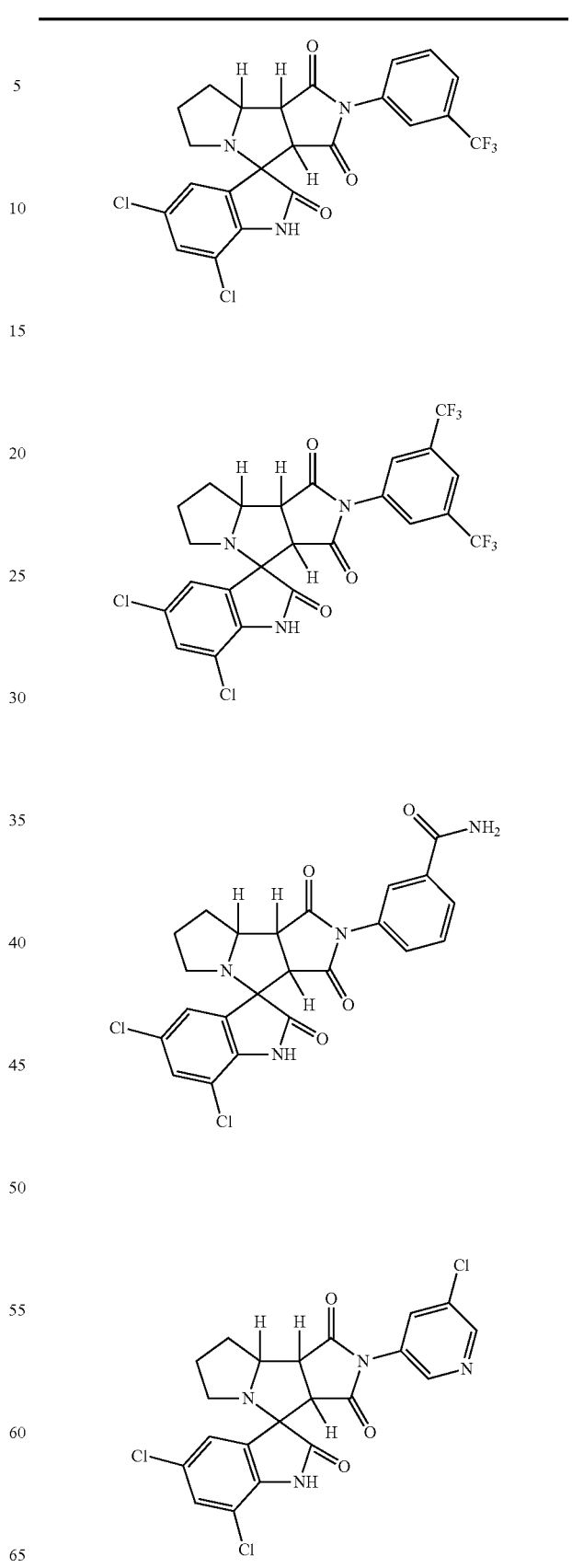

TABLE A-continued

TABLE A-continued
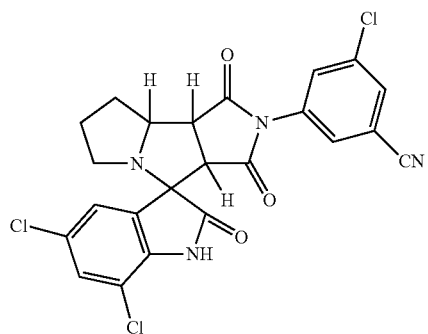 [SMILES: N#Cc1cc(Cl)cc(N2C(=O)C3C4CCCN4C4(C(=O)Nc5c(Cl)cc(Cl)cc54)C3C2=O)c1]
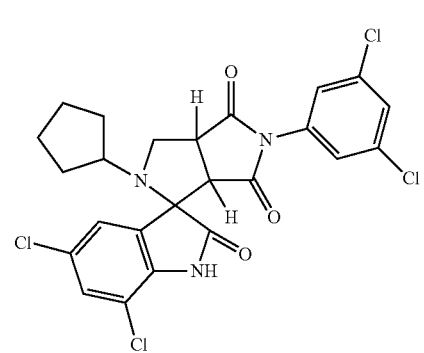 [SMILES: O=C1C2CN(C3CCCC3)C3(C(=O)Nc4c(Cl)cc(Cl)cc43)C2C(=O)N1c1cc(Cl)cc(Cl)c1]
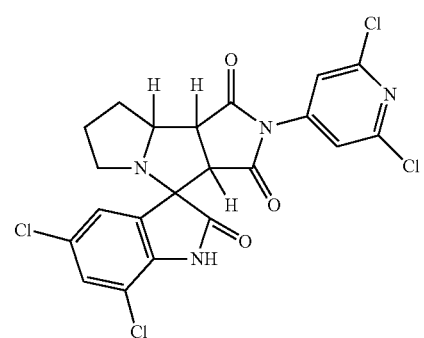 [SMILES: O=C1C2C3CCCN3C3(C(=O)Nc4c(Cl)cc(Cl)cc43)C2C(=O)N1c1cc(Cl)nc(Cl)c1]
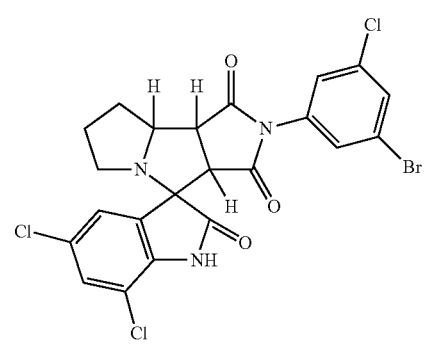 [SMILES: O=C1C2C3CCCN3C3(C(=O)Nc4c(Cl)cc(Cl)cc43)C2C(=O)N1c1cc(Cl)cc(Br)c1]
TABLE A-continued
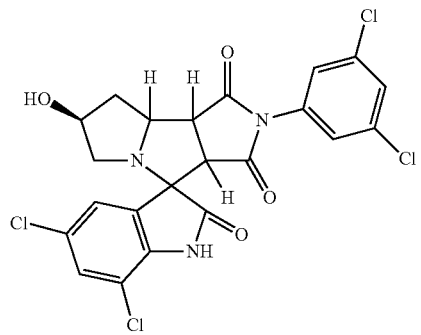
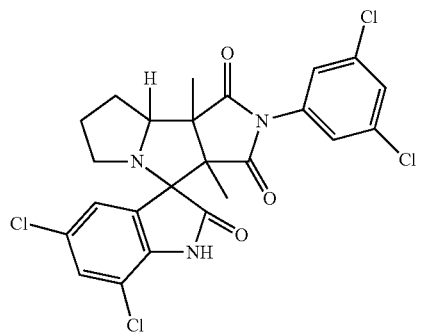 [SMILES: CC12C(=O)N(c3cc(Cl)cc(Cl)c3)C(=O)C1(C)C1(C(=O)Nc3c(Cl)cc(Cl)cc31)N1CCCC12]
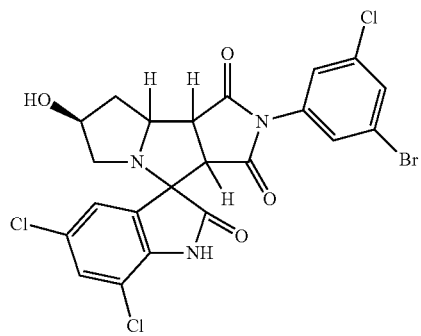
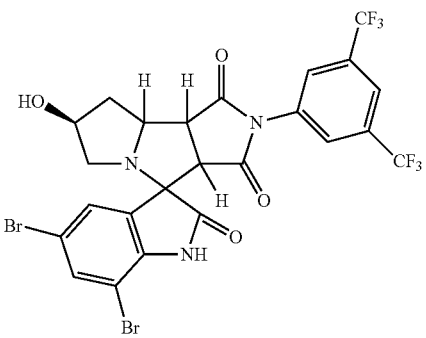 [SMILES: O=C1C2C3C[C@H](O)CN3C3(C(=O)Nc4c(Br)cc(Br)cc43)C2C(=O)N1c1cc(C(F)(F)F)cc(C(F)(F)F)c1]

TABLE A-continued
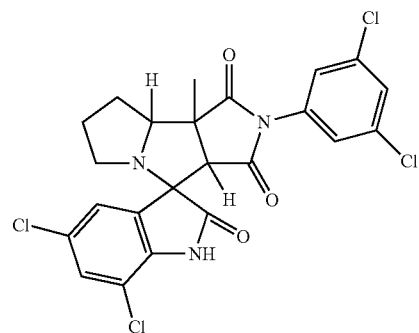 [SMILES: CC12C(=O)N(c3cc(Cl)cc(Cl)c3)C(=O)C1C1(C(=O)Nc3c(Cl)cc(Cl)cc31)N1CCCC12]
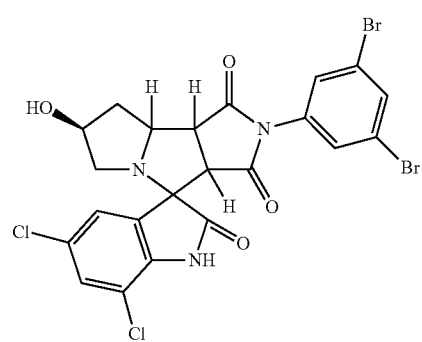 [SMILES: O=C1C2C3C[C@H](O)CN3C3(C(=O)Nc4c(Cl)cc(Cl)cc43)C2C(=O)N1c1cc(Br)cc(Br)c1]
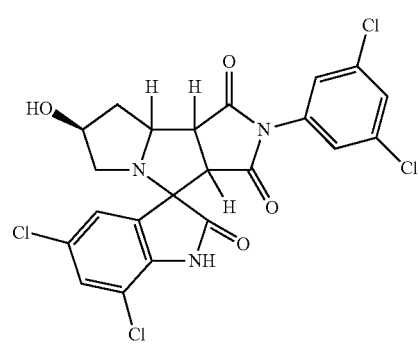 [SMILES: O=C1C2C3C[C@H](O)CN3C3(C(=O)Nc4c(Cl)cc(Cl)cc43)C2C(=O)N1c1cc(Cl)cc(Cl)c1]
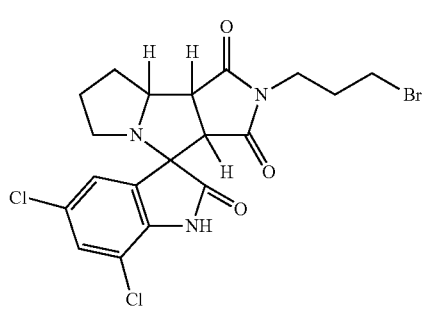 [SMILES: O=C1C2C3CCCN3C3(C(=O)Nc4c(Cl)cc(Cl)cc43)C2C(=O)N1CCCBr]
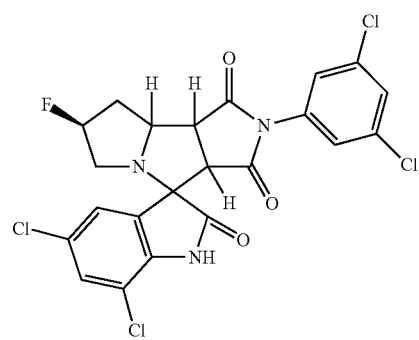 [SMILES: O=C1C2C3C[C@H](F)CN3C3(C(=O)Nc4c(Cl)cc(Cl)cc43)C2C(=O)N1c1cc(Cl)cc(Cl)c1]
TABLE A-continued
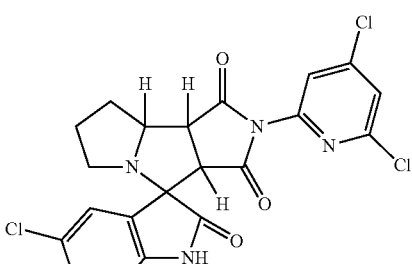
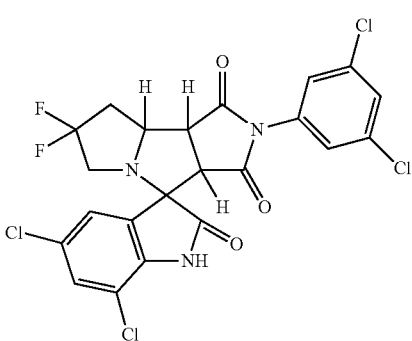 [SMILES: O=C1C2C3CC(F)(F)CN3C3(C(=O)Nc4c(Cl)cc(Cl)cc43)C2C(=O)N1c1cc(Cl)cc(Cl)c1]
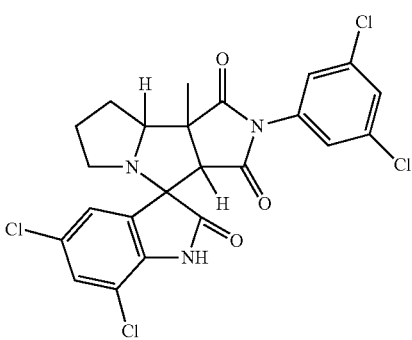 [SMILES: CC12C(=O)N(c3cc(Cl)cc(Cl)c3)C(=O)C1C1(C(=O)Nc3c(Cl)cc(Cl)cc31)N1CCCC12]
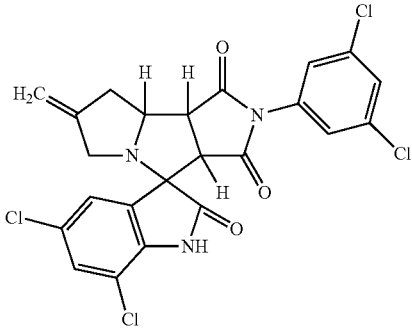 [SMILES: C=C1CC2C3C(=O)N(c4cc(Cl)cc(Cl)c4)C(=O)C3C3(C(=O)Nc4c(Cl)cc(Cl)cc43)N2C1]

TABLE A-continued
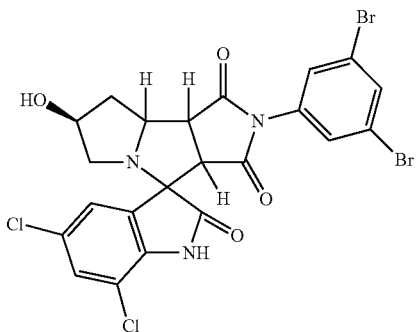 [SMILES: O=C1C2C3C[C@H](O)CN3C3(C(=O)Nc4c(Cl)cc(Cl)cc43)C2C(=O)N1c1cc(Br)cc(Br)c1]
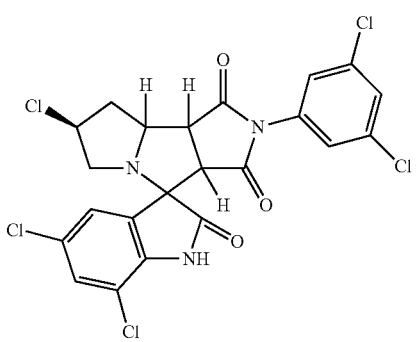
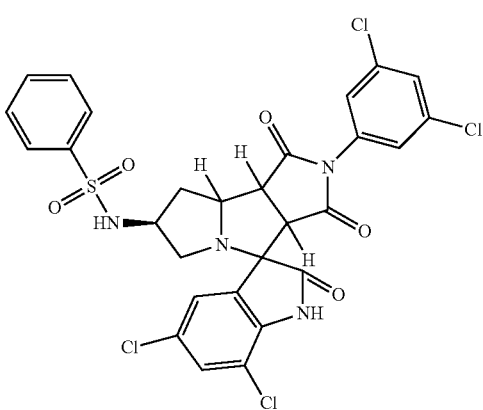 [SMILES: O=C1C2C3C[C@H](NS(=O)(=O)c4ccccc4)CN3C3(C(=O)Nc4c(Cl)cc(Cl)cc43)C2C(=O)N1c1cc(Cl)cc(Cl)c1]
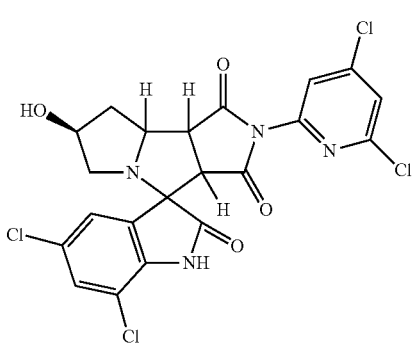
TABLE A-continued
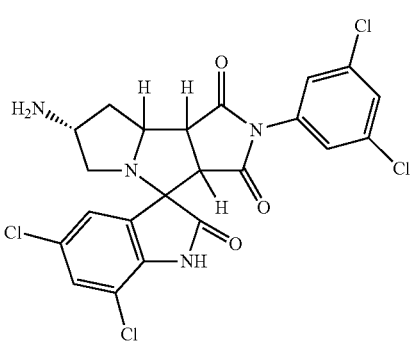 [SMILES: N[C@@H]1CC2C3C(=O)N(c4cc(Cl)cc(Cl)c4)C(=O)C3C3(C(=O)Nc4c(Cl)cc(Cl)cc43)N2C1]
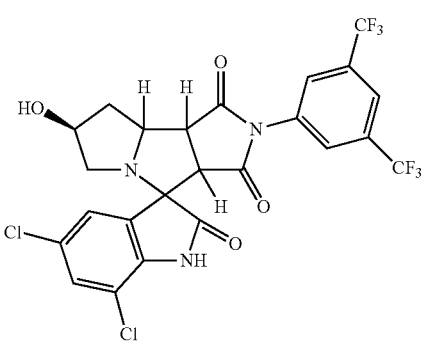 [SMILES: O=C1C2C3C[C@H](O)CN3C3(C(=O)Nc4c(Cl)cc(Cl)cc43)C2C(=O)N1c1cc(C(F)(F)F)cc(C(F)(F)F)c1]
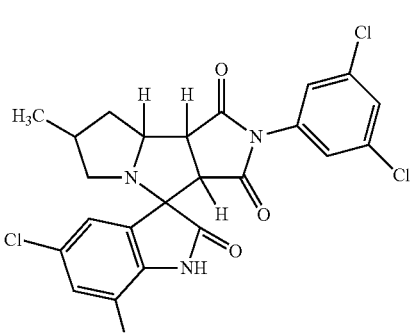
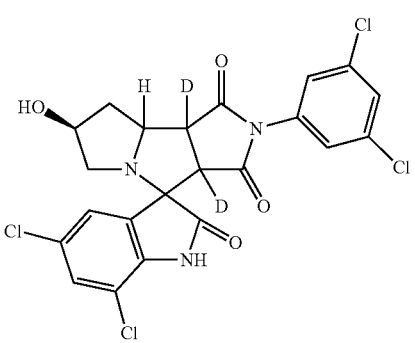 [SMILES: [2H]C12C(=O)N(c3cc(Cl)cc(Cl)c3)C(=O)C1([2H])C1(C(=O)Nc3c(Cl)cc(Cl)cc31)N1C[C@@H](O)CC12]

TABLE A-continued
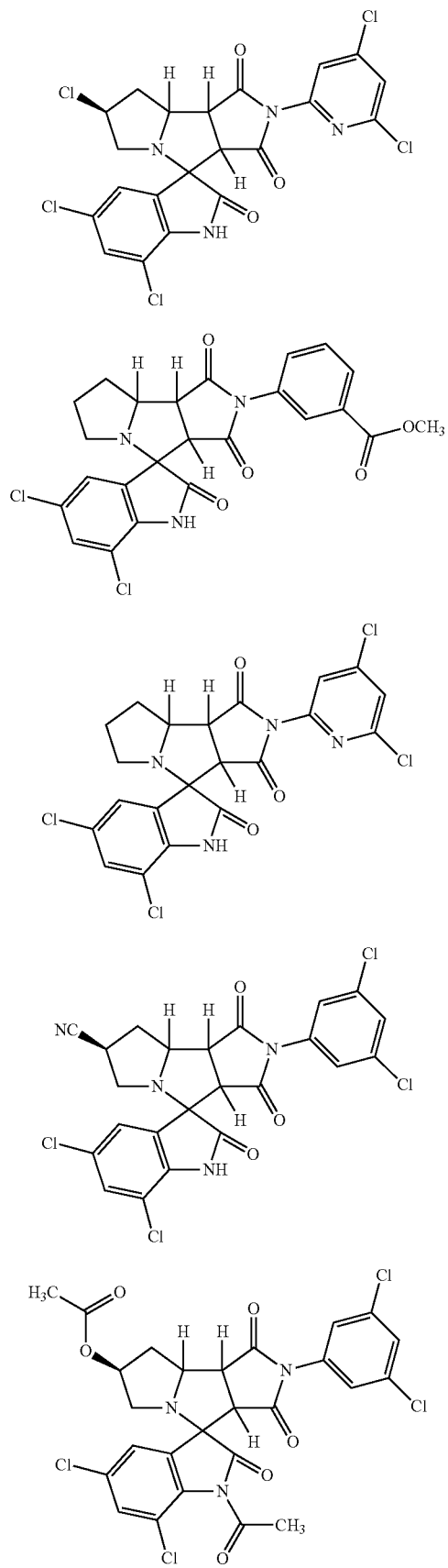
TABLE A-continued
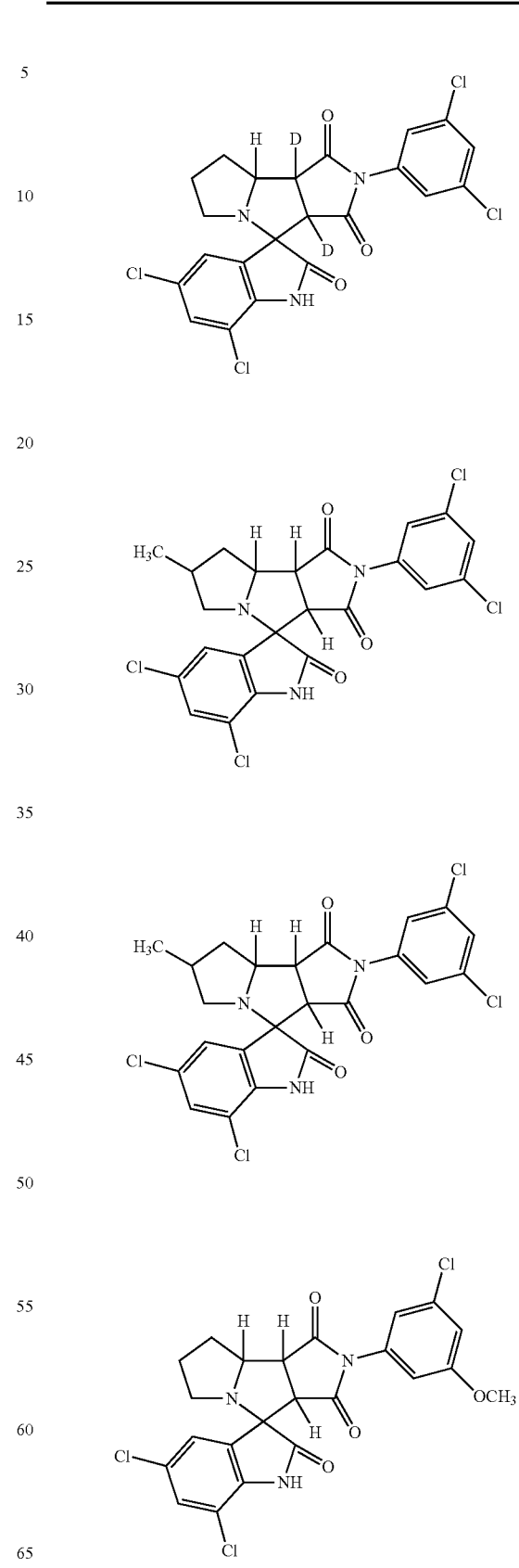

TABLE A-continued
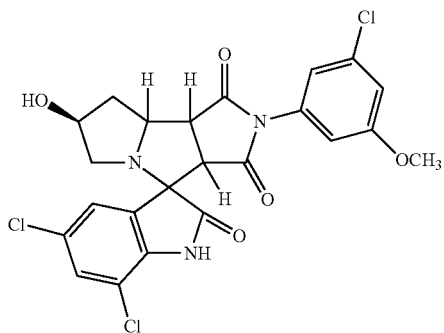 [SMILES: COc1cc(Cl)cc(N2C(=O)C3C4C[C@H](O)CN4C4(C(=O)Nc5c(Cl)cc(Cl)cc54)C3C2=O)c1]
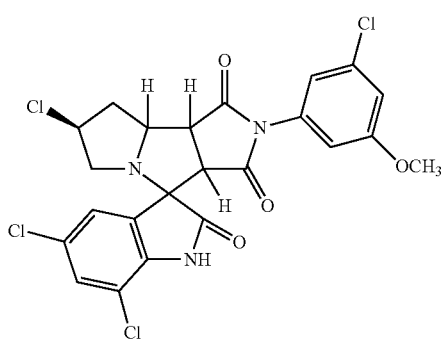 [SMILES: COc1cc(Cl)cc(N2C(=O)C3C4C[C@H](Cl)CN4C4(C(=O)Nc5c(Cl)cc(Cl)cc54)C3C2=O)c1]
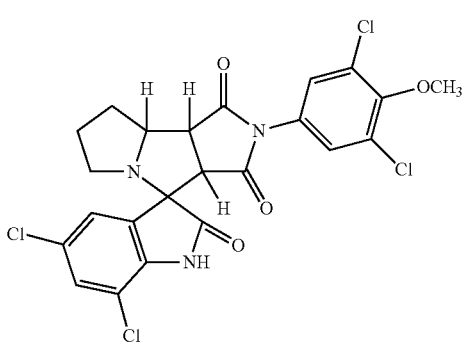 [SMILES: COc1c(Cl)cc(N2C(=O)C3C4CCCN4C4(C(=O)Nc5c(Cl)cc(Cl)cc54)C3C2=O)cc1Cl]
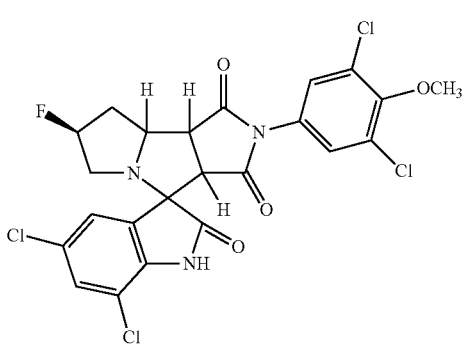 [SMILES: COc1c(Cl)cc(N2C(=O)C3C4C[C@H](F)CN4C4(C(=O)Nc5c(Cl)cc(Cl)cc54)C3C2=O)cc1Cl]
TABLE A-continued
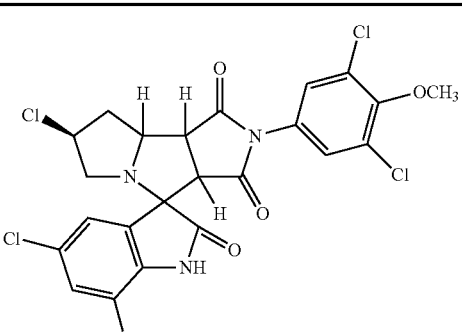
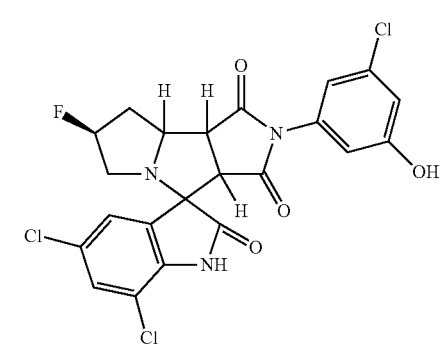 [SMILES: O=C1C2C3C[C@H](F)CN3C3(C(=O)Nc4c(Cl)cc(Cl)cc43)C2C(=O)N1c1cc(O)cc(Cl)c1]
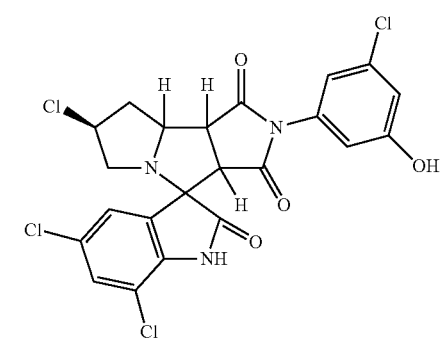 [SMILES: O=C1C2C3C[C@H](Cl)CN3C3(C(=O)Nc4c(Cl)cc(Cl)cc43)C2C(=O)N1c1cc(O)cc(Cl)c1]
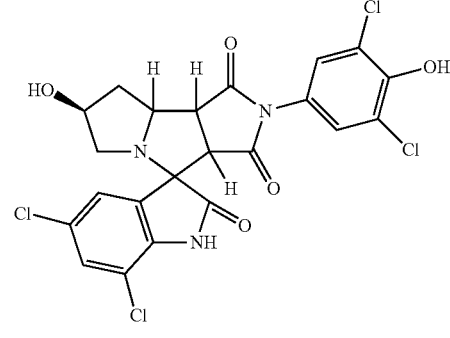 [SMILES: O=C1C2C3C[C@H](O)CN3C3(C(=O)Nc4c(Cl)cc(Cl)cc43)C2C(=O)N1c1cc(Cl)c(O)c(Cl)c1]

TABLE A-continued
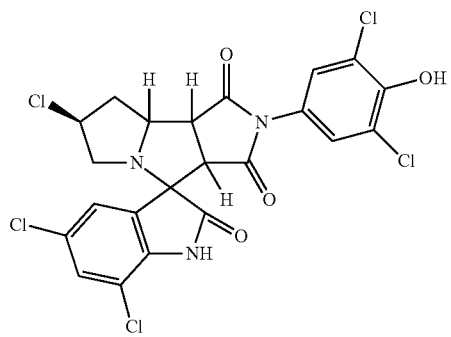 [SMILES: O=C1C2C3C[C@H](Cl)CN3C3(C(=O)Nc4c(Cl)cc(Cl)cc43)C2C(=O)N1c1cc(Cl)c(O)c(Cl)c1]
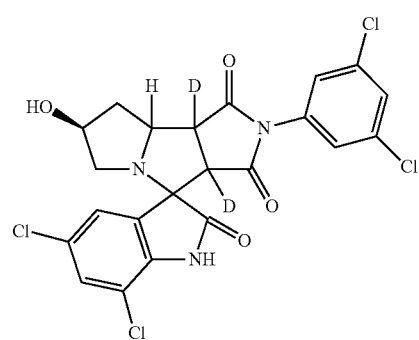 [SMILES: [2H]C12C(=O)N(c3cc(Cl)cc(Cl)c3)C(=O)C1([2H])C1(C(=O)Nc3c(Cl)cc(Cl)cc31)N1C[C@@H](O)CC12]
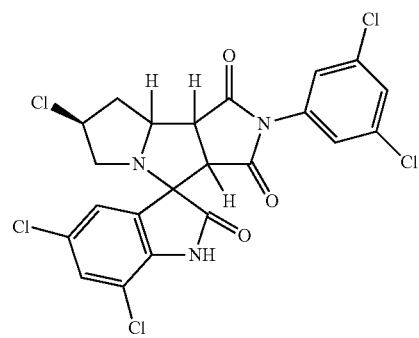 [SMILES: O=C1C2C3C[C@H](Cl)CN3C3(C(=O)Nc4c(Cl)cc(Cl)cc43)C2C(=O)N1c1cc(Cl)cc(Cl)c1]
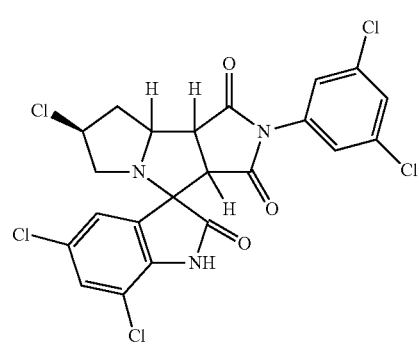
TABLE A-continued
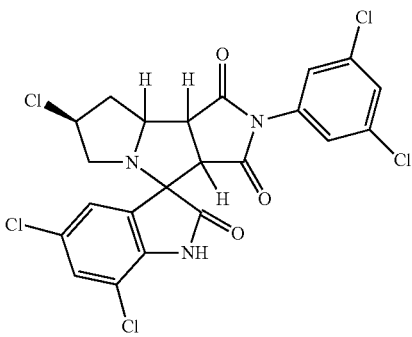
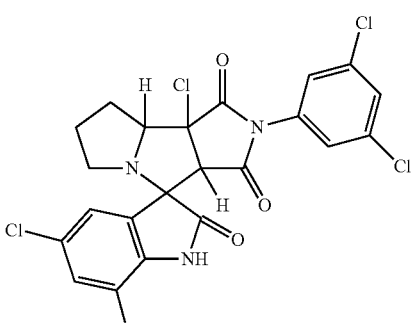
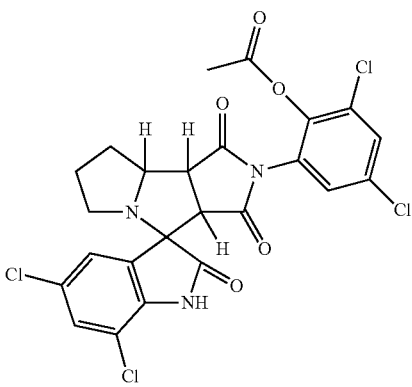 [SMILES: CC(=O)Oc1c(Cl)cc(Cl)cc1N1C(=O)C2C3CCCN3C3(C(=O)Nc4c(Cl)cc(Cl)cc43)C2C1=O]
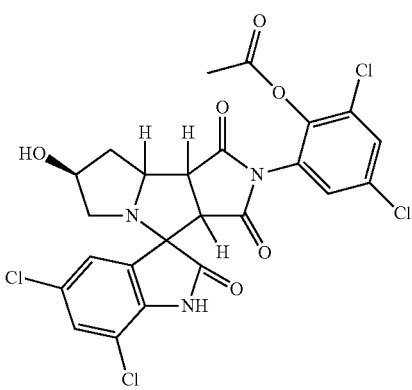 [SMILES: CC(=O)Oc1c(Cl)cc(Cl)cc1N1C(=O)C2C3C[C@H](O)CN3C3(C(=O)Nc4c(Cl)cc(Cl)cc43)C2C1=O]

TABLE A-continued
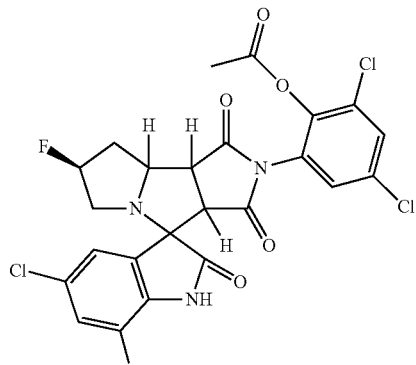
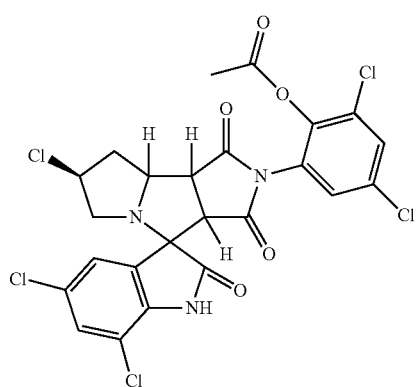
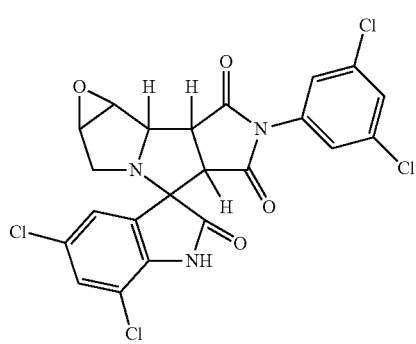 [SMILES: O=C1C2C3C4OC4CN3C3(C(=O)Nc4c(Cl)cc(Cl)cc43)C2C(=O)N1c1cc(Cl)cc(Cl)c1]
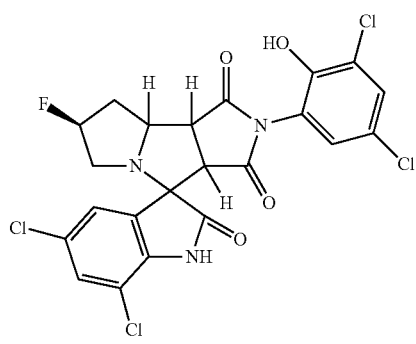 [SMILES: O=C1C2C3C[C@H](F)CN3C3(C(=O)Nc4c(Cl)cc(Cl)cc43)C2C(=O)N1c1cc(Cl)cc(Cl)c1O]
TABLE A-continued
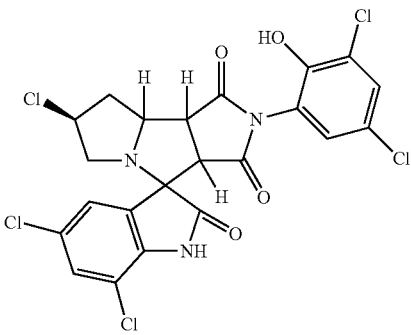 [SMILES: O=C1C2C3C[C@H](Cl)CN3C3(C(=O)Nc4c(Cl)cc(Cl)cc43)C2C(=O)N1c1cc(Cl)cc(Cl)c1O]
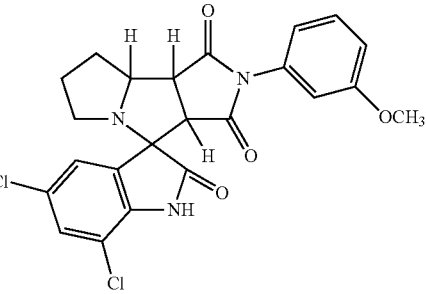
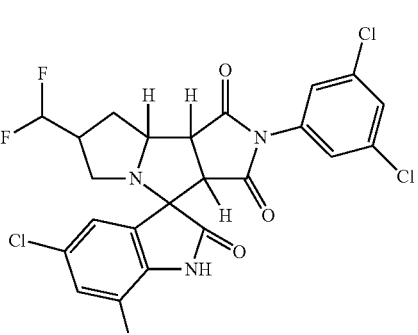
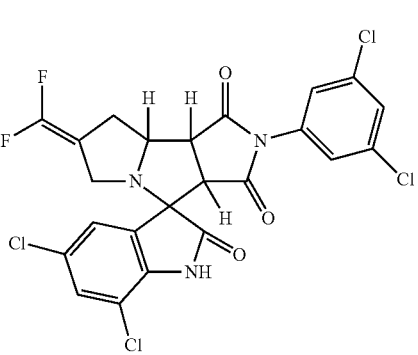 [SMILES: O=C1C2C3CC(=C(F)F)CN3C3(C(=O)Nc4c(Cl)cc(Cl)cc43)C2C(=O)N1c1cc(Cl)cc(Cl)c1]
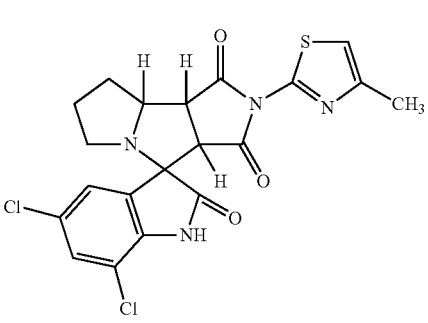 [SMILES: Cc1csc(N2C(=O)C3C4CCCN4C4(C(=O)Nc5c(Cl)cc(Cl)cc54)C3C2=O)n1]

TABLE A-continued
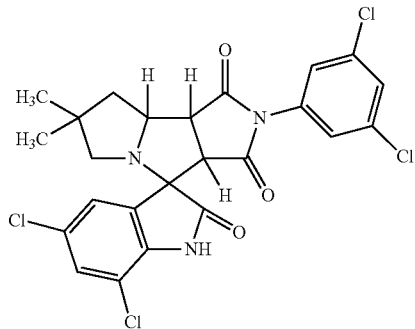 [SMILES: CC1(C)CC2C3C(=O)N(c4cc(Cl)cc(Cl)c4)C(=O)C3C3(C(=O)Nc4c(Cl)cc(Cl)cc43)N2C1]
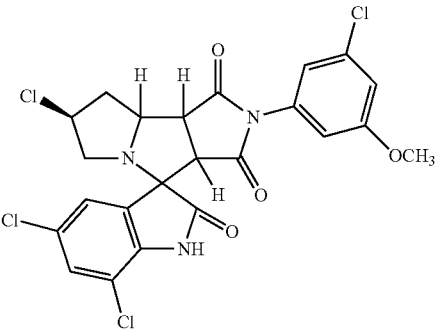
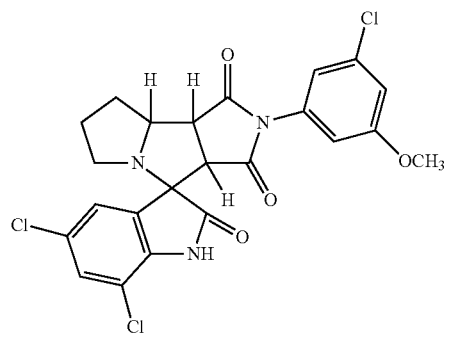 [SMILES: COc1cc(Cl)cc(N2C(=O)C3C4CCCN4C4(C(=O)Nc5c(Cl)cc(Cl)cc54)C3C2=O)c1]
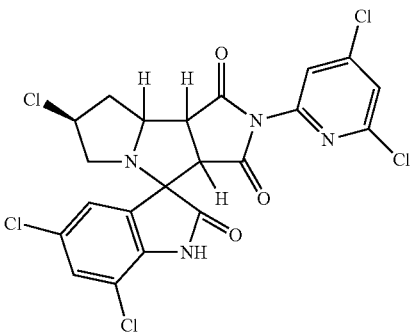
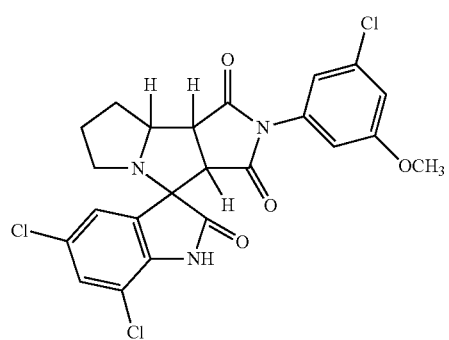 [SMILES: COc1cc(Cl)cc(N2C(=O)C3C4CCCN4C4(C(=O)Nc5c(Cl)cc(Cl)cc54)C3C2=O)c1]
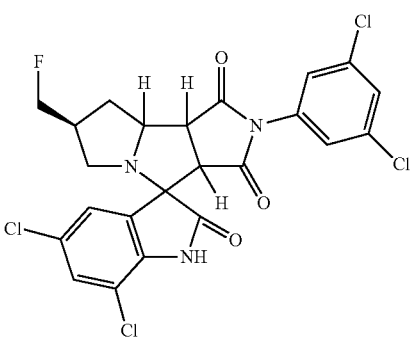
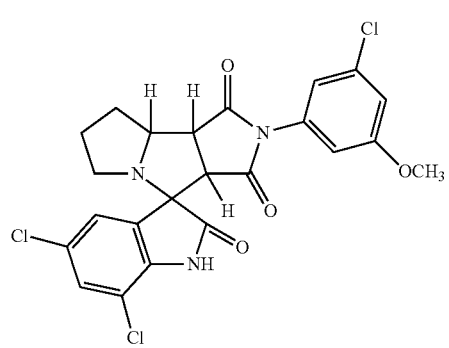 [SMILES: COc1cc(Cl)cc(N2C(=O)C3C4CCCN4C4(C(=O)Nc5c(Cl)cc(Cl)cc54)C3C2=O)c1]
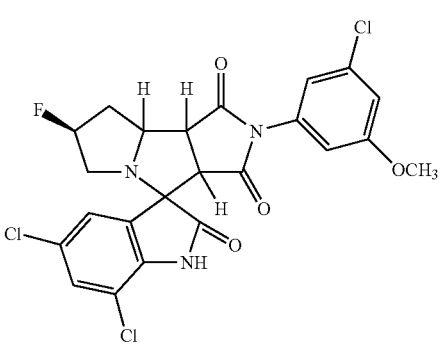 [SMILES: COc1cc(Cl)cc(N2C(=O)C3C4C[C@H](Cl)CN4C4(C(=O)Nc5c(Cl)cc(Cl)cc54)C3C2=O)c1]

TABLE A-continued
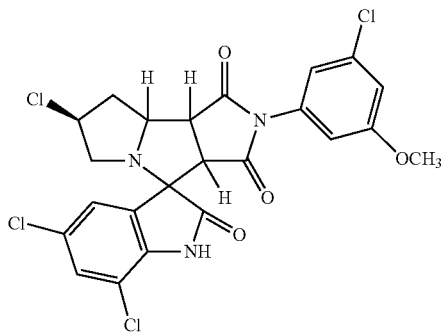 [SMILES: COc1cc(Cl)cc(N2C(=O)C3C4C[C@H](Cl)CN4C4(C(=O)Nc5c(Cl)cc(Cl)cc54)C3C2=O)c1]
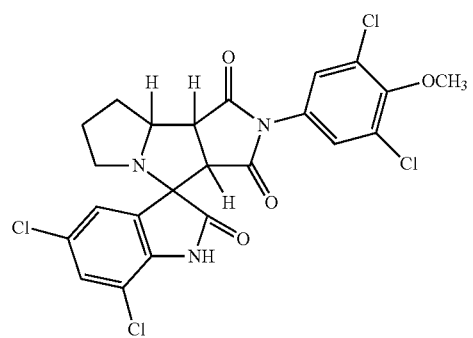 [SMILES: COc1c(Cl)cc(N2C(=O)C3C4CCCN4C4(C(=O)Nc5c(Cl)cc(Cl)cc54)C3C2=O)cc1Cl]
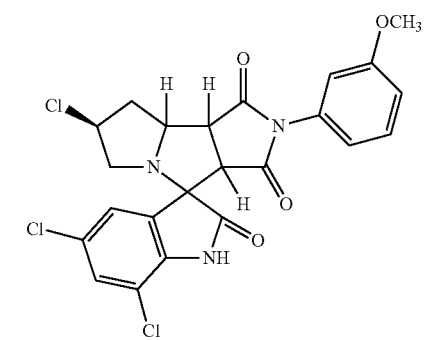 [SMILES: COc1cccc(N2C(=O)C3C4C[C@H](Cl)CN4C4(C(=O)Nc5c(Cl)cc(Cl)cc54)C3C2=O)c1]
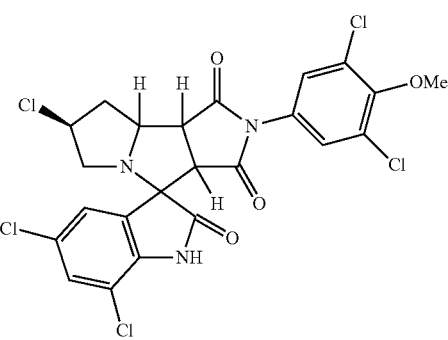 [SMILES: COc1c(Cl)cc(N2C(=O)C3C4C[C@H](Cl)CN4C4(C(=O)Nc5c(Cl)cc(Cl)cc54)C3C2=O)cc1Cl]
TABLE A-continued
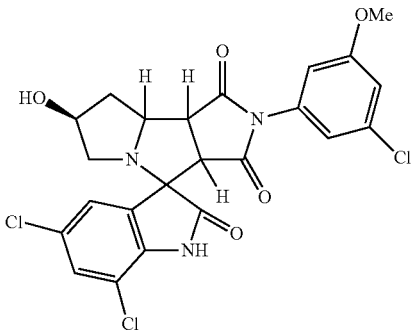 [SMILES: COc1cc(Cl)cc(N2C(=O)C3C4C[C@H](O)CN4C4(C(=O)Nc5c(Cl)cc(Cl)cc54)C3C2=O)c1]
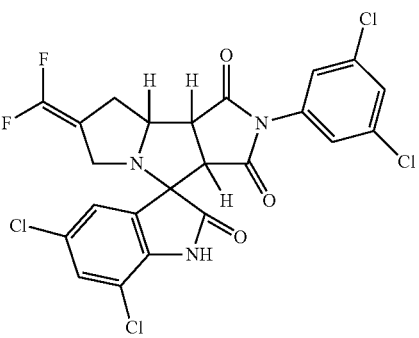
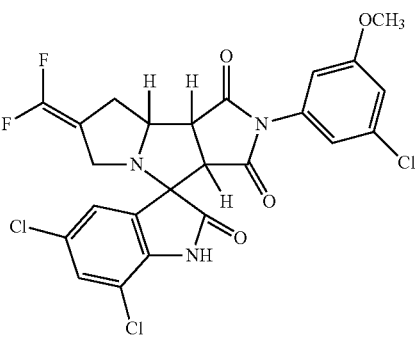
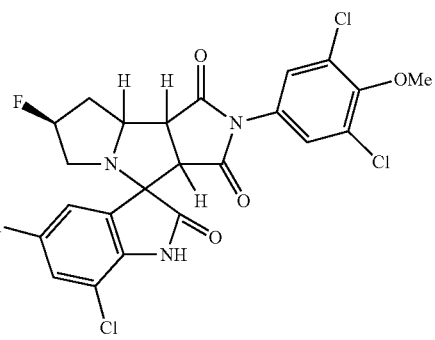

TABLE A-continued
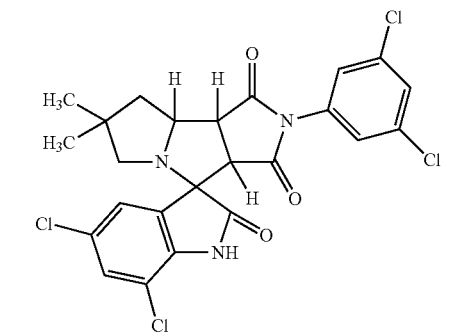 [SMILES: CC1(C)CC2C3C(=O)N(c4cc(Cl)cc(Cl)c4)C(=O)C3C3(C(=O)Nc4c(Cl)cc(Cl)cc43)N2C1]
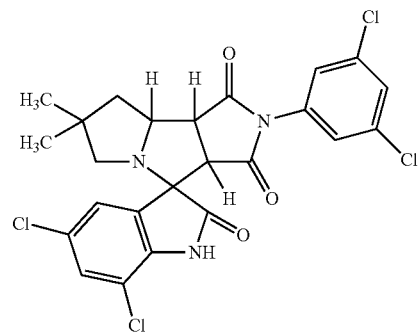 [SMILES: CC1(C)CC2C3C(=O)N(c4cc(Cl)cc(Cl)c4)C(=O)C3C3(C(=O)Nc4c(Cl)cc(Cl)cc43)N2C1]
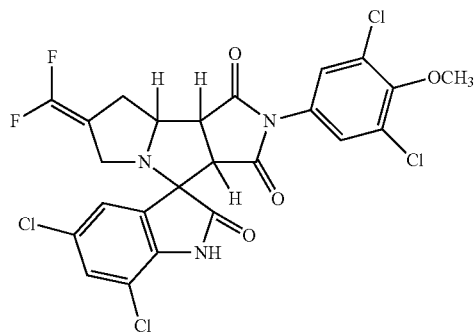 [SMILES: COc1c(Cl)cc(N2C(=O)C3C4CC(=C(F)F)CN4C4(C(=O)Nc5c(Cl)cc(Cl)cc54)C3C2=O)cc1Cl]
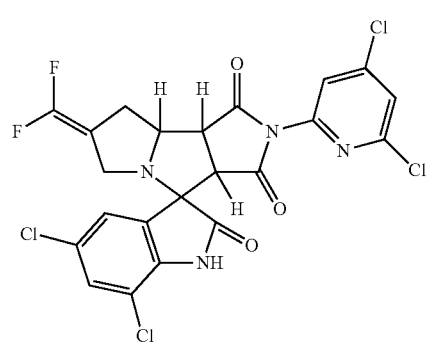 [SMILES: O=C1C2C3CC(=C(F)F)CN3C3(C(=O)Nc4c(Cl)cc(Cl)cc43)C2C(=O)N1c1cc(Cl)cc(Cl)n1]
TABLE A-continued
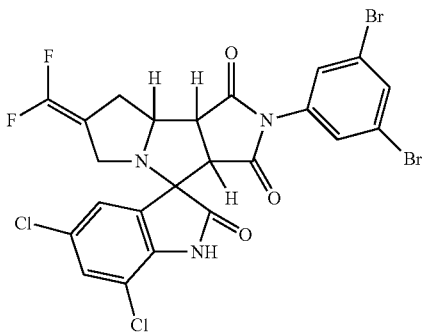
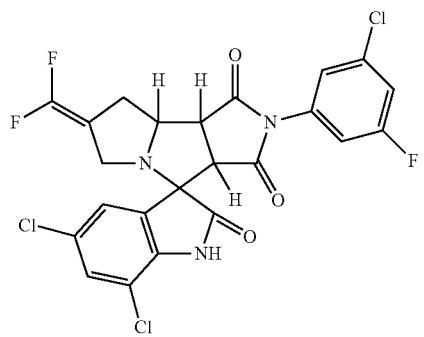 [SMILES: O=C1C2C3CC(=C(F)F)CN3C3(C(=O)Nc4c(Cl)cc(Cl)cc43)C2C(=O)N1c1cc(F)cc(Cl)c1]
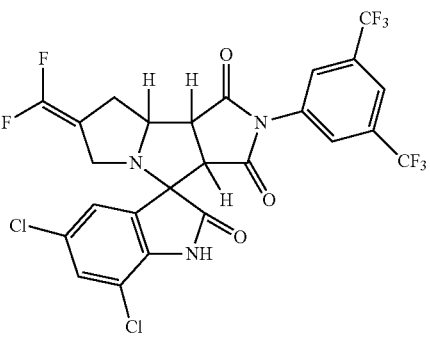 [SMILES: O=C1C2C3CC(=C(F)F)CN3C3(C(=O)Nc4c(Cl)cc(Cl)cc43)C2C(=O)N1c1cc(C(F)(F)F)cc(C(F)(F)F)c1]
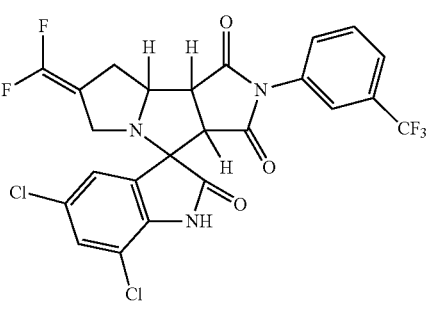 [SMILES: O=C1C2C3CC(=C(F)F)CN3C3(C(=O)Nc4c(Cl)cc(Cl)cc43)C2C(=O)N1c1cccc(C(F)(F)F)c1]
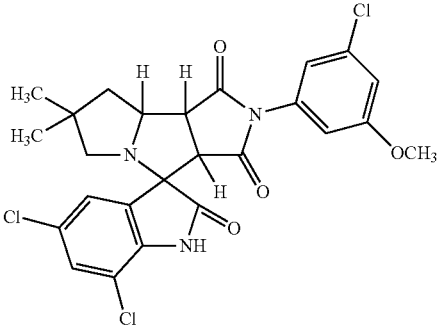 [SMILES: COc1cc(Cl)cc(N2C(=O)C3C4CC(C)(C)CN4C4(C(=O)Nc5c(Cl)cc(Cl)cc54)C3C2=O)c1]

TABLE A-continued
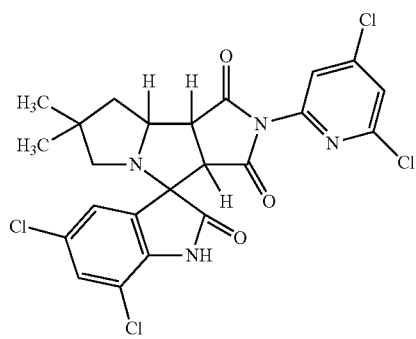 [SMILES: CC1(C)CC2C3C(=O)N(c4cc(Cl)cc(Cl)n4)C(=O)C3C3(C(=O)Nc4c(Cl)cc(Cl)cc43)N2C1]
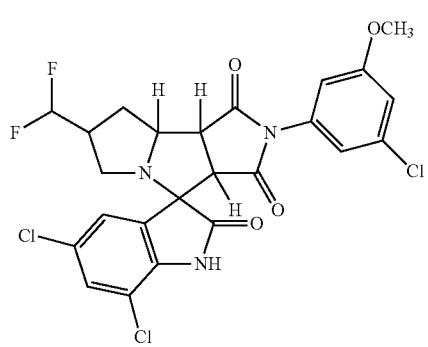 [SMILES: COc1cc(Cl)cc(N2C(=O)C3C4CC(C(F)F)CN4C4(C(=O)Nc5c(Cl)cc(Cl)cc54)C3C2=O)c1]
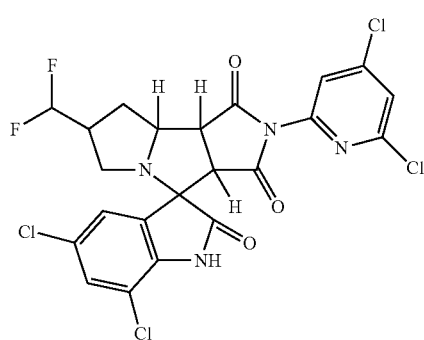 [SMILES: O=C1C2C3CC(C(F)F)CN3C3(C(=O)Nc4c(Cl)cc(Cl)cc43)C2C(=O)N1c1cc(Cl)cc(Cl)n1]
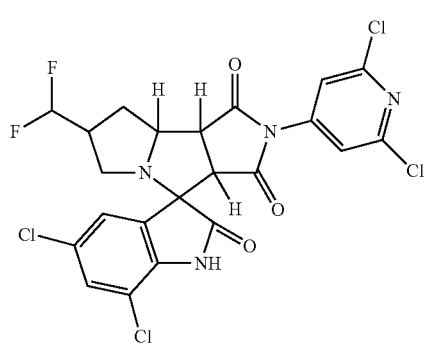 [SMILES: O=C1C2C3CC(C(F)F)CN3C3(C(=O)Nc4c(Cl)cc(Cl)cc43)C2C(=O)N1c1cc(Cl)nc(Cl)c1]
TABLE A-continued
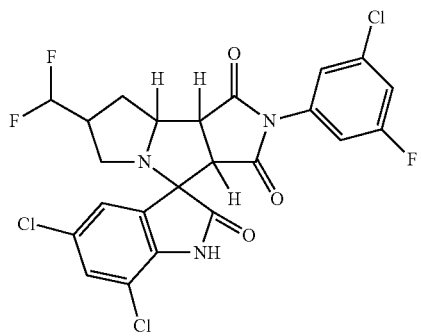 [SMILES: O=C1C2C3CC(C(F)F)CN3C3(C(=O)Nc4c(Cl)cc(Cl)cc43)C2C(=O)N1c1cc(F)cc(Cl)c1]
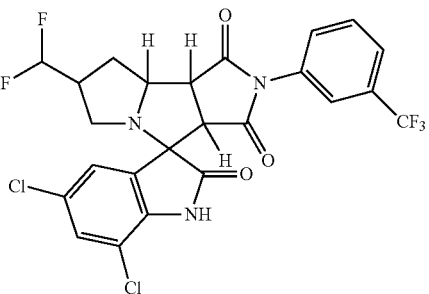 [SMILES: O=C1C2C3CC(C(F)F)CN3C3(C(=O)Nc4c(Cl)cc(Cl)cc43)C2C(=O)N1c1cccc(C(F)(F)F)c1]
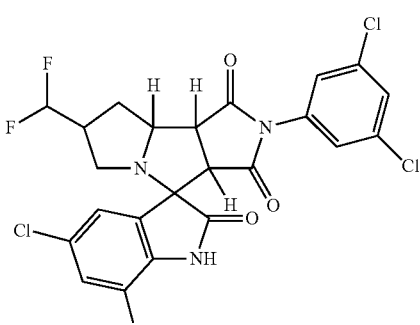
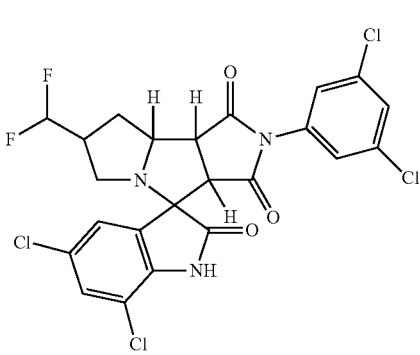 [SMILES: O=C1C2C3CC(C(F)F)CN3C3(C(=O)Nc4c(Cl)cc(Cl)cc43)C2C(=O)N1c1cc(Cl)cc(Cl)c1]
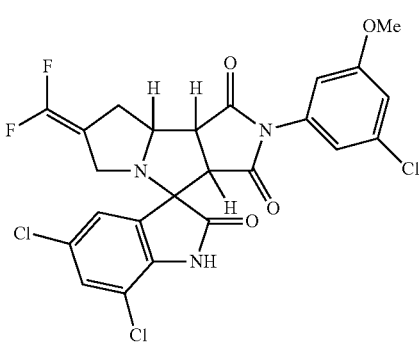 [SMILES: COc1cc(Cl)cc(N2C(=O)C3C4CC(=C(F)F)CN4C4(C(=O)Nc5c(Cl)cc(Cl)cc54)C3C2=O)c1]

TABLE A-continued
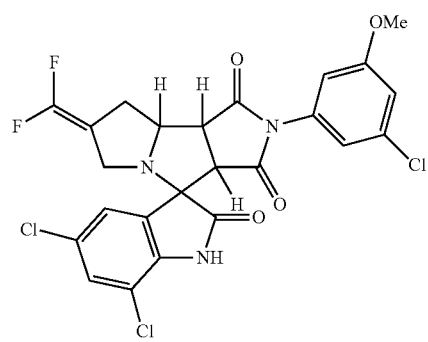 [SMILES: COc1cc(Cl)cc(N2C(=O)C3C4CC(=C(F)F)CN4C4(C(=O)Nc5c(Cl)cc(Cl)cc54)C3C2=O)c1]
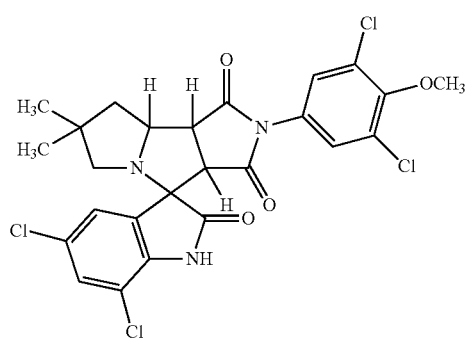 [SMILES: COc1c(Cl)cc(N2C(=O)C3C4CC(C)(C)CN4C4(C(=O)Nc5c(Cl)cc(Cl)cc54)C3C2=O)cc1Cl]
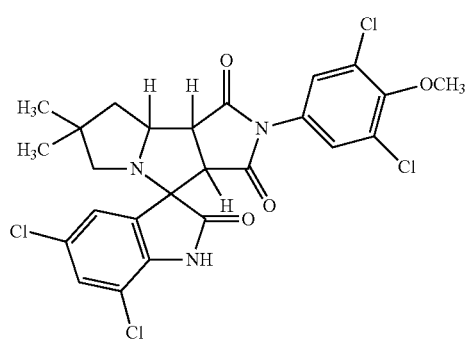 [SMILES: COc1c(Cl)cc(N2C(=O)C3C4CC(C)(C)CN4C4(C(=O)Nc5c(Cl)cc(Cl)cc54)C3C2=O)cc1Cl]
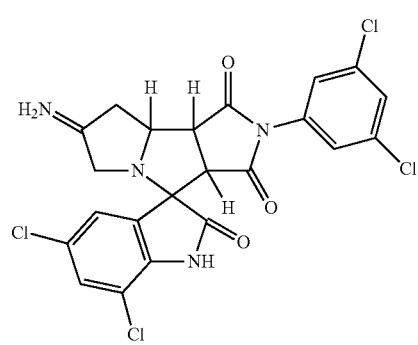 [SMILES: N=C1CC2C3C(=O)N(c4cc(Cl)cc(Cl)c4)C(=O)C3C3(C(=O)Nc4c(Cl)cc(Cl)cc43)N2C1]
TABLE A-continued
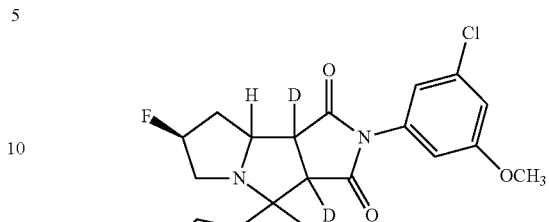
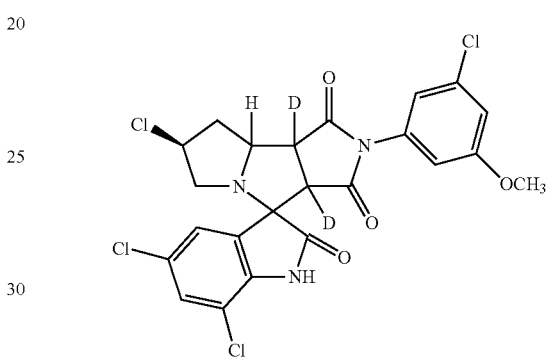
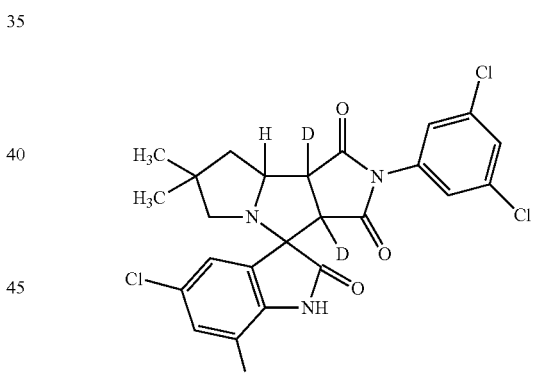
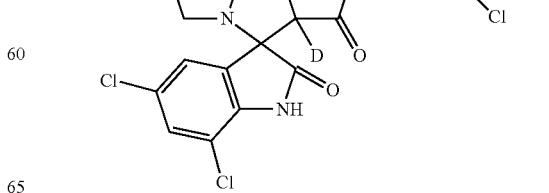

TABLE A-continued
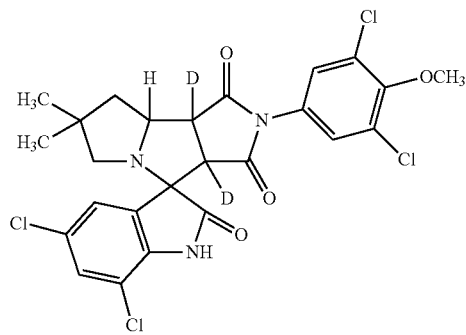 [SMILES: [2H]C12C(=O)N(c3cc(Cl)c(OC)c(Cl)c3)C(=O)C1([2H])C1(C(=O)Nc3c(Cl)cc(Cl)cc31)N1CC(C)(C)CC12]
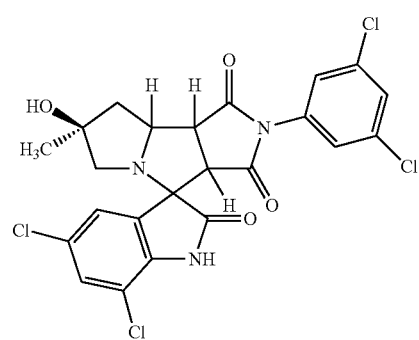 [SMILES: C[C@]1(O)CC2C3C(=O)N(c4cc(Cl)cc(Cl)c4)C(=O)C3C3(C(=O)Nc4c(Cl)cc(Cl)cc43)N2C1]
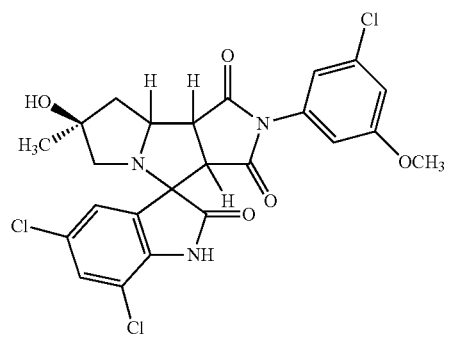
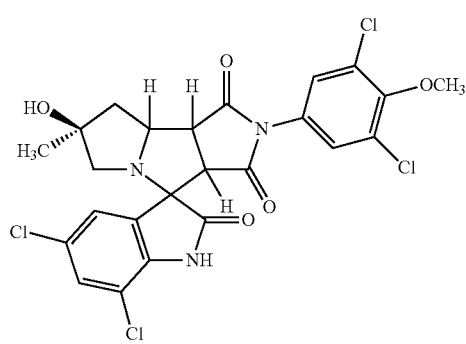 [SMILES: COc1c(Cl)cc(N2C(=O)C3C4C[C@](C)(O)CN4C4(C(=O)Nc5c(Cl)cc(Cl)cc54)C3C2=O)cc1Cl]
TABLE A-continued
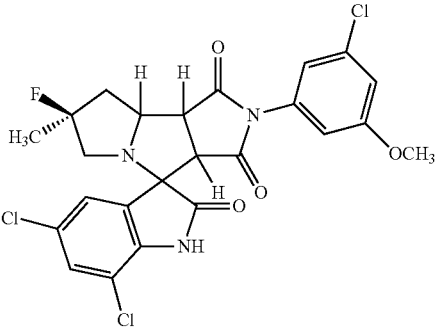 [SMILES: COc1cc(Cl)cc(N2C(=O)C3C4C[C@](C)(F)CN4C4(C(=O)Nc5c(Cl)cc(Cl)cc54)C3C2=O)c1]
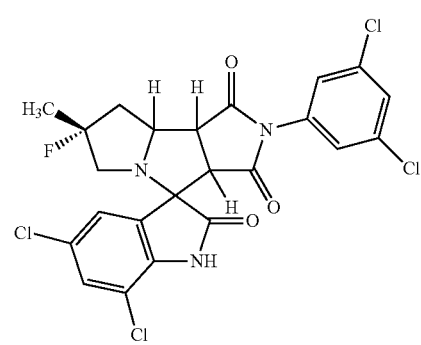
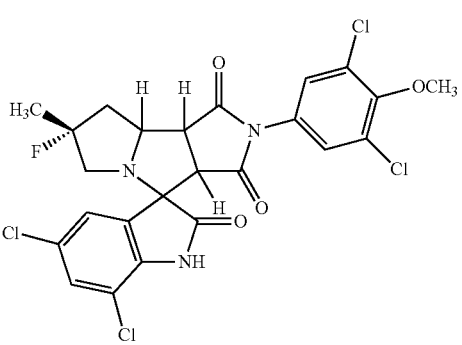 [SMILES: COc1c(Cl)cc(N2C(=O)C3C4C[C@@](C)(F)CN4C4(C(=O)Nc5c(Cl)cc(Cl)cc54)C3C2=O)cc1Cl]
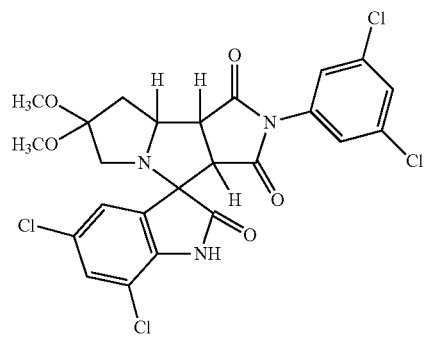 [SMILES: COC1(OC)CC2C3C(=O)N(c4cc(Cl)cc(Cl)c4)C(=O)C3C3(C(=O)Nc4c(Cl)cc(Cl)cc43)N2C1]

TABLE A-continued
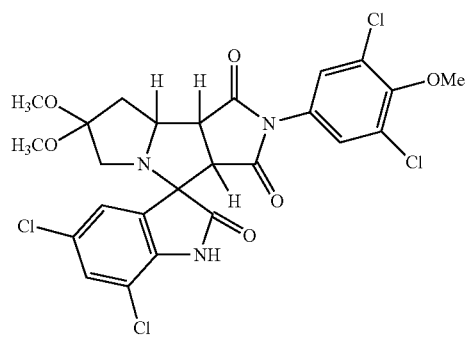 [SMILES: COc1c(Cl)cc(N2C(=O)C3C4CC(OC)(OC)CN4C4(C(=O)Nc5c(Cl)cc(Cl)cc54)C3C2=O)cc1Cl]
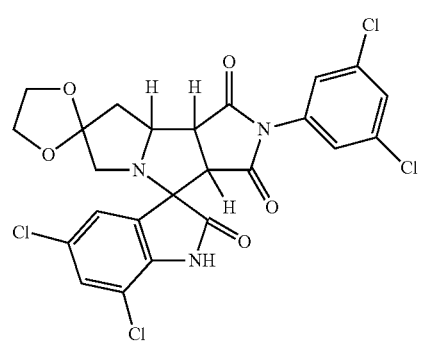 [SMILES: O=C1C2C3CC4(CN3C3(C(=O)Nc5c(Cl)cc(Cl)cc53)C2C(=O)N1c1cc(Cl)cc(Cl)c1)OCCO4]
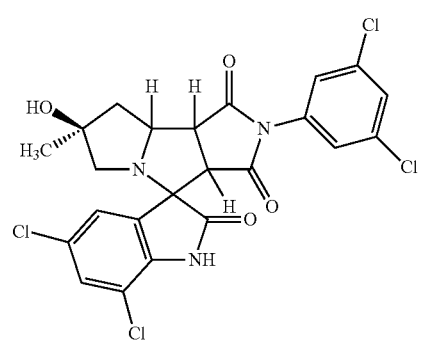 [SMILES: C[C@]1(O)CC2C3C(=O)N(c4cc(Cl)cc(Cl)c4)C(=O)C3C3(C(=O)Nc4c(Cl)cc(Cl)cc43)N2C1]
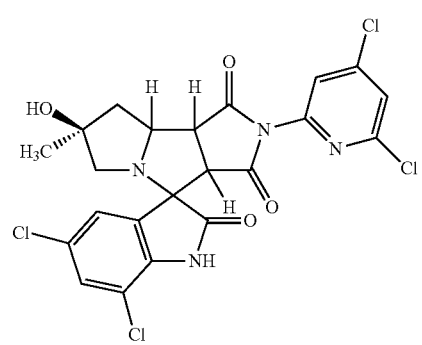
TABLE A-continued
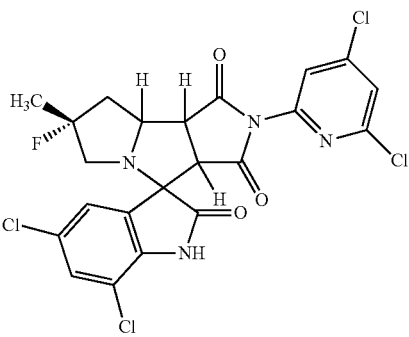 [SMILES: C[C@@]1(F)CC2C3C(=O)N(c4cc(Cl)cc(Cl)n4)C(=O)C3C3(C(=O)Nc4c(Cl)cc(Cl)cc43)N2C1]
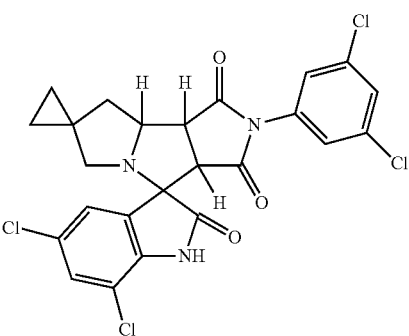 [SMILES: O=C1C2C3CC4(CC4)CN3C3(C(=O)Nc4c(Cl)cc(Cl)cc43)C2C(=O)N1c1cc(Cl)cc(Cl)c1]
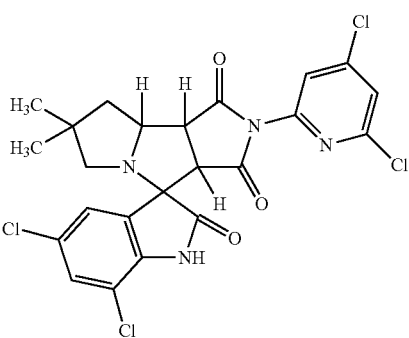 [SMILES: CC1(C)CC2C3C(=O)N(c4cc(Cl)cc(Cl)n4)C(=O)C3C3(C(=O)Nc4c(Cl)cc(Cl)cc43)N2C1]
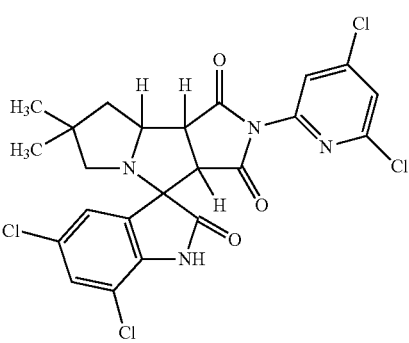 [SMILES: CC1(C)CC2C3C(=O)N(c4cc(Cl)cc(Cl)n4)C(=O)C3C3(C(=O)Nc4c(Cl)cc(Cl)cc43)N2C1]

TABLE A-continued
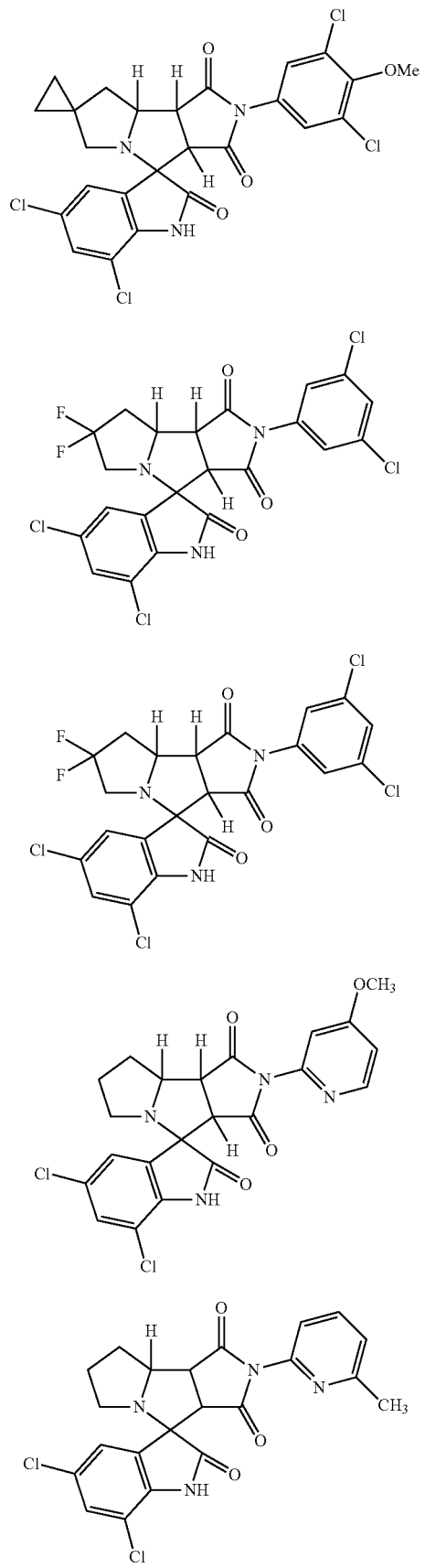
TABLE A-continued
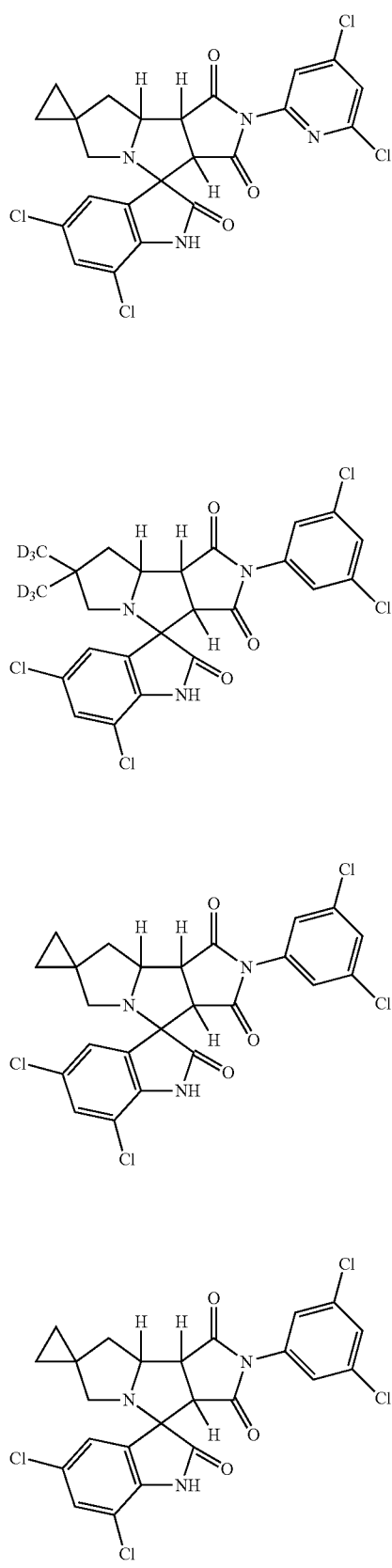

TABLE A-continued
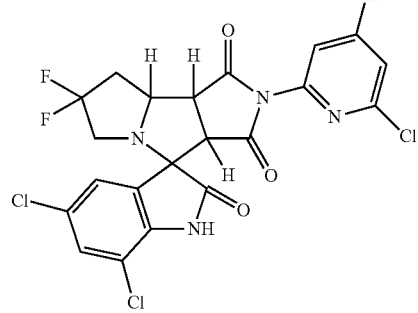
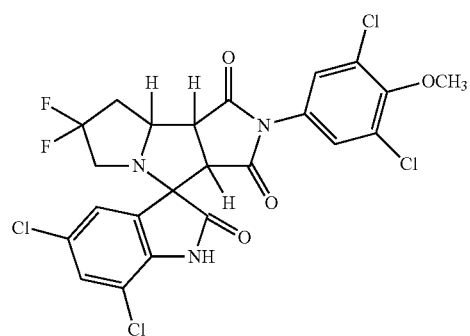 [SMILES: COc1c(Cl)cc(N2C(=O)C3C4CC(F)(F)CN4C4(C(=O)Nc5c(Cl)cc(Cl)cc54)C3C2=O)cc1Cl]
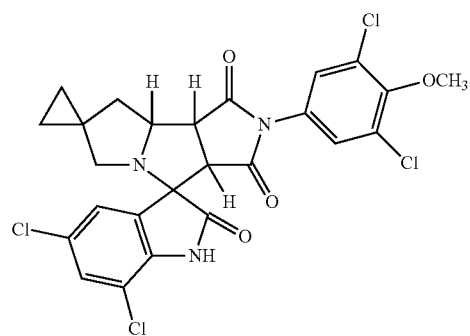 [SMILES: COc1c(Cl)cc(N2C(=O)C3C4CC5(CC5)CN4C4(C(=O)Nc5c(Cl)cc(Cl)cc54)C3C2=O)cc1Cl]
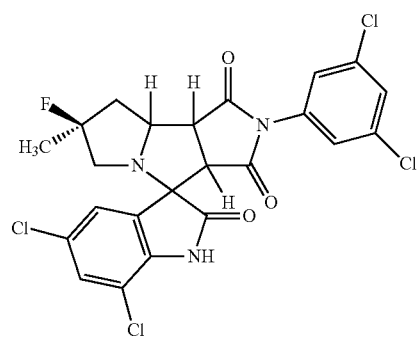
TABLE A-continued
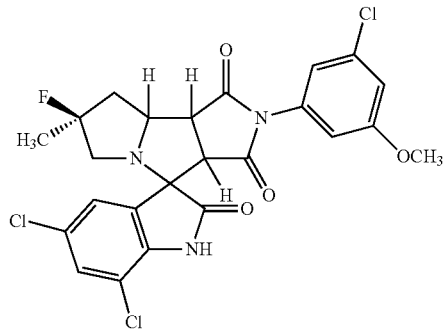 [SMILES: COc1cc(Cl)cc(N2C(=O)C3C4C[C@](C)(F)CN4C4(C(=O)Nc5c(Cl)cc(Cl)cc54)C3C2=O)c1]
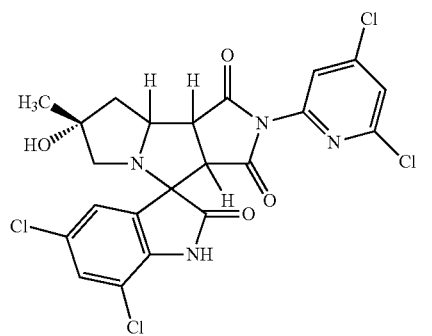 [SMILES: C[C@@]1(O)CC2C3C(=O)N(c4cc(Cl)cc(Cl)n4)C(=O)C3C3(C(=O)Nc4c(Cl)cc(Cl)cc43)N2C1]
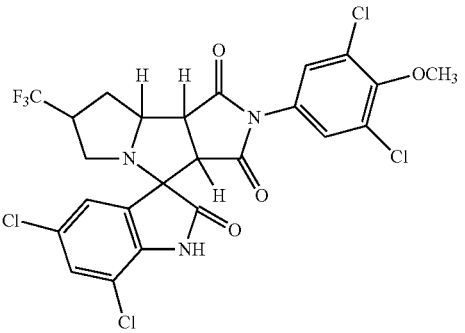 [SMILES: COc1c(Cl)cc(N2C(=O)C3C4CC(C(F)(F)F)CN4C4(C(=O)Nc5c(Cl)cc(Cl)cc54)C3C2=O)cc1Cl]
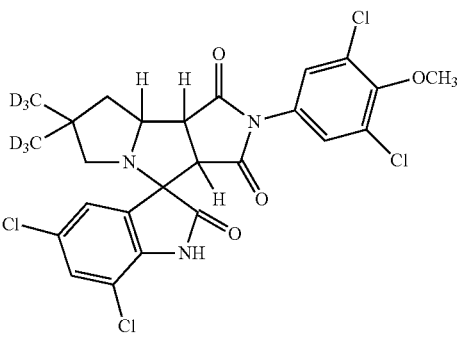 [SMILES: [2H]C([2H])([2H])C1(C([2H])([2H])[2H])CC2C3C(=O)N(c4cc(Cl)c(OC)c(Cl)c4)C(=O)C3C3(C(=O)Nc4c(Cl)cc(Cl)cc43)N2C1]

TABLE A-continued
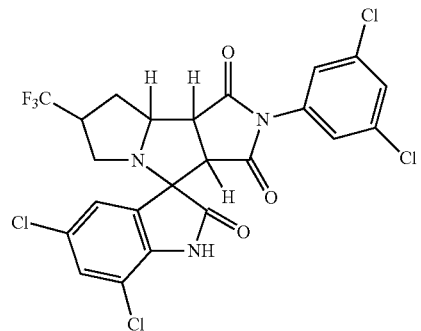 [SMILES: O=C1C2C3CC(C(F)(F)F)CN3C3(C(=O)Nc4c(Cl)cc(Cl)cc43)C2C(=O)N1c1cc(Cl)cc(Cl)c1]
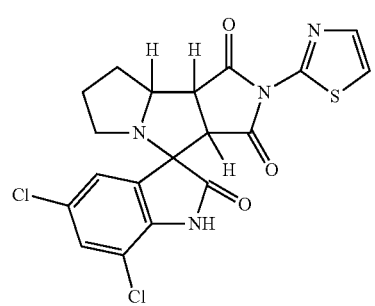 [SMILES: O=C1C2C3CCCN3C3(C(=O)Nc4c(Cl)cc(Cl)cc43)C2C(=O)N1c1nccs1]
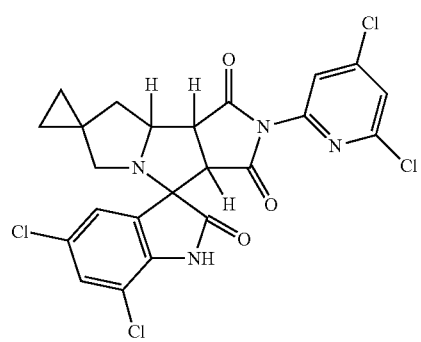 [SMILES: O=C1C2C3CC4(CC4)CN3C3(C(=O)Nc4c(Cl)cc(Cl)cc43)C2C(=O)N1c1cc(Cl)cc(Cl)n1]
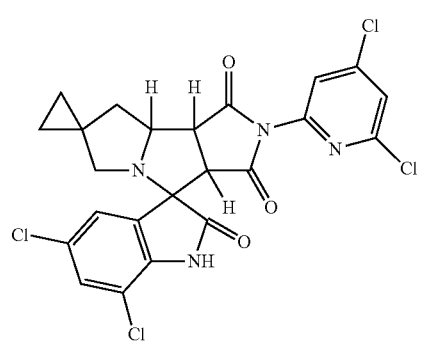
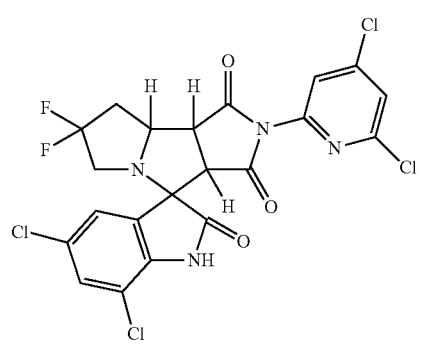 [SMILES: O=C1C2C3CC(F)(F)CN3C3(C(=O)Nc4c(Cl)cc(Cl)cc43)C2C(=O)N1c1cc(Cl)cc(Cl)n1]
TABLE A-continued
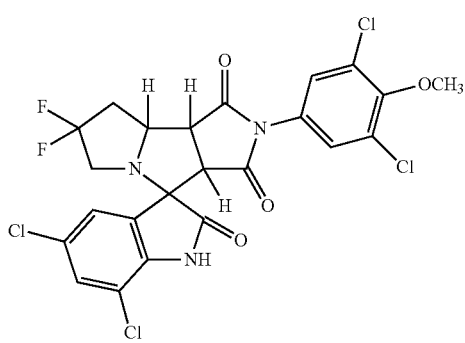 [SMILES: COc1c(Cl)cc(N2C(=O)C3C4CC(F)(F)CN4C4(C(=O)Nc5c(Cl)cc(Cl)cc54)C3C2=O)cc1Cl]
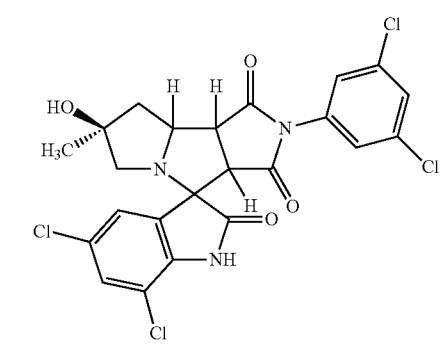 [SMILES: C[C@]1(O)CC2C3C(=O)N(c4cc(Cl)cc(Cl)c4)C(=O)C3C3(C(=O)Nc4c(Cl)cc(Cl)cc43)N2C1]
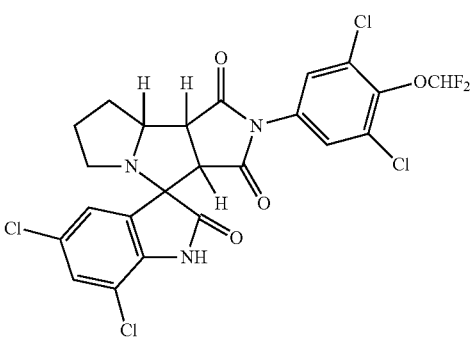 [SMILES: O=C1C2C3CCCN3C3(C(=O)Nc4c(Cl)cc(Cl)cc43)C2C(=O)N1c1cc(Cl)c(OC(F)F)c(Cl)c1]
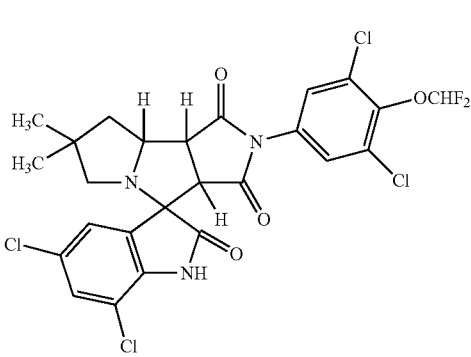 [SMILES: CC1(C)CC2C3C(=O)N(c4cc(Cl)c(OC(F)F)c(Cl)c4)C(=O)C3C3(C(=O)Nc4c(Cl)cc(Cl)cc43)N2C1]

TABLE A-continued
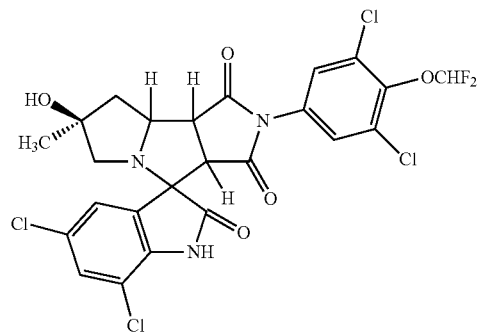 [SMILES: C[C@]1(O)CC2C3C(=O)N(c4cc(Cl)c(OC(F)F)c(Cl)c4)C(=O)C3C3(C(=O)Nc4c(Cl)cc(Cl)cc43)N2C1]
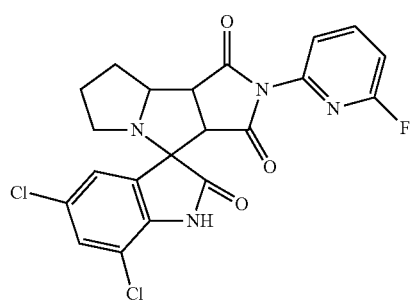 [SMILES: O=C1C2C3CCCN3C3(C(=O)Nc4c(Cl)cc(Cl)cc43)C2C(=O)N1c1cccc(F)n1]
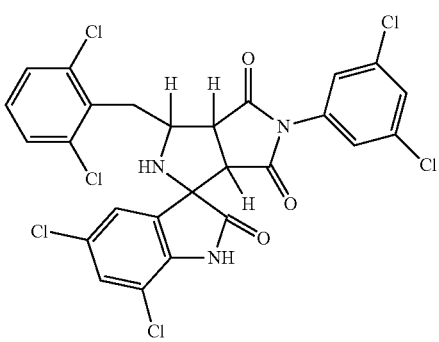 [SMILES: O=C1C2C(Cc3c(Cl)cccc3Cl)NC3(C(=O)Nc4c(Cl)cc(Cl)cc43)C2C(=O)N1c1cc(Cl)cc(Cl)c1]
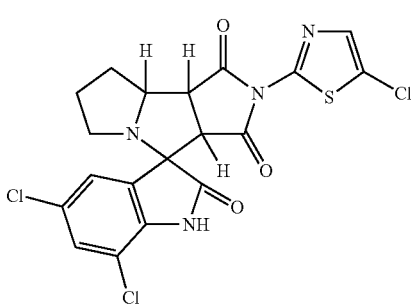 [SMILES: O=C1C2C3CCCN3C3(C(=O)Nc4c(Cl)cc(Cl)cc43)C2C(=O)N1c1ncc(Cl)s1]
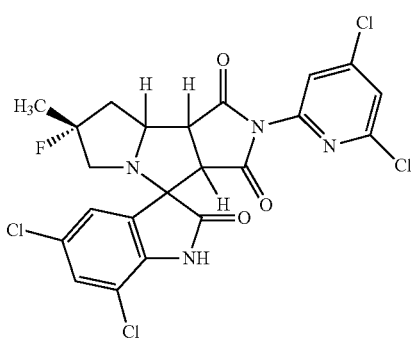 [SMILES: C[C@@]1(F)CC2C3C(=O)N(c4cc(Cl)cc(Cl)n4)C(=O)C3C3(C(=O)Nc4c(Cl)cc(Cl)cc43)N2C1]
TABLE A-continued
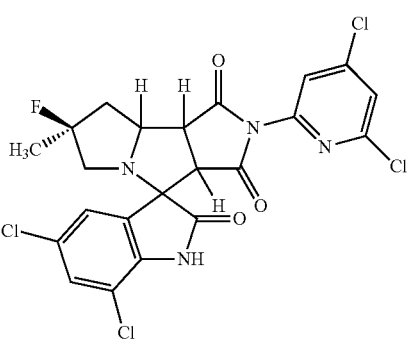 [SMILES: C[C@]1(F)CC2C3C(=O)N(c4cc(Cl)cc(Cl)n4)C(=O)C3C3(C(=O)Nc4c(Cl)cc(Cl)cc43)N2C1]
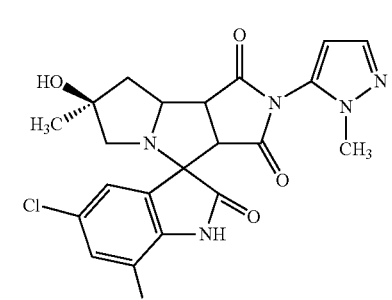
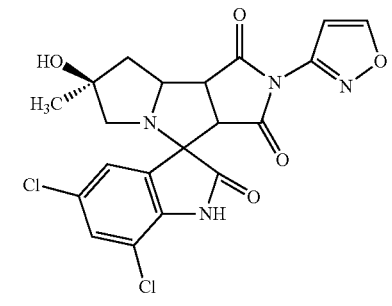 [SMILES: C[C@]1(O)CC2C3C(=O)N(c4ccon4)C(=O)C3C3(C(=O)Nc4c(Cl)cc(Cl)cc43)N2C1]
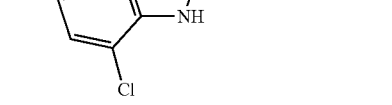

TABLE A-continued
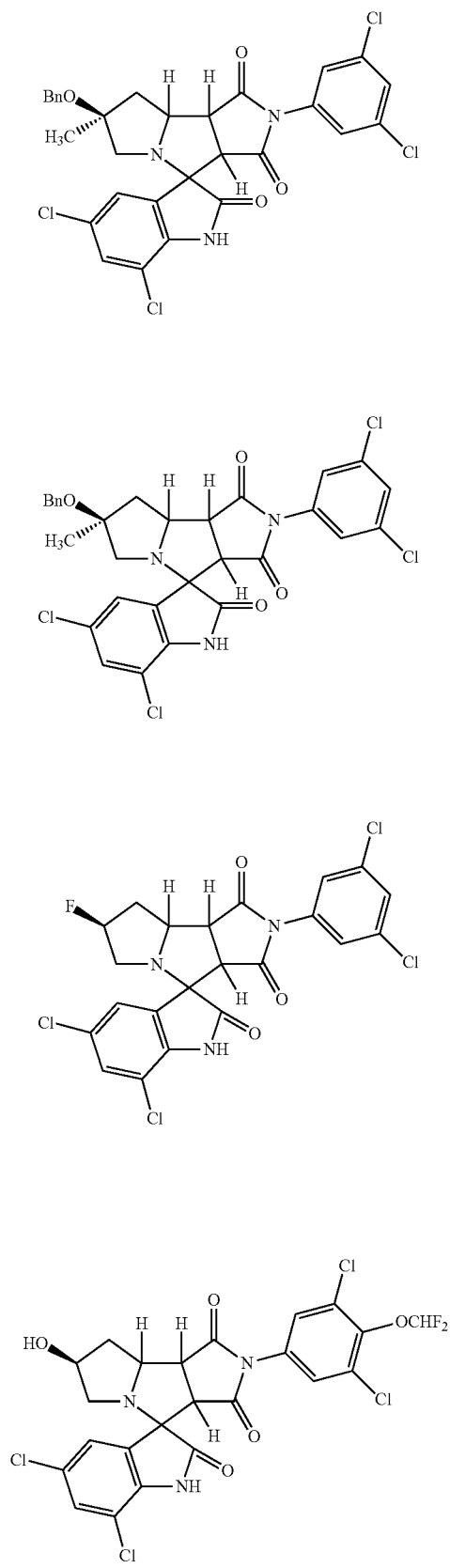
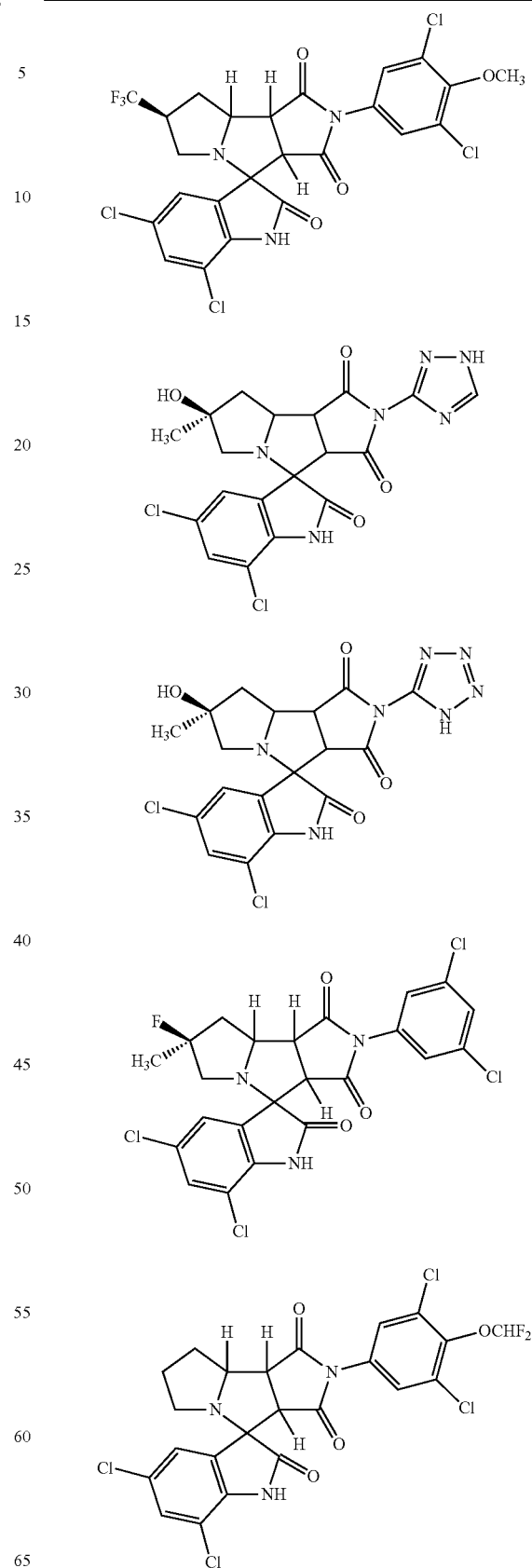

TABLE A-continued
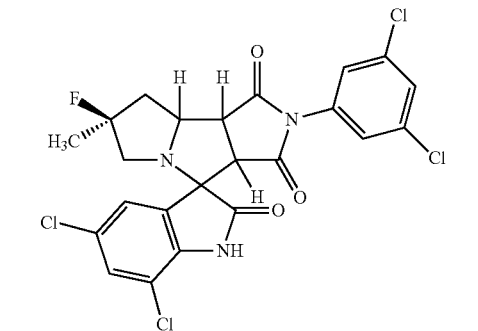 [SMILES: C[C@]1(F)CC2C3C(=O)N(c4cc(Cl)cc(Cl)c4)C(=O)C3C3(C(=O)Nc4c(Cl)cc(Cl)cc43)N2C1]
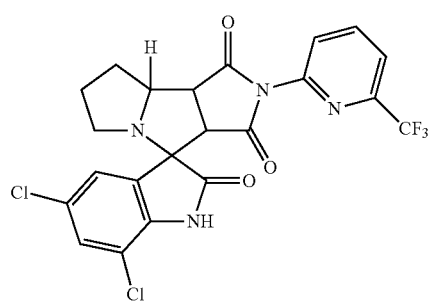 [SMILES: O=C1C2C3CCCN3C3(C(=O)Nc4c(Cl)cc(Cl)cc43)C2C(=O)N1c1cccc(C(F)(F)F)n1]
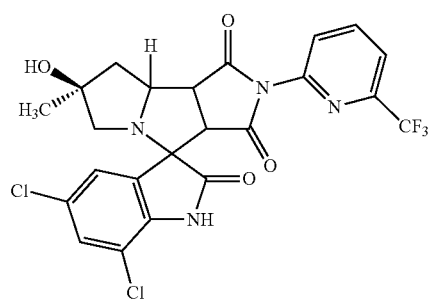 [SMILES: C[C@]1(O)CC2C3C(=O)N(c4cccc(C(F)(F)F)n4)C(=O)C3C3(C(=O)Nc4c(Cl)cc(Cl)cc43)N2C1]
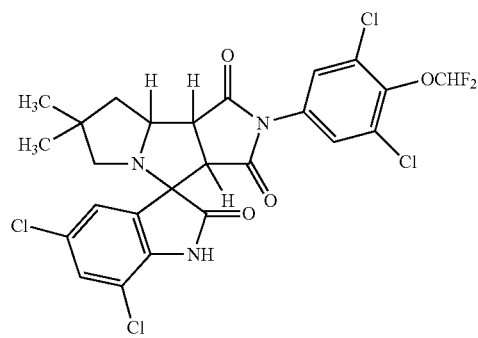 [SMILES: CC1(C)CC2C3C(=O)N(c4cc(Cl)c(OC(F)F)c(Cl)c4)C(=O)C3C3(C(=O)Nc4c(Cl)cc(Cl)cc43)N2C1]
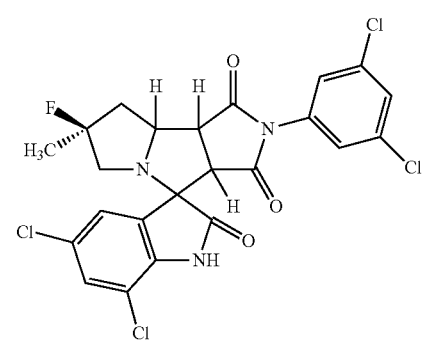 [SMILES: C[C@]1(F)CC2C3C(=O)N(c4cc(Cl)cc(Cl)c4)C(=O)C3C3(C(=O)Nc4c(Cl)cc(Cl)cc43)N2C1]
TABLE A-continued
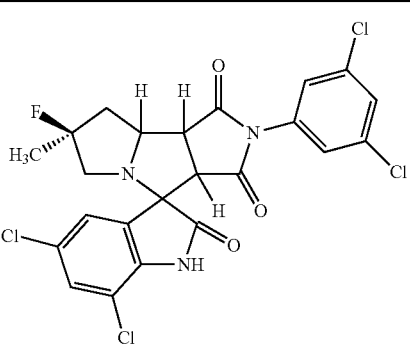
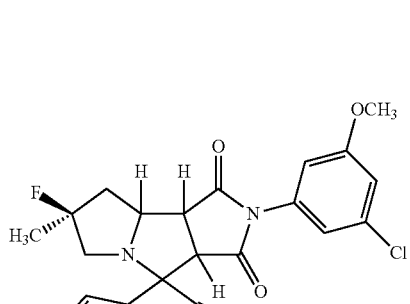
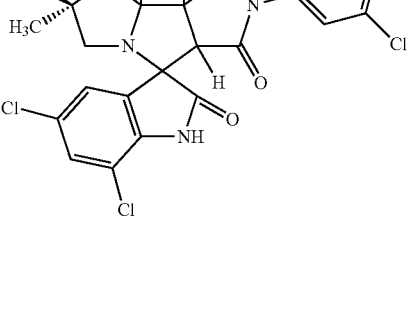
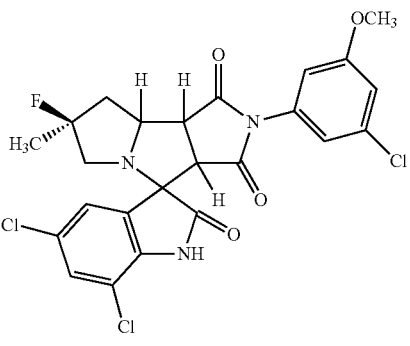 [SMILES: COc1cc(Cl)cc(N2C(=O)C3C4C[C@](C)(F)CN4C4(C(=O)Nc5c(Cl)cc(Cl)cc54)C3C2=O)c1]

TABLE A-continued

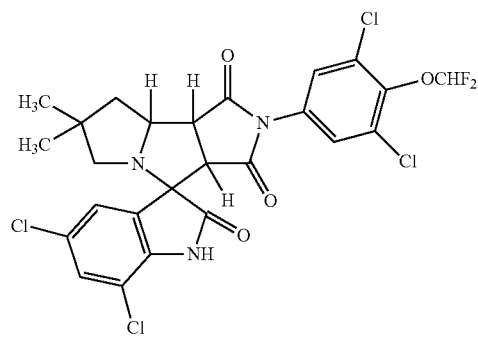 [SMILES: CC1(C)CC2C3C(=O)N(c4cc(Cl)c(OC(F)F)c(Cl)c4)C(=O)C3C3(C(=O)Nc4c(Cl)cc(Cl)cc43)N2C1]

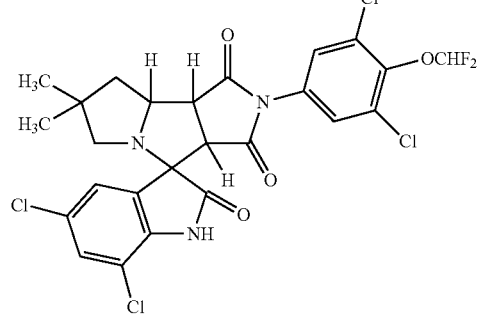

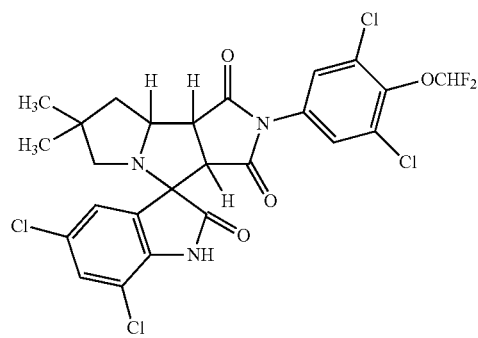 [SMILES: CC1(C)CC2C3C(=O)N(c4cc(Cl)c(OC(F)F)c(Cl)c4)C(=O)C3C3(C(=O)Nc4c(Cl)cc(Cl)cc43)N2C1]

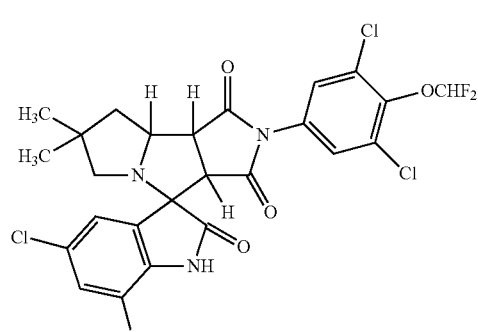

TABLE A-continued

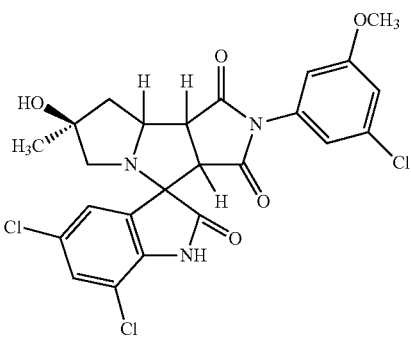 [SMILES: COc1cc(Cl)cc(N2C(=O)C3C4C[C@](C)(O)CN4C4(C(=O)Nc5c(Cl)cc(Cl)cc54)C3C2=O)c1]

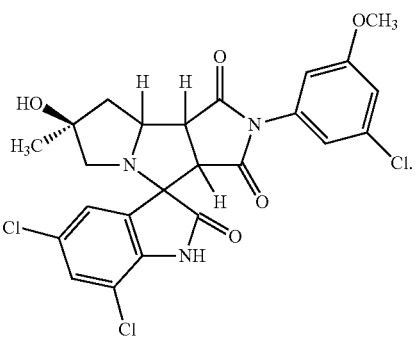 [SMILES: COc1cc(Cl)cc(N2C(=O)C3C4C[C@](C)(O)CN4C4(C(=O)Nc5c(Cl)cc(Cl)cc54)C3C2=O)c1]

3. A pharmaceutical composition comprising a compound of claim 2 and a pharmaceutically acceptable carrier or excipient.

4. A method of treating a disease or disorder mediated by cystic fibrosis transmembrane conductance regulator (CFTR) in a subject in need thereof, comprising the step of administering to the subject a therapeutically effective amount of the composition of claim 2.

5. The compound of claim 1 represented by Formula V, or a pharmaceutically acceptable salt thereof;

Formula V

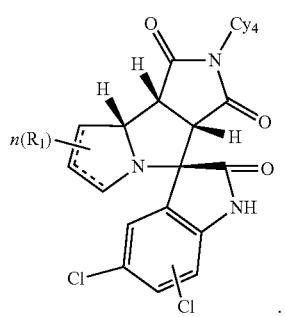

6. The compound according to claim 1, wherein Cy4 is selected from:

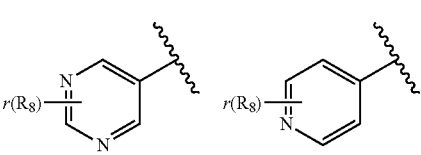

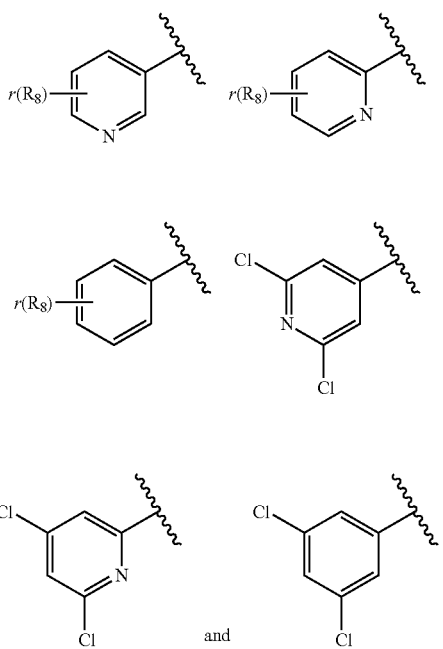

wherein r is selected from 0, 1, 2, and 3; and
R₈ is selected from hydrogen, deuterium, halogen, —OR₁₂, —SR₁₂, —NR₁₀R₁₃, —CF₃, —CN, —NO₂, —N₃, —C(O)OR₁₂, —C(O)R₁₂, —C(O)NR₁₂R₁₃, —S(O)R₁₂, —S(O)NR₁₂, —S(O)₂R₁₂, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl and substituted heteroaryl; alternatively, two R₈ groups together with the atoms to which they are attached form a 3, 4, 5, 6 or 7 membered, optionally substituted carbocyclic, heterocyclic or aryl group.

7. The compound according to claim 1, having the formula:

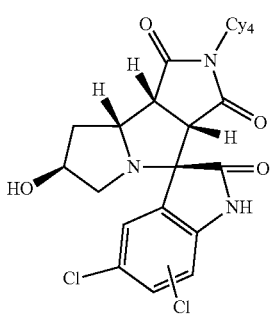

or a pharmaceutically acceptable salt thereof.

8. The compound according to claim 1, having the formula:

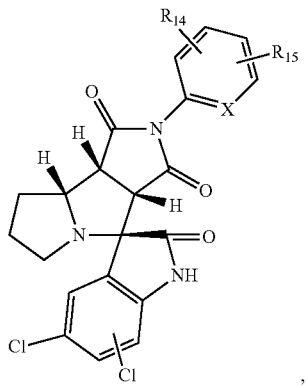

or a pharmaceutically acceptable salt thereof;
wherein
R₁₄ and R₁₅ are each independently selected from the group consisting of hydrogen, deuterium, halogen, —OR₁₂, —SR₁₂, —NR₁₀R₁₃, —CF₃, —CN, —NO₂, —N₃, —C(O)OR₁₂, —C(O)R₁₂, —C(O)NR₁₂R₁₃, —S(O)R₁₂, —S(O)NR₁₂, —S(O)₂R₁₂, alkyl, substituted alkyl, alkenyl, substituted alkenyl, alkynyl, substituted alkynyl, aliphatic, substituted aliphatic, aryl, substituted aryl, heterocyclyl, substituted heterocyclyl, heteroaryl and substituted heteroaryl; alternatively, R₁₄ and R₁₅ together with the atoms to which they are attached form a 3, 4, 5, 6 or 7 membered, optionally substituted carbocyclic, heterocyclic or aryl group; and;
X is N or CR₁₀.

9. The compound according to claim 8, wherein R₁₄ is —Cl, —Br, —F, —CF₃, —OCH₃, —OCH₂CH₃, —OCH₂C(CH₃)₃, —C(O)OCH₃, —CH₃, —CH₂CH₃, or —C(O)NH₂.

10. The compound according to claim 8, wherein R₁₅ is —Cl, —Br, —F, —CF₃, —OCH₃, —OCH₂CH₃, —OCH₂C(CH₃)₃, —C(O)OCH₃, —CH₃, —CH₂CH₃, or —C(O)NH₂.

11. A pharmaceutical composition comprising a compound according to claim 1 and a pharmaceutically acceptable carrier or excipient.

12. The compound according to claim 1, wherein Cy4 is:

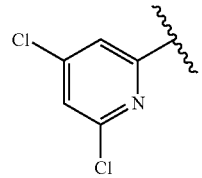

13. The compound according to claim 1, wherein Cy4 is:

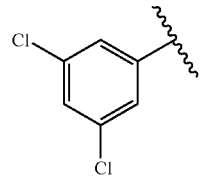

14. The compound according to claim 8, wherein R₁₄ is —Cl.

15. The compound according to claim 8, wherein R₁₅ is —Cl.

16. The compound according to claim 8, wherein $R_{14}$ and $R_{15}$ are —Cl.

17. A method of treating a disease or disorder mediated by cystic fibrosis transmembrane conductance regulator (CFTR) in a subject in need thereof, comprising the step of administering to the subject a therapeutically effective amount of the compound of claim 1.

18. A method of treating cystic fibrosis or a symptom thereof in a subject in need thereof, comprising the step of administering to the subject a therapeutically effective amount of the compound of claim 1.

19. A method of treating cystic fibrosis or a symptom thereof in a subject in need thereof, comprising the step of administering to the subject a therapeutically effective amount of the compound of claim 2.

* * * * *

UNITED STATES PATENT AND TRADEMARK OFFICE
CERTIFICATE OF CORRECTION

PATENT NO. : 10,072,017 B2
APPLICATION NO. : 15/392727
DATED : September 11, 2018
INVENTOR(S) : Michael P. Zawistoski et al.

Page 1 of 2

It is certified that error appears in the above-identified patent and that said Letters Patent is hereby corrected as shown below:

In the Claims

Column 194, Claim 2, Line 56: please delete " 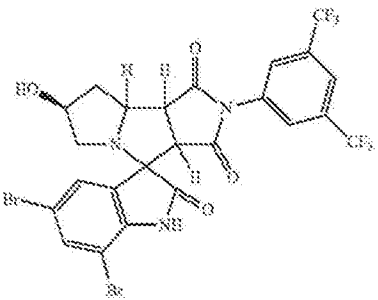 " and replace with -- 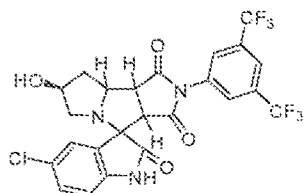 --;

Column 215, Claim 2, Line 54: please delete " 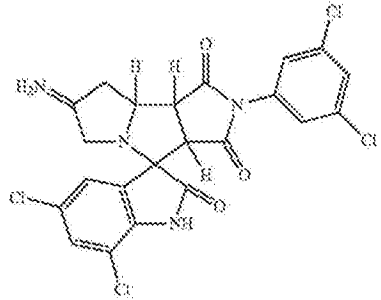 " and replace

Signed and Sealed this
Fourth Day of December, 2018

Andrei Iancu
*Director of the United States Patent and Trademark Office*

CERTIFICATE OF CORRECTION (continued)
U.S. Pat. No. 10,072,017 B2 with -- 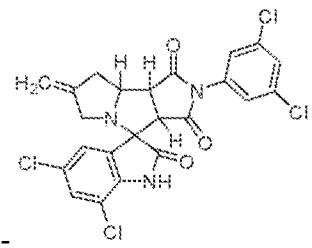 --;

Column 226, Claim 2, Line 20: please delete " 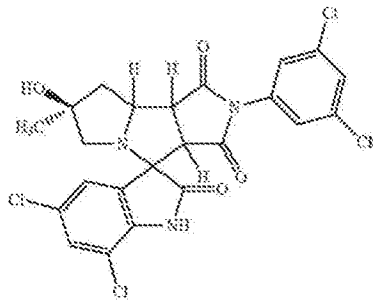 " and replace with -- 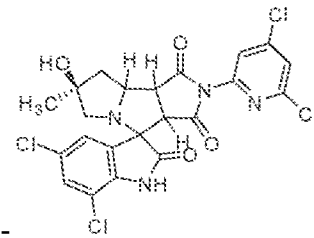 --.